(12) United States Patent
Salahieh et al.

(10) Patent No.: US 8,805,466 B2
(45) Date of Patent: Aug. 12, 2014

(54) LOW PROFILE ELECTRODE ASSEMBLY

(75) Inventors: Amr Salahieh, Saratoga, CA (US);
Jonah Lepak, Santa Cruz, CA (US);
Emma Leung, Sunnyvale, CA (US);
Brian D. Brandt, San Jose, CA (US);
John P. Claude, Redwood City, CA (US); Tom Saul, El Granada, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 248 days.

(21) Appl. No.: 13/106,658

(22) Filed: May 12, 2011

(65) Prior Publication Data

US 2012/0071870 A1   Mar. 22, 2012

Related U.S. Application Data

(63) Continuation-in-part of application No. 12/616,758, filed on Nov. 11, 2009, now Pat. No. 8,295,902.

(60) Provisional application No. 61/113,228, filed on Nov. 11, 2008, provisional application No. 61/160,204, filed on Mar. 13, 2009, provisional application No. 61/179,654, filed on May 19, 2009, provisional application No. 61/232,756, filed on Aug. 10, 2009, provisional application No. 61/253,683, filed on Oct. 21, 2009, provisional application No. 61/334,154, filed on May 12, 2010.

(51) Int. Cl.
*A61B 5/042* (2006.01)
*A61B 18/14* (2006.01)
*A61N 1/05* (2006.01)

(52) U.S. Cl.
USPC .............. 600/374; 600/381; 606/41; 607/122

(58) Field of Classification Search
USPC ...................... 600/374, 381; 606/41; 607/122
See application file for complete search history.

(56) References Cited

U.S. PATENT DOCUMENTS

| 4,547,193 A | 10/1985 | Rydell |
| 4,634,432 A | 1/1987 | Kocak |

(Continued)

FOREIGN PATENT DOCUMENTS

| CN | 1781161 A | 5/2006 |
| DE | 4104092 A1 | 8/1991 |

(Continued)

OTHER PUBLICATIONS

Drafts, Bill; Acoustic wave technology sensors; Sensors Weekly (Questex Media Group); 10 pgs.; Oct. 1, 2000 (http://www.sensorsmag.com/sensors/acoustic-ultrasound/acoustic-wave-technology-sensors-936).

(Continued)

*Primary Examiner* — Lee S Cohen
(74) *Attorney, Agent, or Firm* — Shay Glenn LLP

(57) ABSTRACT

A tissue electrode assembly includes a membrane configured to form an expandable, conformable body that is deployable in a patient. The assembly further includes a flexible circuit positioned on a surface of the membrane and comprising at least one base substrate layer, at least one insulating layer and at least one planar conducting layer. An electrically-conductive electrode covers at least a portion of the flexible circuit and a portion of the surface of the membrane not covered by the flexible circuit, wherein the electrically-conductive electrode is foldable upon itself with the membrane to a delivery conformation having a diameter suitable for minimally-invasive delivery of the assembly to the patient.

22 Claims, 91 Drawing Sheets

(56) References Cited

U.S. PATENT DOCUMENTS

| | | |
|---|---|---|
| 4,692,139 A | 9/1987 | Stiles |
| 4,726,382 A | 2/1988 | Boehmer et al. |
| 4,890,623 A | 1/1990 | Cook et al. |
| 4,968,306 A | 11/1990 | Huss et al. |
| 5,010,895 A | 4/1991 | Maurer et al. |
| 5,041,089 A | 8/1991 | Mueller et al. |
| 5,069,674 A | 12/1991 | Fearnot et al. |
| 5,180,376 A | 1/1993 | Fischell |
| 5,209,741 A | 5/1993 | Spaeth |
| 5,213,576 A | 5/1993 | Abiuso et al. |
| 5,228,442 A | 7/1993 | Imran |
| 5,306,250 A | 4/1994 | March et al. |
| 5,309,910 A | 5/1994 | Edwards et al. |
| 5,311,866 A | 5/1994 | Kagan et al. |
| 5,343,860 A | 9/1994 | Metzger et al. |
| 5,391,200 A | 2/1995 | KenKnight et al. |
| 5,443,470 A | 8/1995 | Stern et al. |
| 5,505,730 A | 4/1996 | Edwards |
| 5,515,848 A | 5/1996 | Corbett, III et al. |
| 5,524,338 A | 6/1996 | Martyniuk et al. |
| 5,540,679 A | 7/1996 | Fram et al. |
| 5,558,672 A | 9/1996 | Edwards et al. |
| 5,562,720 A | 10/1996 | Stern et al. |
| 5,569,241 A | 10/1996 | Edwards |
| 5,571,086 A | 11/1996 | Kaplan et al. |
| 5,571,088 A | 11/1996 | Lennox et al. |
| 5,573,520 A | 11/1996 | Schwartz et al. |
| 5,575,772 A | 11/1996 | Lennox |
| 5,575,788 A | 11/1996 | Baker et al. |
| 5,609,574 A | 3/1997 | Kaplan et al. |
| 5,609,606 A | 3/1997 | O'Boyle |
| 5,626,564 A | 5/1997 | Zhan et al. |
| 5,630,837 A | 5/1997 | Crowley |
| 5,681,308 A | 10/1997 | Edwards et al. |
| 5,715,825 A | 2/1998 | Crowley |
| 5,718,701 A | 2/1998 | Shai et al. |
| 5,735,846 A | 4/1998 | Panescu et al. |
| 5,769,846 A | 6/1998 | Edwards et al. |
| 5,779,698 A | 7/1998 | Clayman et al. |
| 5,836,874 A | 11/1998 | Swanson et al. |
| 5,846,196 A | 12/1998 | Siekmeyer et al. |
| 5,846,238 A | 12/1998 | Jackson et al. |
| 5,846,239 A | 12/1998 | Swanson et al. |
| 5,853,411 A | 12/1998 | Whayne et al. |
| 5,860,974 A | 1/1999 | Abele |
| 5,871,483 A | 2/1999 | Jackson et al. |
| 5,879,348 A | 3/1999 | Owens et al. |
| 5,888,577 A | 3/1999 | Griffin, III et al. |
| 5,904,651 A | 5/1999 | Swanson et al. |
| 5,938,660 A | 8/1999 | Swartz et al. |
| 5,961,513 A | 10/1999 | Swanson et al. |
| 5,991,650 A | 11/1999 | Swanson et al. |
| 6,004,269 A | 12/1999 | Crowley et al. |
| 6,012,457 A | 1/2000 | Lesh |
| 6,024,740 A | 2/2000 | Lesh et al. |
| 6,052,607 A | 4/2000 | Edwards et al. |
| 6,123,718 A | 9/2000 | Tu et al. |
| 6,142,993 A | 11/2000 | Whayne et al. |
| 6,163,726 A | 12/2000 | Wolf |
| 6,164,283 A | 12/2000 | Lesh |
| 6,206,912 B1 | 3/2001 | Goldsteen et al. |
| 6,292,689 B1 | 9/2001 | Wallace et al. |
| 6,402,746 B1 | 6/2002 | Whayne et al. |
| 6,460,545 B2 | 10/2002 | Kordis |
| 6,500,174 B1 | 12/2002 | Maguire et al. |
| 6,514,249 B1 | 2/2003 | Maguire et al. |
| 6,558,378 B2 | 5/2003 | Sherman et al. |
| 6,572,609 B1 | 6/2003 | Farr et al. |
| 6,572,612 B2 | 6/2003 | Stewart et al. |
| 6,595,989 B1 | 7/2003 | Schaer |
| 6,635,054 B2 | 10/2003 | Fjield et al. |
| 6,641,553 B1 | 11/2003 | Chee et al. |
| 6,652,515 B1 | 11/2003 | Maguire et al. |
| 6,660,002 B1 | 12/2003 | Edwards et al. |
| 6,736,811 B2 | 5/2004 | Panescu et al. |
| 6,743,226 B2 | 6/2004 | Cosman et al. |
| 6,771,996 B2 | 8/2004 | Bowe et al. |
| 6,780,183 B2 | 8/2004 | Jimenez, Jr. et al. |
| 6,808,524 B2 | 10/2004 | Lopath et al. |
| 6,814,730 B2 | 11/2004 | Li |
| 6,869,431 B2 | 3/2005 | Maguire et al. |
| 6,872,183 B2 | 3/2005 | Sampson et al. |
| 6,872,206 B2 | 3/2005 | Edwards et al. |
| 6,911,027 B1 | 6/2005 | Edwards et al. |
| 6,942,657 B2 | 9/2005 | Sinofsky et al. |
| 6,978,174 B2 | 12/2005 | Gelfand et al. |
| 7,004,923 B2 | 2/2006 | Deniega et al. |
| 7,048,733 B2 | 5/2006 | Hartley et al. |
| 7,115,122 B1 | 10/2006 | Swanson et al. |
| 7,137,395 B2 | 11/2006 | Fried et al. |
| 7,150,745 B2 | 12/2006 | Stern et al. |
| 7,162,303 B2 | 1/2007 | Levin et al. |
| 7,207,984 B2 | 4/2007 | Farr et al. |
| 7,226,448 B2 | 6/2007 | Bertolero et al. |
| 7,232,437 B2 | 6/2007 | Berman et al. |
| 7,238,179 B2 | 7/2007 | Brucker et al. |
| 7,238,180 B2 | 7/2007 | Mester et al. |
| 7,267,674 B2 | 9/2007 | Brucker et al. |
| 7,286,866 B2 | 10/2007 | Okerlund et al. |
| 7,291,146 B2 | 11/2007 | Steinke et al. |
| 7,310,150 B2 | 12/2007 | Guillermo et al. |
| 7,320,677 B2 | 1/2008 | Brouillette |
| 7,346,381 B2 | 3/2008 | Okerlund et al. |
| 7,357,796 B2 | 4/2008 | Farr et al. |
| 7,365,859 B2 | 4/2008 | Yun et al. |
| 7,366,376 B2 | 4/2008 | Shishkov et al. |
| 7,371,231 B2 | 5/2008 | Rioux et al. |
| 7,382,949 B2 | 6/2008 | Bouma et al. |
| 7,396,355 B2 | 7/2008 | Goldman et al. |
| 7,406,970 B2 | 8/2008 | Zikorus et al. |
| 7,413,568 B2 | 8/2008 | Swanson et al. |
| 7,418,169 B2 | 8/2008 | Tearney et al. |
| 7,429,260 B2 | 9/2008 | Underwood et al. |
| 7,429,261 B2 | 9/2008 | Kunis et al. |
| 7,445,618 B2 | 11/2008 | Eggers et al. |
| 7,447,408 B2 | 11/2008 | Bouma et al. |
| 7,452,358 B2 | 11/2008 | Stern et al. |
| 7,468,062 B2 | 12/2008 | Oral et al. |
| 7,473,251 B2 | 1/2009 | Knowlton et al. |
| 7,481,808 B2 | 1/2009 | Koyfman et al. |
| 7,481,809 B2 | 1/2009 | Stern et al. |
| 7,489,969 B2 | 2/2009 | Knudson et al. |
| 7,507,236 B2 | 3/2009 | Eggers et al. |
| 7,510,555 B2 | 3/2009 | Kanzius |
| 7,519,096 B2 | 4/2009 | Bouma et al. |
| 7,529,393 B2 | 5/2009 | Peszynski et al. |
| 7,538,859 B2 | 5/2009 | Tearney et al. |
| 7,617,005 B2 | 11/2009 | Demarais et al. |
| 7,620,451 B2 | 11/2009 | Demarais et al. |
| 7,653,438 B2 | 1/2010 | Deem et al. |
| 7,669,309 B2 | 3/2010 | Johnson et al. |
| 7,756,583 B2 | 7/2010 | Demarais et al. |
| 7,853,333 B2 | 12/2010 | Demarais |
| 7,937,143 B2 | 5/2011 | Demarais et al. |
| 8,337,492 B2 * | 12/2012 | Kunis et al. ............... 606/41 |
| 2002/0002384 A1 | 1/2002 | Gilson et al. |
| 2002/0095147 A1 | 7/2002 | Shadduck |
| 2003/0097121 A1 | 5/2003 | Jolly et al. |
| 2003/0236443 A1 | 12/2003 | Cespedes et al. |
| 2004/0243118 A1 * | 12/2004 | Ayers et al. ............... 606/21 |
| 2005/0203597 A1 * | 9/2005 | Yamazaki et al. ............... 607/98 |
| 2006/0041277 A1 | 2/2006 | Deem et al. |
| 2006/0100618 A1 | 5/2006 | Chan et al. |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0247701 A1 | 11/2006 | Zacouto |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2007/0078507 A1 | 4/2007 | Zacouto |
| 2007/0112422 A1 | 5/2007 | Dehdashtian |
| 2007/0118094 A1 | 5/2007 | Bingham et al. |

(56) References Cited

U.S. PATENT DOCUMENTS

| | | |
|---|---|---|
| 2007/0129760 A1 | 6/2007 | Demarais et al. |
| 2007/0135875 A1 | 6/2007 | Demarais et al. |
| 2007/0213671 A1 | 9/2007 | Hiatt |
| 2007/0225634 A1 | 9/2007 | Ferren et al. |
| 2007/0244501 A1 | 10/2007 | Horn et al. |
| 2008/0188912 A1 | 8/2008 | Stone et al. |
| 2008/0205481 A1 | 8/2008 | Faries, Jr. et al. |
| 2008/0275445 A1 | 11/2008 | Kelly et al. |
| 2008/0281312 A1 | 11/2008 | Werneth et al. |
| 2008/0281322 A1 | 11/2008 | Sherman et al. |
| 2008/0296152 A1 | 12/2008 | Voss |
| 2009/0024195 A1 | 1/2009 | Rezai et al. |
| 2009/0227885 A1 | 9/2009 | Lowery et al. |
| 2009/0240249 A1 | 9/2009 | Chan et al. |
| 2009/0254142 A1 | 10/2009 | Edwards et al. |
| 2009/0312754 A1 | 12/2009 | Lenihan et al. |
| 2010/0087782 A1* | 4/2010 | Ghaffari et al. .......... 604/103.01 |
| 2010/0204560 A1 | 8/2010 | Salahieh et al. |
| 2010/0331776 A1 | 12/2010 | Salahieh et al. |
| 2011/0034790 A1* | 2/2011 | Mourlas et al. ............... 600/345 |
| 2011/0046600 A1 | 2/2011 | Crank |
| 2011/0077579 A1 | 3/2011 | Harrison et al. |
| 2011/0257622 A1 | 10/2011 | Salahieh et al. |
| 2012/0116438 A1 | 5/2012 | Salahieh et al. |

FOREIGN PATENT DOCUMENTS

| | | |
|---|---|---|
| EP | 0637943 B1 | 4/1998 |
| EP | 0723467 B1 | 4/2002 |
| EP | 0693955 B1 | 1/2003 |
| EP | 1382366 A1 | 1/2004 |
| EP | 2335757 A2 | 6/2011 |
| JP | 2000-504242 A | 4/2000 |
| WO | WO 99/00060 A1 | 1/1999 |
| WO | WO 00/66014 A1 | 11/2000 |
| WO | WO 2009/067695 A1 | 5/2009 |
| WO | WO 2009/132137 A1 | 10/2009 |

OTHER PUBLICATIONS

Salahieh et al.; U.S. Appl. No. 13/748,374 entitled "Intravascular Tissue Disruption," filed Jan. 23, 2013.

Salahieh et al.; U.S. Appl. No. 13/830,624 entitled "Local Sympathectomy for PVD," filed Mar. 14, 2013.

Salahieh et al.; U.S. Appl. No. 61/622,495 entitled "Energy Delivery Device with Rapid Exchange Features," filed Apr. 10, 2012.

Salahieh et al.; U.S. Appl. No. 61/624,206 entitled "Energy delivery device and methods of use," filed Apr. 13, 2012.

Salahieh et al.; U.S. Appl. No. 13/943,633 entitled "Low Profile Electrode Assembly," filed Jul. 16, 2013.

Salahieh et al.; U.S. Appl. No. 14/023,343 entitled "Steerable Deliverey Sheaths," filed Sep. 11, 2013.

Salahieh et al.; U.S. Appl. No. 14/070,232 entitled "Steerable Medical Delivery Devices and Methods of Use," filed Nov. 1, 2013.

\* cited by examiner

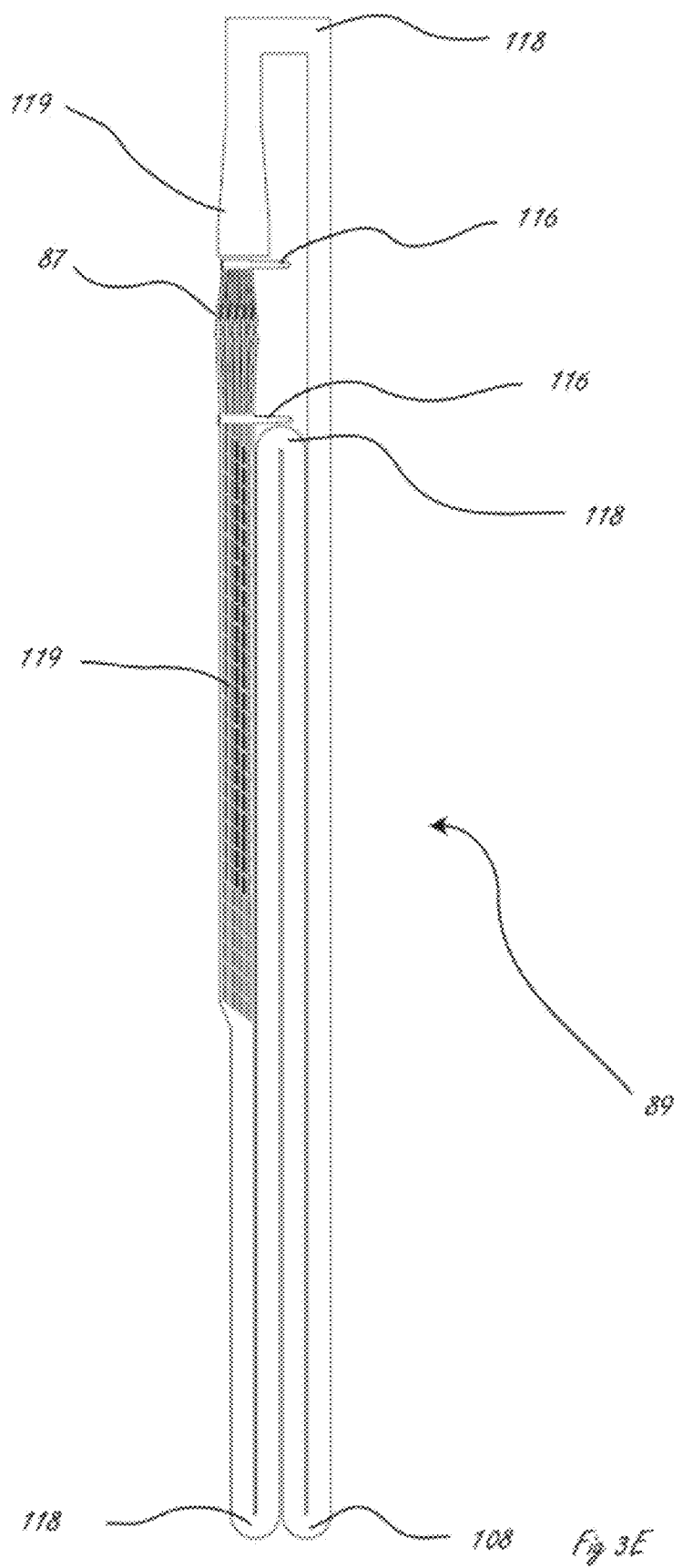

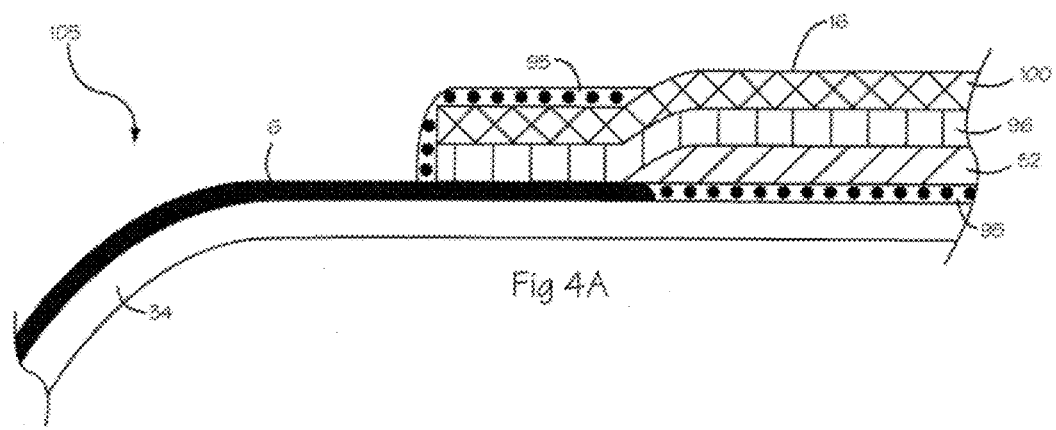
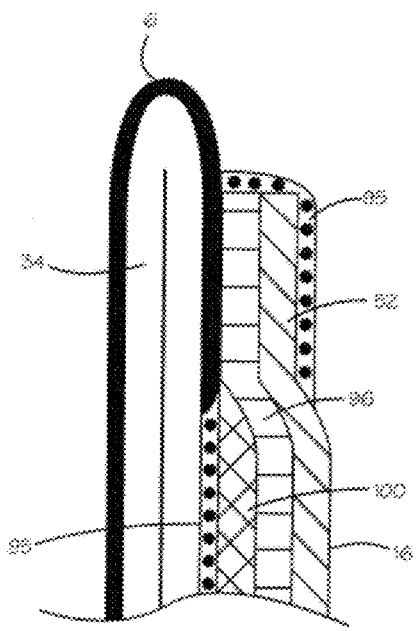 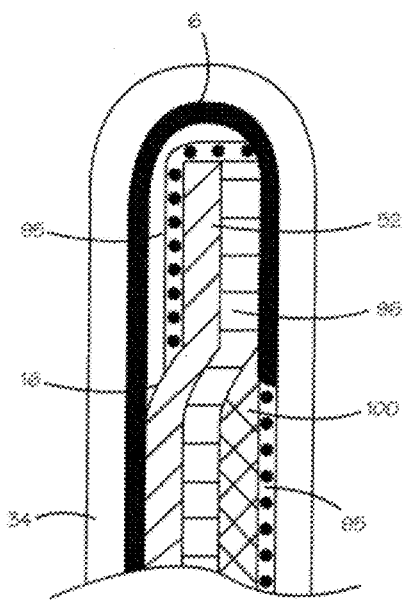
Fig 4A
Fig 4B    Fig 4C

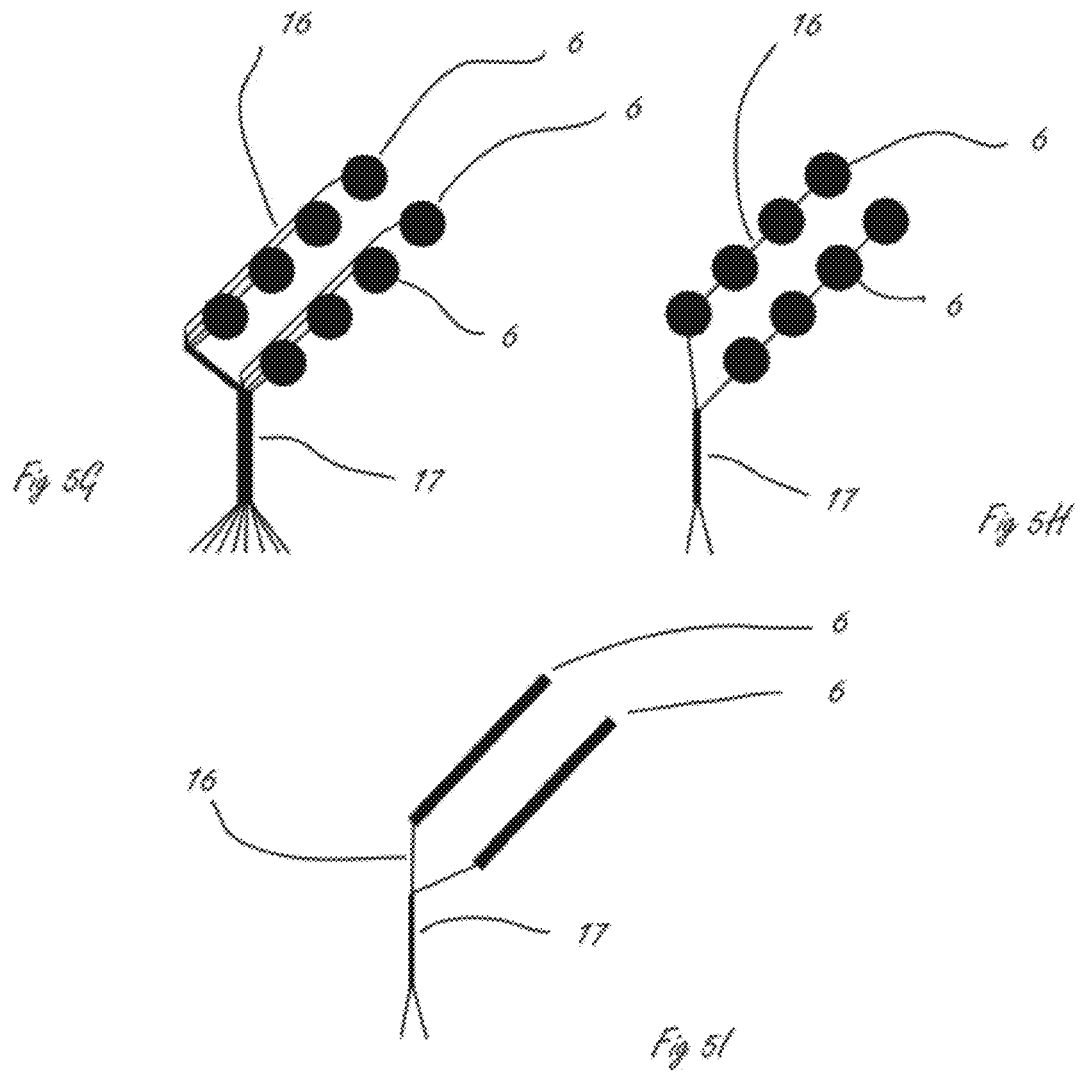

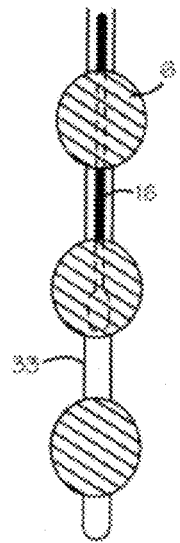 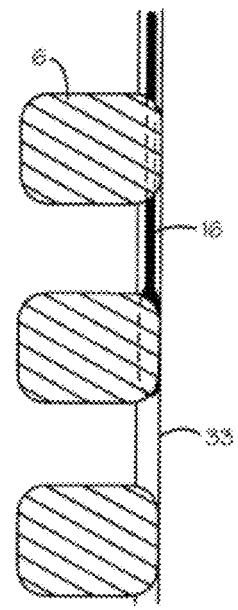
Fig 9A     Fig 9B
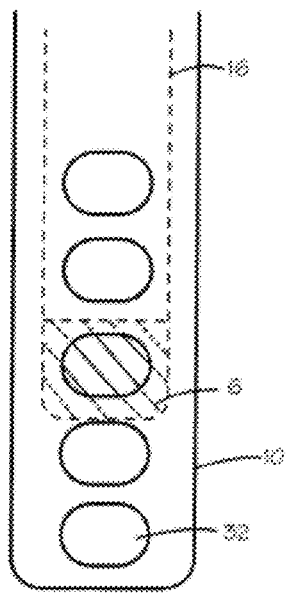 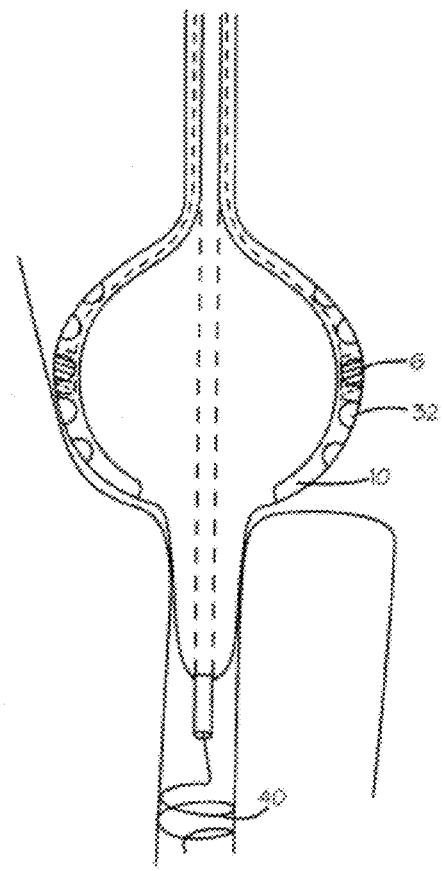
Fig 10     Fig 11

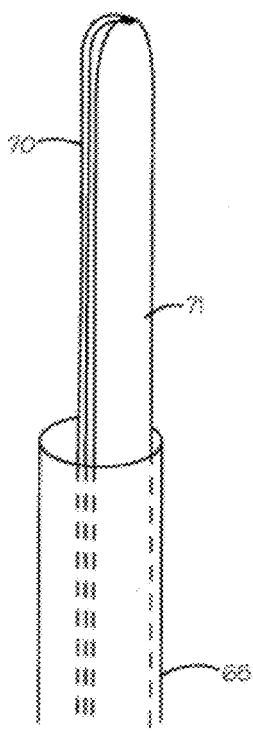
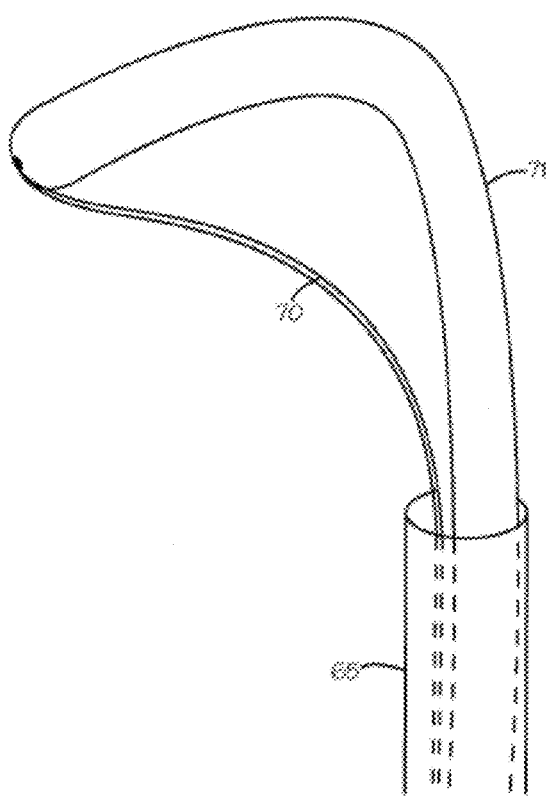
Fig 15A                                   Fig 15B

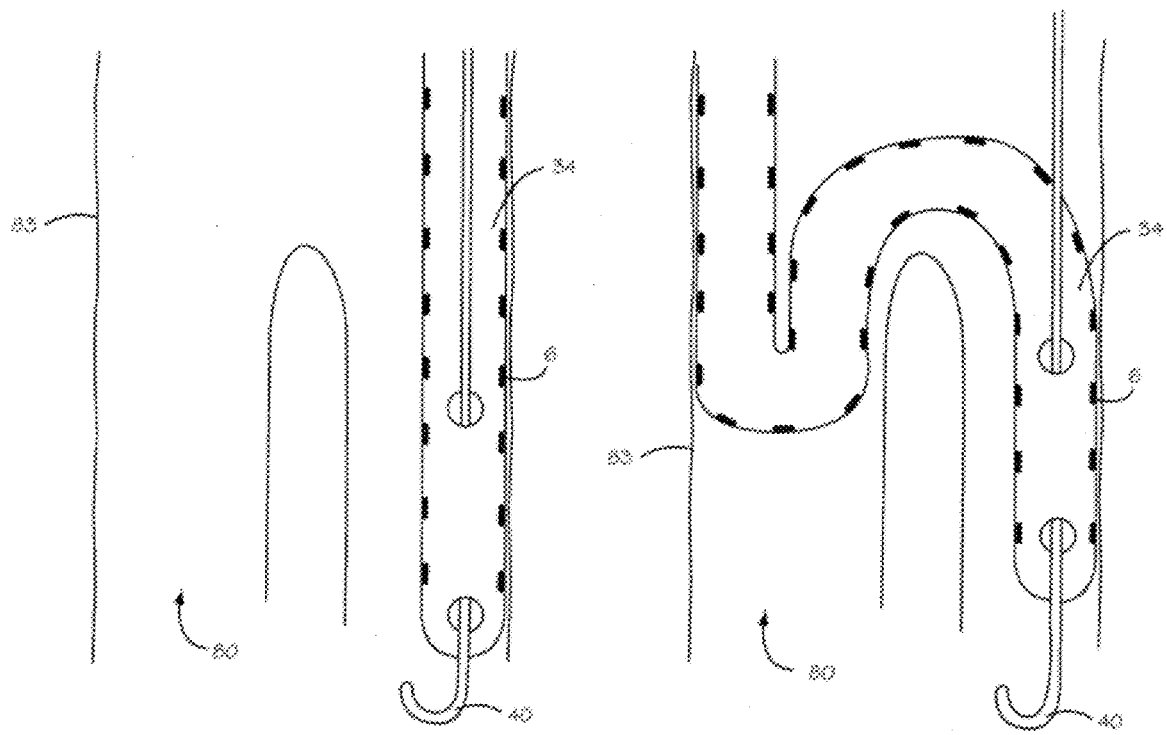
Fig 16A                    Fig 16B

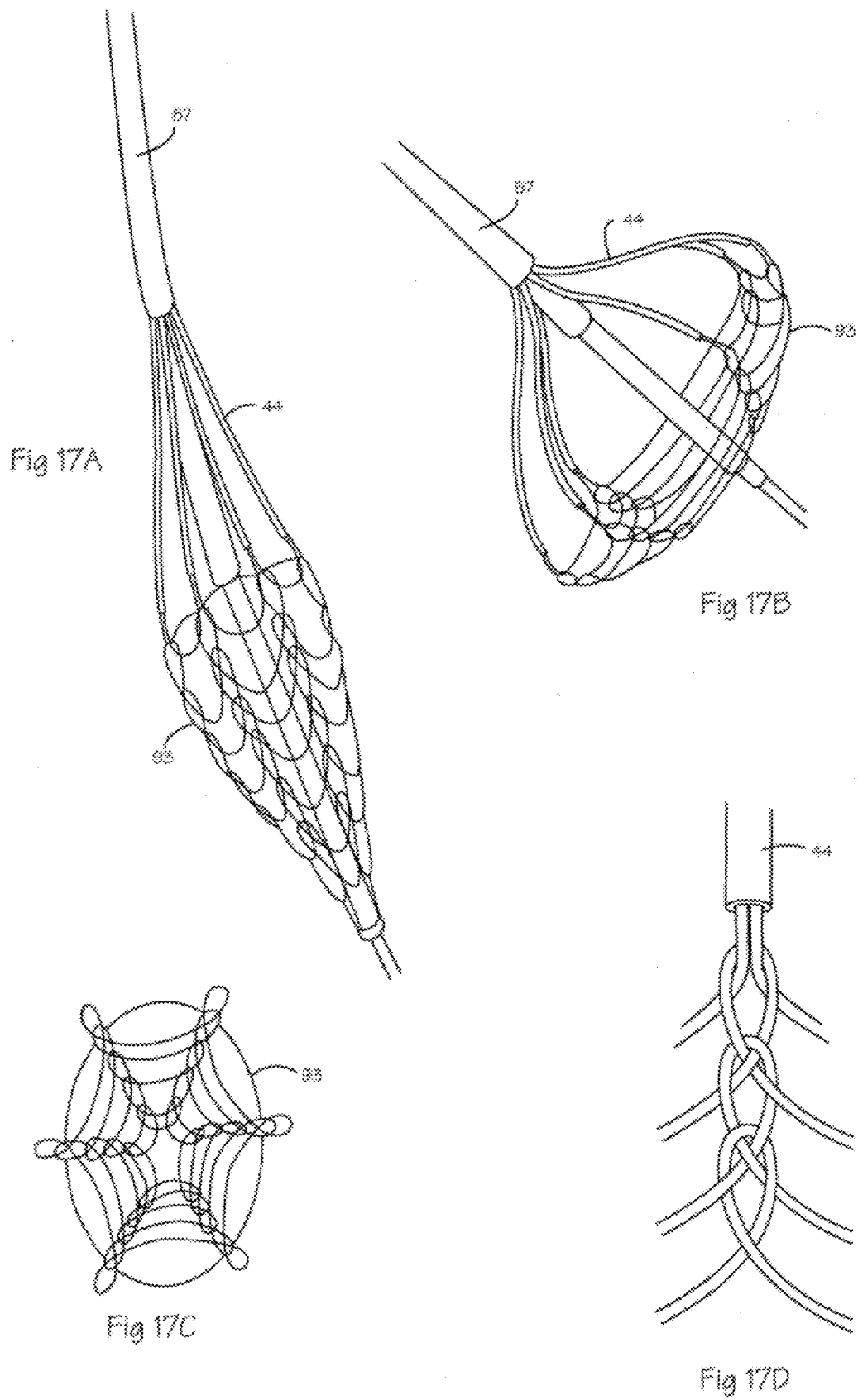

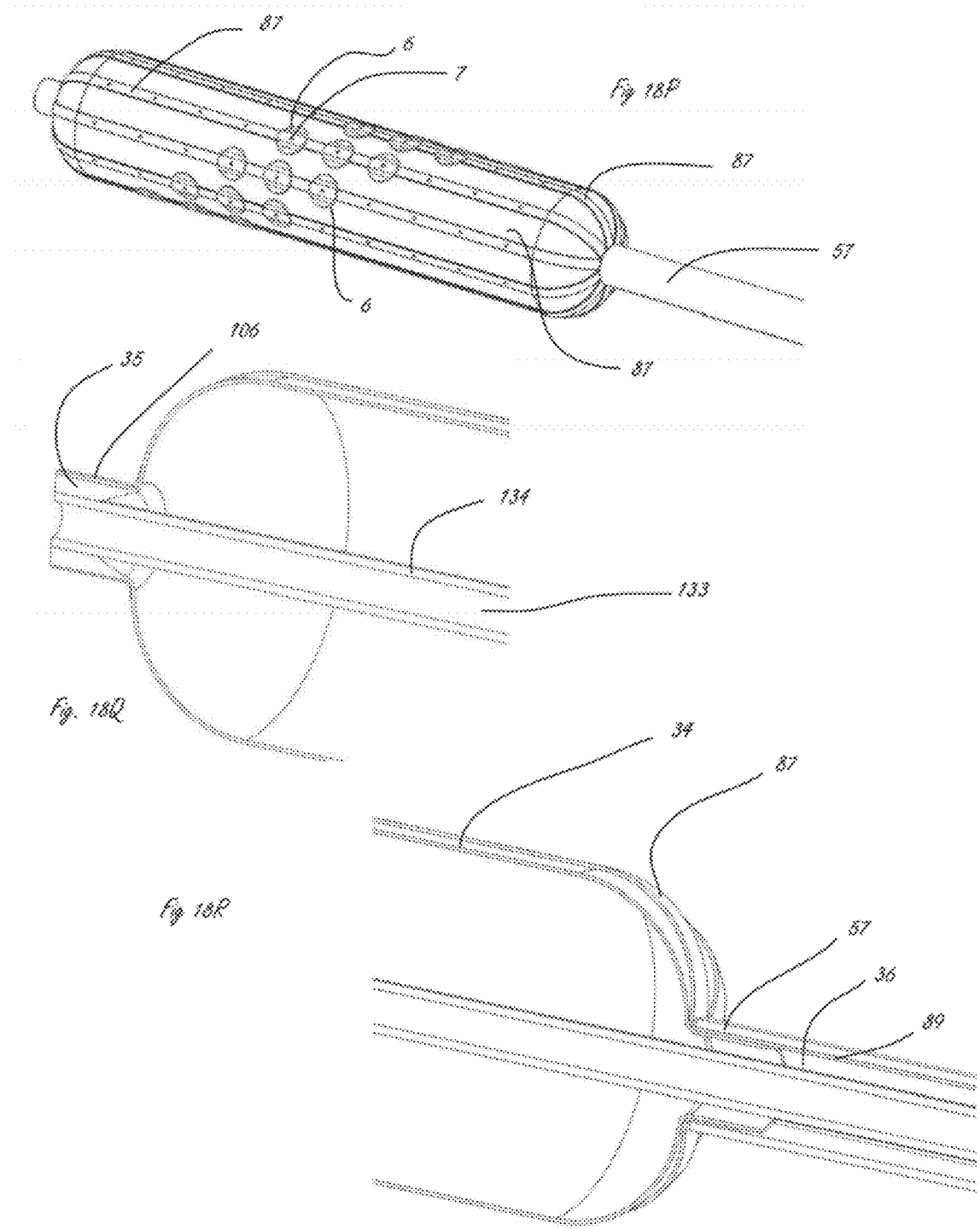

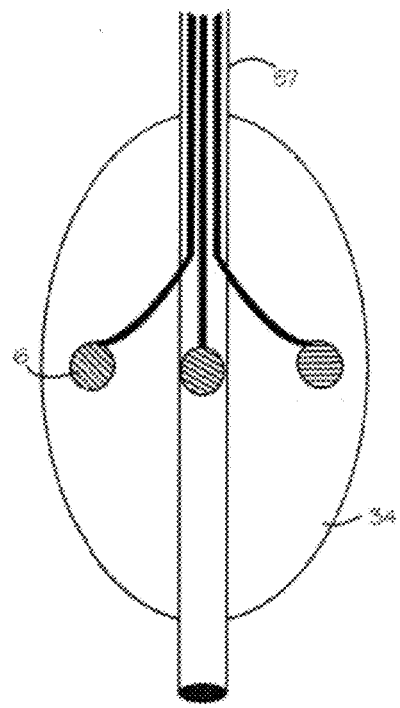
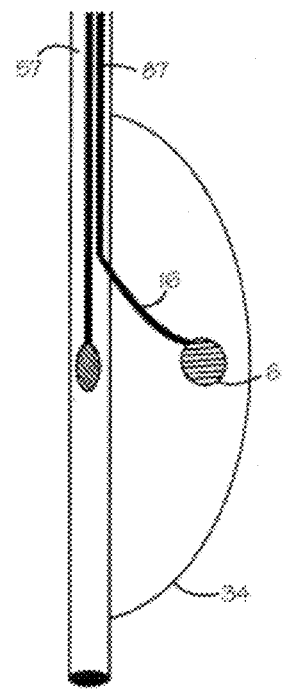
Fig 19A
Fig 19B
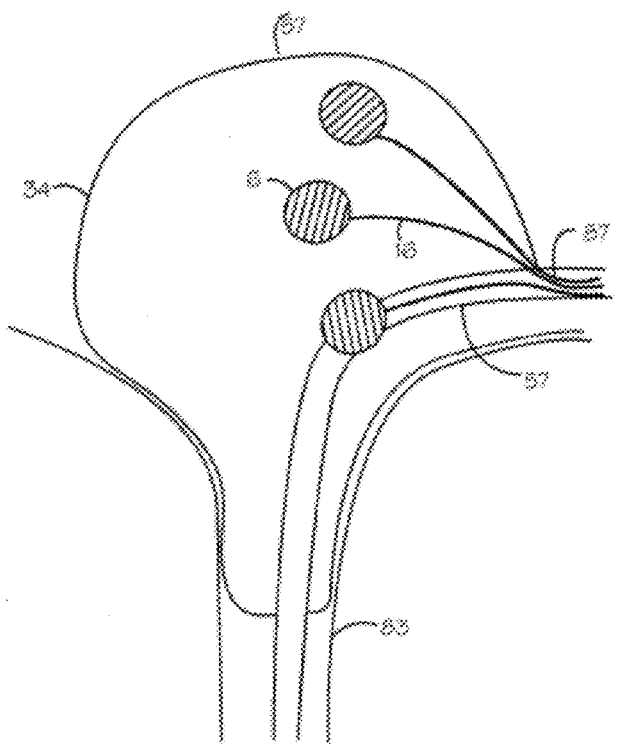
Fig 19C

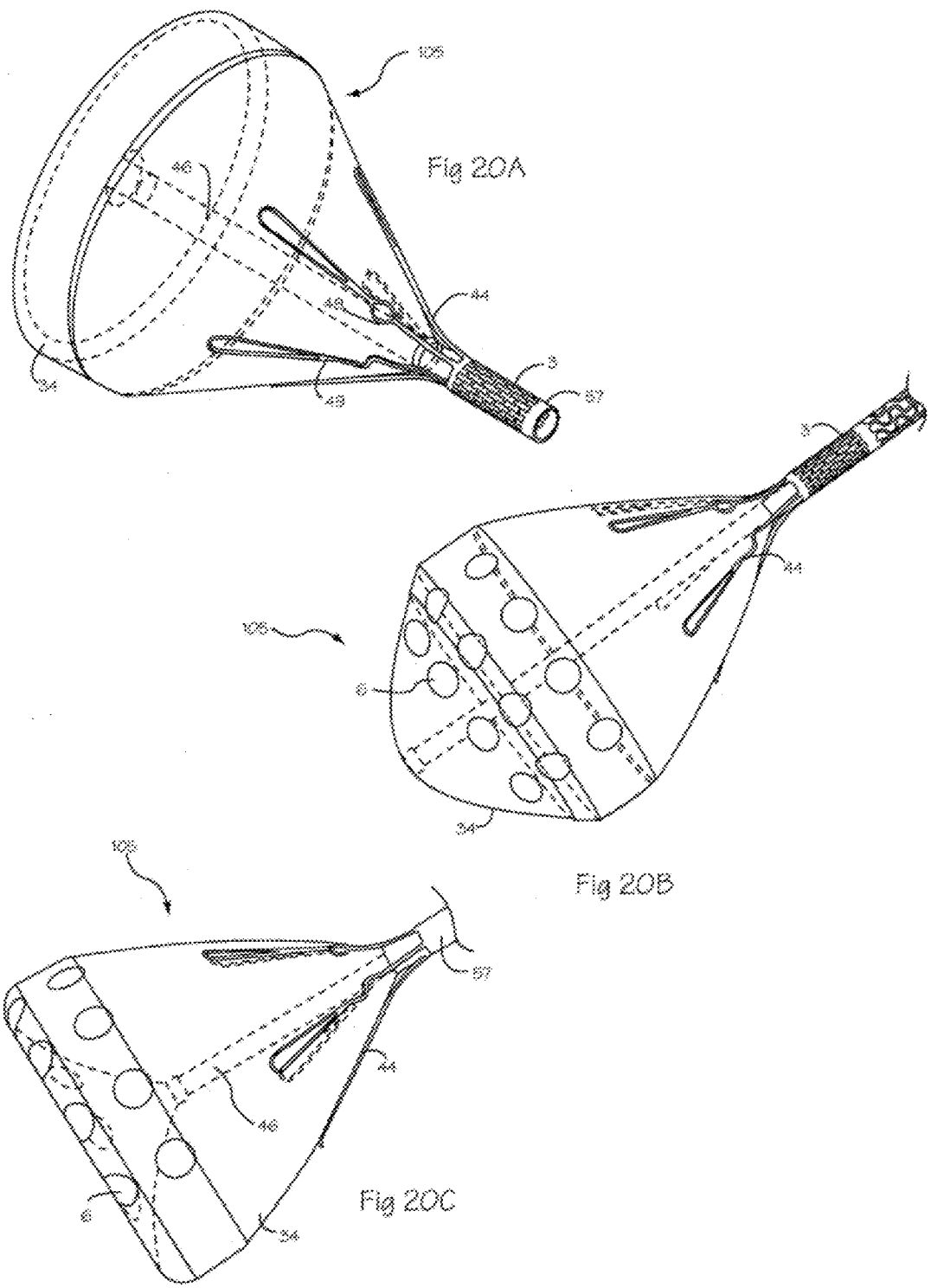

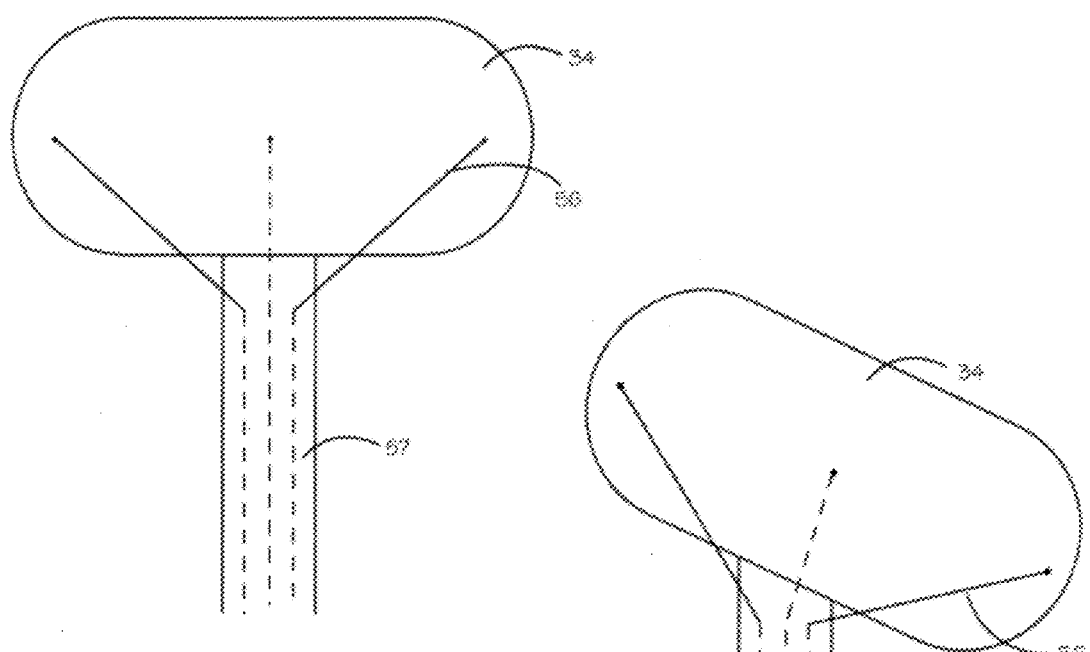
Fig 27A
Fig 27B
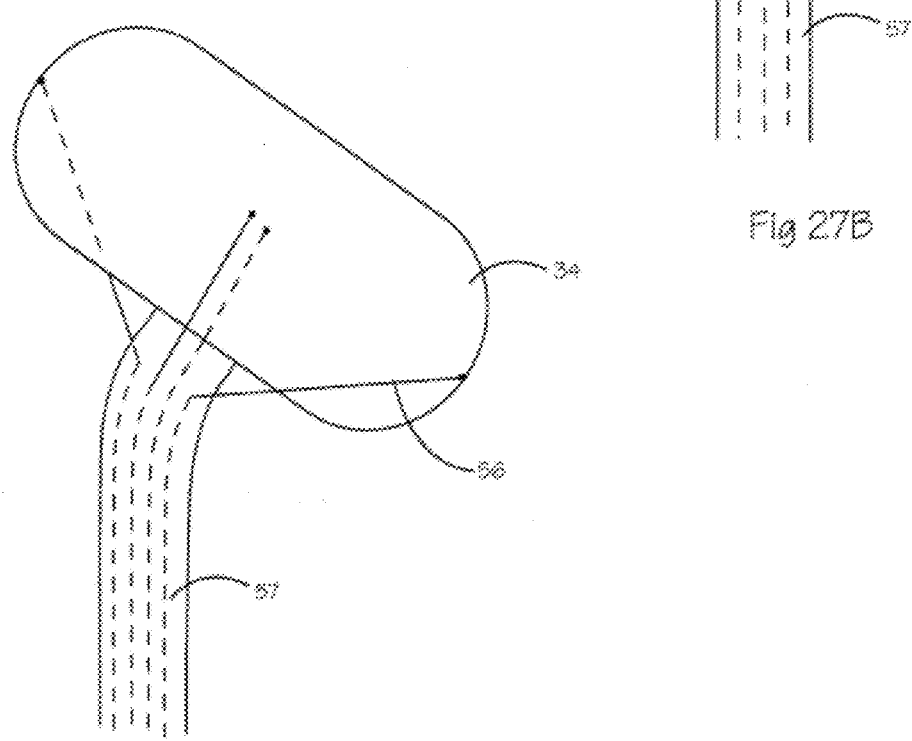
Fig 27C

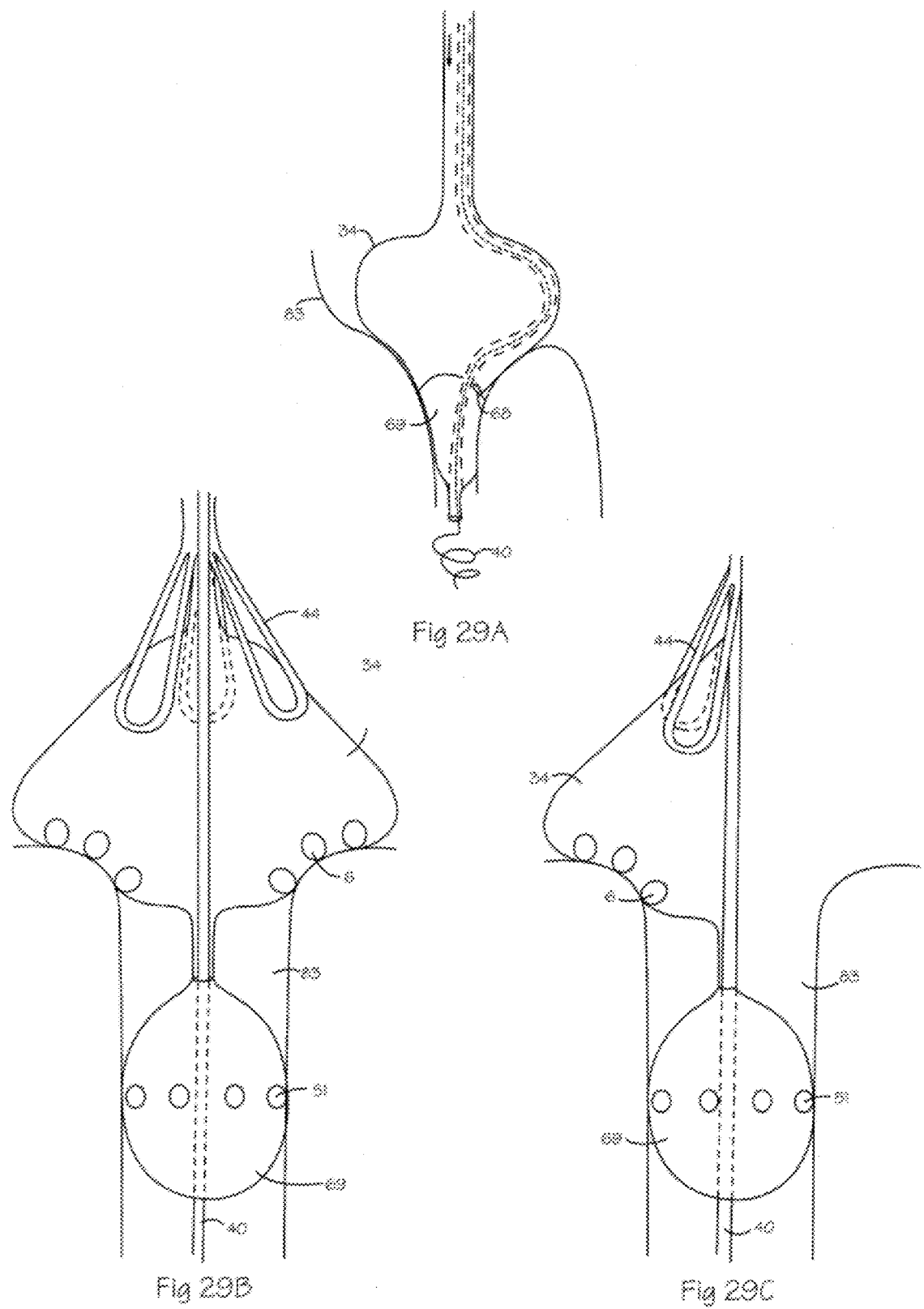

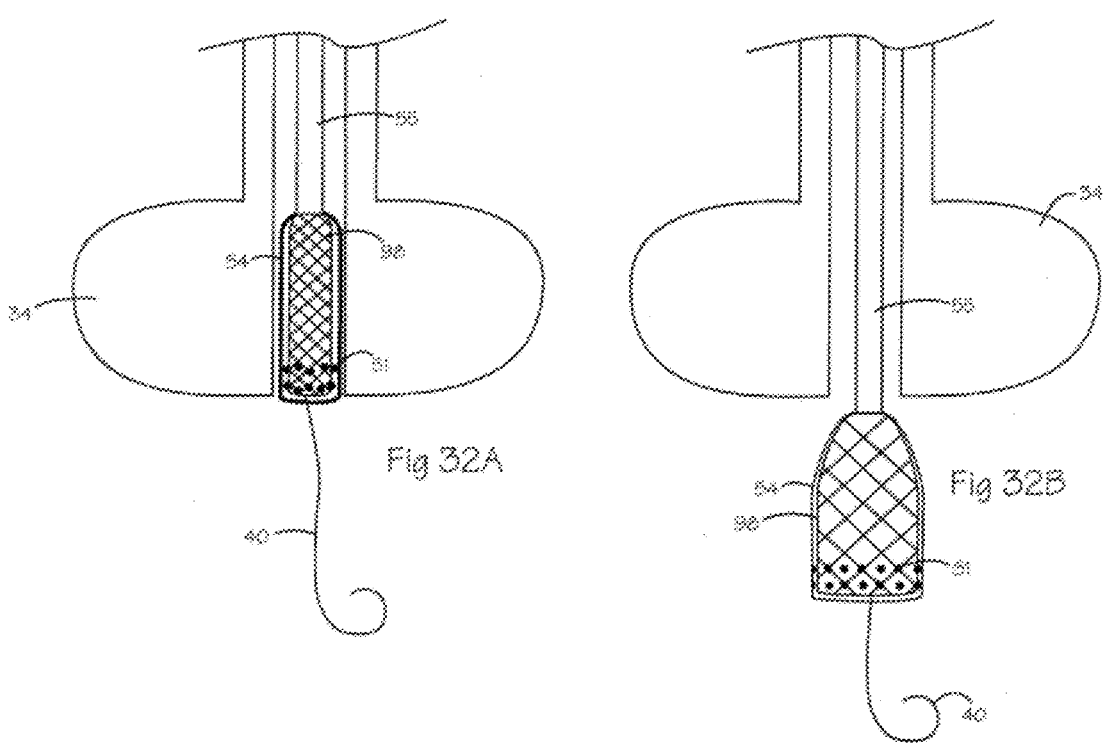

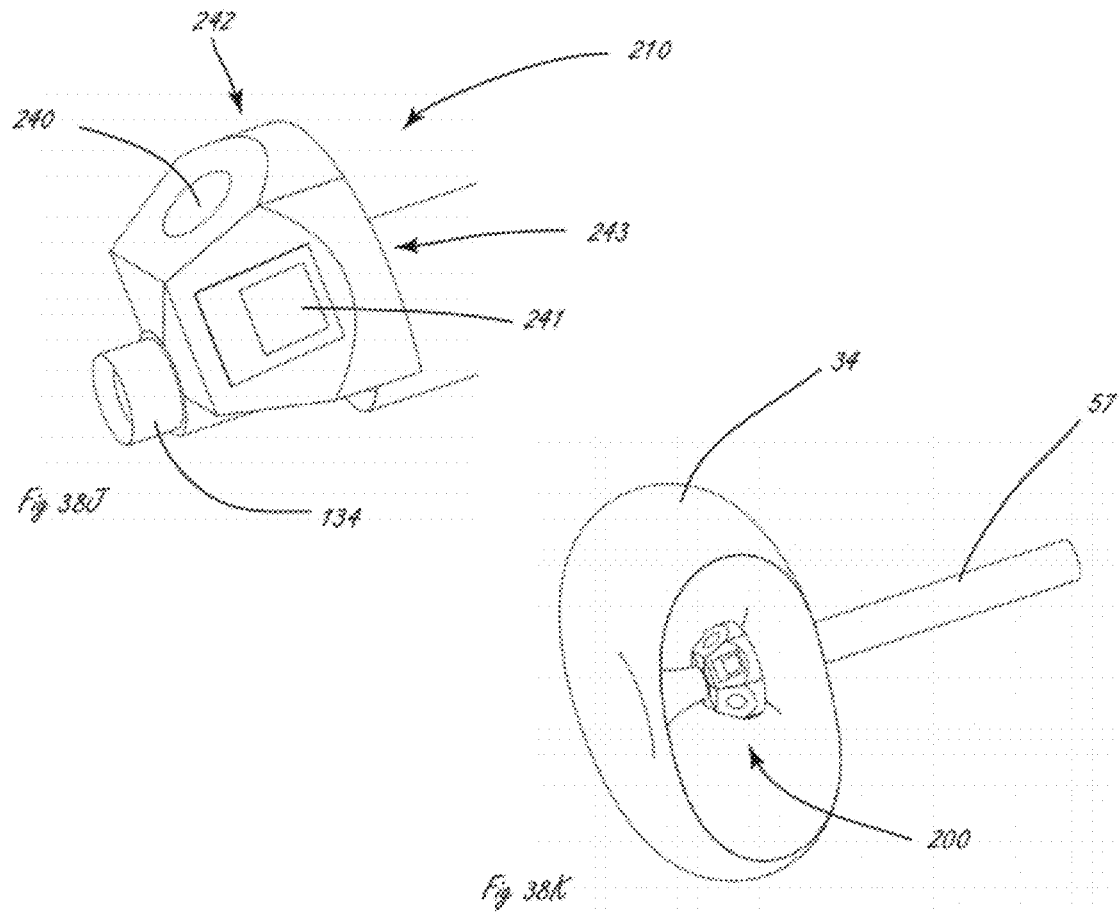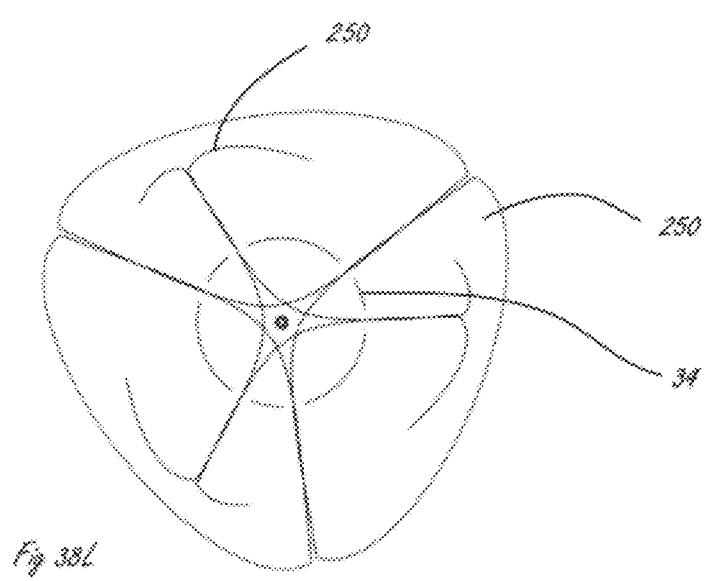

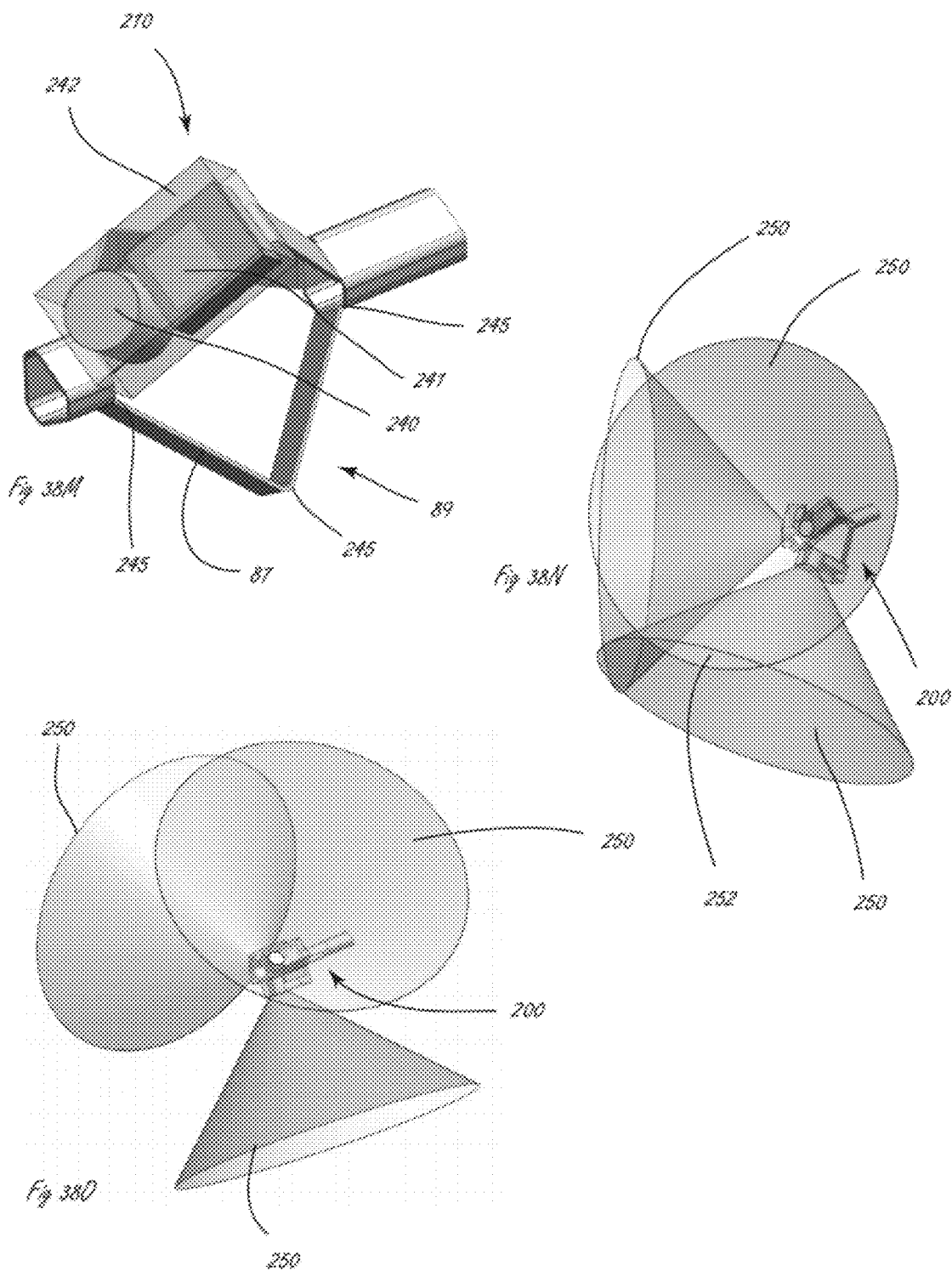

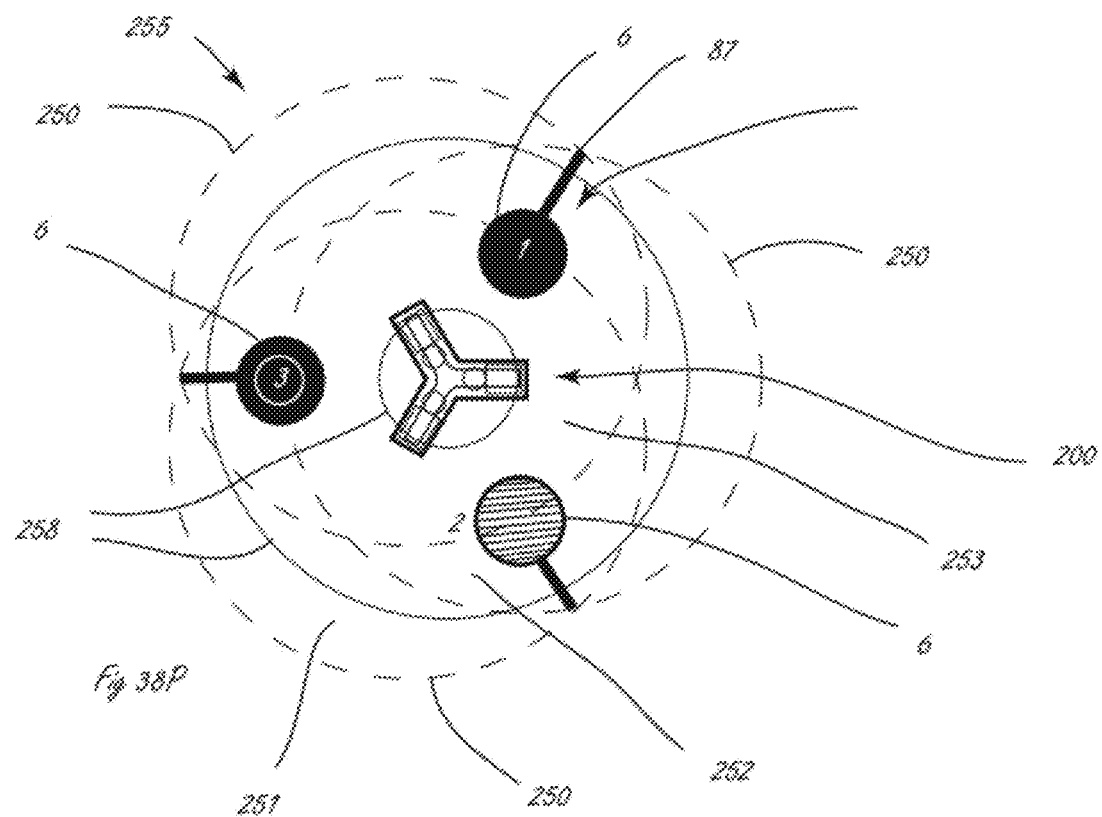
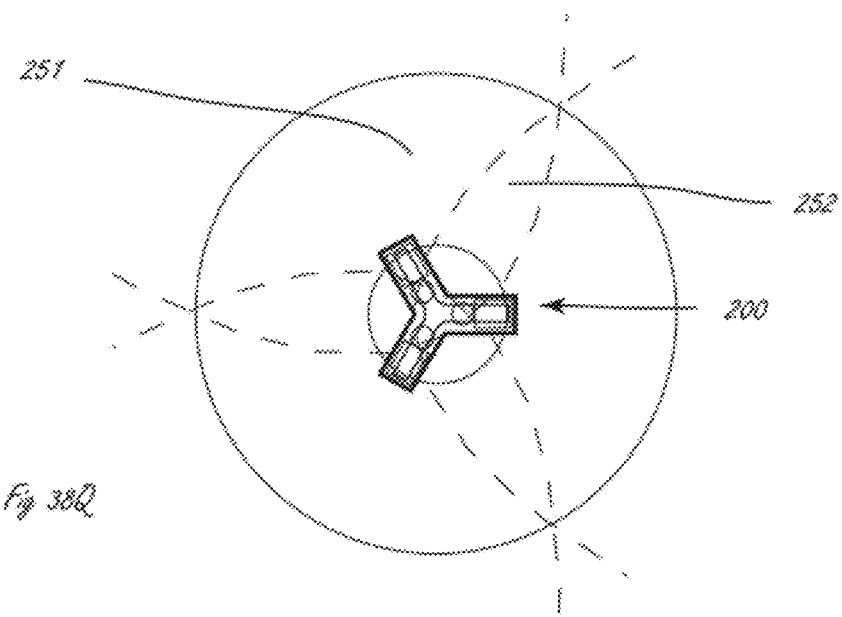

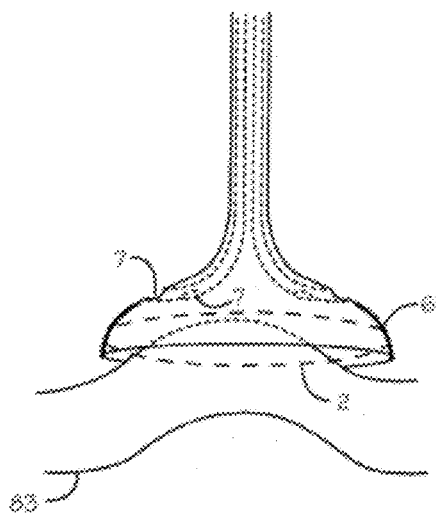
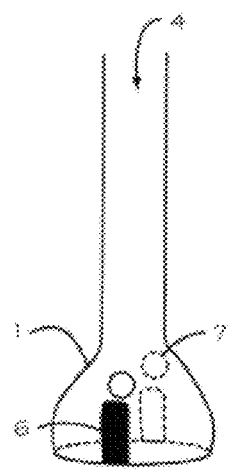
Fig 46A  Fig 46B
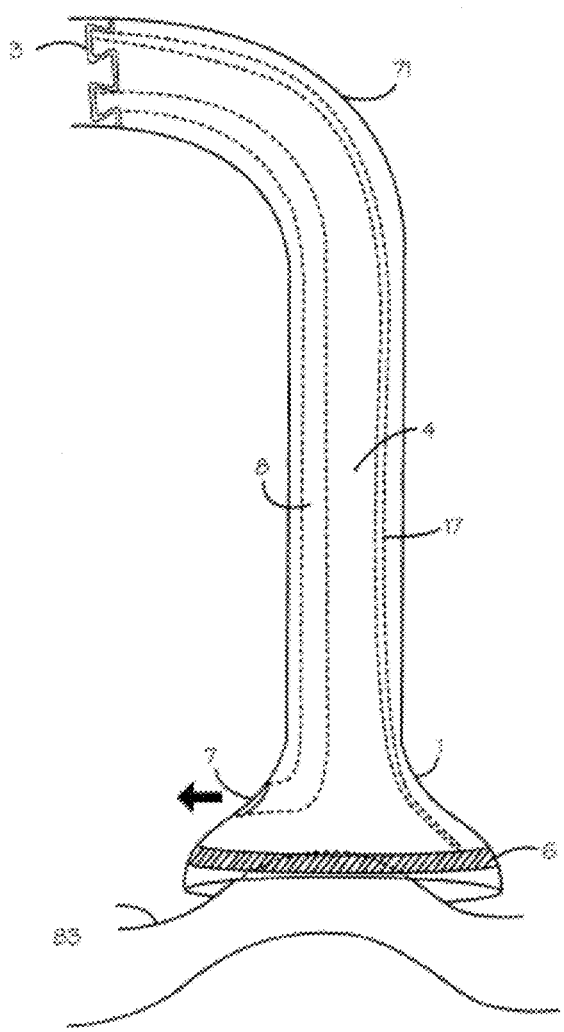
Fig 47

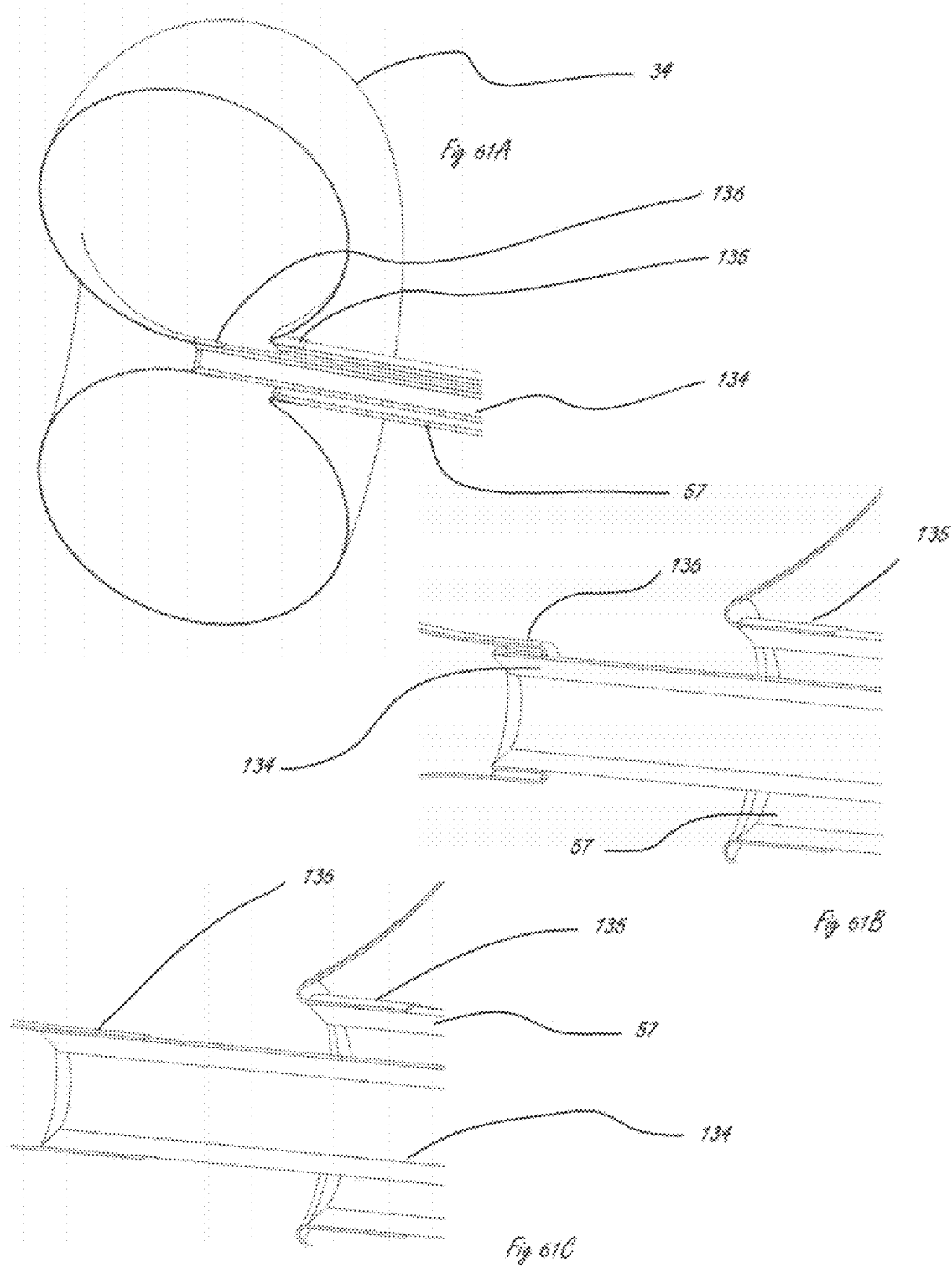

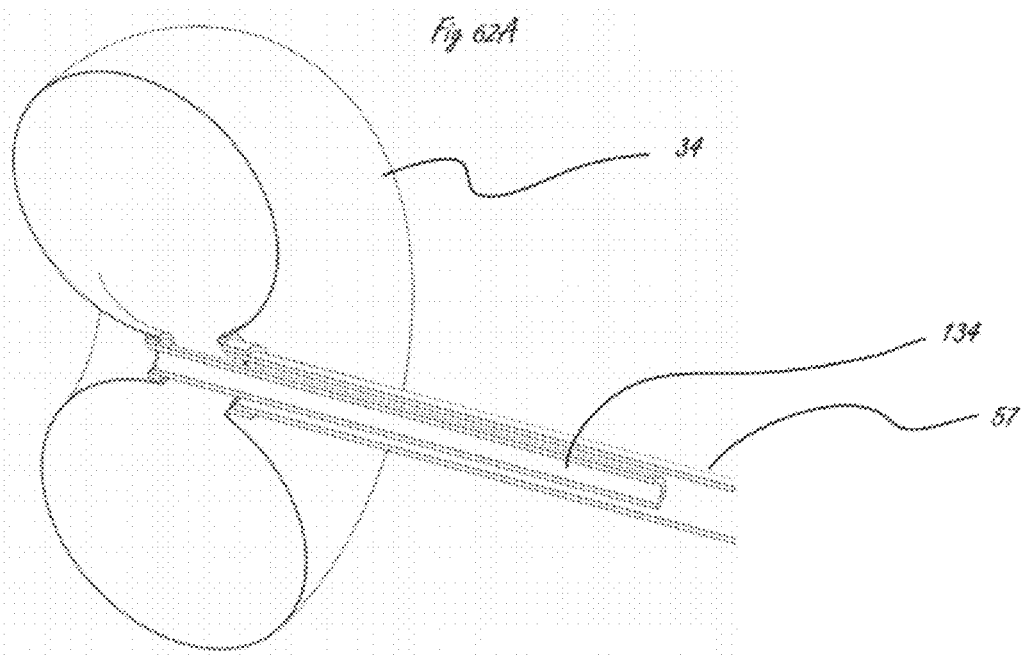
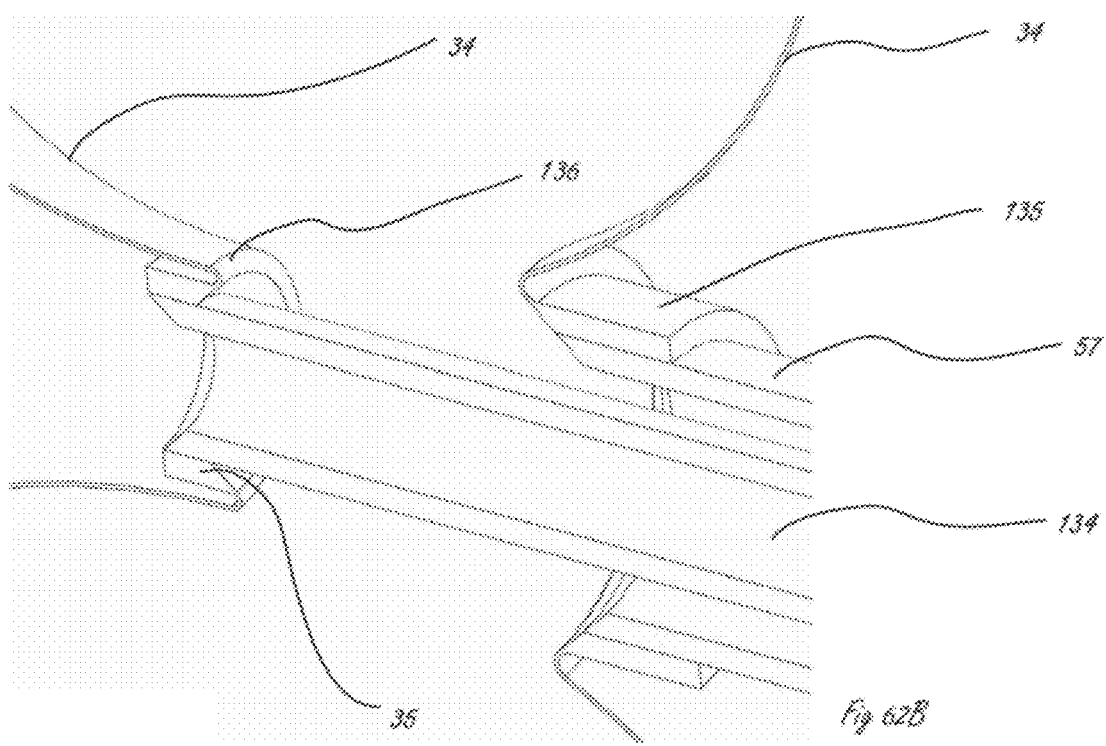

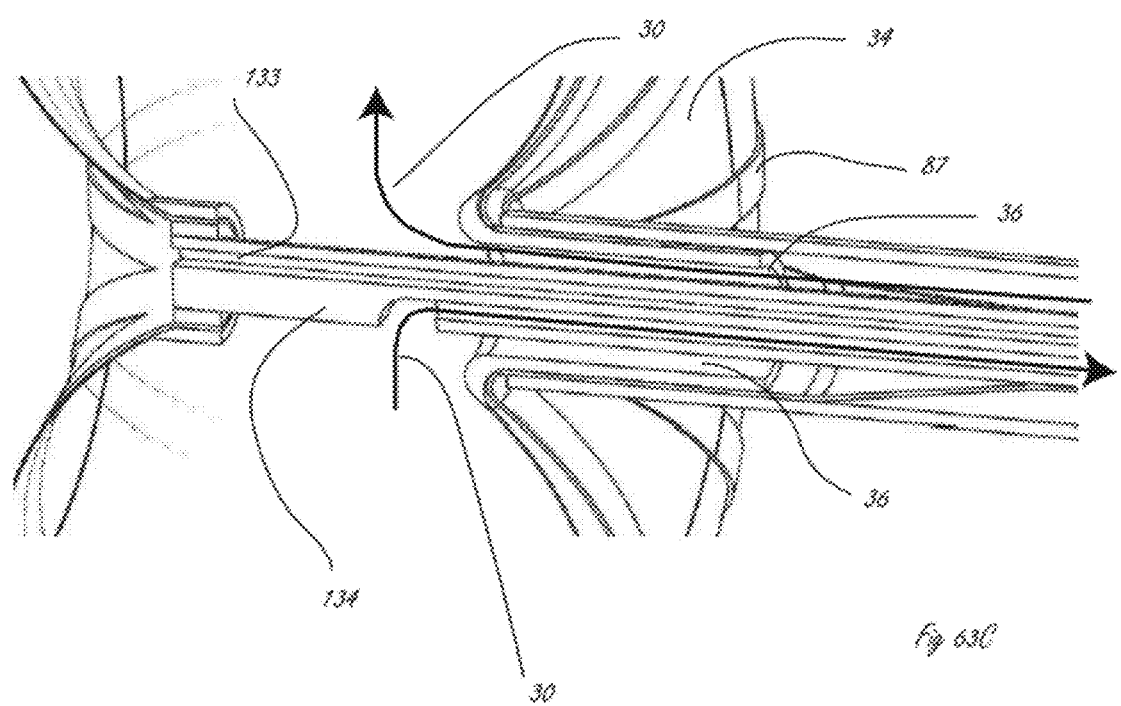

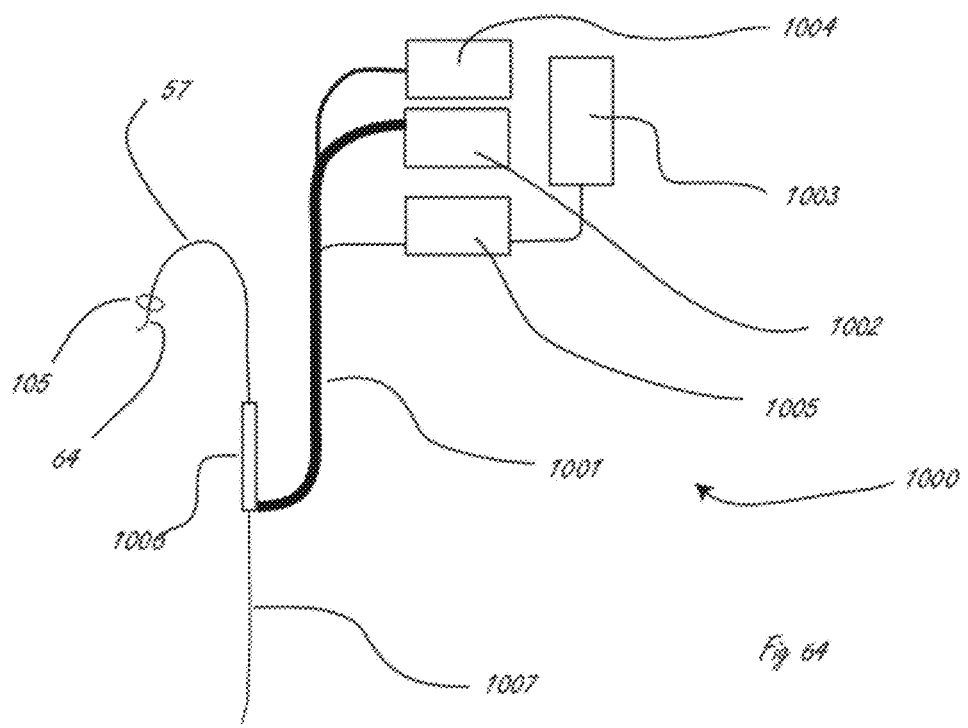
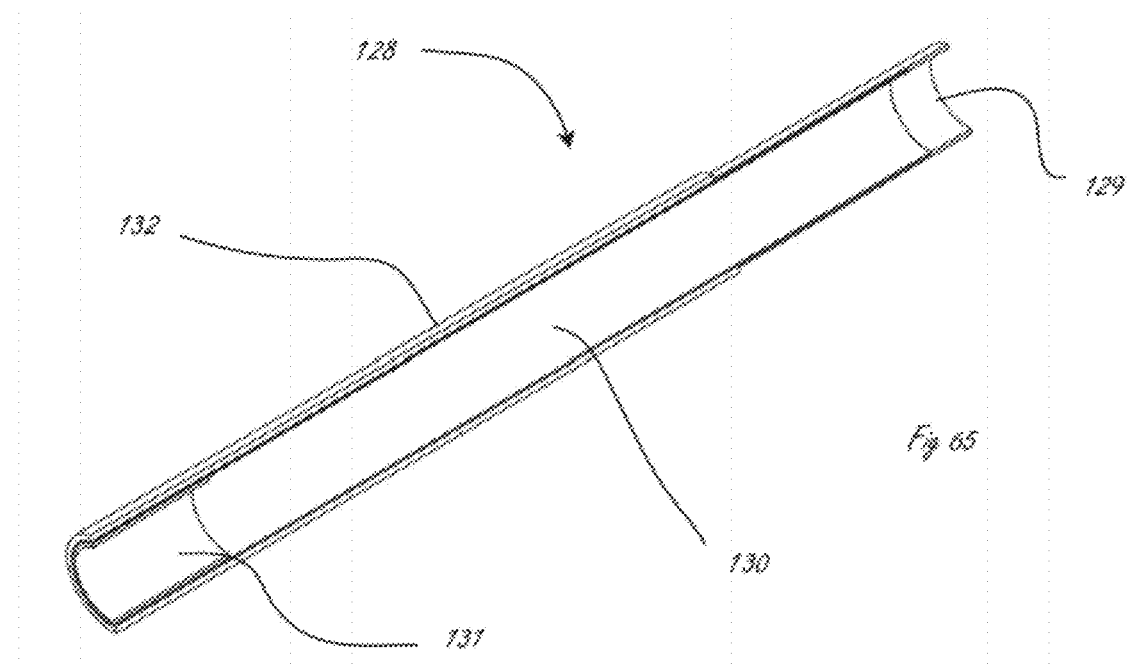

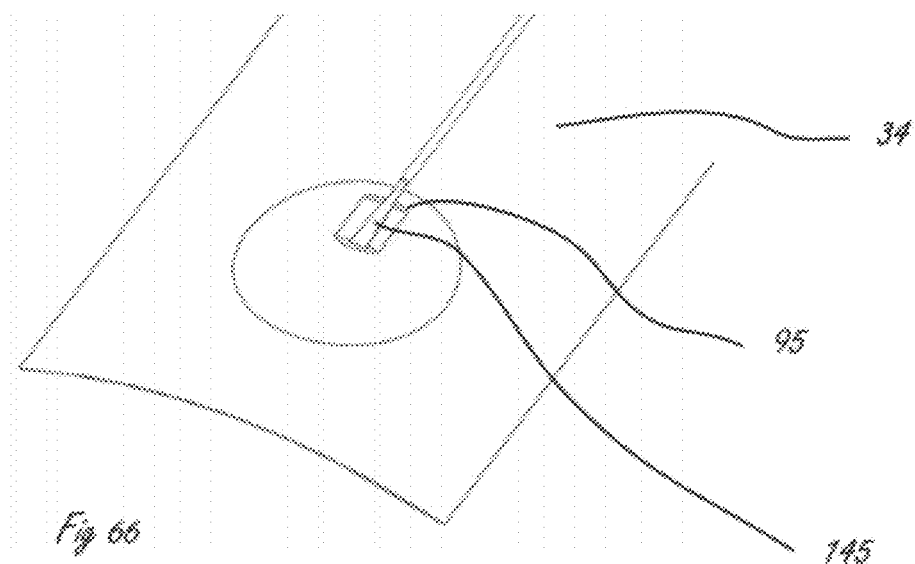

LOW PROFILE ELECTRODE ASSEMBLY

CROSS-REFERENCE TO RELATED APPLICATIONS

This application is a continuation-in-part of U.S. application Ser. No. 12/616,758, filed Nov. 11, 2009, now U.S. Pat. No. 8,295,902; which application claims priority to U.S. Provisional Application No. 61/113,228, filed Nov. 11, 2008, and U.S. Provisional Application No. 61/160,204, filed Mar. 13, 2009, and U.S. Provisional Application No. 61/179,654, filed May 19, 2009; and U.S. Provisional Application No. 61/232,756, filed Aug. 10, 2009; and U.S. Provisional Application No. 61/253,683, filed Oct. 21, 2009; all of which are incorporated herein by reference.

This application claims the benefit of U.S. Provisional Application No. 61/334,154, filed May 12, 2010, the entire content of which is incorporated by reference as if fully set forth herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Energy transmission to tissues can be used to treat a variety of medical conditions. Electrodes can be used to deliver energy to tissues and cells for the purpose of sensing, mapping, ablating, and/or stimulate muscles and/or nerves. Stimulation of muscles and/or nerves can be used to trigger signals to the brain or directly to a specified muscle cell/group. When the treatment requires removing or destroying a target tissue, thermal ablation therapy can be used to heat a target tissue with a surgical instrument such as a needle or probe electrode coupled to an energy source that heats the probe tip, the target tissue, or both. In such cases the thermal energy may be delivered directly by heating or cooling the probe or indirectly by generating energy fields within the tissue which in turn generate heat, or both. Energy fields commonly used to create heat indirectly are RF and acoustic energy fields. The goal for most ablation procedures is to achieve cell death quickly, precisely and with minimal to no collateral damage.

In the case of thermal ablation therapy for terminating destructive cardiac conductive pathways, energy can be delivered to the aberrant cells using minimally-invasive techniques such as an electrode-tip catheter. Pulmonary vein isolation via radio frequency catheter ablation has been demonstrated to be an effective treatment for some patients experiencing atrial fibrillation (AF). The cornerstone of the AF ablation procedures is electrical isolation of relatively large pulmonary vein antra. Ablation of large confluent areas or lines of ablation with older generation AF ablation devices is accomplished by point to point manipulation and RF application with the single electrode tip. The single electrode catheter technique is extremely time-consuming, complex and fraught by subjectivity. Furthermore, efficient and complete mapping of the electrical activity in target tissues often requires the placement of multiple catheters in the left atrium, the use of a 3D-mapping, and/or steering system. It is often desirable to create relatively large surface area lesions with relatively shallow depths of ablation.

Newer larger electrode arrays for "one shot" ablation have been used to improve catheter ablation treatments. These ablation systems have been adopted as a way to provide full contact to tissues having a complex 3-D anatomy and an overall larger lesion area. But known devices incorporate electrodes that are bulky, stiff and limited in their ability to be packed efficiently and effectively into the small space of the treatment catheter. The stiffness of these devices limits conformability against the tissue resulting in the need for additional repositioning and overlapping patterns to ensure uninterrupted lines of ablation.

SUMMARY

One aspect of the disclosure is a catheter and electrode assembly comprising: an elongate catheter body comprising a distal portion; an expandable electrode structure coupled to the distal portion, wherein the expandable electrode structure comprises an expandable membrane with an expanded configuration, and a branched flexible circuit having a substrate layer and planar conducting layer electrically coupled to a plurality of radio frequency ablation electrodes and at least one sensing electrode, wherein in the expanded configuration at least four of the electrodes are disposed in an array on a distal surface of the membrane.

In some embodiments the at least four electrodes are adapted to be substantially coplanar with a distal tip of the catheter body when the membrane is in the expanded configuration.

In some embodiments the at least four electrodes are distal to the distal tip of the catheter when the membrane is in the expanded configuration.

The assembly can additional comprise a first membrane portion comprising at least 15% of the surface area of the membrane that is distal to a distal tip of the catheter body, and wherein the at least four electrodes are disposed on the first membrane portion. In some embodiments at least 10% of the volume of the membrane is distal to a distal tip of the catheter when the membrane is in the expanded configuration.

In some embodiments first and second opposite sides of a surface of the membrane are coupled to the catheter body.

In some embodiments a plurality of perforation holes traverse the membrane.

In some embodiments the assembly further comprises an annular introducer wherein the introducer surrounds the expandable membrane and confines the diameter thereof to less than about 0.2 inches. The introducer can be adapted to engage a collapsed exterior of the expandable membrane and confine a portion of the membrane substantially distal to the distal end of the catheter body.

In some embodiments the expanded configuration is an inflated configuration.

One aspect of the disclosure is a unitary flexible circuit comprising: a proximal end, a distal end, and an intermediate portion, wherein the proximal end is coupled to an electrical source, the intermediate portion is comprised of a plurality of flexible branches separated from one another along their lengths, wherein at least one branch has an insulating layer along a portion thereof and at least one branch is electrically connected to an electrode adapted to deliver radio frequency energy, wherein the flexible branches conform to a portion of a medical device adapted to be minimally-invasively delivered to a location within a subject, and wherein the plurality of branches are coupled to one another distal to the intermediate portion.

In some embodiments the length of at least one branch in the intermediate portion is between about 1 cm and about 5 cm.

In some embodiments the flexible branches conform to a radially outer surface of the portion of the medical device.

In some embodiments the branches of the intermediate portion conform to the portion of the medical device such that they are oriented in a configuration surrounding a longitudinal axis of the medical device. The branches can extend substantially 360 degrees around the longitudinal axis and at least two of the plurality of branches are separated by more than 30 degrees from an adjacent branch. In some embodiments any two branches are separated by more than 10 degrees. In some embodiments any two branches are separated by more than 90 degrees.

In some embodiments the plurality of branches of the intermediate portion are fixed on the medical device such that the medical device maintains the separation between the branches. The portion of the medical device can be an expandable membrane. The orientation of the branches of the intermediate portion can depend on the inflation of the expandable membrane. A portion of the expandable membrane and a portion of a plurality of the branches can be located distally to the distal end when the expandable membrane is in an expanded configuration.

In some embodiments at least two of the branches are comprised of a plurality of electrodes adapted to deliver radio frequency (RF) energy. The distal end can be comprised of a sensing electrode spaced apart from the plurality of electrodes.

In some embodiments the proximal end is coupled to a catheter. The catheter can be sealed along a length thereof extending from the proximal end to the intermediate portion.

In some embodiments at least three branches terminate in a connector at the proximal end. In some embodiment portions of the medical device are adapted to be folded by selective orientation of the plurality of branches.

BRIEF DESCRIPTION OF THE DRAWINGS

These and other aspects will now be described in detail with reference to the following drawings. Generally speaking the figures are not to scale in absolute terms or comparatively but are intended to be illustrative of claimed features. Also, relative placement of features and elements may be modified for the purpose of illustrative clarity.

FIGS. 3A-3E illustrate top views of various embodiments of a flex circuit.

FIGS. 4A-4C illustrate cross-sectional views of an embodiment of an electrode assembly in different folding configurations.

FIGS. 5A-5I illustrate various exemplary electrode patterns and electrode shapes.

FIGS. 9A-9B illustrate various electrode configurations and activation mechanisms.

FIG. 10 illustrates an embodiment of electrode activation using an electrode sleeve.

FIG. 11 illustrates another embodiment of electrode activation using an electrode sleeve.

FIGS. 15A-15B illustrate embodiments of an electrode assembly having a cylindrical electrode element within a sheath.

FIGS. 16A-16B illustrate embodiments of an electrode assembly having a cylindrical electrode element.

FIGS. 17A-17G illustrate embodiments of an electrode assembly having an expandable electrode structure.

FIGS. 19A-19F illustrate embodiments of an electrode assembly having an expandable electrode structure that can be deployed asymmetrically and/or can be of various shapes.

FIGS. 20A-20C illustrate embodiments of an electrode assembly having an expandable electrode structure that can be deployed into various shapes.

FIGS. 27A-27C illustrate embodiments of a steerable catheter having a membrane mounted thereto and steerable elements mounted to the membrane.

FIGS. 29A-29C illustrate embodiments of an electrode assembly integrated with additional expandable structures that can be used for mapping and/or anchoring.

FIGS. 32A-32B illustrate an embodiment of a self-expanding mapping electrode structure.

FIGS. 38J-R illustrate exemplary optic structures and exemplary expandable membranes.

FIGS. 46A-46B illustrate embodiments of a suction tip anchoring and electrode assembly.

FIG. 47 illustrates an embodiment of a suction tip anchoring and electrode assembly.

FIG. 61A-61C illustrates two embodiments of an electrode supporting membrane and shaft interface.

FIG. 62A-62B illustrates an alternate embodiment of an electrode supporting membrane and shaft interface.

FIG. 63A-63C illustrates an alternate embodiment of an electrode supporting membrane and shaft interface.

FIG. 64 illustrates a system for using an electrode assembly.

FIG. 65 illustrates a sheathing device.

FIG. 66 illustrates a means of fabricating an electrode.

DETAILED DESCRIPTION

The use of minimally-invasive electrode devices, especially those for use in regions of the body having somewhat complicated 3-D anatomy, has been hindered by the conformability, flexibility and overall profile of the device as well as the electrode stimulation, ablation, mapping effectiveness. Disclosed herein are devices having electrode assemblies that incorporate one or more flexible electrodes deposited over one or more flex circuits positioned on a deployable, flexible membrane. The flexible electrodes can be used to sense, map, ablate, or stimulate muscles and/or nerves. Energy transmission through the electrodes can be accomplished over large surfaces such as the lining within an organ or selective regions for treatment of tumors, for example. Stimulation of muscles and/or nerves can be used to trigger signals to the brain or directly to a specified muscle cell/group. The electrode assemblies can also be used as temporary implants for the purpose of providing or generating thermal energy for a specified period of time, such as can be needed for stimulation of nerves and/or muscles. It should be appreciated that the electrodes and electrode assemblies described herein can be used for a variety of functions as is known in the art, including but not limited to, ablation, mapping, sensing, and/or stimulating a variety of cells types and tissue types. When an electrode is described herein to perform a particular function, such as ablation, it should not be construed to mean the electrode is incapable of performing another electrode function such as mapping, sensing or stimulating.

The electrode assemblies described herein are readily conformable, foldable and have a very low profile for minimally-invasive procedures as well as a large overall surface area. The electrode assemblies described herein allow for superior apposition to the target site and limit the number of catheter manipulations required. Further, the electrode assemblies described herein can greatly reduced procedure times and reduce the necessary skill level required to achieve successful results.

Although the devices, assemblies and methods of the present disclosure are at times described in terms of mapping, ablating or sensing tissue which creates aberrant electrical signals in the heart, it should be appreciated that the devices described herein can be used to treat a variety of conditions through sensing, mapping, ablation and/or stimulation in a variety of anatomical locations and that other indications are considered herein. The devices, assemblies and methods described herein are not limited to treating cardiac conditions or any other particular indication and can be used for any treatment in which an energy delivery system is indicated, and in particular, a minimally-invasive treatment.

Figure 1A:
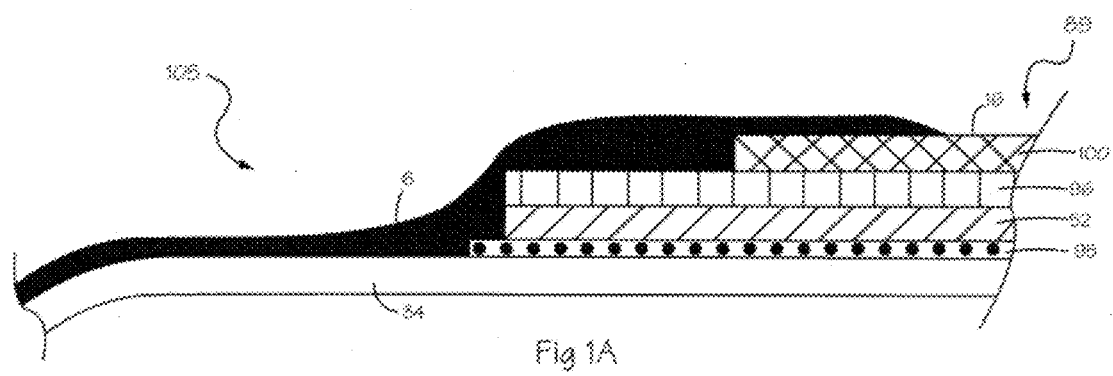
FIGS. 1A-1B show enlarged, cross-sectional schematic views of an embodiment of an electrode assembly.
Figure 1B:
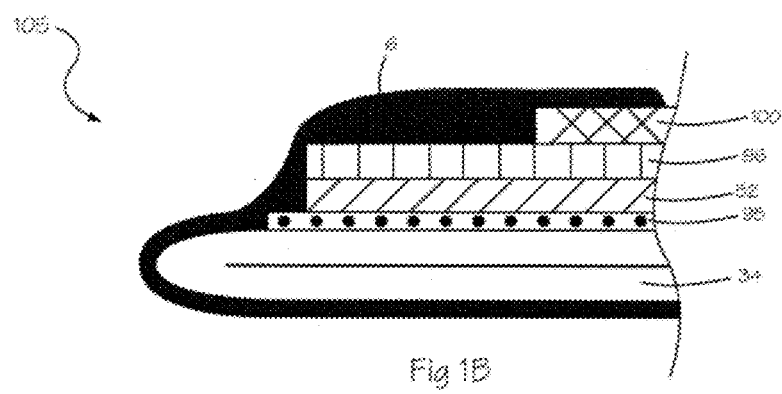
Figure 1C:
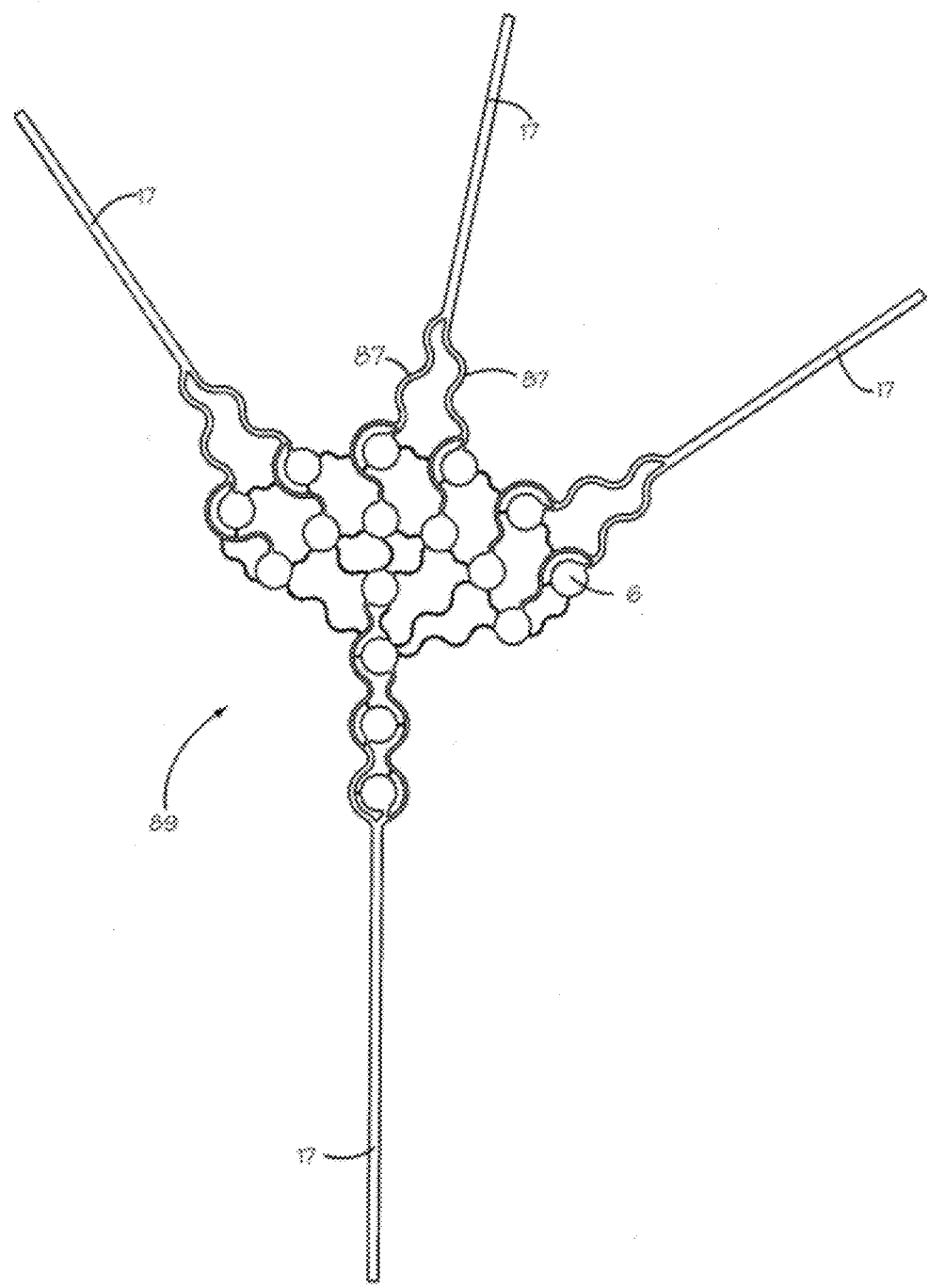
FIG. 1C illustrates an embodiment of a flex circuit for an electrode device.

FIGS. 1A-1B show enlarged, cross-sectional schematic views of an embodiment of an electrode assembly 105. The electrode assembly 105 can include a flexible membrane 34, one or more flex circuits 89 and one or more electrodes 6. The flex circuit 89 can include a base substrate 52, a conducting layer 96 and a dielectric layer 100. As shown in FIG. 1C, the flex circuit 89 can diverge from one or more main branches 17 into multiple distal branches 87, each having one or more conductive traces 16 (not shown) which each lead to one or more conductive pads 59 (not shown). The flex circuit 89 as shown in FIG. 1C can be wrapped around an expandable membrane, such as a balloon (see FIG. 23G or 23H), so that the main branches 17 come together at the shaft. In an embodiment, each conductive trace 16 can include at least two conductive pads 59. The conductive pad 59 can be a region of the conductive trace 16 that has an exposed, non-insulated portion of the conducting layer 96. The electrode 6 can be electrically coupled to the flex circuit 89 via the conductive pad 59 (not shown) of the conductive layer 96. The base substrate 52 can also have a wider surface for better adhesion of the flex circuit 89 to the membrane 34. With a larger base substrate surface, the conductive pad 59 can have a larger surface to electrically connect to the electrode 6. It should be appreciated that the embodiment of the electrode assembly shown in FIGS. 1A-1C is exemplary and that variations in the structure, shape, and relative positions of the components are possible.

Figure 1D:
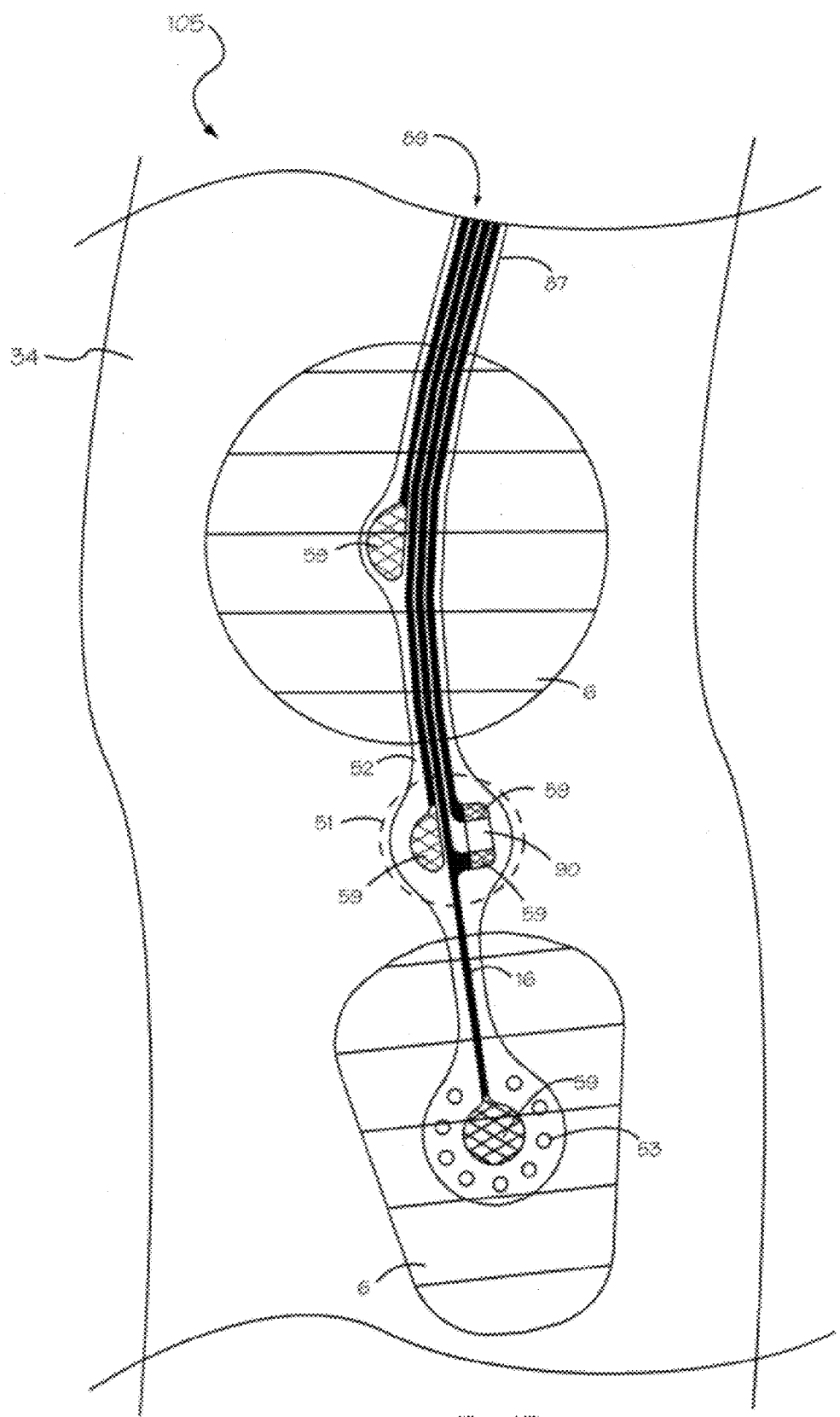
FIG. 1D illustrates an embodiment of an electrode assembly including a membrane, flex circuit and electrodes.

Each electrode 6 can be a thin, electro-conductive film that covers at least a portion of the flex circuit 89 and a portion of the outer surface of the membrane 34. FIG. 1D illustrates a portion of a membrane 34 supporting a one distal branch of the flex circuit 87. The figure shows two electrodes 6 that overlap separate conductive pads 59 of the flex circuit 89, the corresponding conductive traces 16, and a portion of the flex circuit distal branch 87. The electrode 6 can have a surface area or diameter that is significantly larger than the conductive pad 59. Because the electrode 6 has a larger surface area it also covers a portion of the membrane 34 not covered by the conductive pad 59 or the flex circuit distal branch 87.

The electrode assembly 105 can be deployed to deliver energy to a target tissue. When deployed, each electrode 6 on the membrane 34, both alone and in combination, can cover a relatively large surface area of the membrane 34 with which to contact target tissues. Despite the large overall surface area of the electrodes 6 and the components of the flex circuit 89 covering the flexible membrane 34, the electrode assembly 105 can be compactly folded into a small diameter such that the electrode assembly 105 can be delivered, for example, through small access channels for minimally-invasive delivery.

Flexible Electronics

The electrode devices described herein incorporate flexible electronics that are foldable to a very low profile for minimally-invasive delivery in contrast to a relatively stiff and bulky electrode assembly. Upon reaching the target tissue, the electrode devices described herein can unfold to reveal a very large surface area electrode assembly that can be readily conformable with the target tissues.

Flex Circuit

As mentioned above, the electrode assembly 105 of the devices described herein can include one or more branching flex circuits 89. The flex circuit 89 can include a base substrate 52, a conducting layer 96 and a dielectric layer 100 as will be discussed in more detail below. Still with respect to FIG. 1D, the flex circuit 89 can include one or more main proximal branches 17 (not shown) that can divide into multiple conductive distal branches 87. Each distal branch can contain multiple conductive traces 16, each having one or more conductive pads 59. The conductive pad 59 has an electrically-conductive region formed by exposure of the conducting layer 96 upon removal of a portion of the overlying insulating dielectric layer 100. The exposed portion of conductive layer 96 can contact the conductive film electrode 6. The conductive pad 59 can be a region of the conductive trace 16 that has a larger surface area due to a larger base substrate layer 52 and insulating dielectric layer 100 (not shown). The method of conductive trace 16 termination is created as known in the art. These regions of wider and larger surface areas can be used for better adherence to the membrane.

As shown in FIG. 1C, the distal branches 87 of the flex circuit 89 can form a pattern of distal branches 87 that can spread out across the membrane 34. The branching pattern can vary and includes a fractal, self-repeating pattern or other symmetrical pattern, as well as an unsymmetrical pattern. The flex circuit 89 can include branches that are sinusoidal in shape so that some elongations between electrodes can be achieved. Multiple flex circuits 89 can be used to accommodate for the quantity and location of the multiple electrodes 6. Some elements of the flex circuitry 89 can have bridging elements 88 that facilitate handling during manufacturing (see FIG. 3C).

As shown in FIGS. 2A-2E, the flex circuit 89 and multiple conductive traces 16 can be constructed using laminations of various materials, but generally includes a base substrate 52, an electrically conductive layer 96 and an electrically insulating layer 100. In an embodiment, the multiple conductive traces 16 include a bottom insulating substrate layer 52, a middle conductive layer 96 and a top insulating dielectric layer 100. The dielectric or top insulating layer 100 can be removed as is known in the art to expose a small region of the conductive layer 96. For example, a laser can be used to remove the dielectric layer 100 by etching as will be discussed in more detail below. In other embodiments, an adhesive layer can be used between the layers described above. In other embodiments, multiple layers of conductivity and/or dielectric and/or adhesive can be included.

The materials used in the laminations of the flex circuit 89 can vary. The base substrate layer 52 and the electrically insulating layer 100 can be a material such as, but not limited to, a thin flexible plastic substrate, polyimide, polyester, PET (polyethylene terephthalate), PEEK (polyaryletheretherketone), PTFE (polytetrafluoroethylene), PEN (polyethylene naphthalate), LCP (liquid crystal polymer), PIC (photoimageable coverlay), thin epoxy glass, polyimide glass, acrylic adhesive or other material. In an embodiment, the substrate or bottom insulating layer 52 and the dielectric or top insulating layer 100 can be the same materials. In another embodiment, the substrate and the dielectric layers are different materials. For example, the substrate can be polyimide and the dielectric can be polyimide glass or similar material.

The conductor or conductive layer 96 can be a material such as, but not limited to, a metal or metal foil of copper, gold, silver, tin, nickel, steel, cupronickel (copper-nickel alloy), KOVAR (nickel-cobalt ferrous alloy) or other material. In an embodiment, more than one conductive material can be used in the conductive layer 96. In an embodiment, a conductive layer 96 of copper can be plated with a thin layer of an additional conductive material at the conductive pad 59. In an embodiment, the thin layer of additional conductive material can be gold. The flex circuit and its components can be manufactured using techniques as known in the art.

Still with respect to FIGS. 2A-2E, the flex circuit 89 and associated conductive traces 16 and conductive pads 59 can be coupled to the membrane 34 by a variety of techniques known in the art to affix a metallic or polymer, shaped member onto another surface as are known in the art. For example, an adhesive film 95 or other material can be used to adhere the bottom layer of the flex circuit 89 to the membrane 34 as will be discussed in more detail below. The adhesive film 95 can be conductive or non-conductive. For example, an adhesive 95 that is conductive can be laid over portions of the electrodes to adhere to the exposed conductive layer 96. Adhesive 95 that is not conductive can be used to bond the rest of the components to the membrane 34, for example to secure an end region of the flex circuit 89 to the membrane 34. The flex circuit 89 can be direct formed into the membrane 34 as will be discussed in detail below. Alternatively the conductive layer may be plated directly onto the substrate without the use of an intervening layer of adhesive.

Although the conductive layer 96 can be relatively narrow, it can also have a surface that is somewhat planar, as opposed to having a cylindrical geometry. The planar surface of the conductive layer 96 can have a width and thickness that is optimized for carrying current to the electrodes 6. Further, the plurality of conductive traces 16 can be grouped to create a planar surface width optimized to bond the flex circuit 89 to the membrane 34. The flex circuit 89 can also include one or more holes 53 incorporated through the base substrate 52 and the insulating layer 100 to allow for adhesive to wick through to improve adhesion of the flex circuit 89 to the membrane 34 (see FIG. 1D).

Figure 2A:
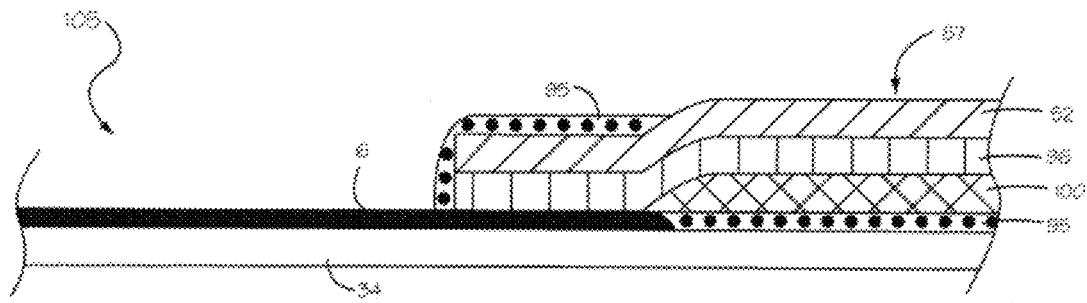
FIGS. 2A-2E illustrate cross-sectional views of various embodiments of an electrode assembly.

FIGS. 2A-2E illustrate various lamination configurations of the flex circuit and electrode assembly 105. The lamination configurations are exemplary and variations are possible. FIG. 2A shows an adhesive layer 95 that is electrically non-conductive adjacent to the electrode 6 and covers a portion of the membrane 34 and the flex circuit distal branch 89. The conductive section of the conductive layer 96 contacts the electrode 6. An adhesive layer 95 can also be applied over the top of the flex circuit distal branch 87 near an end where it contacts the electrode 6 to secure the end of the distal branch 87 to the membrane 34. The adhesive applied over this portion can be conductive to increase the surface area of the electrode 6. In other embodiments, the electrode 6 itself can also serve as an adhesive for portions of the flex circuit 89 when conductivity is desired.

Figure 2B:
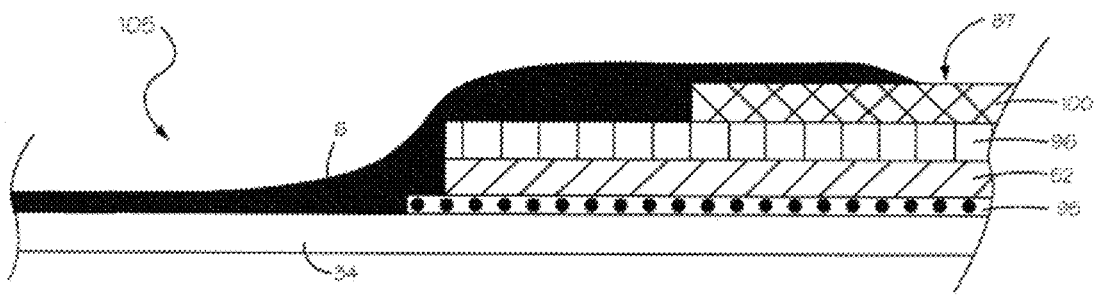
Figure 2C:
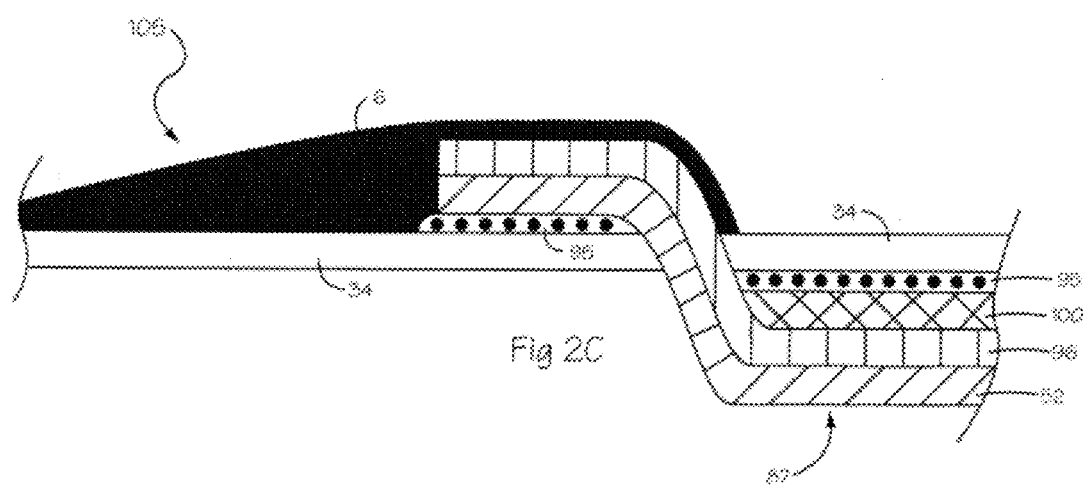
Figure 2D:
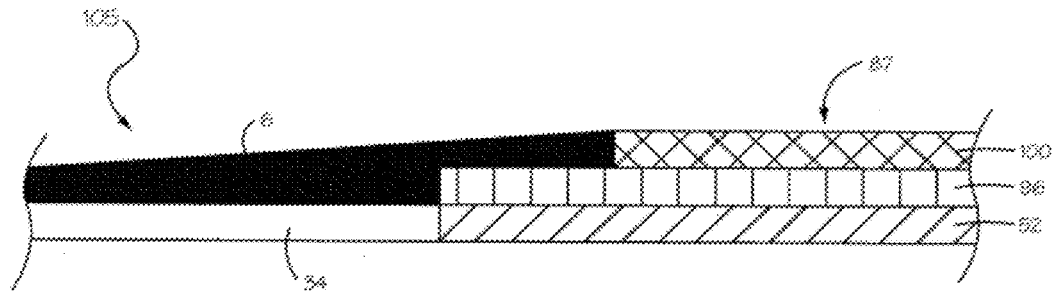
Figure 2E:
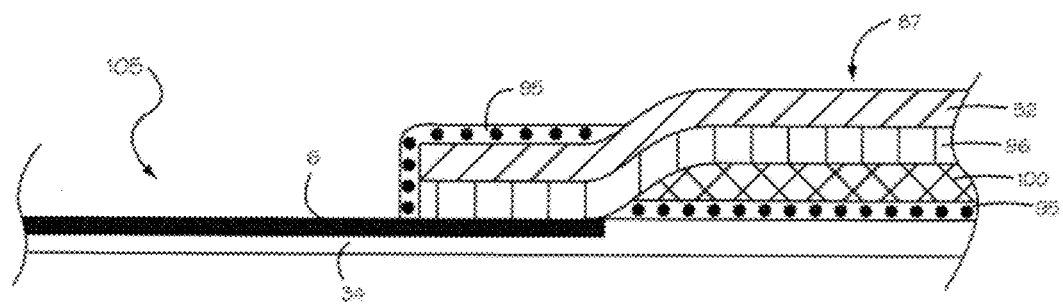

FIG. 2B shows a conductive trace 16 bonded to a membrane 34 using an adhesive 95. An exposed portion of the conductive layer 96, such as where the insulating layer 100 has been removed, can face away from the membrane 34 surface such that it does not come in direct contact with the membrane 34. Since the conductive layer 96 faces away from the membrane 34, a non-conductive adhesive can be applied. The electrode 6 covers the exposed portion of the conductive layer 96 as well as a portion of the membrane 34 and flex circuit distal branch 87. FIG. 2C shows the distal branch 87 of a flex circuit 89 that is adhered to a region of an inner surface of the membrane 34 as well as the outer surface of the membrane 34. The flex circuit distal branch 87 pierces through the membrane surface. In an embodiment, an adhesive layer 95 is not used to fix the flex circuit 89 to the inner surface of the membrane 34. The adhesive in this case can be non-conductive as the conductive layer 96 faces away from the membrane 34. FIGS. 2D-2E shows the distal branches of flex circuit 89 directly coupled to a membrane structure 34. FIG. 2D shows a membrane 34 encapsulating of the base substrate 52 of the flex circuit 89. The exposed conductive layer 96 is covered by the electrode 6 which also covers part of the membrane. FIG. 2E shows an electrode 6 embedded within the membrane 34 and the conductive layer 96 of the flex circuit 89 covering a portion of the electrode such that the electrode 6 and exposed conductive layer 96 are in contact.

Figure 2F:
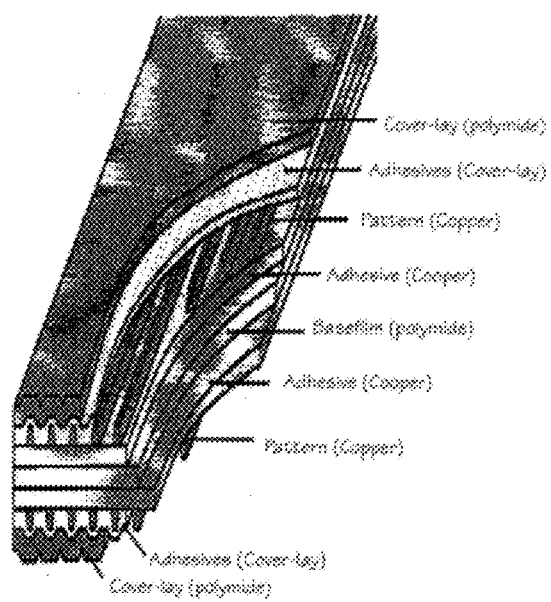
FIG. 2F illustrates a cross-sectional view of an existing flex circuit.

The flexible and thin components of the flex circuit 89 contribute to the low profile and low bulk of the electrode assembly 105 such that it can fold to a very small profile for minimally-invasive delivery. The flex circuit 89 can be affixed to the membrane 34 such that the membrane 34 and electrodes 6 undergo preferential folding, for example between or across the flex circuits 89. The folding can occur in an organized, controlled and repetitive manner. The flex circuit 89 can aid in better packing as it straightens out during folding and encourages the membrane to do the same. FIG. 2F shows an embodiment of an existing flex circuit with multiple layers of conductive, adhesive and dielectric layers.

Figure 3A:
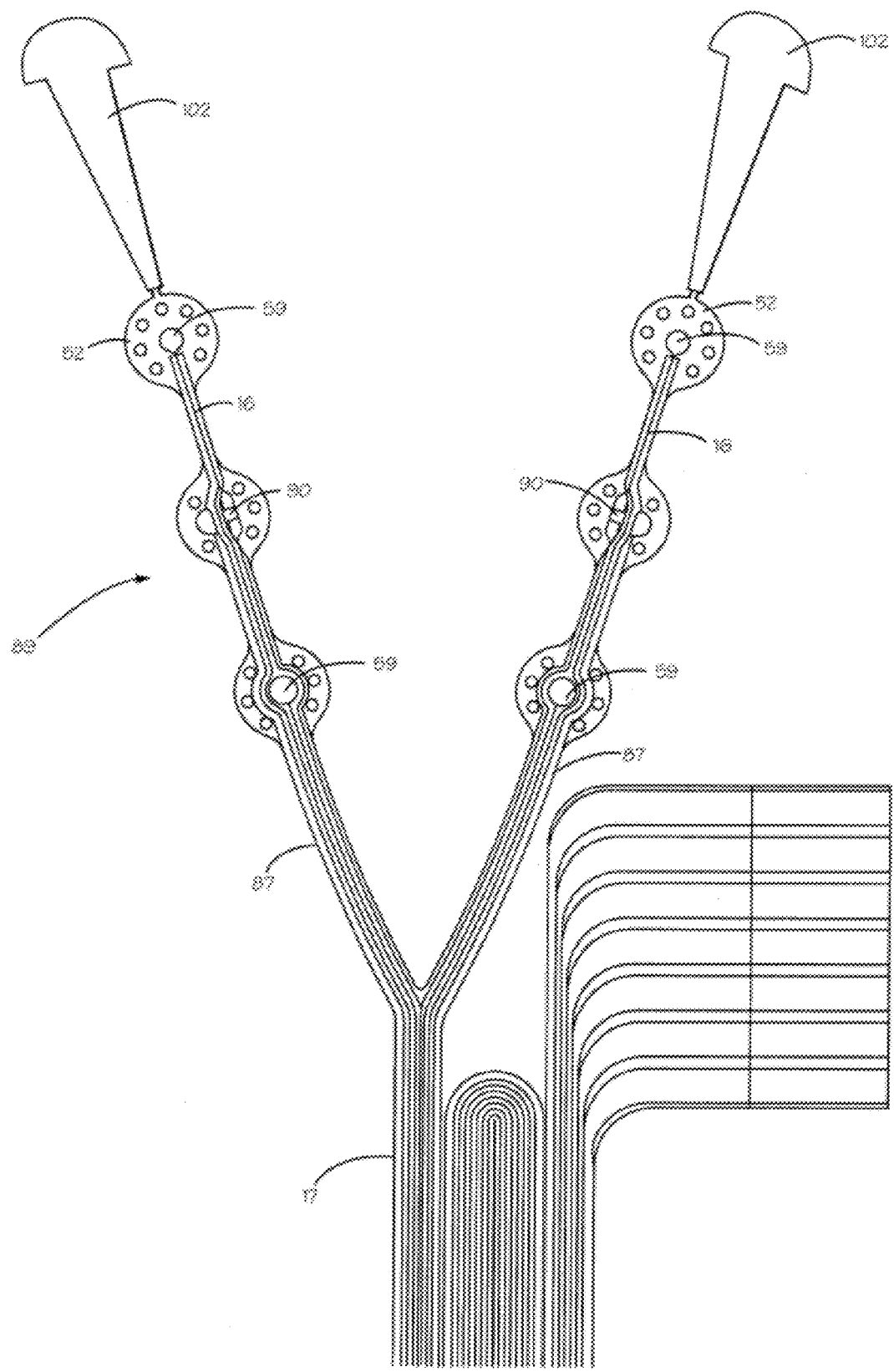
Figure 3B:
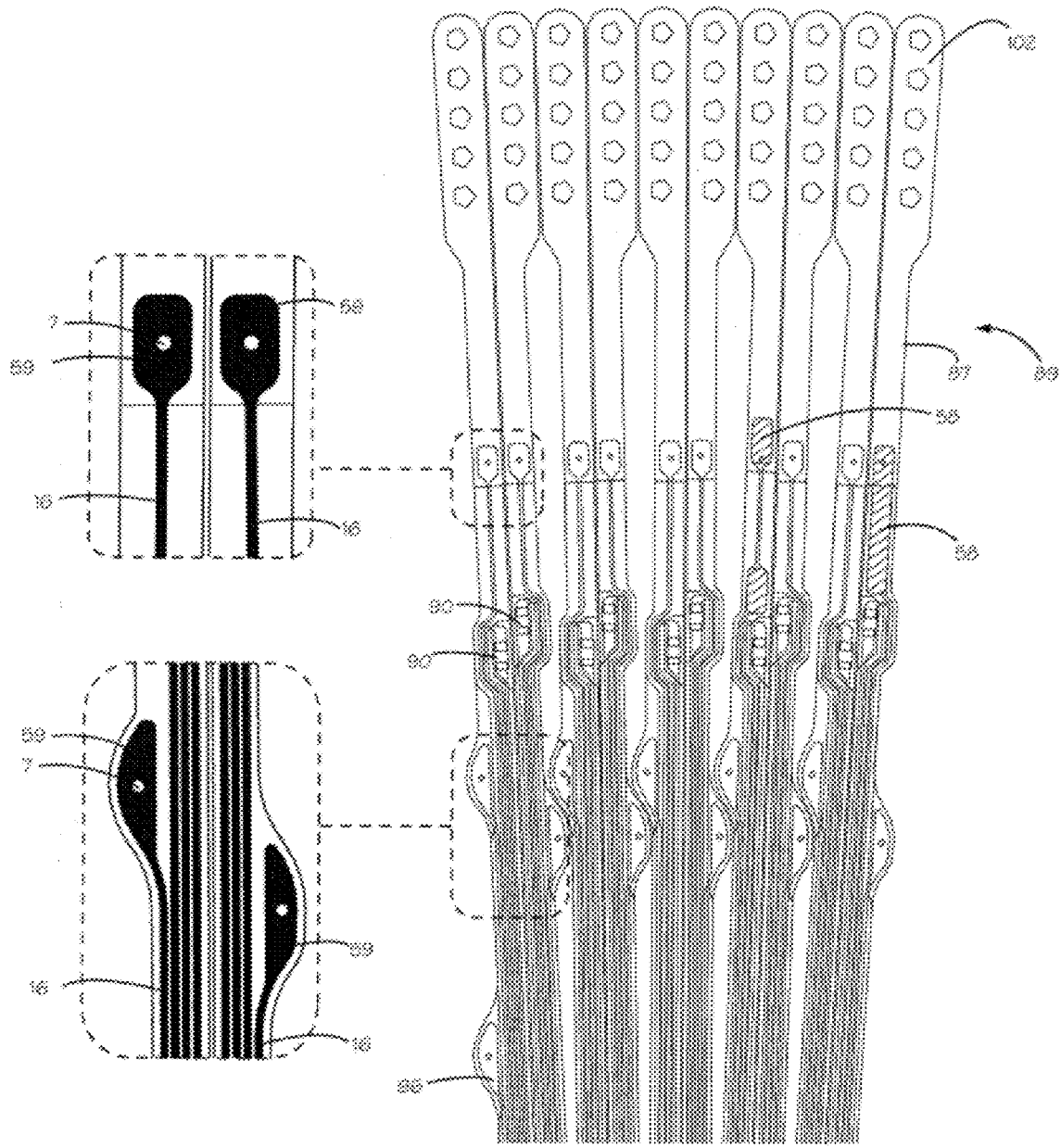
Figure 3C:
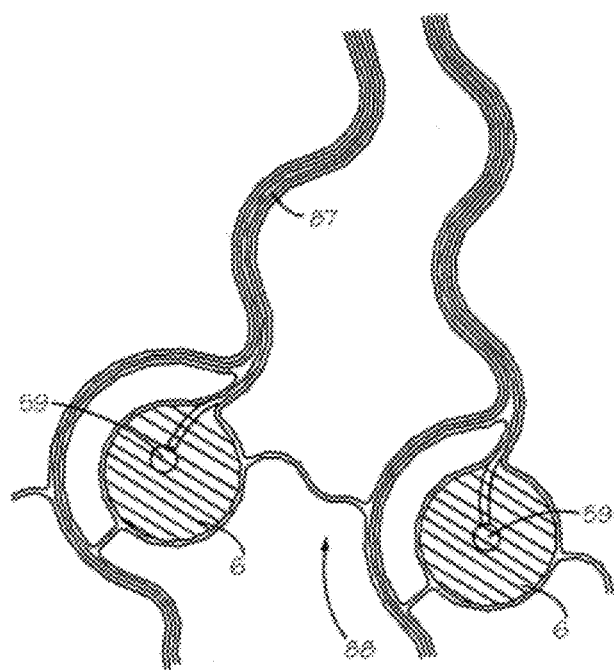

FIGS. 3A-3B show two embodiments of a flex circuit that can be used to power the electrodes described herein. The embodiments of 3A and 3B are exemplary and are not intended to be limiting. FIG. 3A shows a flex circuit 89 that includes an array of distal branches 87 extending from a proximal main flex circuit lead 17 toward the distal end. The distal branches 87 can split forming a Y-junction. This allows the flex circuit 89 to continue at various angles from the main flex circuit lead 17 and can be used to wrap a membrane 34, for example an expandable balloon-shaped membrane, at different latitudes along the surface. The distal branch 87 which can contain multiple conductive traces 16 can be electrically insulated through the length of the flex circuit 89 and the conductive layer 96 exposed at specific points on the flex circuit 89, for example at a conductive pad 59 surrounded by an area of enlarged width or diameter substrate layer 52 and dielectric 100 (not shown). The substrate layers 52 are shown including holes 53 through the substrate 52 and insulating dielectric layer 100 (not shown) to facilitate attachment with, for example an adhesive. The embodiment of the flex circuit 89 illustrated in FIG. 3A can power four electrodes (not shown) via the four conductive pads 59. The embodiment is shown as including two temperature sensors 90, but it should be appreciated that fewer or more than two temperature sensors 90 can be included. It should be understood that the temperature sensor also requires a conductive pad 59 for power. The conductive traces for the temperature sensors 90 can also be used to simultaneously power a mapping electrode (not shown). In an embodiment five flex circuits 89 can be used to power twenty ablation electrodes, ten mapping electrodes and ten temperature sensors 90.

FIG. 3B shows a different embodiment of the flex circuit 89 in which all the flex circuits are integrated into a single piece that can be split into all the distal branches 87 needed to power the electrodes 6. The flex circuit 89 in this embodiment is a single unit that is split into a number of branches. These branches 87 can be connected to one another via a small bridge 88 on the substrate at various points throughout the length of the flex circuit 89 (see FIG. 3C). The flex circuit 89 can be rolled up into a small profile to insert the flex circuit 89 into a catheter for assembly. Since the flex circuit 89 can be split into branches 87, these cuts help facilitate the flexing and bending necessary for assembly and during use. The flex circuit 89 can be placed inside a catheter and at the distal end; each branch 87 can peel away at the distal end to form a Y-junction as shown in FIG. 3A. The flex circuit 89 can then be attached to the membrane 34 at the various desired positions. The flex circuit 89 can also include staggered conductive pads 59. Staggering the position of the conductive pads 59 can aid in providing a low profile to reduce a stack up of the regions of enlarged width or diameter substrate 52. The distal end region of the branches 87 can contain an extra amount of length to be used as sacrificial tabs 102. These sacrificial tabs 102 can be used to provide for consistent tensioning of the flex circuit branches 87 during assembly. The tabs 102 can be mounted to an assembly fixture (see FIG. 59) to ensure the locations of each tab 102 and each branch 87 of the flex circuit 89 is properly positioned relative to the membrane 34 and/or shaft 57.

Figure 3D:
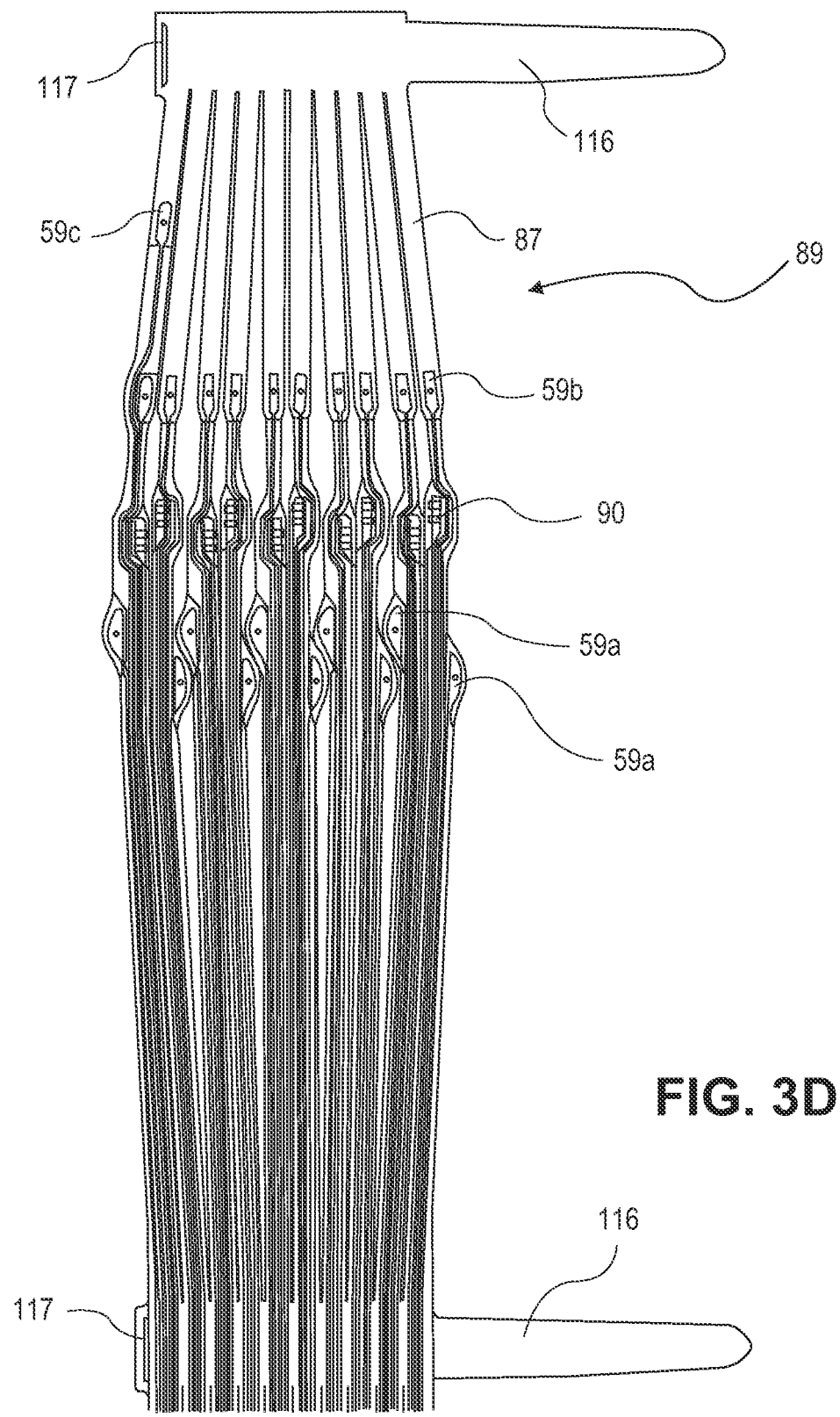

FIG. 3D shows an alternate embodiment of the distal end of the flex circuit shown in FIG. 3B. In this embodiment the branches 87 are separated as in the flex circuit of FIG. 3B but, in contrast to the embodiment of FIG. 3B, are again remerged into a single length of substrate, tab 116 (at the top in the figure), at the very distal end of the flex circuit. This tab 116 wraps the distal end around a shaft, thereby forming a ring structure at the distal end of the flex circuit that may be locked in place. Incorporated in tab 116 is slot 117 into which the free section of tab 116 can be slipped and affixed, thereby forming a ring of substrate material. Also incorporated in the flex circuit of FIG. 3D is an additional tab 116 and slot 117 at the proximal end of the branches (shown at the bottom of the figure). The section between the two attachment tabs 116 is the intermediate portion. In such an embodiment the flex circuit may be affixed to the membrane 34 of an expandable element continuously on the surface of membrane 34 or at multiple points on membrane 34, or may be affixed only at the proximal and distal edges of the membrane 34. Such an embodiment can have advantages both in manufacturing and packing relative to delivery. Also shown in FIG. 3D are staggered conductive pads 59a, 59b, and 59c.

The intermediate portion is comprised of a plurality of individual branches separated from one another along their lengths, wherein at least one branch has an insulating layer along a portion thereof and at least one branch is electrically connected to an electrode adapted to deliver radio frequency energy. The plurality of branches, as shown, are coupled to one another distal to the intermediate portion where they are separated along their lengths.

FIG. 3E is an exemplary complete flex circuit element 89 viewed from the substrate side which incorporates the distal end of the flex circuit 89 illustrated in FIG. 3D. Flex circuit 89 incorporates bends 118 which facilitate the manufacture of flex circuit 89. During assembly of the electrode assembly, bends 118 are folded such that flex circuit 89 may be wrapped around or within a shaft of the delivery system. In such a fashion the flex circuit can span from the electrodes of the electrode assembly to a connector at a handle (not shown) into which flex circuit interface 119 is connected. A flex circuit of a length greater than about 12 inches can therefore be manufactured on a surface which is no greater than about 12 inches in any dimension. In some instances it may be desirable to create multiple segments of flex circuit 89 and connect them as part of the catheter fabrication process. In such cases the flex circuit may be segmented normal to primary direction of the conductors. Convenient locations for such segments to start and end are at the folds 108, in which case the number of connections could replace a same number of folds. The connections thus knit the segments into a unitary structure. Alternatively the direction of segmentation can be parallel to the primary direction of the conductors, in which case the segments would travel the same length as the single structures previously described. Tabs 116 can be modified to interface between segments thus allowing the segments to be knit into a unitary structure.

In some embodiments the length of at least one branch in the intermediate portion is between about 1 cm and about 5 cm.

The circuit shown in FIG. 3E may alternatively be printed on a tubular substrate which is the full unfolded length of the circuit. In such an embodiment the tubing base substrate may be slotted in areas requiring expansion or additional flexibility. Circuit printing techniques such as those used in InkJet Flex circuits can be used in these embodiments. Alternatively, the circuit can be printed on one full length of the circuit, eliminating the need for bends. If incorporated, the folds allow for printing on more readily available fabrication equipment.

In some situations where the number of electrodes and ancillary sensors is minimal the flex circuit may be replaced by wires affixed to the flexible membrane 34. FIG. 66 illustrates such an arrangement. In such cases a wire lead which has been coined at its distal end to create a thin section of sufficient flexibility and surface are to act as the electrode of the flex circuit. Coined wire 145 can replace a flex circuit branch 87. The coined wire 145 may be affixed to flexible membrane 34 using an adhesive film 95. The coined wire 145 may be affixed over an electrode with a conductive adhesive as shown or may be affixed with a non-conductive adhesive and the electrode fabricated over the adhered coined wire 145 (not shown). The sensor leads can be treated in the same fashion if required.

Electrodes

One or more electrodes 6 can contact specified non-insulated sections of a conductive trace 16 of the flex circuit 89, the conductive pad 59, as well as a portion of the deployable membrane 34 and insulated portion of the flex circuit 89. The electrodes 6 can be a thin film material that can be repeatedly folded such that the electrode 6 and membrane 34 can be compacted into a small diameter for minimally-invasive delivery. The conductive material of the electrode 6 has a relatively large surface area compared to the conductive pad 59 it contacts, which provides for a large overall electrode area.

Despite this large surface area, the electrodes 6 do not significantly increase the stiffness of the membrane 34 and can fold with the membrane 34. FIGS. 4A-4C show an embodiment of the interface bond where the membrane 34 is manufactured separately from the flex circuit 89 and the electrode 6. The electrode 6 can be deposited such that it contacts specified non-insulated section of the conductive layer 96 and a portion of the membrane 34. FIG. 4A shows a slight curvature in the membrane 34 and how the electrode 6 can follow this curvature. FIG. 4B shows the electrode 6 folded away from the membrane 34 whereas FIG. 4C shows the electrode 6 folded inwards and possibly contacting itself. Despite the large surface area covered, the thin electrode 6 and the membrane 34 can still be folded (see FIGS. 4B and 4C). The electrode 6 can fold and flex to substantially the same extent as the membrane 34, even a region of the membrane 34 not covered by an electrode layer, such that the electrode 6 does not impede the flexibility of the membrane 34 or the electrode assembly 105. It should be appreciated that the electrode 6 can fold upon itself along with the membrane 34, although folding can also occur between the electrodes 6. The ability to fold can allow for a lower device profile.

The materials used to create the electrodes 6 can vary. The electrodes 6 can be a thin film of an electro-conductive or optical ink. The ink can be polymer-based for better adhesion to the membrane. The electrode material can be a biocompatible, low resistance metal such as silver, silver flake, gold, and platinum which are additionally radiopaque. Inks may additionally comprise materials such as carbon and/or graphite in combination with the more conductive materials already described. The addition of carbon and/or graphite can increase the conductivity of the polymer matrix. When incorporated as fibers the carbon and/or graphite add additional structural integrity to the ink electrode. Other fiber materials may be substituted to attain the same end. When the electrode material is not particularly radiopaque, additives such as tantalum and tungsten may be blended with the electrode material to enhance radiopacity. An example of an electro-conductive ink is provided by Engineered Conductive Materials, LLC (ECM) which is a polyurethane-based silver loaded ink.

Another example is Creative Materials Inc., which manufactures conductive inks, films, as well as radiopaque inks. As mentioned above, the electrodes 6 can be applied to the membrane 34 and flex circuit 89 using an adhesive. Alternatively, the electrode material can have adhesive properties or be an adhesive-loaded with conductive particles such as silver flakes such that the electrodes 6 can adhere the components of the flex circuit 89 to the membrane 34. If an additional adhesive layer is used to adhere the electrode 6 to the membrane 34 and flex circuit 89, the adhesive layer can include a conductive or non-conductive material. The electrodes formed with electro-conductive or optical ink or thin metal film can be visualized under fluoroscopy to provide a general sense of the shape of the membrane and location of the electrode. To enhance visualization under fluoroscopy, radiopaque additives can be included in the electrode material or radiopaque markers laid out next to, on top or below the electrodes as will be discussed in more detail below.

The electrode material can be deposited using a variety of techniques known in the art including, but not limited to, printing, pad printing, screen printing, silk screening, flexography, gravure, offset lithography, inkjet, painting, spraying, soldering, bonding deposited using touch-less technologies or otherwise transferred onto the surface of the membrane 34. In an embodiment, the electrode 6 can be formed by depositing an electrically conductive coating or layer by spraying a designated surface region. Alternatively, the electrode can be formed by depositing the electrically-conductive material onto a region of the membrane 34 by vacuum deposition or printing the electrically conductive material on the designated surface region. This provides an electrically conductive coating of a desired thickness and a relatively uniform electrode through the desired area. Printing processes can include pad printing, screen printing and the like. Touch-free technologies such as positive material deposition of ink such as from a syringe or similar device can also be used to transfer conductive film or ink onto the membrane or substrates that are sensitive to pressure.

The electrodes can also be made using thin, conductive adhesive film or gel that can be cut to the shape of the electrodes and serve as an adhesive for the flex circuit when conductivity is desired. The conductive adhesive gel can be mixed with conductive particles for conductivity and disposed over the substrate and UV cured.

Each region of electrically conductive material can be deposited over and electrically connected to a specified conductive pad 59 of the flex circuit 89 and coupled to the surface of the membrane 34. The electrodes can be formed by using a mask (chemical or mechanical) over the membrane during the deposition process, which can deposit electrode material over the membrane and the mask alike. Once the deposition process is completed, the masking can be removed as is known in the art. An alternate technique can be used where automated robotic systems are programmed to precisely and accurately spray only the desired electrode surfaces without the presence of a mask. This technique can have multiple movable axes such as the Engineering Fluid Dispensing Inc. dispensing robots (East Providence, R.I.).

The flex circuit 89 components can be bonded before, during or after deposition of the electrodes 6 to the membrane 34, for example, using an adhesive or thermal bond or the like as described above. The electrically conductive layer 96 of the flex circuit distal branches 87 can be exposed by etching away a portion of the dielectric layer 100.

Figure 5A:
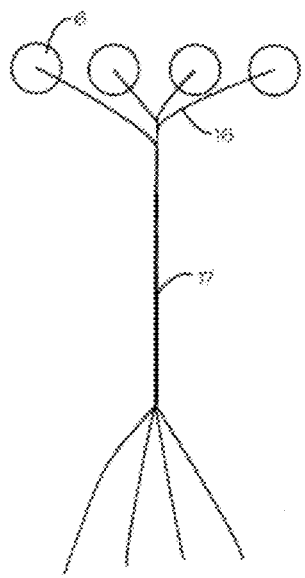
Figure 5B:
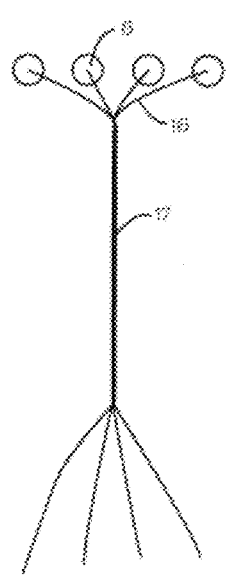
Figure 5C:
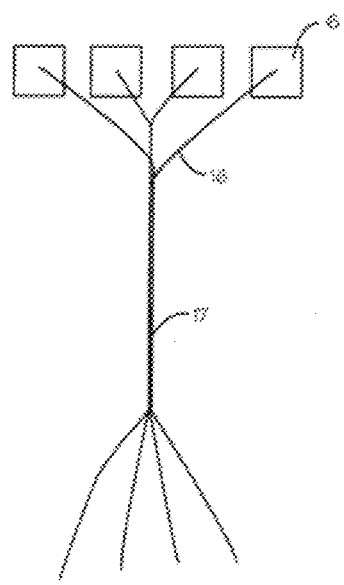
Figure 5D:
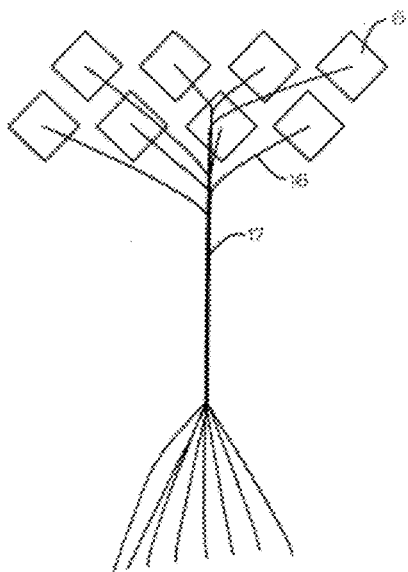
Figure 5E:
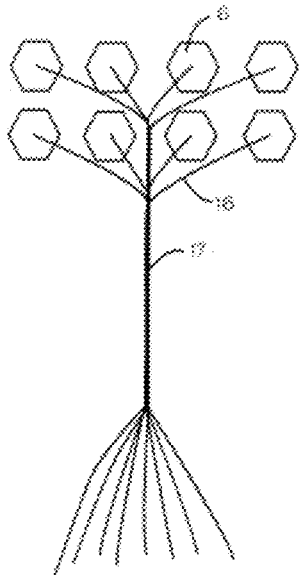
Figure 5F:
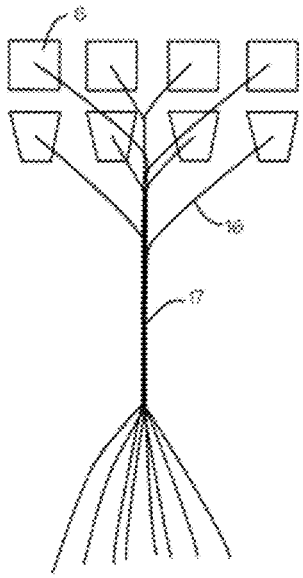

The shape and pattern of electrodes 6 created can vary. The surface area, shape and pattern of the electrodes 6 can influence the amount of energy applied and the ablation line created. FIGS. 5A-5I illustrate various electrode patterns and electrode shapes considered herein including, but not limited to, circular, rectangular, octagonal, polygonal etc. The shape and pattern of the electrodes 6 deposited on the membrane 34 can be selected depending upon the intended application of the electrode assembly. A square electrode, for example, can be better suited for interpolation based on image projection analysis, such as to reproduce the shape of deployable membrane 34 in a mapping and identification software algorithm. One or more rows of electrodes 6 can be used. Each row of electrodes 6 can have the same shape or can vary in shape and size. Spacing between the electrodes 6 within the same row or spacing between the rows can alter the depth and quality of lesion created. The rows of electrodes can have electrodes that line up or can be staggered as shown in FIG. 5D. The electrodes 6 can be arranged in patterns that wrap around the flexible membrane structure to provide rings of electrodes as in FIG. 5A through 5F, or on "diagonals" such that when wrapped the electrode pattern will form helices. Patterns of electrodes may in addition be addressable by the RF power source individually as in FIG. 5G and others, or in groups as in FIGS. 5H and 5I. The electrode pattern may incorporate a single ring as illustrated in FIGS. 5A-5C, or they may incorporate two rows as in FIGS. 5D-5F, or they may incorporate more than two rows. The electrodes 6 can also be deposited in a variety of other locations on the deployable membrane 34 as will be described in more detail below.

Helical patterns of the electrodes have particular advantage when used to create lesions in body lumens, for example the pulmonary veins. In such situations there is a risk that if the lesions were created as a ring on a single plane normal to the long axis of the vessel or lumen, swelling of the lumen resulting from the ablative injury or the subsequent healing might stenos at a ring lesion. By wrapping the electrodes as indicated in FIGS. 18P and 18S the impact of any resultant stenosis associated with each lesion are not allowed to become additive. A single helical electrode energized in a monopolar fashion, or two helical electrodes spaced apart, as in FIG. 5G, may have advantages with regard to simplicity of the RF source, speed of application, and minimal fabrication costs. These configurations, however, have limitations when the uniformity of lesion, and the ability to modify the lesion in response to feedback acquired from sensing electrodes, to be described as described elsewhere herein, are primary to effective therapy.

With reference to the uniformity of lesion, as the electrode surface increases the uniformity of tissue contact across the electrode can be lessened. This variation can be minimized by using a flexible electrode on a flexible membrane, also described elsewhere herein. However, as the surface area of the electrode grows, and or the aspect ratio for of the electrode increases, as in the long helical elements just described, the uniformity of contact become less controllable. As the contact area varies the current gradients and possibly total current delivered, depending on system design, will vary. Since the amount, and spacial distribution, of current transmitted to the tissue from the electrode control the size and depth of the resultant lesion, it is often more advantageous to use multiple smaller individually addressable electrodes. In addition to helical patterns of electrodes, rectilinear arrays may be used where the helical lesion pattern is created by addressing an appropriate pattern of electrodes, either individually or in pairs depending whether monopolar or bipolar energy is used. None helical patterns will have similar advantage to those stated for the helical pattern when their projection on a plane normal to the long axis of the lumen are continuous and closed, The spacing between electrodes is another important characteristic which can be used to control the volume of the lesion. As such, although not pictured, the present description anticipates various spacing and arrangements of addressability not specifically illustrated or described herein.

Figure 12:
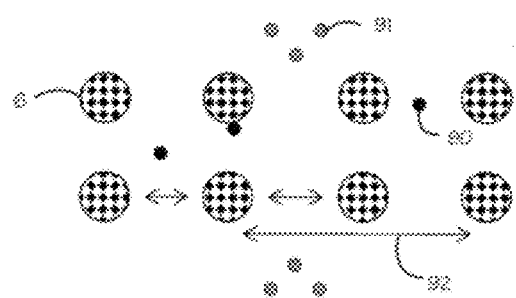
FIG. 12 shows an embodiment of an electrode pattern that can be used for ablation.

FIG. 12 shows an embodiment of a pattern of electrodes 6. The pattern shown in FIG. 12 is exemplary and variations in the pattern are possible. Current 92 can be passed between adjacent electrodes 6 and/or overlap an electrode 6 to reach the next electrode 6 to create the desired ablation line. Each of the electrodes 6 can be created as a solid pattern, a set of concentric circles or other geometric shape, or a set of lines intersecting or not. The surface area, shape and internal pattern of the electrodes can influence the density of the current and burn line created. These features can also affect the amount of current and power required as well as duty cycle and/or pulse wave modulation. There can be more than one row of electrodes 6 to allow the user to actively select which region to use for creating the ablation lesion and avoid having to exactly position the device and or manipulate to create the proper ablation line. The ablation line can be created in a desirable location using techniques that are easy and fast and without the need for tedious repositioning.

The multiple electrodes 6 deposited on the membrane 34 can collectively create a large electrode array of energy-transmitting elements. This electrode array can form a variety of patterns across the membrane 34 and has an energy-transmitting surface area. The electrode array pattern and energy-transmitting surface area can vary. In an embodiment, the energy-transmitting surface area covers at least about 10% of the membrane surface area to be selectively activated. In an embodiment, the energy-transmitting surface area can cover about 25% of the membrane surface area. In another embodiment, the energy-transmitting surface area can cover approximately 50% of the membrane surface area. The energy-transmitting surface area can be a factor of the physical surface area of each individual electrode within the energy-transmitting array as well as the projection of the expected ablation surface area based on the electrode pattern spacing. The preferred energy-transmitting surface area percentage can also vary depending upon the indication being treated. For example, for the treatment of atrial fibrillation the energy-transmitting surface area can cover at least 25% of the membrane surface to be selectively activated. In another embodiment, the energy-transmitting surface area can cover greater than 40% of the membrane surface to be selectively activated. These percentages are provided for example and can vary. The large energy-transmitting surface area allows the membrane surface to selectively ablate more tissue simultaneously without the need for repositioning. Generally, the lesion site can be slightly larger than the energy-transmitting surface area.

Figure 6A:
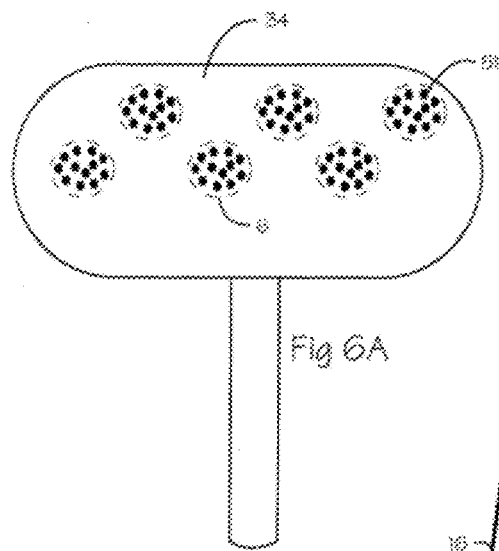
FIGS. 6A-6B illustrate groupings of multiple smaller electrodes creating a larger electrode.
Figure 6B:
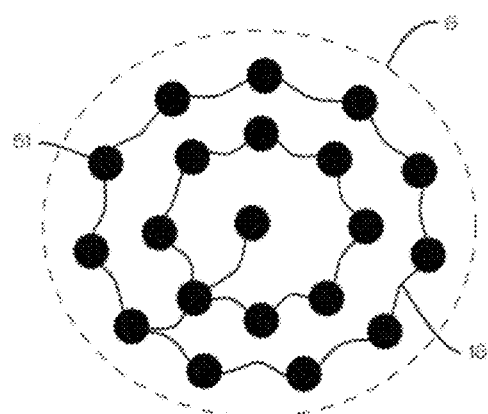
Figure 6C:
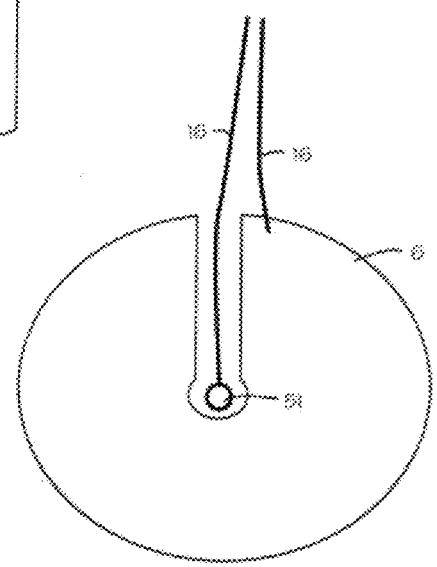
FIG. 6C illustrates an embodiment of an electrode that includes a small mapping electrode.
Figure 6D:
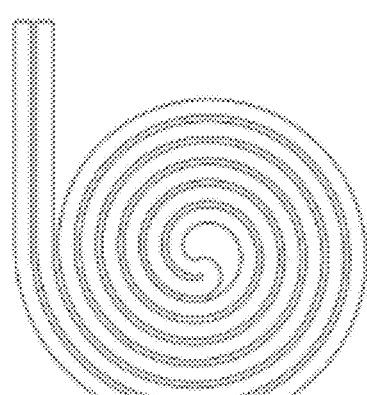
FIG. 6D illustrates an embodiment of an electrode configured as a dual spiral with the inner ends merged.

Each electrode 6 can also be a grouping of multiple smaller electrodes 51 such as the embodiments shown in FIGS. 6A-6B. Each of the smaller electrodes 51 can be connected by the conductive traces 16 of the flex circuit 89 as shown in FIG. 6B to form a larger electrode 6. Alternatively, the smaller electrodes 51 can be independently activated for mapping electrical signals as may be needed in some indications such as the treatment of atrial fibrillation. The traces 16 can be created as a sinusoidal line, for example, to allow for some elongation of the expandable element so that the individual electrodes can spread farther apart and the electrodes become substantially larger. As shown in FIG. 6B, traces 16 allow for uniform elongation in all directions. Alternatively, the traces 16 can allow for elongation in specified directions. The surface area, shape and pattern of the electrodes can influence the amount of energy transmitted to the target tissue. Measurement with smaller electrodes 51 can provide higher resolution and accuracy of the signal location, which can be useful for example in mapping aberrant signals. FIG. 6C illustrates an embodiment of an electrode 6 that includes a small electrode 51 located at the center of the larger electrode 6. Each of the electrodes is connected to their individual traces 16. This embodiment can be used to confirm conduction block such as during treatment of atrial fibrillation by comparing conductivity before and after ablation or by moving the electrode structure further into the pulmonary vein for measurements. FIG. 6D illustrates an embodiment of an electrode 6 configured as a dual spiral with the inner ends merged. This embodiment can be used when the resistance of the electrode is required to be monitored such as when the electrode is used as a temperature sensor in conjunction with its electrode function as discussed elsewhere herein. In such a configuration the long path of the trace forming the electrode is contained in a small area. Arranging the electrode as a long path allows changes in the resistance as different areas of the electrode have comparable effects on the overall resistance of the electrode.

Figure 7A:
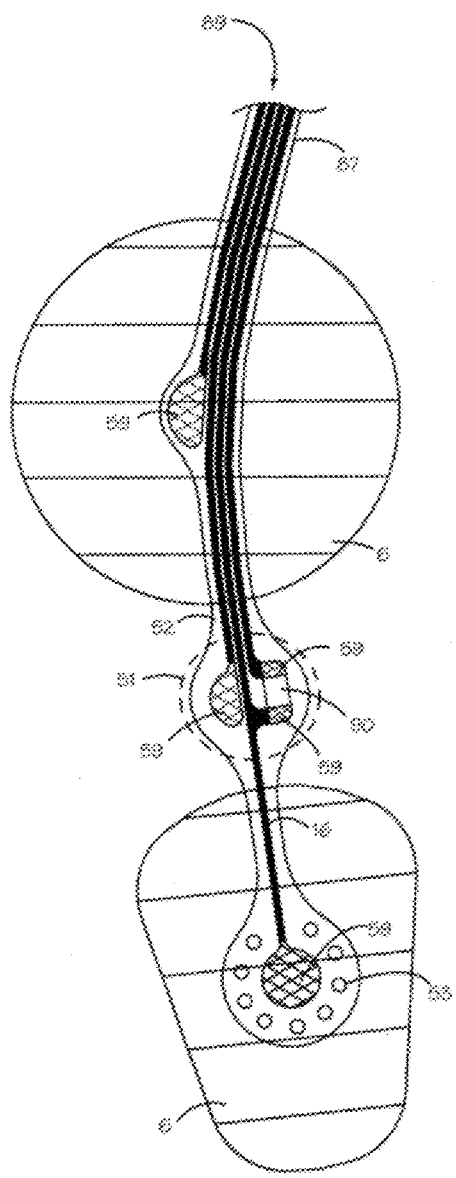
FIGS. 7A-7E illustrate various embodiments of electrodes and a flex circuit having mapping electrodes and temperature sensors.
Figure 7B:
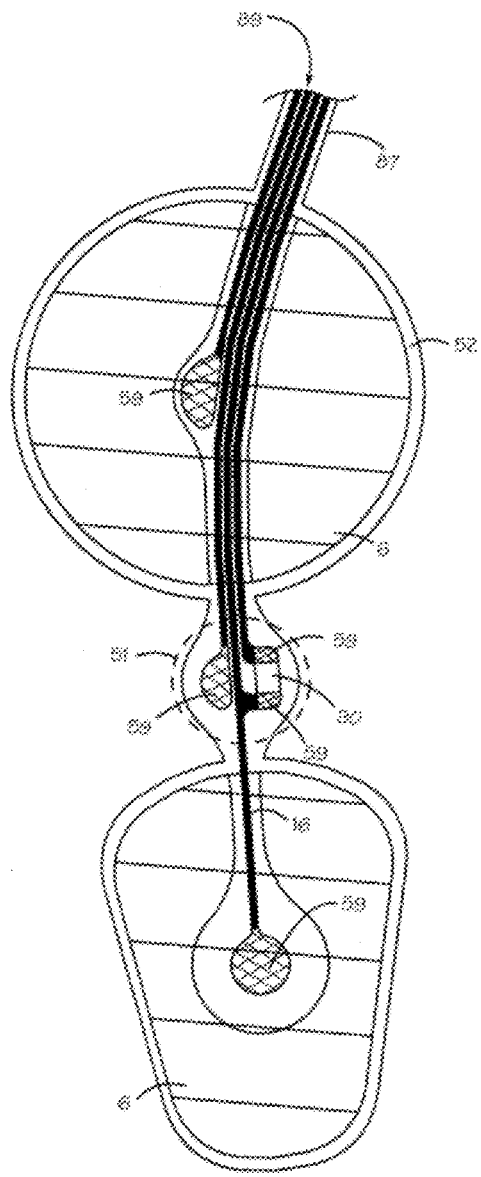
Figure 7C:
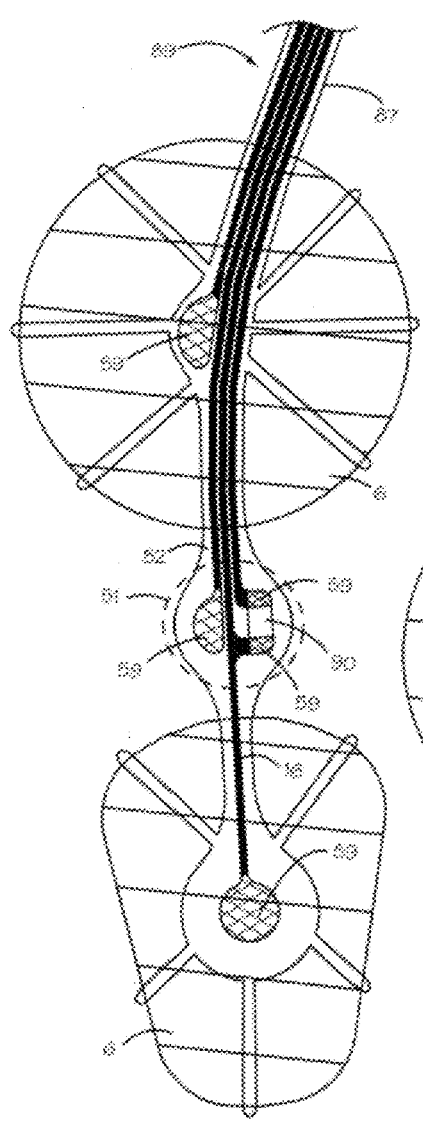

The electrode 6 can be a thin, flexible film that is deposited over a portion of the flex circuit 89 as well as a portion of the membrane 34. As discussed briefly above and shown as an example in FIGS. 7A-7E, each of the electrodes 6 has dimensions that exceed those of the conductive pad 59 or the conductive trace 16 of the flex circuit 89 such that the electrode 6 covers an area of the membrane 34 on which the flex circuit 89 is mounted. FIG. 7A shows the substrate layer 52 of the flex circuit 89 following and outlining the conductive traces 16. The electrodes 6 can extend beyond the substrate layer 52 onto the underlying membrane 34 to provide a large surface for the electrode 6 to contact the tissue. This is in contrast to many devices known in the art which use the small, non-insulated portion of the flex circuit itself as the electrode element. Larger surface area and bigger overall electrodes 6 allow the electrode assembly 105 of the devices described herein to transmit energy deeper and with less risk of gaps in the energy transmission line. To increase the durability of the electrodes 6, the substrate layer 52 can be extended over portions of the electrodes 6. This can restrict elongation on sections of the membrane where the electrodes 6 are located and can ensure, for example predictable ablation lesion size and quality. FIG. 7B shows the substrate layer 52 can extend to outline the shape of the electrodes 6 to be deposited. FIG. 7C shows the substrate layer 52 can have finger-like extensions or struts that can extend to the edge of the electrodes 6. A combination of any of the above can also be used.

The dimensions of the electrode 6 can vary. In an embodiment, each electrode 6 can be between about 0.015 to 0.050 mm in thickness. In an embodiment, each electrode 6 is less than 0.025 mm in thickness. In an embodiment, each electrode 6 can have an overall surface area of between 3 and 36 mm2. In an embodiment, each electrode 6 can have a size that is approximately about 2 mm round. In comparison, each conductive trace 16 can be between about 0.05 mm and 0.10 mm in width and between about 0.02 and 0.05 mm in thickness. Each conductive pad 59 can be between about 0.05 and 0.70 mm in width and between about 0.02 and 0.05 mm in thickness. In an embodiment, each conductive pad 59 can have an overall surface area of between about 0.002 and 0.450 mm2. In an embodiment, the conductive pad 59 can be approximately 0.5 mm round. It should be appreciated that the aforementioned dimensions are exemplary and that variations are possible.

The relative dimensions of the electrode 6 and portions of the flex circuit 89, such as the conductive pad 59, can also vary. In an embodiment, the surface area of each electrode 6 as it relates to the surface area of its associated conductive pad 59 can be described in terms of a ratio and can be at least about 14:1. In another embodiment, the ratio of electrode width to conductor width can be about 13:1. The relative dimensions between the electrode assembly components can also vary depending upon the indication being treated. For example, atrial fibrillation-specific devices the ratio of surface area of electrode 6 to surface area of conductive pad 59 can be at least about 44:1. The conductive pad 59 can be approximately 0.5 mm round and the electrode can be a minimum of approximately 3×3 mm or 3.4 mm round for a 44:1 ratio. For an electrode having an area of 4 mm round, the ratio can be approximately 62:1. For an electrode having an area of 5 mm round, the ratio can be approximately 95:1. For an electrode having an area of 3×5 mm, the ratio can be approximately 74:1. For an electrode having an area of 5×5 mm, the ratio can be approximately 123:1. In another embodiment, the ratio of electrode width to conductor width on the flex circuit can be approximately 35:1. The conductor width can be 0.07 mm and a minimum width of the electrode can be 3 mm for a 3×3 mm electrode. In another embodiment, the electrode can have a surface area of at least about 9 mm$^2$ (3.4 mm round) and an electrical conductor of between about 0.025 to 0.050 mm maximum thickness. This combination results in a flexible electrode that has a large surface area yet is connected to a very thin conductive trace. It should be appreciated that the aforementioned relative dimensions are exemplary and that variations are possible.

The energy delivered by the electrodes 6 can vary. The energy can include direct current (DC), alternating current, radiofrequency (RF) energy, for example in a monopolar or bipolar energy configuration, microwave, high voltages. When using RF and or high voltages the energy levels can be adjusted to cause thermal damage by increasing the tissue temperature to above 42° C. or by creating high voltage gradients to bring about irreversible electroporation (IRE). Microwave and RF energy can use the application of thermal energy for cell necrosis while IRE can use high voltage electrical pulses to create cell permeability leading to cell death. Voltage energy can be delivered in very high voltage dosage in short bursts. Use of bipolar RF energy prevents the current from traveling through the bloodstream and reduces the risk of charring and thrombus. Bipolar energy also removes the effect of blood flow on the energy delivery compared to monopolar and generally provides more consistent results. The electrode assembly 105 can be used exclusively in the bipolar configuration without using the monopolar configuration to minimize or eliminate current transfer through the bloodstream. The energy applied during an energy transmission period can be in the form of high energy and low energy cycles (on/off) or alternating high and low temperatures.

Figure 8:
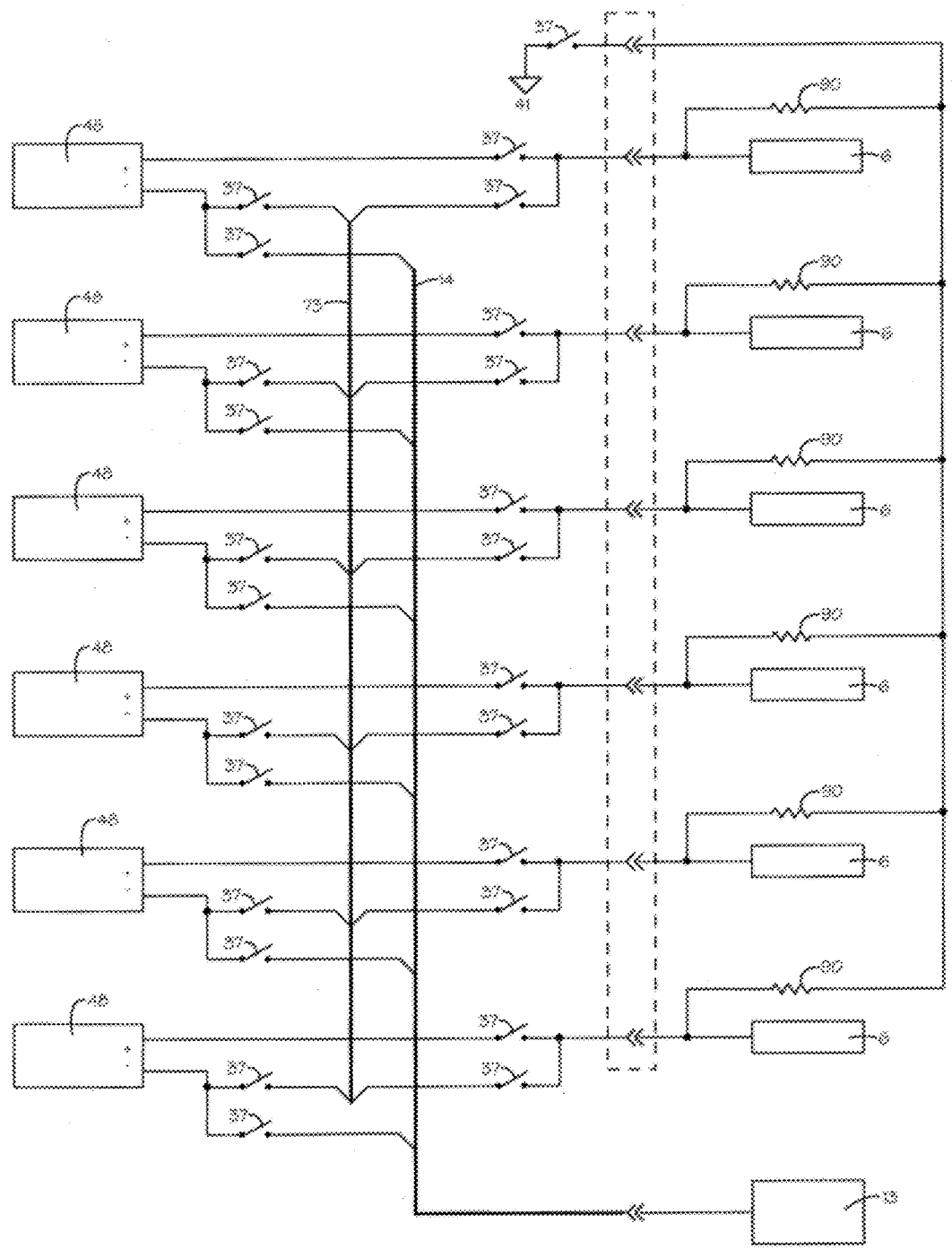
FIG. 8 illustrates an embodiment of the flex circuitry wiring.

FIG. 8 illustrates an embodiment of the flex circuitry wiring for the electrodes 6. Each electrode 6 can be connected to an RF amplifier 48. Each electrode 6 can be individually turned on and off for monopolar or bipolar energy transmission. For monopolar, the electrodes 6 can be connected via a monopolar bus line 14 to a patient return electrode 13 and can be individually or simultaneously activated by switches 37. For bipolar, the electrodes 6 can be connected via a bipolar bus line 73 and can be individually or simultaneously activated by switches 37. Variations in the manner of connection between the electrodes are possible. As will be discussed in more detail below, temperature sensors 90 can be included in the electrode assembly 105 and can share an RF conductive trace with an adjacent electrode 6. This allows for dual use of the conductors which reduces the overall bulk and profile of the device. It also eliminates the need for an additional assembly junction on the membrane during manufacturing and allows for a narrower flex circuit and lower profile. It should be appreciated that the electrodes 6 can also be used for mapping as will be discussed in more detail below.

The electrodes 6 can include a variety of activation mechanisms. Multiple electrodes 6 can be individually connected to a single flex circuit 89 and can be individually controlled and individually activated for a more precise energy transmission via an electronic control box. Alternatively, the electrodes 6 can have a physical movable activation means, such as a conductive wire, which can be electrically connected to an array of electrodes in series. FIGS. 9A-9B, for example, show a conductive trace 16 that can be a movable wire housed within a lumen 33. The trace 16 can contact individual electrodes 6 located in series and activate them individually or in unison. This can allow a user to create a burn pattern precisely where needed without having to move the membrane 34 to a different position. FIG. 10 shows another embodiment of a selective activation mechanism which includes an electrode sleeve 10. A conductive trace 16 can be advanced distally or withdrawn proximally within a lumen of the electrode sleeve 10. The distal end of the conductive trace 16 can have a region of exposed conductive layer 96 covered by an electrode 6 that can selectively contact the tissue to be ablated through the openings 32 of the electrode sleeve 10. This configuration can allow the user to position the electrode device once and tune the position of the electrodes 6 with the least amount of manipulation. This minimizes the amount of risk of trauma and injury to the patient as well as reduces the time of the procedure. FIG. 11 shows an embodiment in which the electrode sleeve 10 having movable traces 16 is mounted to a surface of a membrane 34 such as a balloon.

The electrodes 6 described herein can have low thermal mass or inertia for quick heating and quick heat dissipation. This low thermal mass provides a more consistent and predictable temperature and energy delivery as well as a more accurate measurement of temperature and better user control of the energy. One or more temperature sensors 90 can be mounted directly on the flex circuit 89 adjacent or over the electrodes 6 to provide feedback during use of tissue temperature such that power, current, duty cycle can be modulated and maintained within a specified temperature or temperature range. The temperature sensors 90 considered herein can include surface mount thermistors, thermocouples or other resistance temperature detectors or platinum resistance thermometers. The temperature sensor 90 can be bonded to the conductive trace 16, for example, with an adhesive.

Figure 13A:
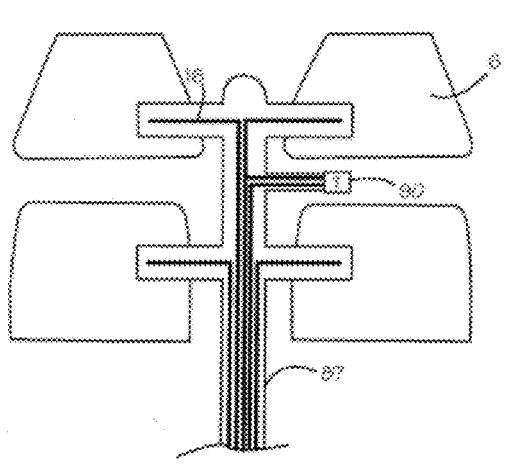
FIGS. 13A-13B illustrate embodiments of a flex circuit at the electrodes.
Figure 13B:
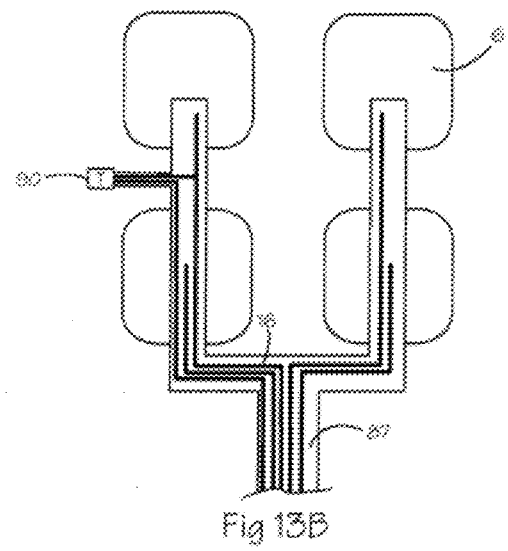

The number and pattern of temperature sensors 90 included in each flex circuit 89 can vary. FIG. 12 shows an embodiment of an electrode 6 and temperature sensor 90 pattern where the temperature sensor is located between two electrodes 6, between four electrodes 6 or in contact with one electrode 6. FIGS. 13A-13B show other embodiments of an electrode assembly including a distal branch 87 and branching conductive traces 16 of a flex circuit 89 contacting multiple electrodes 6 and a temperature sensor 90. Each electrode 6 can be connected to one conductive trace 16 stemming from the distal branch 87. The temperature sensor 90 can share the conductive trace 16 with the electrode 6 and be positioned near where the electrode 6 is touching the tissue. For example, a temperature sensor 90 can have a common ground and each end can be connected to one of the electrodes 6 and switched/multiplexed with RF power. The dual usage for the trace 16 between temperature sensors 90 and electrodes 6 reduces the overall profile of the electrode assembly 105. Fewer connections results in less material and less bulk of the device, better packing and ease of manufacture.

The electrodes may be configured to provide the temperature sensing function thereby replacing some or all of the temperature sensors described herein. Such configurations include using the inherent temperature coefficient of resistance ("tempco") of the electrode as a means to characterize the electrode temperature. Conductive ink ECM CI-1036 configured as a 0.3 mil thick electrode demonstrates a linear tempco of 0.005 ohms/degree C. over the range of 30 to 60 degree C. This is very close to the 0.006 ohms/degree C. associated with silver. Copper or aluminum with temperature coefficients approximately 0.004 ohms/degree C. coated with silver or gold to protect the electrode and improve biocompatibility are additional material useful for such temperature sensing electrodes. Platinum with a tempco of approximately 0.004 ohms/degree C. is yet another material useful for such purposes. These materials may be used in any of the other electrode configurations described herein. Alternatively the electrodes may be comprised as a conductive ink modified to have a nonlinear tempco within the desired temperature control range and exhibiting a large change in tempco at a predetermined control temperature with in this range. In such configurations the size, shape, loading, and composition of the conductive particles and the matrix polymer may be adjusted to create such a transition. In particular, as the matrix expands at the rate associated with its coefficient of thermal expansion, the overlap and contact area between particles is abruptly reduced, thereby abruptly increasing the electrical resistance. In such configurations the electrode can act as its own temperature regulator.

In configurations using the electrode as a temperature sensor the return line associated with the separate temperature sensors may be used as a return line for measuring the temperature of the electrode. The return line can be gated in such a fashion that it is an open circuit when delivering RF and a closed circuit during a measurement period. Alternatively the temperature sensor has a very nonlinear tempco within the control range; a return line is not required. In this situation the inherent increase in resistivity of the electrode when used as a temperature sensor, or that of an ancillary temperature sensor when in use, may be used to limit the delivery of RF energy after a control temperature maximum has been attained.

Figure 7D:
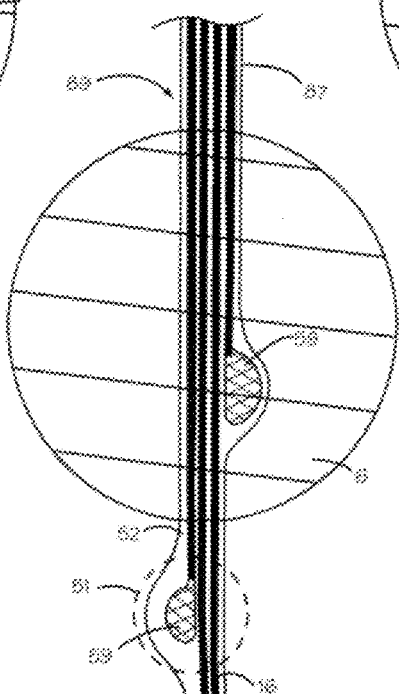
Figure 7E:
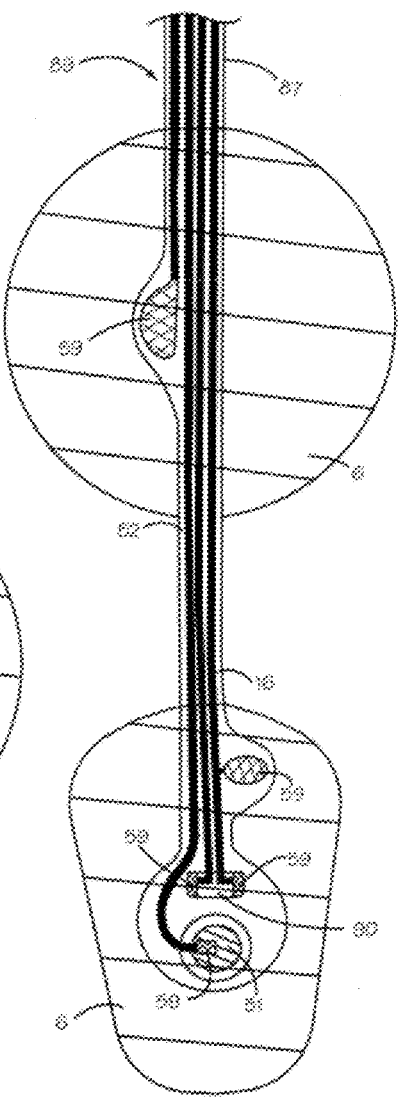

The location, distribution throughout the flex circuit 89 and number of temperature sensors 90 incorporated with the electrode assembly 105 can vary. In an embodiment, the temperature sensors 90 can be adjacent, directly covering, or in between the electrodes 6. FIG. 7A shows a temperature sensor 90 located in between two electrodes 6. In a non-limiting example, the temperature sensor 90 can be generally less than 1 mm away from the electrode 6. The trace connected to the temperature sensor 90 can be shared with the trace 16 for the adjacent electrode 6. FIGS. 7D and 7E shows an embodiment of an electrode assembly 105 where the temperature sensor 90 is located at the center of an electrode 6 instead of between two electrodes. The temperature sensor 90 may be electrically isolated from the electrode 6. One or more temperature sensors 90 can be used per pair of electrodes 6. In an embodiment, at least 10 temperature sensors 90 can be included for temperature control.

Deployable Membrane

The electrode assembly 105 also includes a deployable, flexible membrane 34 to which the flex circuit 89 and electrodes 6 can be coupled. When deployed, the membrane 34 can deliver energy through the large surface area of the electrodes 6 to a target tissue. The deployed membrane 34 and electrodes 6 can ablate tissue over a large zone or area in a variety of patterns, for example circumferential, curved and linear patterns, as will be discussed in more detail below. Despite the large overall surface area of the membrane 34 covered by the electrodes 6 and the flex circuit 89, the membrane 34 can be readily conformable to the target tissue to be ablated and also compactly folded into a small diameter such that the electrode assembly 105 can be delivered, for example, through small access channels for minimally-invasive delivery.

The structure of the membrane 34 can vary including, but not limited to a membrane sheet, cylinder, tube, inflatable, expandable, or fellable structure, such as a balloon, or braided mesh and the like. In an embodiment, the electrode assembly includes a deployable membrane that is formed into a linear structure or a cylindrical tube such as a cylindrical electrode element 34 as shown in FIGS. 16A-16B. The cylindrical membrane 34 can have multiple electrodes 6 deposited along its length in varying patterns. The membrane 34 can be steered and manipulated, for example to ablate two anatomical regions simultaneously. The membrane 34 can include sections of varying flexibility and stiffness for the ability to steer. The distal end of the membrane 34 can be manipulated with a guidewire 40 for proper placement at or near the target tissue 80, for example into a vessel such as the pulmonary vein for the treatment of atrial fibrillation. A region of the membrane 34, for example a middle region, can be highly flexible such that by pushing a handle (not shown) distally the middle region of the membrane 34 can bend and be directed toward another anatomical region, for example such as inserted into an adjacent vessel (FIG. 16B). This can be useful, for example, when ablating a region between the two pulmonary veins that can have highly irregular anatomy that is difficult to access. The membrane 34 can also be inflated or expanded to contact the vessel wall 83 and anchor the device in place as will be discussed in more detail below. The cylindrical electrode element 34, which is located on the electrode catheter 71, can be advanced through a sheath 65, such as a transseptal sheath (see FIGS. 15A-15B). The user can control the distal end of the electrode sheath 76 via a pull tether 70 at the proximal end of the electrode catheter 76. Pull tether 70 can be concentric and housed within the electrode catheter 76 in some portion more proximal than what would be protruding from the transseptal sheath 65.

Figure 14A:
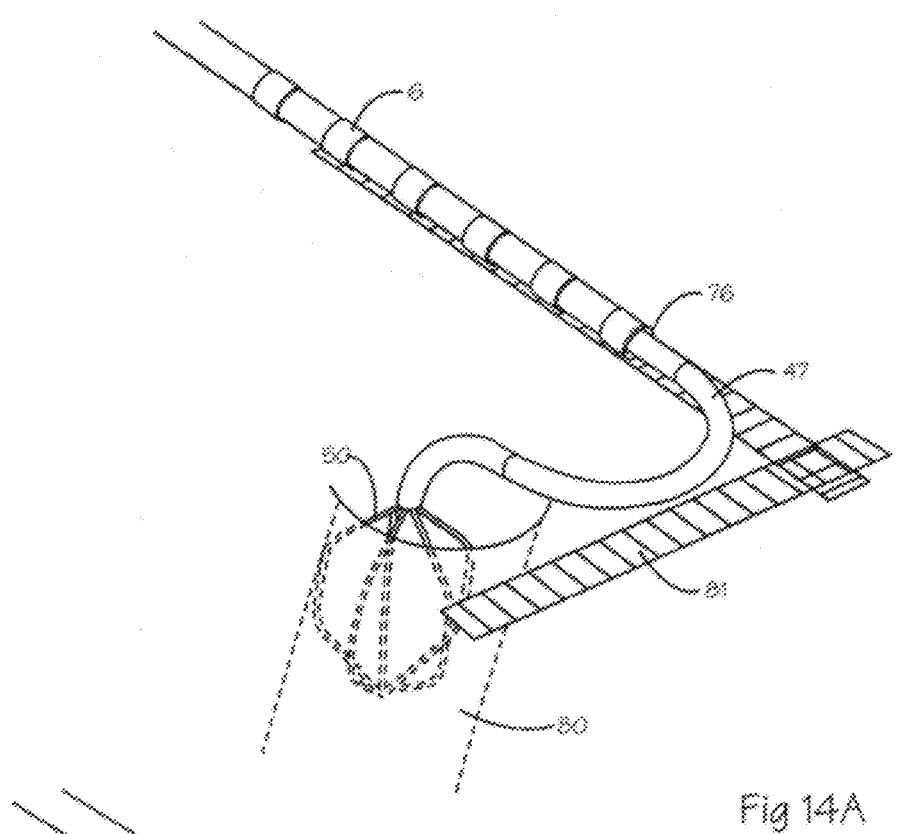
FIGS. 14A-14B illustrate embodiments of an electrode assembly having a cylindrical electrode element and an electrode sheath.
Figure 14B:
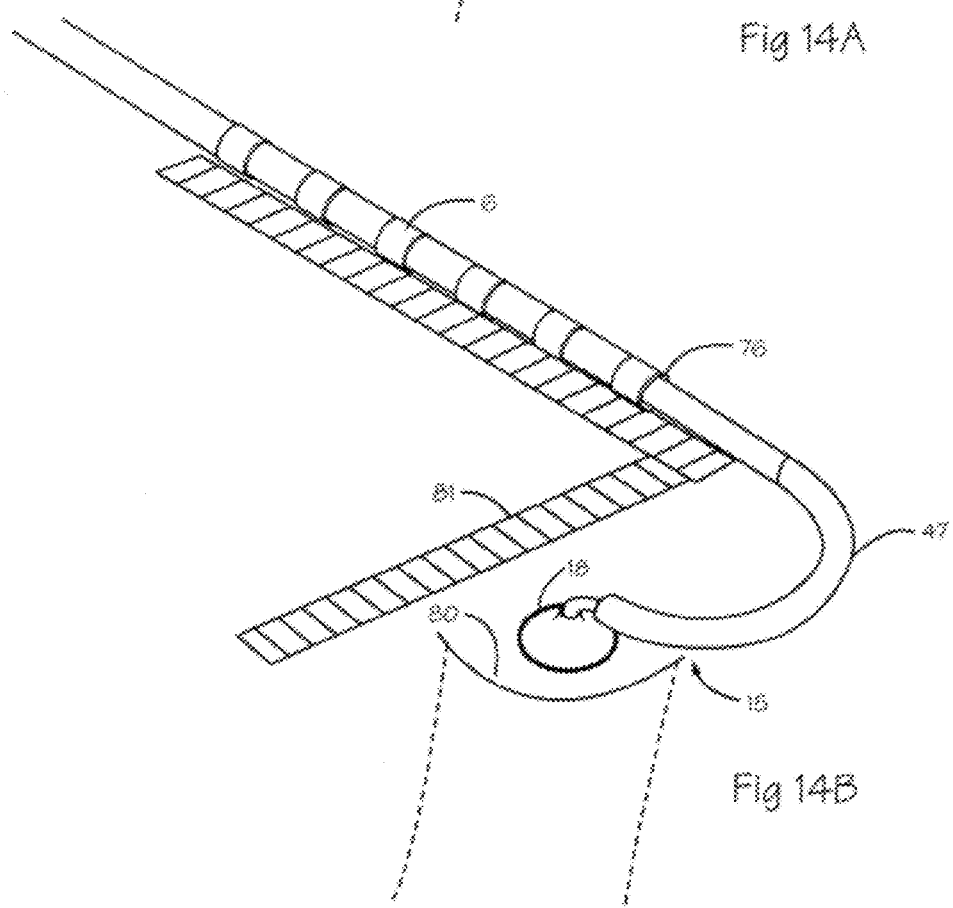

In one embodiment, the electrode catheter 71 can be housed within an electrode sheath 76 as shown in FIGS. 14A-14B. In an embodiment, one or more electrodes 6 can be positioned on an outer surface along the length of the electrode sheath 76. The electrode catheter 71 can be used in conjunction to electrode sheath 76 to transmit thermal energy in multiple locations. In another embodiment, the electrode sheath 76 can slide over a steerable guide catheter 47 anchored in place, for example using an anchoring basket 50 or a suction tip 18 at the end of an anchoring catheter 15 to anchor onto neighboring tissue such as the myocardium near the pulmonary vein 80. The steerable guide catheter 47 can be used to position the electrode sheath 76 to produce the desired treatment lines 81. It should be appreciated that the electrode sheath 76, the electrode catheter 71 and steerable guide catheter 47 can be incorporated into a single catheter configuration.

The membrane 34 of the electrode assembly 105 can have an expandable structure (self-expanding or otherwise) that can place the electrodes in full contact with tissues. The membrane 34 of the electrode assembly 105 can have an expandable structure that is closed or fluid-tight, such as a balloon or a cylindrical tube. The membrane 34 of the electrode assembly 105 can also span or have an expandable structure that is open, such as a woven, braided, stent or basket-like expandable structure as shown in FIG. 17A-17D. In an embodiment, the expandable structure 93 can radially expand to an open state (self-expanding or user-operated). The expandable structure 93 can be surrounded by the electrode assembly 105 such that the flexible, outer membrane 34, flex circuit 89 and electrodes 6 are disposed thereon. The expandable structure 93 can be attached to a catheter 57 via distal support elements 44. In one embodiment the flexible membrane 34 can surround the expandable structure 93 while attached by sutures at the intersections of the distal support elements 44 and the expandable structure 93. In another embodiment, the membrane 34 may be weaved through some or all the loops of the expandable structure 93 while allowing sufficient material for elongation and movement of the expandable structure 93. The electrodes (not shown) can also be mounted over a single wire or over the intersection of wires or both. The expandable structure 93 can be flexible and conform to a variety of anatomical shapes. FIG. 17A shows the expandable structure 93 in a relatively elongated state with a lower profile more suitable for insertion and removal through a small access channel or sheath. FIG. 17B shows the expandable structure 93 in its fully expanded state that can be used or is suitable for energy transmission. A guidewire (not shown) can be used when ablating, for example around the pulmonary vein. When the guidewire is retracted, the distal end of the expandable structure 93 can be used to ablate tissue. FIGS. 17C and 17D show close-up views of an embodiment of the woven loops of the expandable structure 93. The expandable structure 93 can be a shape memory material such as Nitinol.

Figure 17E:
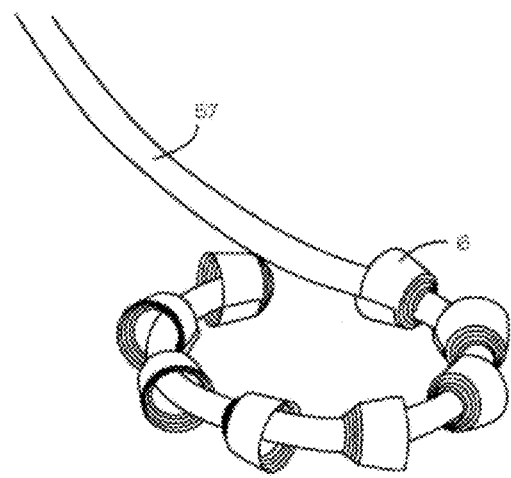
Figure 17F:
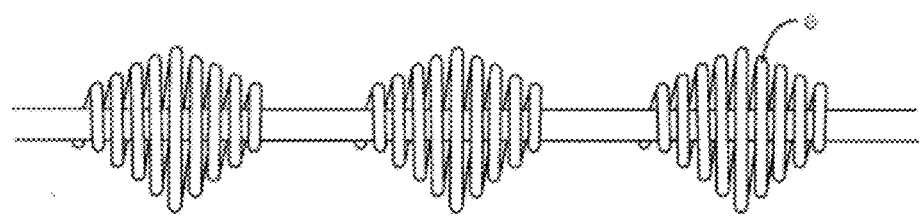
Figure 17G:
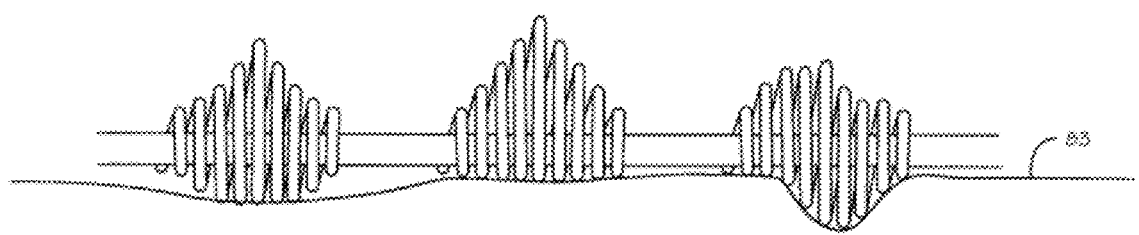

In another embodiment, shown in FIGS. 17E-17G, a catheter 57 can have one or more electrodes disposed on an expandable structure. The configuration of the expandable element can vary including a flat wire or coil. Once deployed the diameter of the electrode 6 can be larger than the diameter of the catheter body 57. This promotes optimum contact with the tissue 83 to be ablated or mapped. Additionally, these "spring" electrodes can be constructed for self-adjustment within their range of movement to conform to a variety of anatomies. A pressure or movement sensitive mechanism can be incorporated at each electrode in order to provide feedback to the user about tissue contact prior to device activation. A flexible membrane 34 can also be placed over these spring elements with the electrodes disposed on the membrane.

The flexible membrane 54 can be disposed around an expandable structure 98 that is self-expanding such as a braid, coil or the like, as shown in FIGS. 60A-60D. Electrodes 6 may be arranged over the tubular thin walled membrane 54. A sheath 31 can cover the electrodes and support structure for a low profile delivery. Once inside the desired location, the sheath can be pulled back, exposing the structure 98 and the electrodes 6. The membrane 54 can be attached to one or both ends of the support structure 98. An exemplary benefit of this approach is that the device does not occlude the anatomy during ablation. The structure is open through its longitudinal length and thus allows for the flow of fluid or gas. This eliminates a concern especially when treating blood vessels. The membrane can also include holes, slits, or ports which allow for additional fluid or gas passage to minimally interfere with anatomical flows.

Figure 60A:
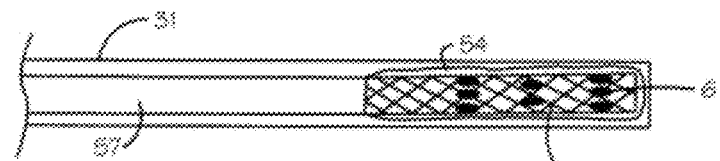
FIG. 60A-60D illustrate a flexible membrane incorporating electrodes disposed around an expandable structure.
Figure 60B:
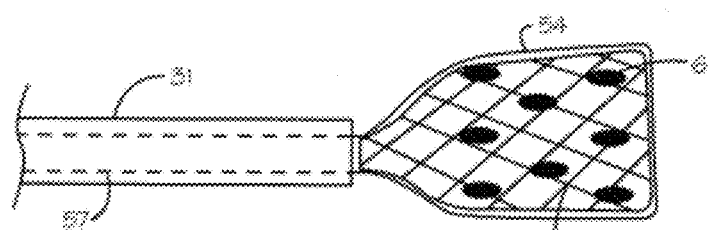
Figure 60C:
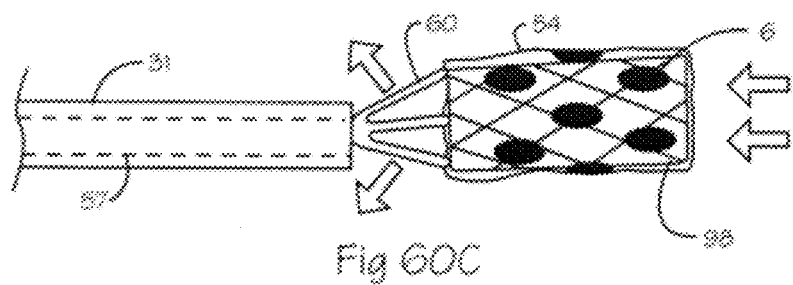
Figure 60D:
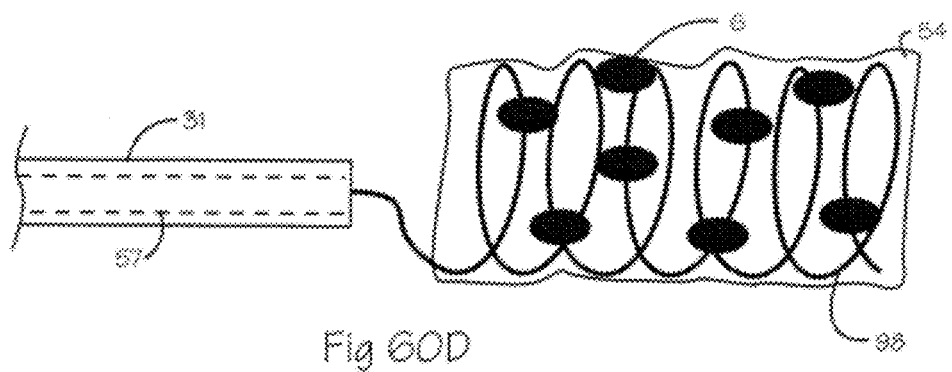

FIGS. 60A and 60B show an embodiment of this design. The structure 98 is directly attached to the catheter shaft 57 which creates a funnel shape at the junction of the shaft and the structure. This facilitates sheathing and unsheathing of the structure. FIG. 60C shows another embodiment in which a coupling element 60 connects the shaft 57 and the structure 98, which allows for full expansion of the support structure 98 at the distal and proximal end and thus fully expansion of the electrode-carrying membrane 54. A depiction of the flow of blood is indicated with arrows in FIG. 60C. FIG. 60D illustrates a thin wall membrane 54 with electrodes 6 supported by a coil support structure 98. This embodiment allows for a very small profile in that a coil can be sheathed into an essentially linear structure. To prevent distortion of the electrodes, the membrane 54 in this particular embodiment may be attached at only the proximal end or otherwise contain compliant sections not directly affecting the electrodes during sheathing.

Figure 18A:
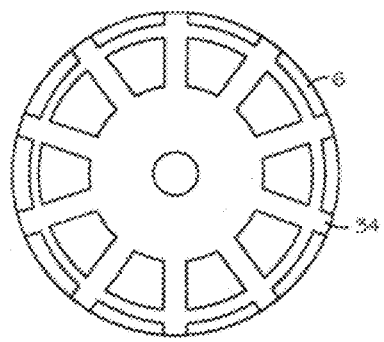
FIGS. 18A-18S illustrate embodiments of an electrode assembly having an expandable electrode structure.
Figure 18B:
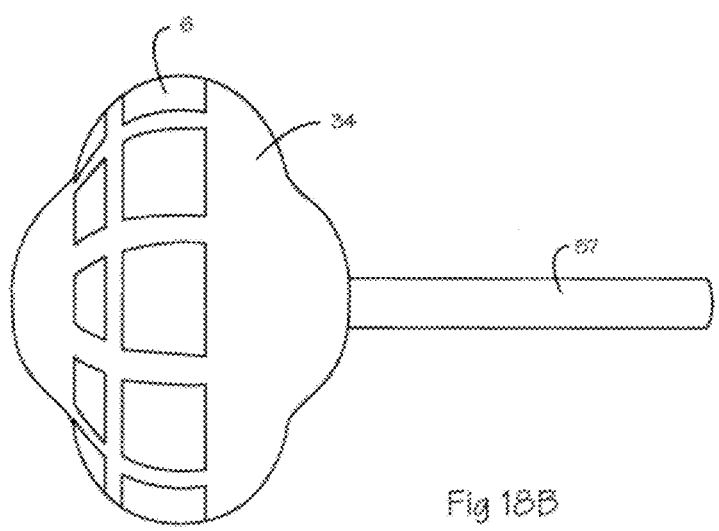
Figure 18C:
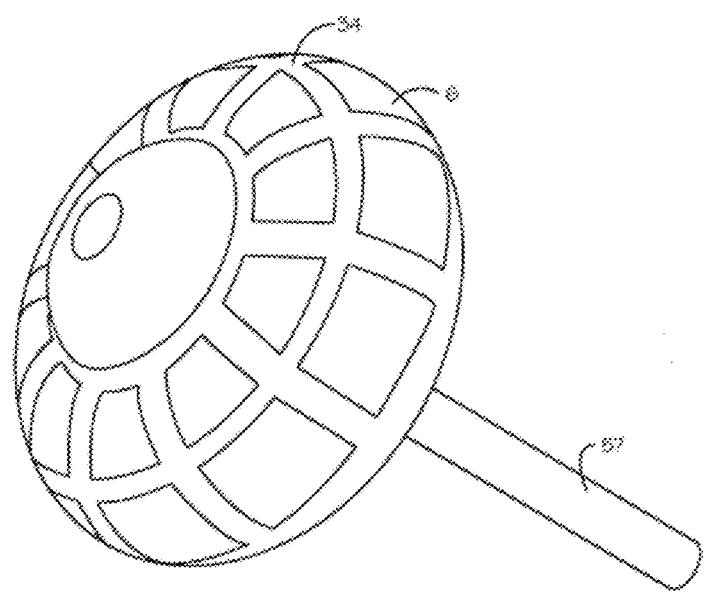
Figure 18D:
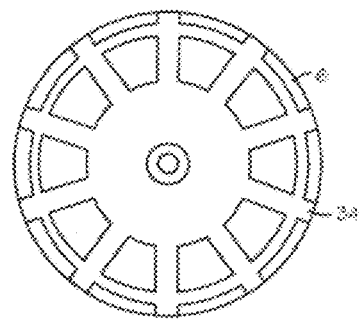
Figure 18E:
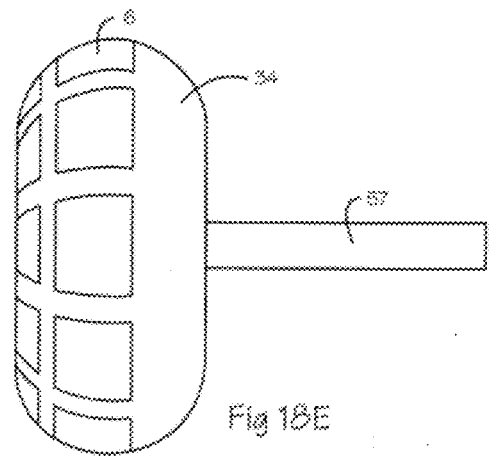
Figure 18F:
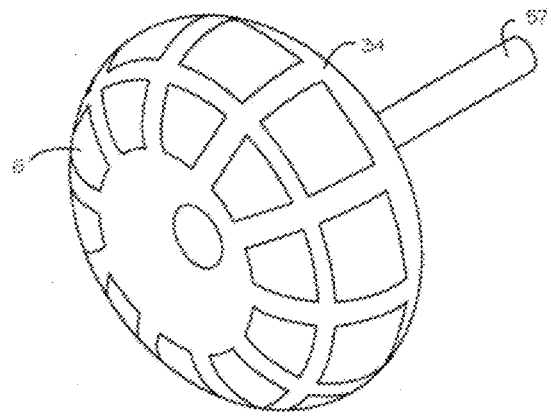
Figure 18G:
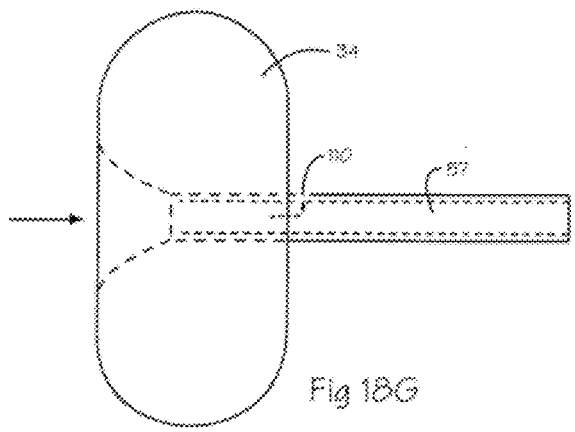

The electrode assembly can include a perfusion balloon and catheter configuration in which blood flow is not restricted by the presence of the device. The assembly can include a large inner lumen which allows the use of a guidewire and is large enough to also accommodate for flow of fluid, such as blood. FIG. 18G illustrates one such embodiment. The flow of blood indicated by arrows can enter the guidewire lumen and exit a hole 110 that can be located just proximal to the membrane 34 on the shaft 57.

The membrane 34 of the electrode assembly 105 can also have a closed, expandable structure, such as a balloon as shown in FIGS. 18A-18M. The membrane 34 can have an expandable structure that is fluid-tight such that it can be filled with a liquid or gas to expand or inflate it. The membrane can be expanded using a variety of techniques such as by filling with a gas or liquid, such as saline, a radiopaque dye, cooling fluid, blood-safe gas and the like. The expandable structure can also be self-expanding. The membrane 34 can be covered by multiple electrodes 6 and can be coupled near its proximal region to a distal end of a catheter 57. The distal and proximal regions of the membrane structure 34 shown in FIGS. 18A-18C protrude outwards forming smaller domes, which can provide convenience for manufacturing. FIGS. 18D-18M illustrate other embodiments of an electrode assembly 105 where the membrane 34 has a continuous smooth surface and no protrusions or domed regions at its distal and proximal end regions. The distal end of the membrane 34 can be flat or as shown in FIGS. 18F and 18G drawn into itself creating a concave surface at its distal end. The surface of the membrane can be that portion of the membrane that is expandable upon introduction of fluid and that typically expands from proximal and distal points of attachment to the catheter body.

Figure 18H:
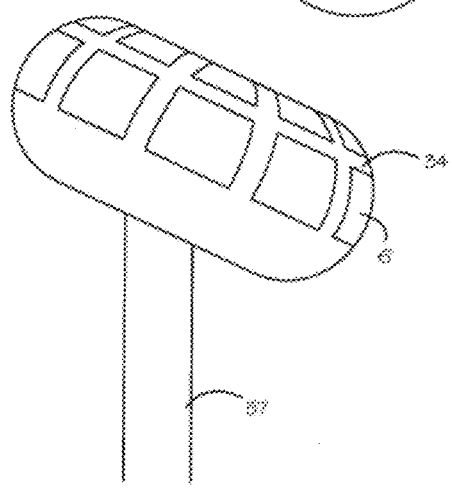
Figure 18I:
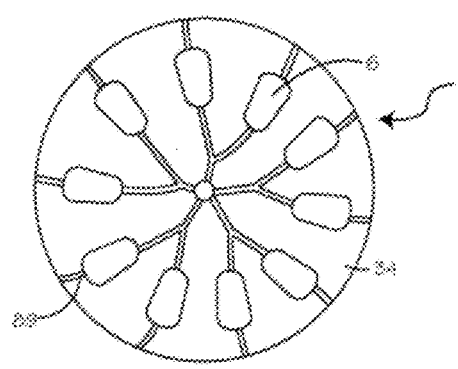
Figure 18J:
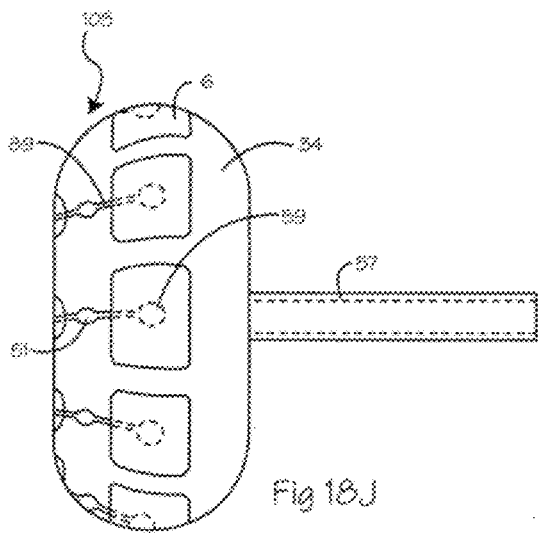
Figure 18K:
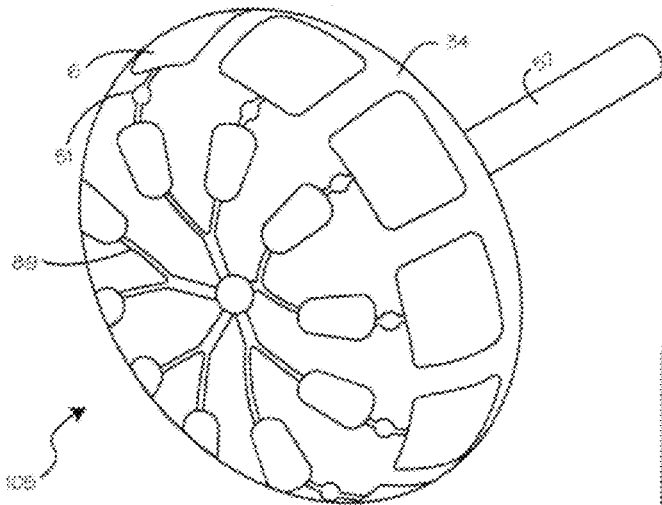
Figure 18L:
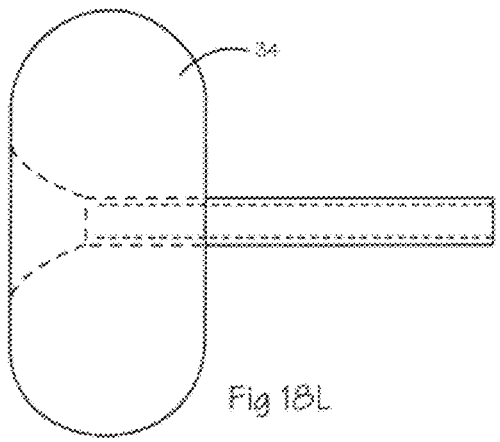

FIGS. 18I-18M show various views of an embodiment of the deployable membrane 34 of the electrode assembly 105 that has a fluid-tight expandable structure. The deployable membrane 34 can have multiple electrodes 6 electrically connected via one or more flex circuits 89. As shown in FIG. 18I, each flex circuit 89 can be routed through the shaft 57 and can exit or emerge from the inner diameter of the membrane 34 at a distal end region and split into two at a Y-junction. This allows a single flex circuit 89 to be positioned at different latitude positions on a membrane 34. FIG. 18J shows an embodiment of the conductive pad 59 that can be used to electrically connect the electrodes 6. FIG. 18K shows an embodiment of a mapping electrode 51 that is smaller and in between the larger electrodes 6. FIG. 18L shows an embodiment of the distal end region of the membrane 34 that can be drawn into itself creating a concave surface.

The flex circuit shown and described with reference to FIG. 3E can be seen in FIGS. 18N and 18O incorporated into a deployed electrode assembly at the end of a shaft 57. The circuit includes an intermediate portion with a plurality of branches separated along their lengths. In this embodiment branches 87 are equally spaced from adjacent branches along an equator defined by the toroid-shaped membrane 34 in the expanded configuration shown. The branches are affixed in a uniformly distributed fashion around the equator of the toroid-shaped membrane 34 in the expanded configuration shown. The branches are flexible and conform to membrane 34. Three rings of electrodes 6 can be seen, a single ring electrode at the distal end of the expandable member interfaced with conductive pad 59c (shown in other embodiments herein), a ring of ten individual electrodes interfaced with conductive pads 59b (shown in other embodiments herein), and an additional ten electrodes interfaced with conductive pads 59a (shown in other embodiments herein). The device also includes thermistor elements 90 interposed between electrode elements interfaced with the conductive pads.

Figure 18M:
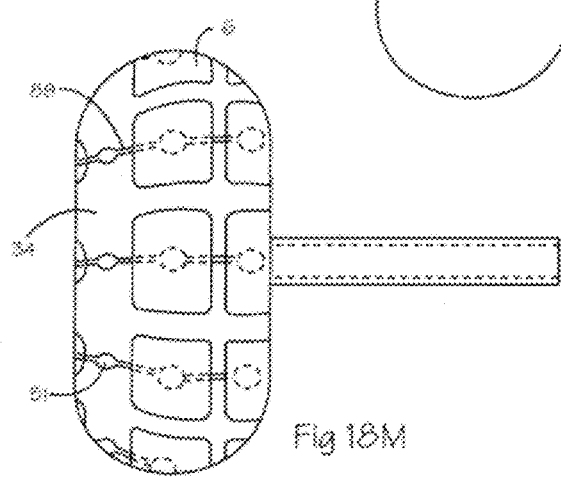
Figure 18N:
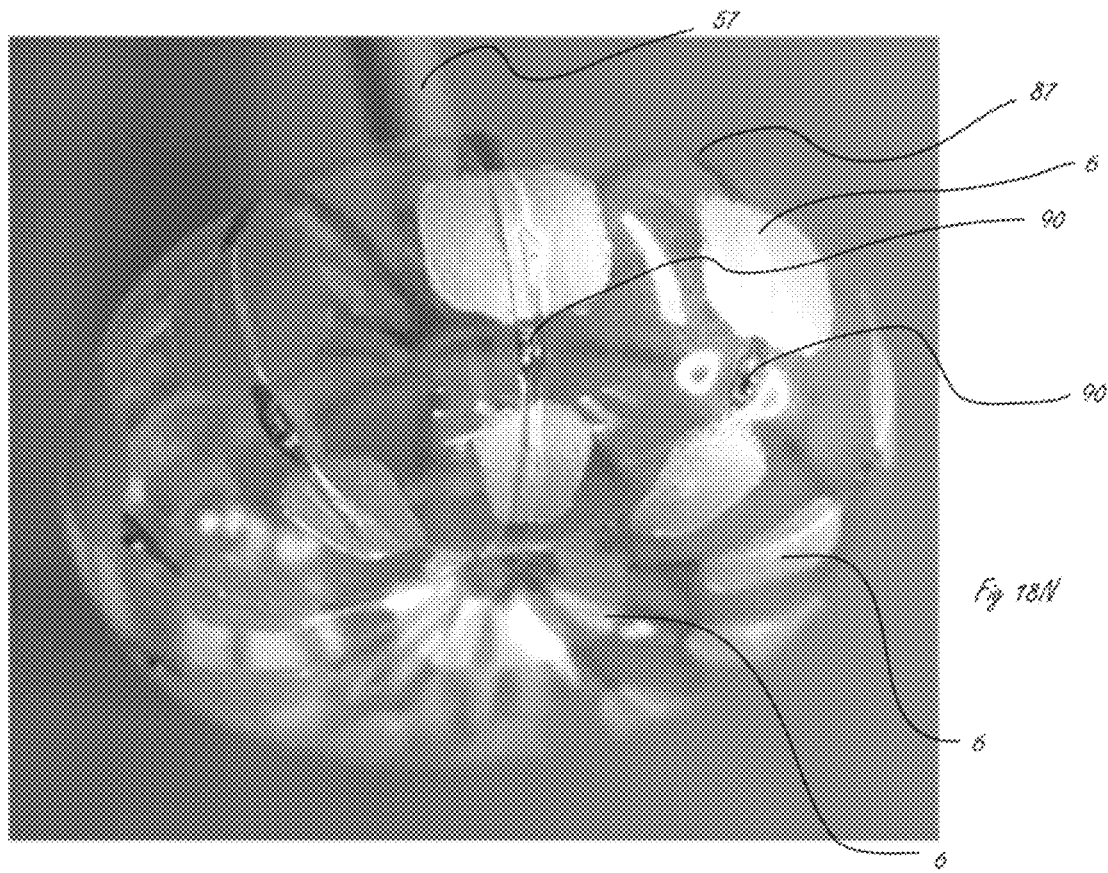
Figure 18O:
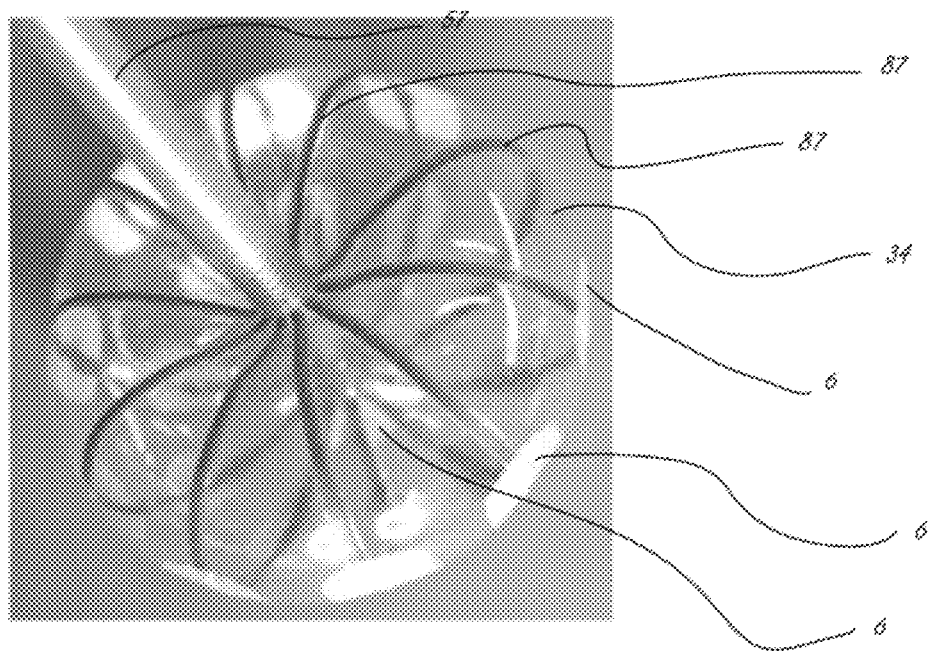
Figure 188:
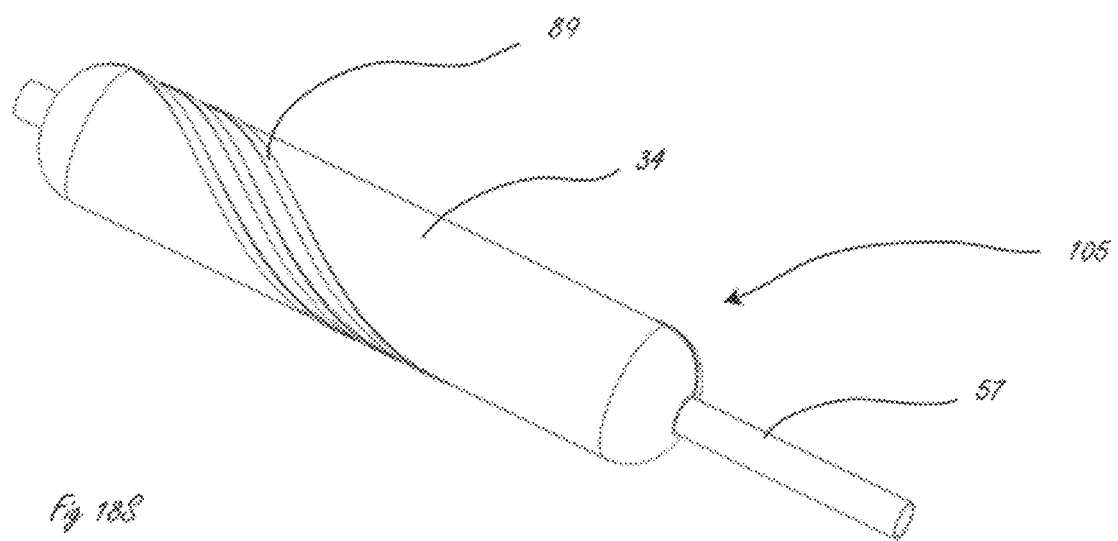

In FIGS. 18N and 18O, the branches are coupled to the membrane such that they conform to the membrane and are uniformly spaced from one another in the membrane's expanded configuration. In an end view of the expanded device (looking in the distal-to-proximal direction), at least two adjacent branches define an angle greater than 30 degrees. In some embodiments at least two adjacent branches can be separated by more than about 10 degrees. In some embodiments at least two branches are separated by more than about 90 degrees. In alternative embodiments the branches are not uniformly spaced from one another, such that two branches define a first angle and two branches define a second angle, wherein the first angle is different than the second angle.

The branches are flexible, allowing them to conform to the radially outer surface of the membrane in FIGS. 18N and 18O. The branches extend substantially 360 degrees around the longitudinal axis of the shaft and are uniformly spaced from one another.

In FIGS. 18N and O the plurality of branches of the intermediate portion are fixed on the expandable membrane and the membrane maintains the separation between the branches. The configuration of the expandable membrane can at least partially define the angles between the branches of the intermediate portion and/or the orientation of the branches on the membrane.

In some embodiments at least three branches terminate in a connector at the proximal end of the flexible circuit.

In the embodiment in FIGS. 18N and O portions of the branches are folded by selective orientation on the flexible expandable membrane.

The flex circuit 89 can wrap around the membrane 34 to power the electrodes as shown in FIG. 18J. The flex circuit 89 can extend to the proximal end of the membrane 34 and/or into the distal end of the shaft 57 as shown in FIG. 18M. Extending the flex circuit to the joint where the shaft 57 and the membrane 34 meet can increase the robustness and ease of manufacturing the electrode assembly 105. The flex circuit main leads can be inserted within the inner diameter of the shaft and bonded in place. This can be beneficial for preventing de-lamination of the flex circuit main leads 17, such as during the sheathing process. These sections of the flex circuit 89 can power another set of electrodes located at or near the proximal end of the membrane 34. With a toroidal-shaped, closed membrane 34, the location of the electrodes 6 face away from the distal portion of the membrane 34, such that they face in a proximal direction towards the shaft 57 of the assembly 105. This configuration can be useful in reaching target tissues that are located directly through an access point, such as for example the septum once a catheter crosses the septum to enter the left atrium.

The shape of the expandable membrane 34 can vary including, but not limited to, cylindrical, spherical, toroid, doughnut-like, conical, branched, pronged and other geometries. As shown in FIGS. 18D-18M, the expandable membrane 34 has a toroid shape. This shape provides for better maneuverability of the distal tip due to the relatively short longitudinal length of the structure. A cylindrical shaped expandable membrane 34 incorporated in electrode assembly 105 is illustrated is illustrated in FIGS. 18P through 18S. In FIG. 18P the distal branches 87 of flex circuit 89 have a configuration similar to that illustrated in FIGS. 3D and 3F, where the distal branches are longer to accommodate the cylindrical shaped expandable membrane 34. An alternative configuration to the longitudinally oriented distal branches 87 of flex circuit 89 is shown in FIG. 18S. In this configuration the distal branches are wound about the cylindrically shaped expandable membrane 34. Note that in FIG. 18S only the substrate layer of the flexible circuit 89 have been illustrated, but all of the features associated with the other flex circuits herein described can be incorporated in the flex circuit of FIG. 18S. The electrode assembly of 18P can be populated such that an electrode is associated with any combination of locations indicated by the irrigation holes shown. Using such an electrode assembly, a number of helical lesion patterns of different orientation and pitch can be created specific to the particular luminal site under treatment, without the need to reposition the electrode structure.

FIG. 18H illustrates the swiveling action the toroid shaped membrane structure can achieve. Because the longitudinal length of the membrane structure on the catheter shaft is relatively short, the membrane structure can move relative to the shaft without bending the shaft. When the membrane structure is used in a semi-inflated state, this allows for greater motion or swiveling of the membrane structure on the shaft. Further, a smaller membrane structure 34 can be used, which although it may be subject to more frequent manipulation of the electrode assembly 105 during the procedure it can allow for easier manipulation especially in smaller and/or tight anatomies. Electrode assemblies having small membrane structures 34, such as shown in FIGS. 22A to 22B and FIGS. 26A to 26C, can be useful for touch-ups during the procedure or during follow-up procedures.

The deployable membrane 34 can have an expandable structure that is symmetrical such as shown in FIG. 19A. The electrodes 6 can be evenly distributed across the membrane 34 where they can be connected to their individual conductive traces 16 stemming from the distal flex circuit branches 87. The distal branches 87 connect to the main flex circuit leads 17 (not shown) which can be routed through the catheter 57 such that they can connect at a proximal region for example at a handle. The deployable membrane 34 can also have an asymmetrical configuration as shown in FIGS. 19B and 19C. An asymmetrical structure can reduce bulk and can allow for easier manipulation and positioning of electrodes. FIG. 19C shows the asymmetrical membrane structure conforming to tissue 83 such as the pulmonary vein. In atrial fibrillation applications, for example, the deployable membrane 34 having an asymmetrical structure can involve two or more different applications of energy and rotations of the membrane 34 to completely isolate the pulmonary vein. The asymmetrical structure can allow for better rotation control and placement of the electrodes 6 against the tissue 83.

Figure 19D:
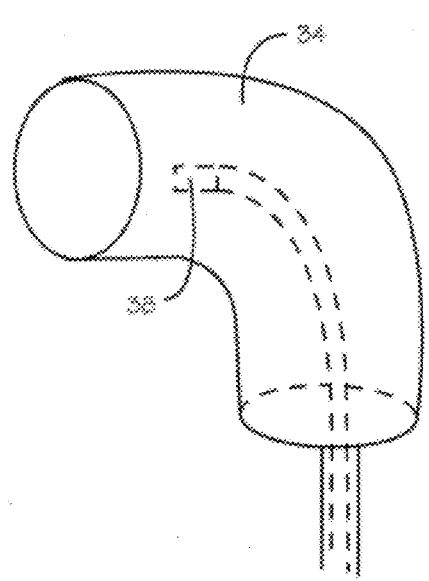
Figure 19E:
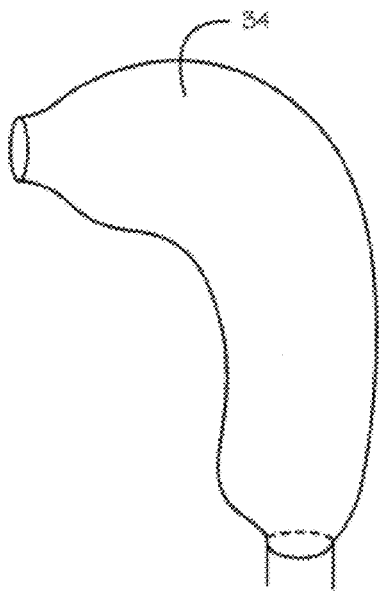
Figure 19F:
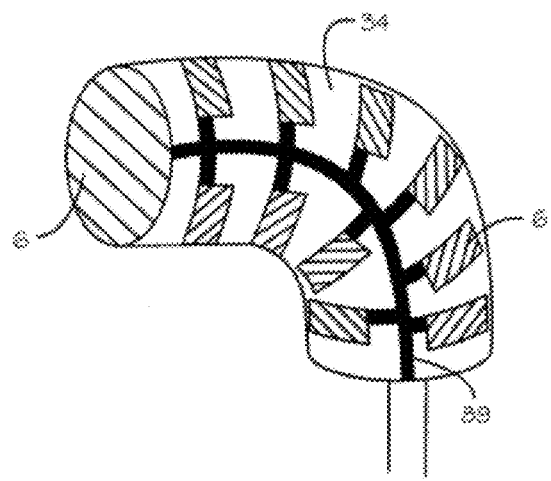
Figure 21A:
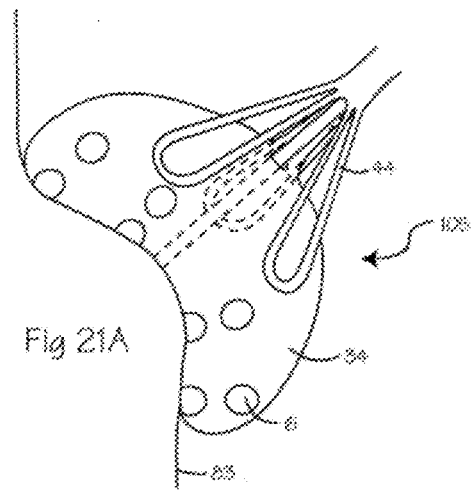
FIGS. 21A-21E illustrate the tissue conformability of embodiments of the expandable electrode structure.
Figure 21B:
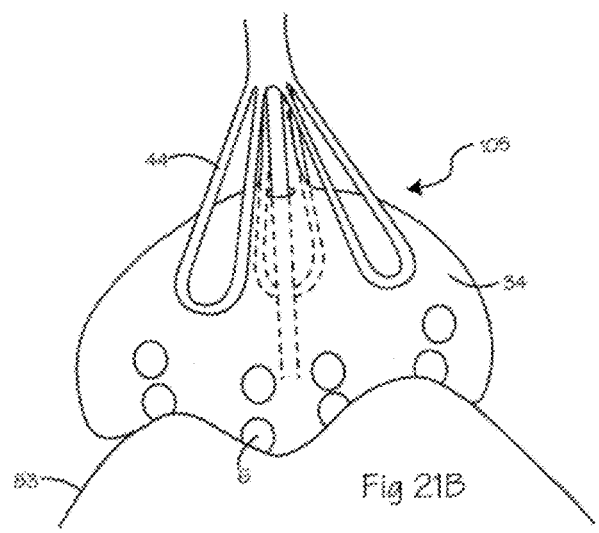
Figure 21C:
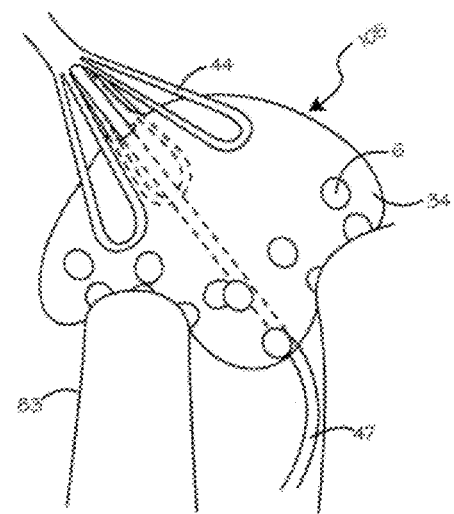
Figure 21D:
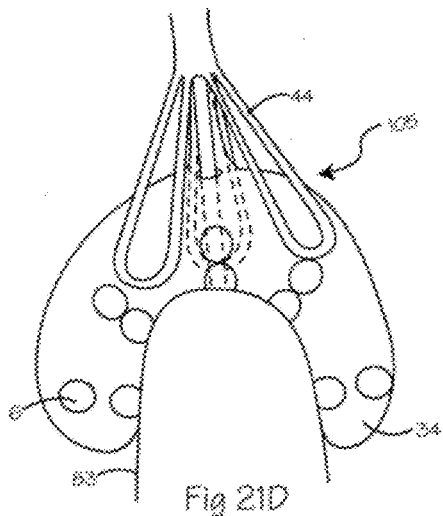
Figure 21E:
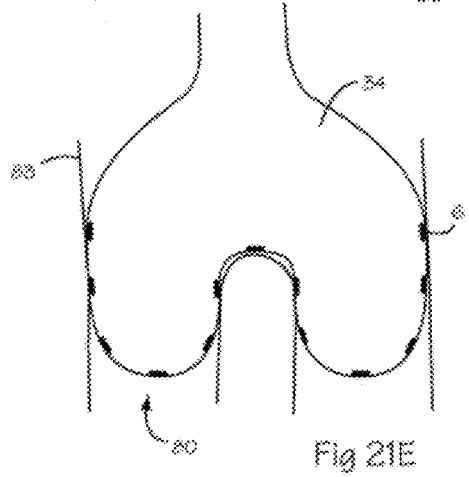

The electrode assembly 105 can include an enclosed membrane 34 and can be of any shape or form, one of which can be a cylindrical shaped balloon. The membrane 34 can further be shaped to maintain a curved position or include one or more pull wires. FIGS. 19D-19F show alternative embodiments for a membrane 34 for an ablation assembly 105 including one that has a flat distal end surface and one that is more conical. It should be appreciated that other variations of the membrane shape can be possible. The length of the membrane 34 can be shorter or longer and the shape can be straight or contain any amount of curvature. The electrode assembly 105 can include a flex circuit 89 which powers one or more electrodes 6. The electrodes 6 can be laid out in an asymmetrical pattern of electrodes 6 on the inside of the curve versus the outside of the curvature. The distal end of the membrane 34 can also include a single large electrode 6 as shown in FIG. 19F. Fiber optic scopes 38 can be included to the electrode assembly 105 as well as shown in FIG. 19D.

The shape of the membrane 34 can be changed or adjusted before, during or after use. FIGS. 20A-20C show an embodiment of an electrode assembly 105 having a deployable membrane 34 that can be expanded into a balloon shape. The deployable membrane 34 is coupled at an outer surface of its proximal region to support arms 44 extending from the distal end of the steerable catheter 57. The membrane is coupled at its distal region to a shaft 46 that extends through and translatable relative to the steerable catheter 57. The shaft 46 can translate from a proximal position in which the membrane 34 is folded distal to the catheter 57 and shaft 46. The shaft 46 can also translate to a distal position in which the membrane 34 expands into an enlarged structure and exposes the most distal electrodes suitable for energy transmission as seen in FIG. 20B. The shape of the membrane 34 can be varied depending upon the position of the shaft 46 relative to the catheter 57. For example, the membrane 34 can have a fully rounded configuration as shown in FIG. 20B or a distally flattened configuration such as shown in FIG. 20A or a distally concave configuration as shown in FIG. 20C or anywhere in between. This allows for positioning and exposure of the electrodes as needed to fully contact the target tissue.

The membrane 34 and electrode assembly 105 can conform to three-dimensional anatomy for optimum tissue contact and energy transmission. Good apposition of the membrane allows for better contact of the electrodes 6 to the surface of the tissue. The membrane 34 having an expandable structure as described above can be expanded to a variety of conformations, shapes and have a range of diameters over a relatively low range of pressures. In an embodiment the membrane can be radially expanded such that it fits and conforms within two regions of the anatomy simultaneously (for example see FIG. 16B). In another embodiment, the membrane 34 can have a large distal diameter (for example FIGS. 18A-18M) and/or can be tapered, or funnel-shaped (for example FIGS. 20A-20C). This allows for a better conformation to circumferential geometries, for example regions near the ostia of a pulmonary vein.

FIGS. 21A-21E illustrate how a membrane 34 having an expandable balloon-type structure can conform to tissue 83 having a variety of anatomical shapes. The membrane 34 can be semi- or non-compliant, but can still conform to target tissues depending the degree to which it is filled. In an embodiment, the deployable membrane 34 can be non-compliant and have an expandable, closed structure that is only partially filled. Partial filling of a non-compliant, closed structure can allow it to properly conform to the target tissue despite the non-compliant properties of the membrane material itself. In another embodiment, the deployable membrane 34 has an expandable, closed structure and a relatively short longitudinal length. In this embodiment, partial filling of the structure such as with a fluid, gas or liquid results in a conformability and swiveling steerability. The membrane 34 can have an expandable, closed structure that is branched or can split into two branches at its distal end upon expansion. In the expanded state, electrodes 6 on each of the branches can be in contact with the tissue 83 during energy transmission (see FIG. 21E). The pronged or two-leg shape can aid in reaching irregular surfaces between, for example two vessels such as the carina between the pulmonary vein 80.

Figure 22A:
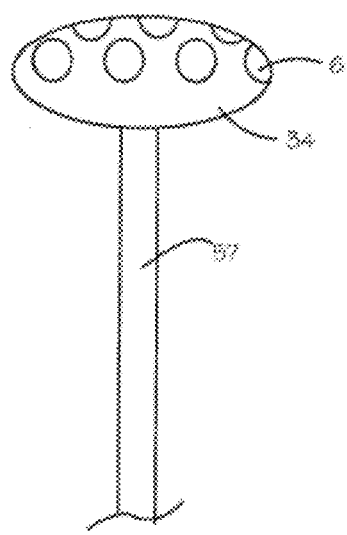
FIGS. 22A-22C illustrate embodiments of electrode deposition onto a deployable membrane.
Figure 22B:
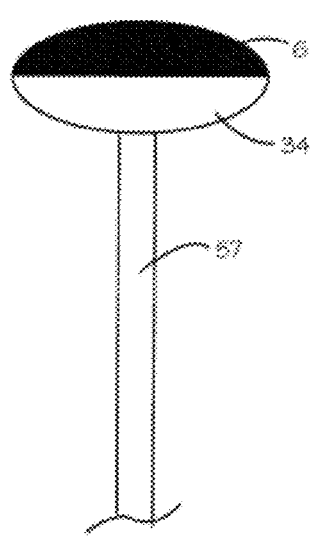
Figure 22C:
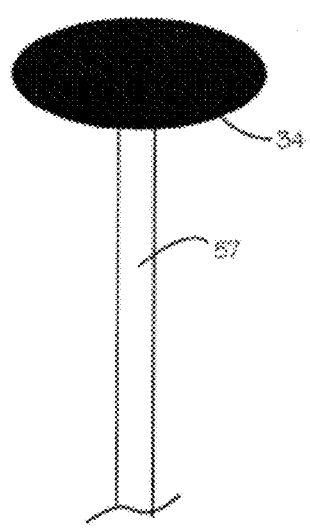

As described above, the electrodes 6 can be deposited on the membrane 34 as well as on a portion of the flex circuit 89. The membrane 34 can include multiple electrodes 6 or the membrane 34 can have a single electrode 6 covering a portion or the entire membrane 34. For example, FIG. 22A shows a membrane 34 having multiple electrodes 6. FIG. 22B shows a single electrode 6 covering a distal portion of the membrane 34. FIG. 22C shows a single electrode 6 that surrounds the entire outer surface of the membrane 34. Further, the membrane 34 can be impregnated with conductive material which then can become the electrode. It should be appreciated that the size of the membrane 34, in particular an enclosed membrane such as the balloon shape shown in FIGS. 22A-22C, can be of any size and shape. A small balloon size can be used for treatment of small anatomical sites or for touch-up/follow-up secondary treatments.

In addition to the variation in the number of electrodes 6 deposited on the membrane 34, the location and pattern of electrode deposition can vary as well. For example, as shown in FIGS. 18A-18C the electrodes 6 can be positioned on a section of the membrane structure 34 having the largest diameter upon expansion. The distal domed region can include electrodes 6 for the purpose of mapping, sensing, stimulating and/or ablation. FIGS. 18D-18M illustrate other embodiments of the membrane 34 having electrodes 6 positioned circumferentially from the largest diameter section of the membrane structure 34 to the flat region at the distal end. As another example, in the treatment of atrial fibrillation the electrodes can be positioned on the membrane structure to optimize contact with the antrum of the ostium. The electrodes 6 can also be placed at the proximal end of the membrane 34 as shown in FIG. 18M to ablate or map structures in anatomical locations such as the septum as described above.

The materials of the membranes 34 described herein can vary. Generally, the membrane material is thin, readily foldable into a low profile and refoldable after expansion. The materials can be elastic, inelastic, stretchy, non-stretchy, compliant, semi-compliant, or non-compliant. In an embodiment, the membrane 34 has an expandable structure and can be constructed of materials such as those materials used in the construction of balloon catheters known in the art, including, but not limited to polyvinyl chloride (PVC), polyethylene (PE), cross-linked polyethylene, polyolefins, polyolefin copolymer (POC), polyethylene terephthalate (PET), nylon, polymer blends, polyester, polyimide, polyamides, polyurethane, silicone, polydimethylsiloxane (PDMS) and the like. The membrane 34 can be constructed of relatively inelastic polymers such as PE, POC, PET, polyimide or a nylon material. The membrane 34 can be constructed of relatively compliant, elastomeric materials including, but not limited to, a silicone, latex, urethanes, or Mylar elastomers. The membrane 34 can be embedded with other materials such as for example, metal, Kevlar or nylon fibers. The membrane 34 can be constructed of a thin, non-extensible polymer film such as polyester or other flexible thermoplastic or thermosetting polymer film. In one embodiment the flexible membrane 34 can be 0.001" to 0.002" in thickness to provide sufficient burst strength and allow for foldability. In some embodiments it is preferable to have the electrode mechanical properties as close to the membrane mechanical properties as possible. One way of providing this is to use an inelastic membrane that will not stretch as it is expanded. This helps secure the branches to the membrane.

Low Profile Folding and Delivery Conformation

The electrode assemblies and devices described herein incorporate a design and structure that are optimized for low bulk and low profile folding. The electrode assemblies and devices described herein can be used, for example in minimally-invasive delivery of energy transmission to tissues. The construction of the electrode devices, such as the routing of the flex circuit main leads through the device, also can contribute to the low bulk and low profile of the device.

Figure 23A:
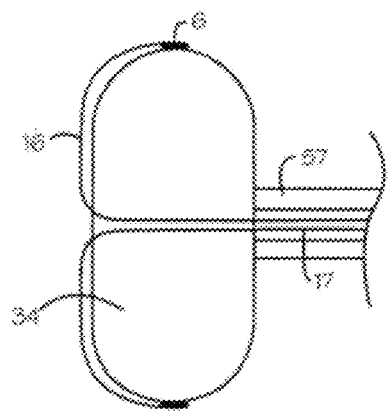
FIGS. 23A-23H illustrate embodiments of flex circuit routing through an electrode device and electrode deposition onto a deployable membrane.
Figure 23B:
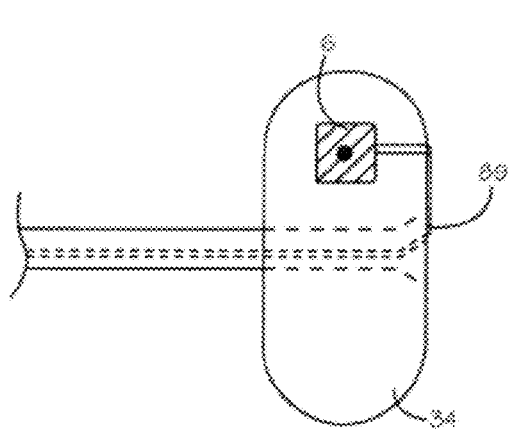
Figure 23C:
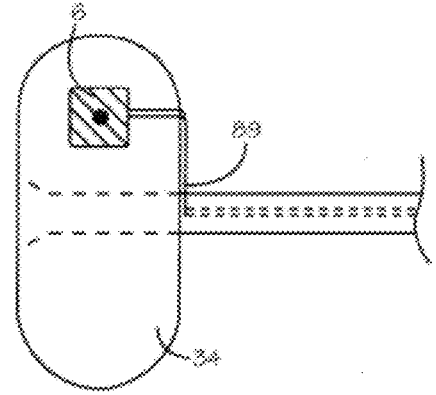
Figure 23D:
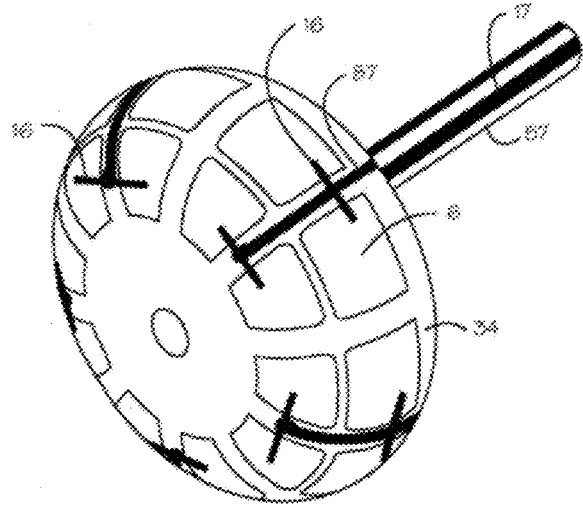
Figure 23F:
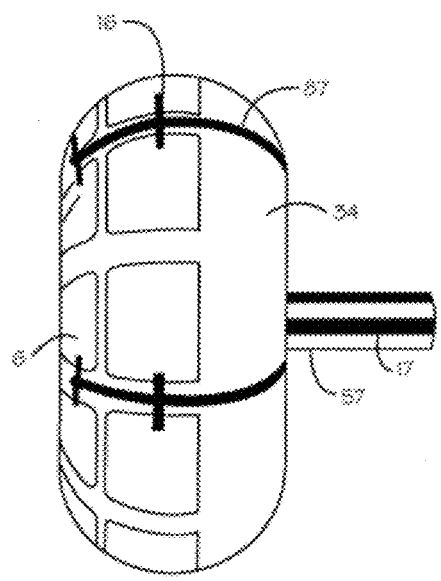
Figure 23E:
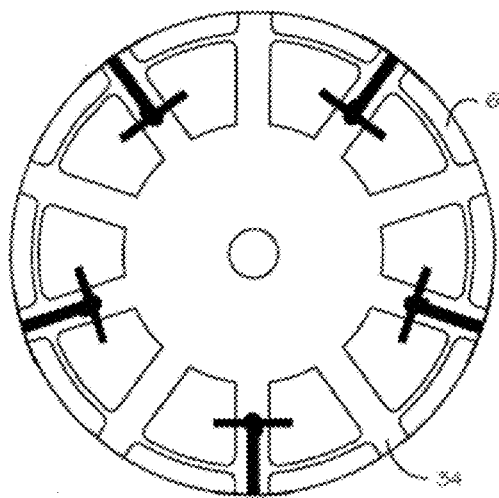

A deployable membrane 34 having an expandable structure can be mounted at a distal end of a catheter 57 configured for percutaneous delivery (see FIGS. 23A-23H). The flex circuit main leads 17 of the flex circuit 89 can extend from a handle (not shown) and be routed through an inner lumen of the catheter 57. The flex circuit main leads 17 can emerge out of the inner lumen of the catheter 57 as well as the inner diameter of the deployable membrane 34 at a distal end region as shown in FIGS. 23A and 23B. Alternatively, the flex circuit main leads 17 can emerge from a proximal end region as shown in FIG. 23C-23H. The flex circuit main leads 17 can be kept together until they emerge out of the catheter 57 where they may branch out into their respective distal branches 87. The distal branches 87 can immediately branch out into multiple conductive traces 16, which can be attached to an outer surface of the membrane 34. Other configurations of the flex circuit main leads 17 and distal branches 87 are possible, the distal branch 87 can continue to the distal tip of the balloon for example.

Figure 23G:
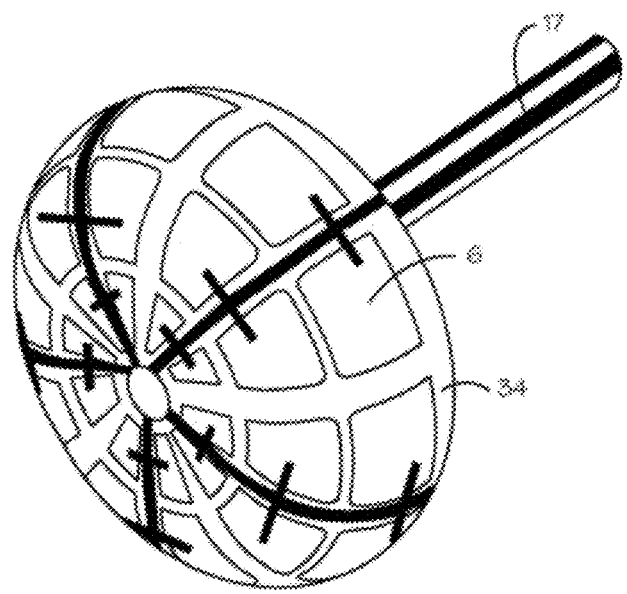
Figure 23H:
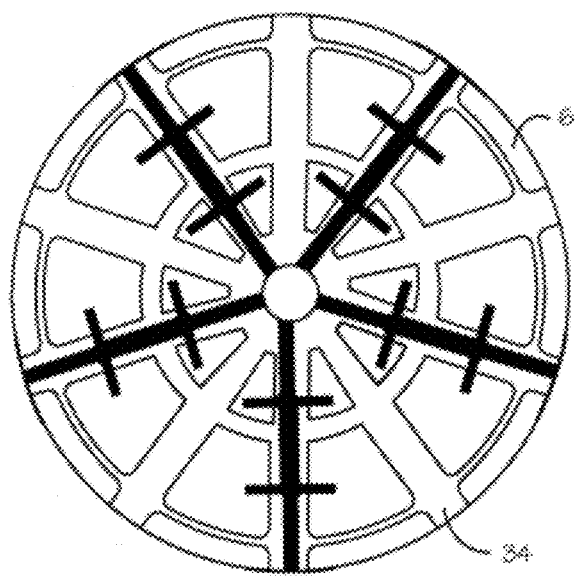

During manufacturing, the membrane 34 can be mounted on a temporary mandrel support having inflation ports to maintain a constant expanded state during assembly. The flex circuit can have branches with sacrificial tabs 102 (see FIGS. 3A and 3B) that can be mated to an assembly fixture for consistent tensioning of all branches of the flex circuit 89 during assembly. Adhesive can be applied to the inner surface of the flex circuit that will be in contact with the membrane 34. This can be accomplished through the use of a robotic system that can apply precise volume of adhesive and precise locations on the flex circuit. The main leads 17 of the flex circuit 89 can exit at or near the distal end of the shaft 57 or the proximal end of the flexible membrane 34 and extend distally (see FIGS. 23C-23H). Electrodes 6 can be positioned at or near the distal end of the membrane 34. They can be positioned as two distal-most electrodes for each branch of the flex circuit as shown in FIGS. 23G-23H. It should be appreciated that the flex circuit 89 and the electrodes 6 can vary in the power configuration and layout. For example, the end of each flex circuit 89 can terminate with one large electrode 6 instead of two smaller electrodes 6.

Folding of the deployable membrane 34 can occur distal to the end of the catheter 57. A shaft 46 (see FIGS. 20A-20C) can be withdrawn in a proximal direction to fold the membrane 34 distal to the end of the shaft 46 and catheter 57. The folds of the membrane 34 do not therefore contribute to bulk and overall diameter of the catheter 57. Alternatively, in other embodiments and membrane shapes, the shaft 46 can be extended fully distally while elongating the membrane 34 (in particular an elastic membrane) to minimize bunching of the membrane material. An outer sheath (not shown) can additionally be used to cover the folded up membrane 34 providing the electrode assembly 105 with a smooth outer surface for better delivery, for example through the vasculature. The deployable membrane 34, electrodes 6 and flex circuits 89 can all fold up such that they fit inside a specified sheath size appropriate for the anatomical site to the treated. This allows for a smaller diameter of catheter shaft and, in turn, a very low profile delivery configuration of the device, which minimizes the trauma and risk of complications.

Figure 24A:
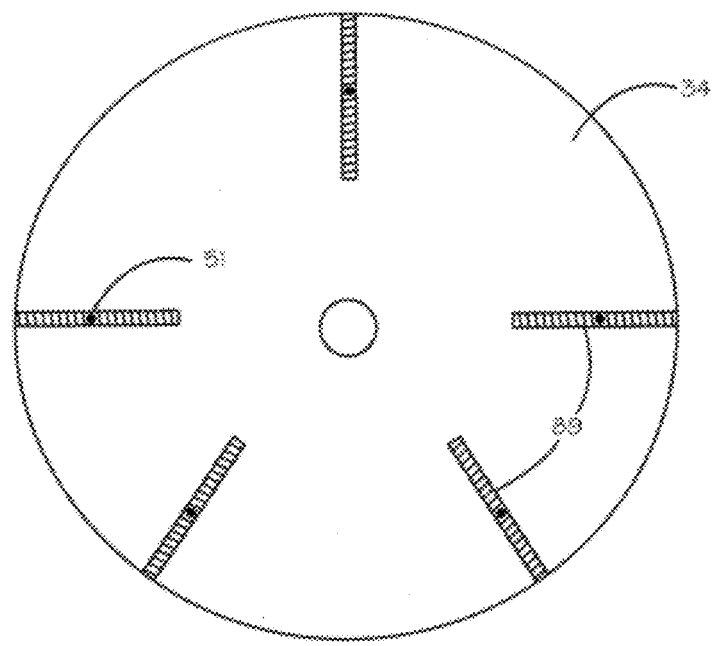
FIGS. 24A-24B illustrate folding of an embodiment of a deployable membrane having flex circuits attached thereto.
Figure 24B:
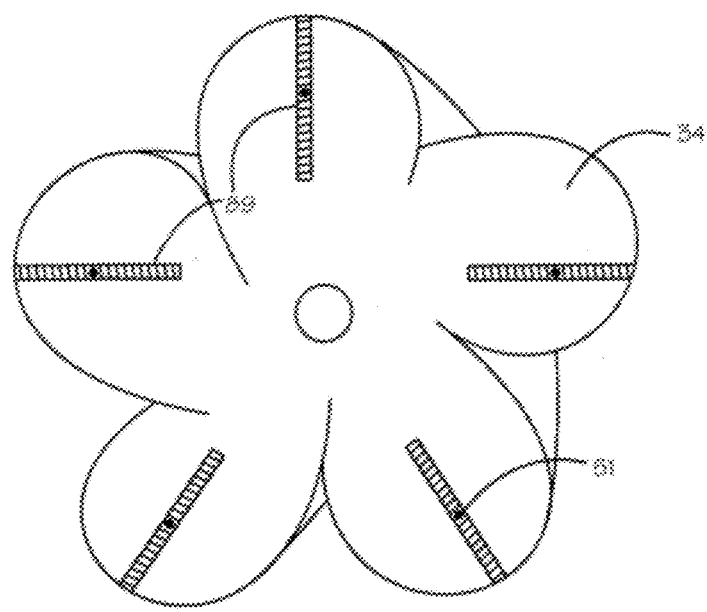

As shown in FIGS. 24A-24B, the membrane 34 can fold preferentially, for example along, between or across the flex circuits 89 and electrodes 6 when deflated or in the unexpanded state. The folding can occur in an organized, controlled, predictable and repetitive manner. The flex circuit 89 can also act to influence folding along a preferential folding line and provide for or aid in better packing of the electrode assembly into a low profile delivery configuration.

Catheter

As described above, the electrode assemblies described herein can be mounted onto a catheter configured for percutaneous delivery. Control of the movement of catheters in general can be somewhat difficult due to the elongated, tubular structure. To provide sufficient control over the movement, the catheters described herein can be somewhat rigid, but not so rigid as to prevent navigation of the catheter through the body to arrive at a precise location. Further, the catheter should not be so rigid that it could cause damage to portions of the body being treated or through which it is passed. The catheters described herein can be manufactured of a variety of materials known in the art of percutaneous catheters including extruded polyether block amid (PEBAX) or other polymeric materials such as polyurethane, polycarbonate, nylon, FEP, PTFE, LDPE, and HDPE. The catheters described herein can be reinforced as known in the art such as with a braided or coiled layer of stainless steel to increase torsional rigidity. Other reinforcement materials and constructions can be used both metallic and polymer based. The catheters can also be formed to a desired shape, such as a curved tip, for ease of placement into the proper orientation. One typical method of shaping a catheter is through thermal re-forming of an extruded catheter which can be done pre- or post-assembly of the catheter. The catheter needs to be of sufficient length and adequate diameter to reach the target tissue through known access points without causing trauma to the tissue during introduction and tracking through the anatomy.

Figure 25A:
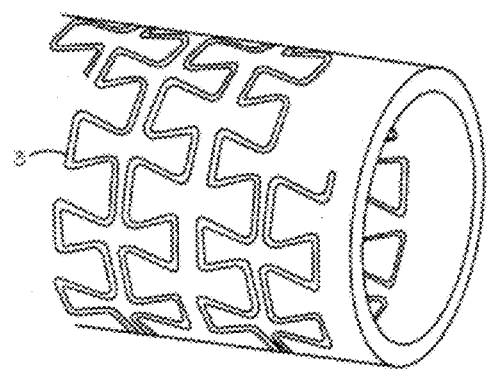
FIGS. 25A-25C illustrate embodiments of a catheter having features to improve flexibility and torque control.
Figure 25B:
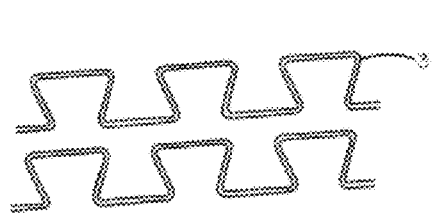
Figure 25C:
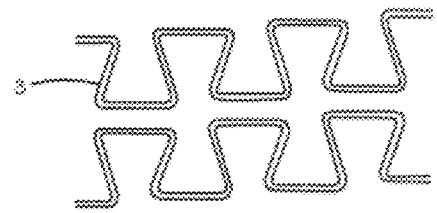

The catheters described herein can include a laser cut region 3 in a variety of patterns, such as an interlocking zigzag pattern or similar, to optimize flexibility while resisting compression and tension (see FIG. 25A). FIG. 25B shows a close-up of a laser cut region 3 having teeth lined up at every row. FIG. 25C shows a close-up of a laser cut region 3 of the catheter having teeth lined up at every other row. This pattern can be more resistant to tension or compression compared to the pattern of FIG. 25B. This laser cut region 3 can be added to any of the catheters described herein such as the guide catheter or electrode catheter or other catheter to increase the ease of use and improve manipulation of the electrode assembly 105. The laser cut region 3 can be constructed of metallic or polymeric material and an addition to the catheter or part of the catheter structure.

Figure 26A:
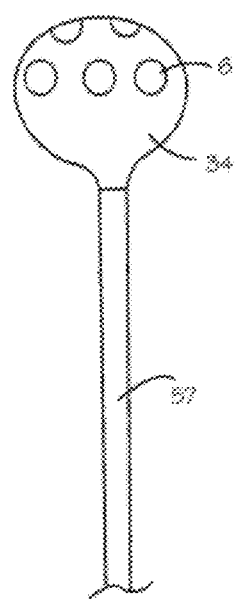
FIGS. 26A-26C illustrate embodiments of a steerable catheter having a membrane mounted thereto.
Figure 26B:
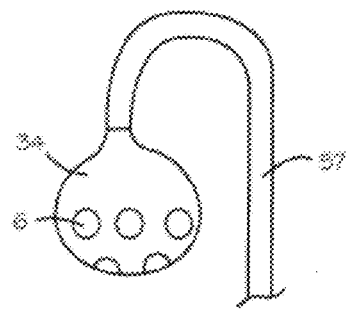
Figure 26C:
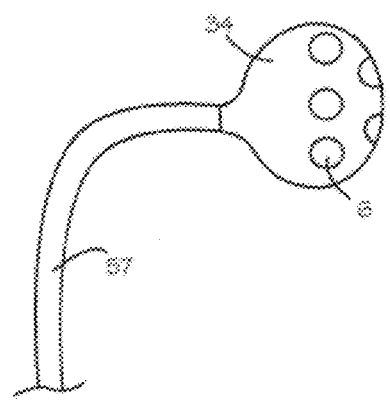

The catheters described herein can be steerable in multiple directions and can be held at various degrees of bend during the procedure as shown in FIG. 26A-26C. Generally steerable shafts or sheaths allow for motion at the distal end of the catheter itself. External elements distal to the shaft or sheath tip can move indirectly. Furthermore, a steerable shaft located within a steerable sheath can result in a loss of function as the shaft is constrained within the sheath. Embodiments described herein allow for steering of the distal most element of the shaft, for example a membrane attached to the shaft.

In an embodiment, the support arms 44 can be used to aid in maneuvering the catheter shaft 57 in a distal and proximal direction. As shown in FIGS. 20A-20C, the membrane 34 was coupled to the catheter shaft 57 using one or more support elements 44 extending from the distal end of the catheter 57 to provide better control of positioning and orientation of the electrode assembly 105 against the tissue. The support elements 44 can be a shape memory material such as Nitinol and can have radiopaque visual orientation markers 49 in the form of a specific shape or element on the support elements 44 or the materials may in themselves be radiopaque. These can be used to identify the orientation of the device as will be described in more detail below.

FIGS. 27A-27C show various embodiments of a steerable or deflectable catheter 57 having a membrane 34 mounted on its distal end. The embodiments of FIGS. 27A-27C are examples and other embodiments are possible. Steering elements 56 can be placed on the membrane 34 to allow for precise control and placement of the membrane 34. These elements 56 can be attached to the membrane 34, directly or indirectly, anywhere distal to the junction of the membrane 34 and catheter shaft 57. The use of the steering elements 56 allows for easier use of the device especially in more tortuous anatomies. The elements 56 can be used in a pulling configuration and/or have the ability to push. The ability to steer at the membrane 34 eliminates any constriction an outer sheath or a traditional steerable shaft (not shown) may have on the full range of motion. The ability to steer distal to the junction enhances the overall maneuverability of the device. Multiple steering elements 56 spaced equally or not can be used to allow for the desired degree of maneuverability. FIGS. 27A and 27B show the use of three steering elements 56. In an embodiment, when one of the steering elements 56 is pulled (FIG. 27B), only the membrane 34 is deflected. The catheter 57 remains unchanged or flexes just slightly. FIG. 27C shows a membrane 34 with four steering elements 56 mounted on a steerable catheter 57. In this embodiment, when the steering element 56 is pulled, the membrane 34 and the distal end of the catheter 57 can both flex. In an alternative embodiment, only the membrane 34 can flex.

The catheter shaft can also include an anchoring system for stability and orientation. For example, suction can be applied through the shaft to stabilize the device over a specific region on the tissue. The catheter shaft can also be used to inflate the expandable membrane structure with a gas or fluid. This will be described in more detail below.

Assessment and Control of Energy Transmission to Tissue

Excessive energy applied to tissues can cause collateral damage such as charring and clotting. Conversely, the lack of good apposition of electrodes to target tissues can result in sub-optimal transmission of energy particularly in anatomical areas having complex three-dimensional geometries. As such, assessing the progress of energy transmission as well as adjusting and controlling the energy delivered can be used, particularly without the need for removing the device is beneficial. The devices described herein can include other features to assess and control the energy transmission in real-time. For example, the devices described herein can include temperature sensors, mapping electrodes, irrigation mechanisms, visualization systems, radiopaque markers, fiber optics, pressure sensors, heat dissipation pattern recognition software, impedance measurement software, anchoring mechanisms and other control mechanisms as will be described in more detail below. With reference to temperature measurement, the electrode assembly 105 or the distal end of the catheter shaft may incorporate a microwave radiometer which can monitor temperature remote form the sensor within a target tissue. This is in contrast to more traditional temperature sensors such as thermistor or thermocouples which require contact with the tissue of which the temperature is being monitored. Such a sensor is especially useful when the target tissue volume is within a tissue mass and not on the surface to which the ablative elements are in contact. Such a technology is described in US Patent Application Pub. No. 2009/0312754, which is incorporated by reference in its entirety.

Pressure sensors can be mounted within the electrode assembly 105 or in the irrigation pump 1005. Such sensors will allow for control of the pressure internal to inflatable structure 34 of the electrode assembly 105. The output of such devices can help the user to understand contact pressure. Additionally, such pressure information can be used to control the conformability of the expandable structure. In particular by maintaining the internal pressure of the expandable structure a level where tension in the walls of the structure are minimal when the structure is not in contact with any tissue structure, the walls and affixed electrode will be more conformable to the target tissue structures on application by the user. Such pressure control will also enhance the swiveling action described with reference to the toroidal structure of FIG. 18H.

Pressure sensors can also be used to monitor that electrode irrigation through irrigation holes 7 is maintained and properly functioning when the system is run under flow control. Holes can be sized and distributed such that within a given pressure range the flow rate of irrigation fluid is maintained within predetermined boundaries. Alternatively, two flow sensors and a restrictor may be used as a flow monitor to verify proper system performance. Irrigation flow ranges will depend on the particular device and its intended use. Flow ranges of particular merit are in the range of 0.1 to 0.4 mL/min/mm^2.

Figure 63A:
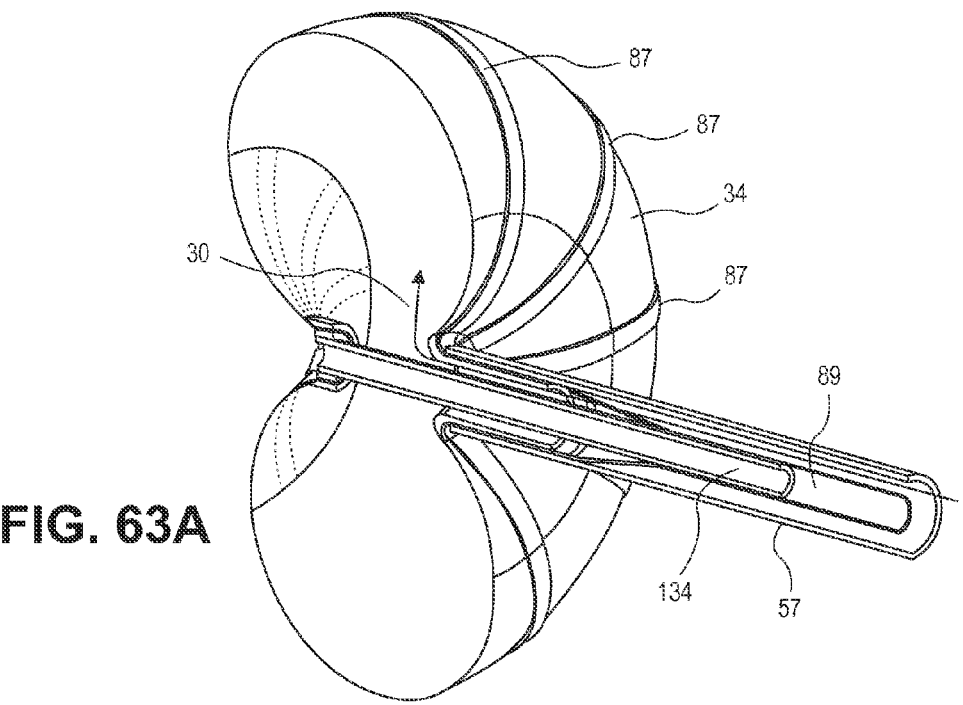
Figure 63B:
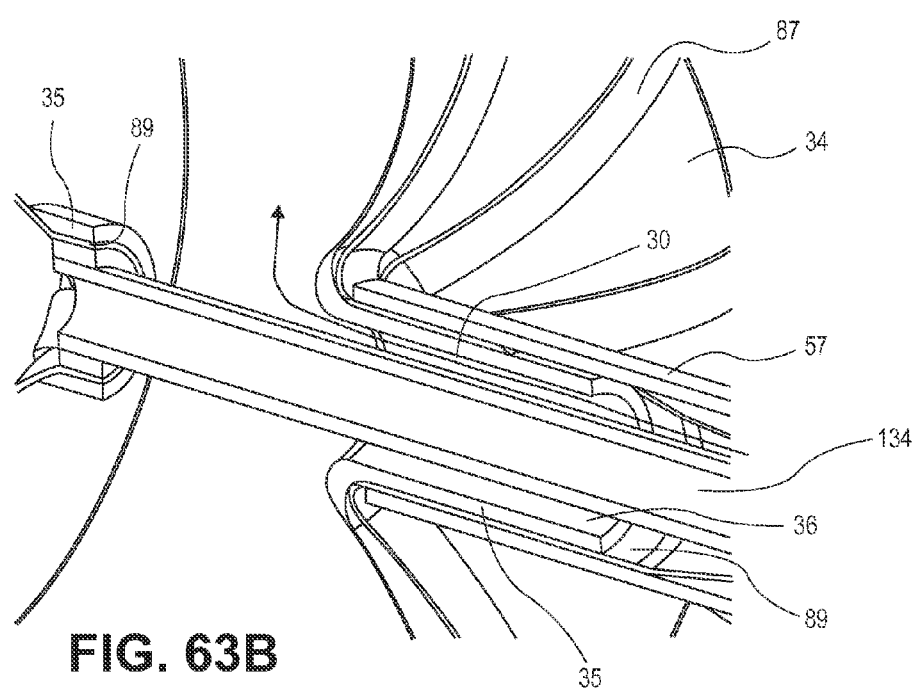

Cooling procedures, either by direct irrigation at or near the electrodes or circulating cooling fluids through the expandable structure, are especially useful when the target tissue is not at the surface to which the electrodes are in closest proximity, but deeper into the adjoining tissue. Cooling the expandable structure or the irrigation fluid can allow for higher energy delivery while protecting the tissue near or in contact with the expandable structure while still allowing damage to tissue further away from the electrode. One such embodiment which allows for irrigation is shown in FIG. 63A. The membrane 34 is attached to the outer shaft 57 at the proximal end and to inner shaft 134 at the distal end, the inner shaft 134 being of a smaller diameter than the shaft 157 allows for passage of saline 30 in between the two shafts. The ends of the membrane may be thickened sections 35. In this particular embodiment, the flex circuit 89 is affixed to the inner catheter 134 and the distal branches of the flex circuit 87 are affixed to the membrane 34. Passage of saline 30 or other irrigation fluid is allowed as the flex circuit is slotted in the transition region. A close-up of the construction of FIG. 63A is shown in FIG. 63B. The distal branches of the flex circuit 87 are attached to the outside of the membrane 34, so the transition from the attachment to the inner shaft 134 to attachment to the outer shaft 57 occurs at or near the membrane junction. This transition section will also contain the slotted features for saline passage. The membrane at this attachment point is not attached to the inner shaft 134 which allows the space necessary for saline 30 to flow through into the membrane and provide a cooling mechanism.

FIG. 63C shows an alternate embodiment which can be used both for the irrigation and for recirculation of a cooling fluid. This embodiment expands on the previously described embodiment in FIGS. 63A and 63B, by incorporating an inner shaft 134 with two lumens, one of which is used as a return for the cooling fluid. The membrane is inflated with saline 30 via the inflation lumen 36 and, saline 30 exits via the opening into the flow return lumen of the inner shaft 134. The other lumen in the inner shaft 134 is used as guide wire lumen 133. Inner shaft 134 and the guidewire lumen 133 may be separate entities of a multi-lumen catheter. Irrigation may also be incorporated with a circulating fluid cooling system by additional saline exit holes at the membrane as previously disclosed. Irrigation and recirculation cooling are facilitated by the irrigation pump 1005 and irrigation source 1003 depicted in FIG. 64. In situations where only irrigation is provided these system components may be replaced with a spring loaded syringe.

Figure 67A:
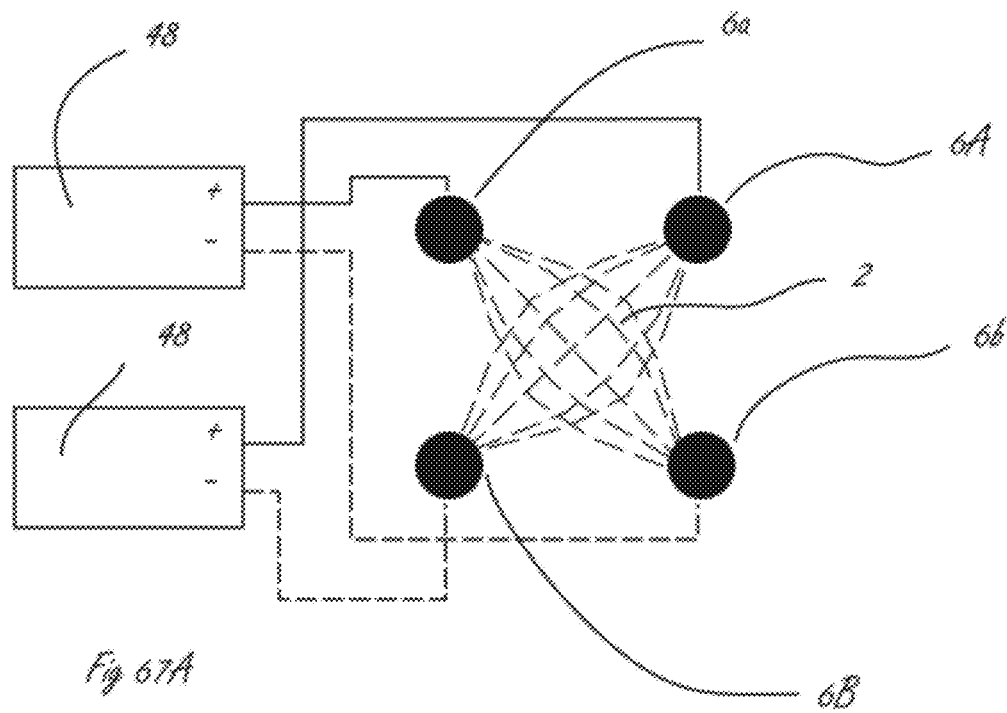
FIGS. 67A-67B illustrate arrangements of RFG electrode interfacing.
Figure 67B:
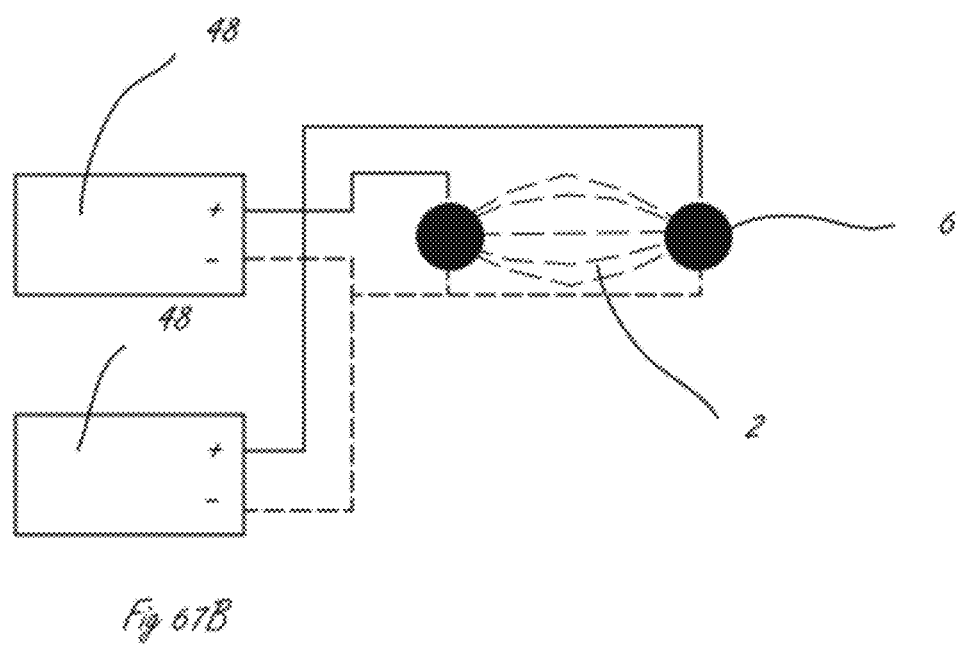

In combination with the cooling procedures just described the configuration of the power source and means of power application to the electrodes and thereby the tissue can play a significant role in protecting the tissue more proximal to the electrodes allowing the generation of ablative energy deeper into the tissue. With reference to RF ablation and cooling by irrigation or recirculation, the two generator (RFG) electrode configurations presented in FIG. 67A-67B are of particular interest. In FIG. 67B is presented a somewhat traditional RFG arrangement. Two RFGs 48 are connected to two electrodes 6 and when properly energized current 2 travels between the electrodes. In this configuration the negative outputs are connected in common across the bank of RFG's powering the electrodes. In such a configuration, pulsing RF will allow tissue closest to the cooling means to dissipate heat energy without heating the cooling means. The heat generated deeper into the tissue during the on time of the pulse is dissipated more slowly as the thermal resistance between it and the cooling means is higher thereby minimizing substantial heating of the tissue surface proximal to the electrodes. In FIG. 67A, an alternate arrangement of RFG electrode interfacing is presented. In this configuration each RFG 48 interfaces across a pair of electrodes 6. Each RFG 48 and its paired electrodes 6 are completely isolated from one another. Sets of paired electrode are energized simultaneously. In such a configuration the current 2 in the area between the electrodes 6 is doubled there by increasing the power by a factor of 4. As illustrated only current at the surface of the tissue is portrayed, but in fact the effect is occurring in 3 dimensions. Combinations of these techniques may be used to more effectively ablate tissues further from the electrodes while providing some protection to the tissue in close proximity.

It should also be appreciated that a variety of elements are described herein and that they can be used individually or in a variety of combinations. Features described herein in the context with or respect to one device, assembly or system can be implemented separately or in any suitable sub-combination with other devices, assembly or systems.

Sensing Electrodes

The devices described herein can include one or more electrodes that can be used for a variety of functions, including but not limited to ablation, sensing, stimulating and/or mapping. Mapping electrodes can be used, for example, to sense intrinsic cardiac activity and measure the conduction block during and/or after ablation for the treatment of atrial fibrillation. In an embodiment in which atrial fibrillation is being treated, mapping electrodes can be incorporated to measure EKG during the procedure without the need to introduce a separate device. The variety of electrodes can be deposited using the same or similar techniques and materials as described above.

In an embodiment, the electrode assembly includes a combination of mapping and ablation electrodes. The mapping electrodes can be interspersed between the ablation electrodes on the electrode assembly. For example, a small mapping electrode 51 can be positioned in the middle of a larger ablation electrode 6. Each of the ablation 6 and mapping electrodes 51 can be connected to their own individual trace 16. The configuration of mapping electrodes 51 can allow for confirmation of conduction block by comparing conductivity before and after ablation. Further, the proper number of these mapping electrodes 51 can help identify the direction of electrical signals to confirm proper conduction block. In an embodiment, at least 10 small electrodes can be dedicated for mapping. In another embodiment, at least 20 small electrodes can be dedicated for mapping. The mapping electrodes can be evenly spaced and arranged in a pattern similar to the ablation electrodes. In addition, the larger ablation electrodes can also provide mapping capabilities but the smaller mapping electrodes provide a more accurate measurement.

One or more mapping electrodes 51 can be incorporated with the flex circuit 89. As shown in FIG. 7A-7E, mapping electrodes 51 can be connected to the flex circuit 89 via a conductive pad 59. The mapping electrode 51 can be located on top of or in between two electrodes 6, such as ablation electrodes, and remain electrically isolated from the electrodes 6. Each of the ablation electrode 6 and the mapping electrode 51 can have their individual conductive traces 16. The mapping electrode 51 can be about the same size as its conductive pad 59 or can be laid over both the conductive pad 59 and the temperature sensor 90, if in proximity. The temperature sensor 90 and corresponding conductive traces 16 can be insulated from the mapping electrode by a non-conductive adhesive for example. As shown in FIG. 7E, the mapping electrode 51 can be positioned more distally on the flex circuit such that less advancement of a catheter is needed for measurement of an electrical signal when measuring inside the pulmonary vein.

Figure 28A:
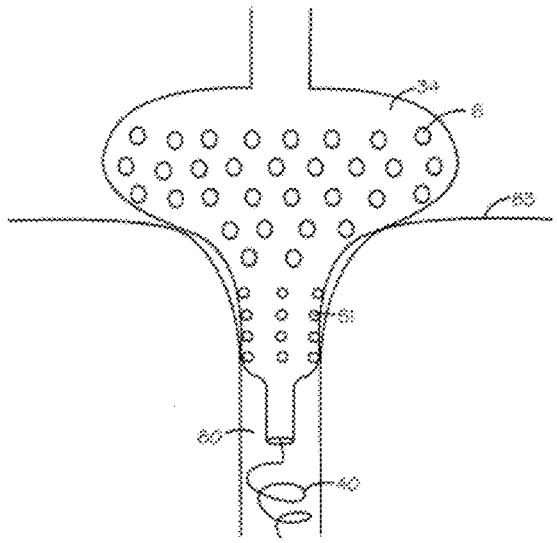
FIGS. 28A-28F illustrate an embodiment of an expandable electrode structure having mapping and ablation electrodes deposited thereon.
Figure 28B:
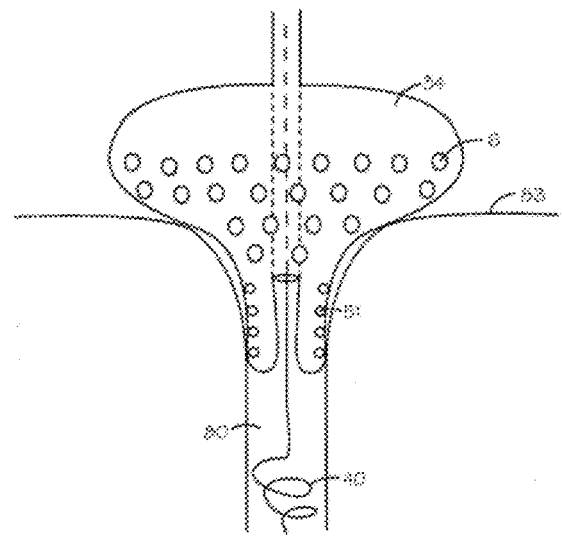

In an embodiment, a mapping electrode 51 can be positioned on an expandable membrane 34 having ablation electrodes 6. FIGS. 28A-28D show embodiments of an expandable, closed membrane structure engaged in the pulmonary vein 80. The membrane 34 can include multiple electrodes 6 deposited thereon. Some electrodes 6 can be deposited on a region of the membrane that has a larger diameter. This region of the membrane 34 can be more proximal and, for example, contact the antrum of the pulmonary vein 80 to create an energy transmission line on the tissue 83. The smaller mapping electrodes 51 can be deposited near a distal region of the membrane 34 for mapping electrical activity originating from the veins. A guidewire 40 is shown and can be used for better positioning of the membrane 34. FIG. 28B shows an alternate embodiment in which the guidewire lumen is retracted proximally to decrease the size of the mapping section of the membrane 34. This can allow for mapping in smaller anatomical regions.

Figure 28C:
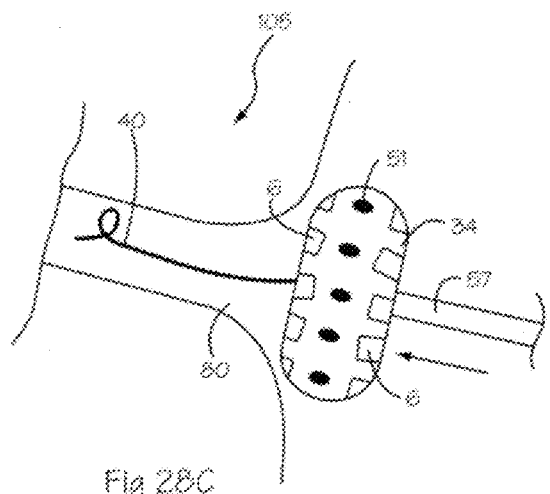
Figure 28D:
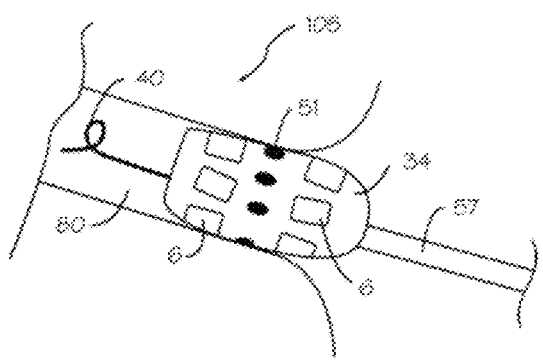
Figure 28E:
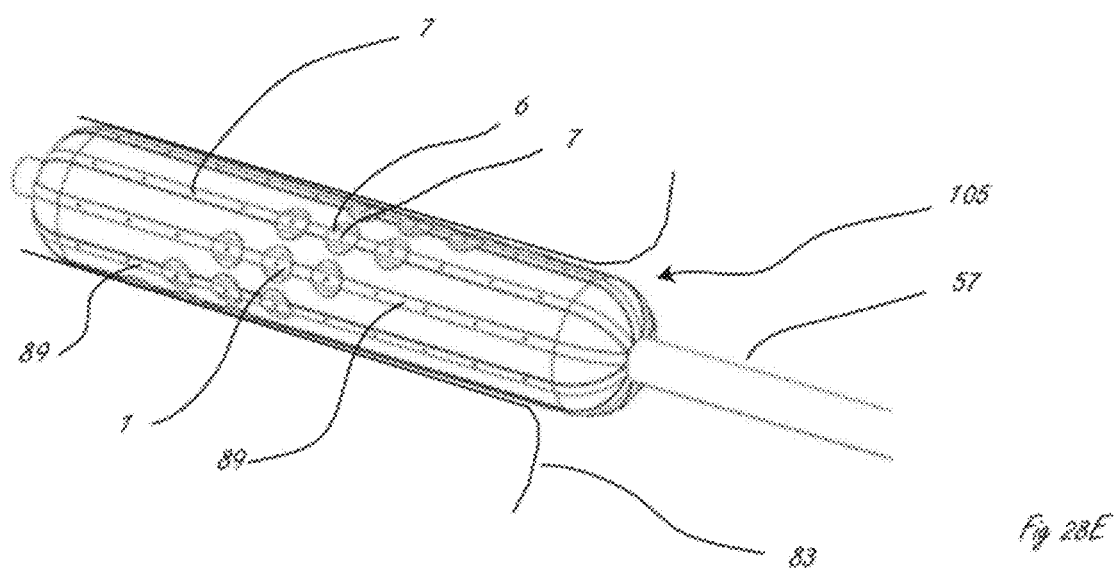
Figure 28F:
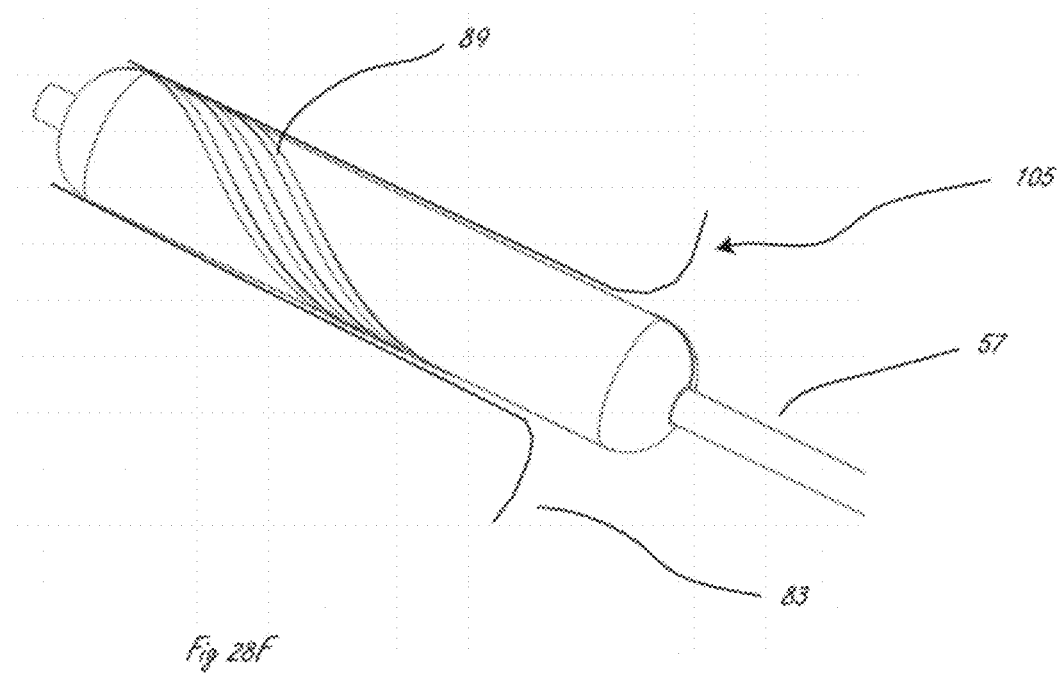

In another embodiment, the mapping electrodes can be positioned on an expandable membrane 34 having the mapping electrodes 51 between the ablation electrodes 6. FIGS. 28C-28D illustrate an electrode assembly 105 which is partially deflated prior to introduction into the pulmonary vein 80. Once inside the pulmonary vein 80, the electrode assembly 105 can be re-inflated if necessary to ensure good tissue contact of the mapping electrodes 51. A guidewire 40 is shown and can be used for better positioning of the membrane 34. FIGS. 28E-F illustrate an embodiment where ablation electrodes and mapping elements are helically arrayed around the cylindrical electrode structure of FIG. 18P. In this embodiment the mapping electrodes are arranged in a helical pattern between two sets to ablation electrodes.

In an embodiment, folding of the electrode assembly 105 and deflation of the expandable membrane 34 exposes the mapping electrodes 51 (see FIGS. 24A-24B). The electrode assembly 105 can fold preferentially when the expandable membrane 34 is deflated. The deflated assembly with exposed mapping electrodes 51 can be inserted into the pulmonary veins and used to map the electrical signals. Once mapping is performed, the membrane 34 of the electrode assembly 105 can be re-expanded or re-inflated allowing for the ablation electrodes 6 to be used at their full size. During deflation, the membrane 34 can begin to fold at areas of the membrane 34 not covered by the flex circuit or areas adjacent to the flex circuits 89. The electrodes 6 can also fold in this process as the electrodes 6 are flexible and carry similar mechanical properties as the bare membrane 34. FIG. 24A shows an expanded membrane 34 ready for ablation. The flex circuits 89 are shown to contain one mapping electrode 51 each, although there can be one or more mapping electrodes 51 per flex circuit 89. FIG. 24B shows the membrane beginning to fold, initially at the sections not covered by a flex circuit such that the flex circuits 89 remain exposed. It is important to note that the membrane may not be fully deflated for this procedure. Also, re-inflation of the membrane once inside the pulmonary vein is possible to ensure the mapping electrodes 51 are in full contact with the tissue.

The mapping electrodes 51 can also be positioned on a device separate from the ablation assembly such as a second expandable structure as shown in FIGS. 29A-29C. FIG. 29A shows an example of a two balloon integrated ablation and mapping system having a separate balloon for mapping 69. This second balloon 69 can have a separate inflation hole 68. The guidewire lumen can be located on one side of the balloon 69 to allow for better control of the balloon 69 position. The second balloon 69 can also be used to anchor the electrode assembly during use. FIGS. 29B and 29C show a proximal ablation balloon 34 coupled to a distal mapping balloon 69. The two balloons can be part of a single catheter or can be separate devices. Each of the balloons can include electrodes for ablation and/or mapping, or electrodes to perform other functions such as sensing or stimulating. A guidewire 40 can be used for example to center the mapping balloon 69 for better positioning of the mapping electrodes 51.

Figure 30:
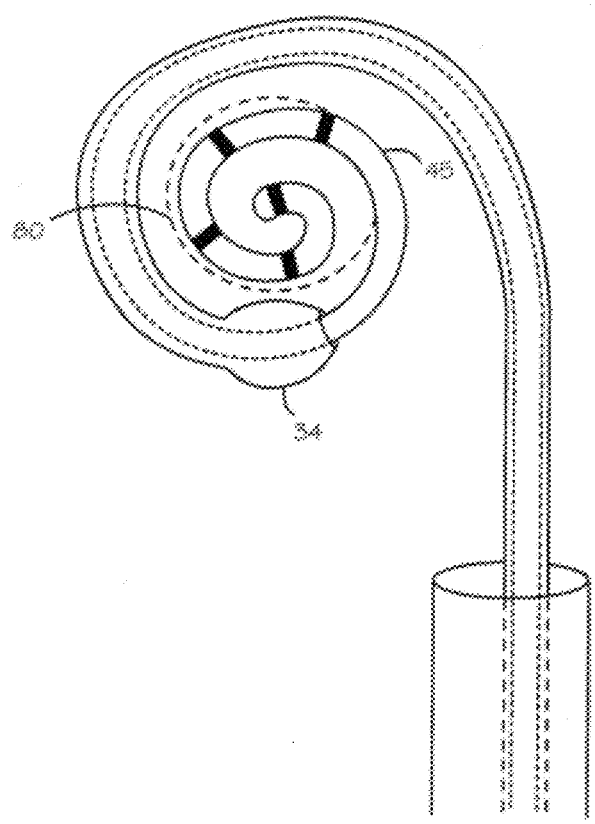
FIG. 30 illustrates an embodiment of an electrode assembly integrated with a mapping catheter.
Figure 31A:
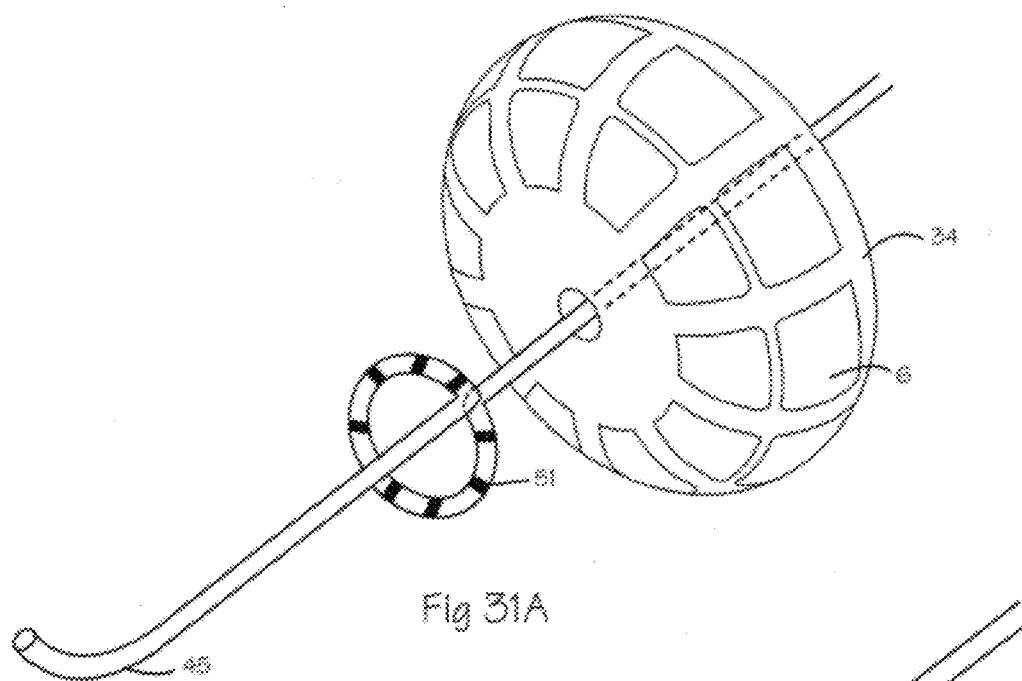
FIGS. 31A-31B illustrate an embodiment of a linear mapping electrode catheter.
Figure 31B:
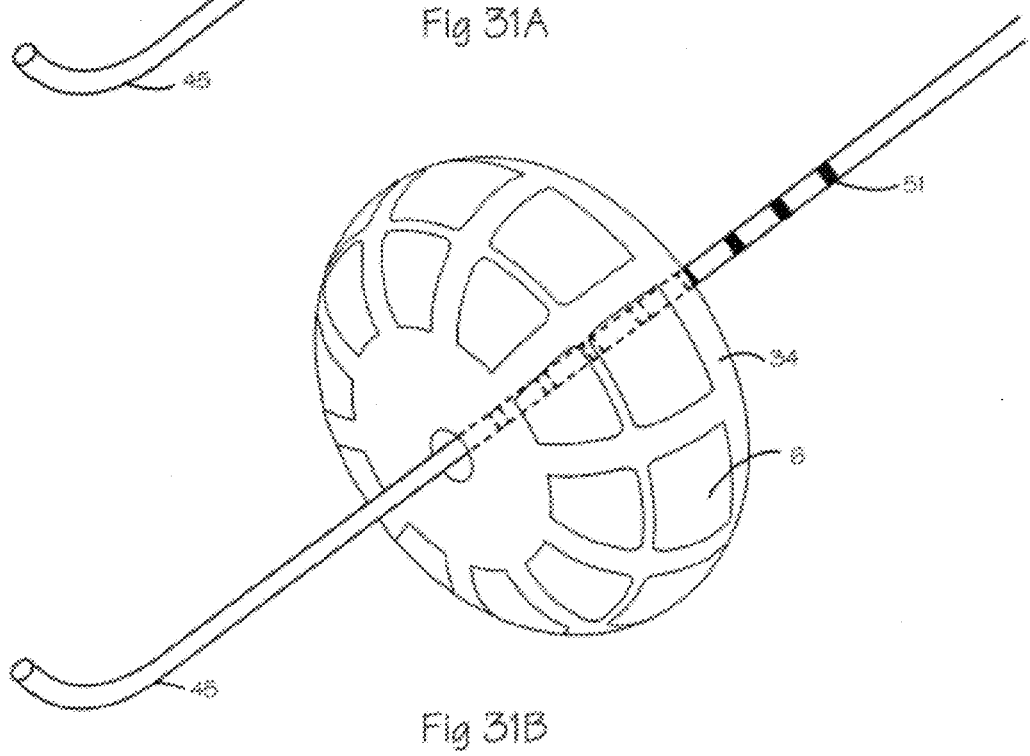

In an embodiment, the mapping electrode structure can be a tubular structure such as a mapping catheter 45 as shown in FIG. 30. The catheter 45 can serve as a guidewire for the ablation assembly as well as provide mapping information. The distal end of the mapping catheter 45 can wrap around an inside surface of the pulmonary vein 80 and measure electrical signals. FIGS. 31A-31B also show a linear mapping electrode catheter 45. The mapping catheter 45 can be used also as a guidewire and can be the same diameter and length of a standard guidewire. In an embodiment, the mapping catheter 45 can be between about 0.035" and 0.038". In an embodiment, the diameter of the mapping catheter 45 does not exceed 0.035" and can be interchanged with a conventional 0.035" guidewire. The mapping catheter 45 can be manufactured of a flexible outer shell with an inner diameter that allows for a core element (not shown) to be inserted which will determine the shape, size, and stiffness of the catheter. As shown in FIG. 31A, the core can create a loop shape on the catheter 45 where the mapping electrodes 51 can be located. The loop as shown in FIG. 31A can be off-center or centered. The loop shape of the catheter 45 can be adjustable in size and can conform to the pulmonary vein for mapping. A section distal to the electrodes 51 can be atraumatic and behave like a standard guidewire tip and terminate as a standard guidewire, for example a J-tip as shown. The distal end can be closed such that it does not allow the core to protrude beyond the tip. A steerable element (not shown) can be included to manipulate the distal end of the catheter.

The mapping electrodes 51 can be deposited using the same or similar techniques and materials as the electrodes described above. The electrodes 51 can be formed with electro-conductive ink which can be painted, printed, sprayed, deposited or otherwise transferred onto the catheter as described above with respect to the ablation electrodes. The ink can include radiopaque additives for visualization under fluoroscopy or a radiopaque ink pattern can be included adjacent to or on top or below the electrodes. A thin, conductive film and/or conductive adhesive gel can be cut into strips and wrapped around the catheter to serve as the mapping electrodes 51. Use of a conductive adhesive film or gel can also serve to secure the end of the flex circuit. The conductive adhesive can be created by mixing conductive particles, such as silver flakes, into a flexible adhesive.

During mapping, the catheter 45 can be extended distal to the expanded membrane 34 as shown in FIG. 31A. If not in use, the shaped section of the mapping catheter 45 can be retracted into or proximal to the expanded membrane 34 as shown in FIG. 31B. A mapping wire can be the same diameter of a guidewire. In an embodiment, the proximal handle end of the mapping wire can be detachable to allow for other devices to be inserted over the mapping wire.

In another embodiment, the mapping electrode structure can include a scaffold or braided, self-expanding structure 98 that can be pushed distal to an expanded membrane 34 and electrode assembly 105 as shown in FIG. 32A-32B. The mapping structure 98 can be covered by a membrane 54 and can include one or more mapping electrodes 51. In its retracted configuration as shown in FIG. 32A, the mapping structure 98 can be elongated, narrow and positioned within the guidewire lumen. The mapping structure 98 can be attached to a moving element 55. The lumen can remain open for a guidewire 40 to travel through. When mapping is performed, the mapping structure 98 can be pushed distal to the expanded membrane 34 and can self-expand (see FIG. 32B). The mapping structure 98 can have a tapered or funnel-shaped structure near where it attaches to the moving element 55. The funnel shape can allow for easier retraction of the mapping structure 98. Mapping electrodes 51 can be mounted on the expanding portion of the mapping structure 98 in a variety of patterns, such as a single or multiple rows.

Figure 33A:
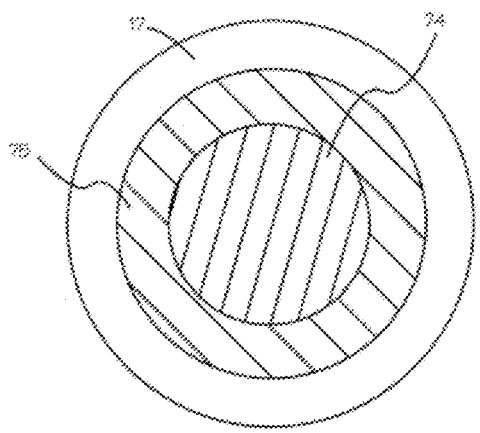
FIGS. 33A-33D illustrate embodiments of a mapping electrode structure.
Figure 33B:
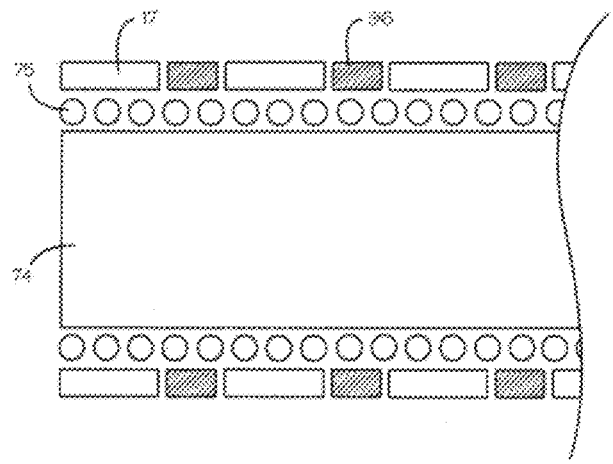
Figure 33C:
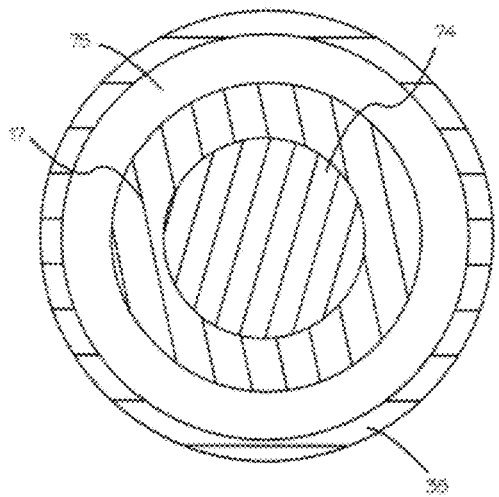
Figure 33D:
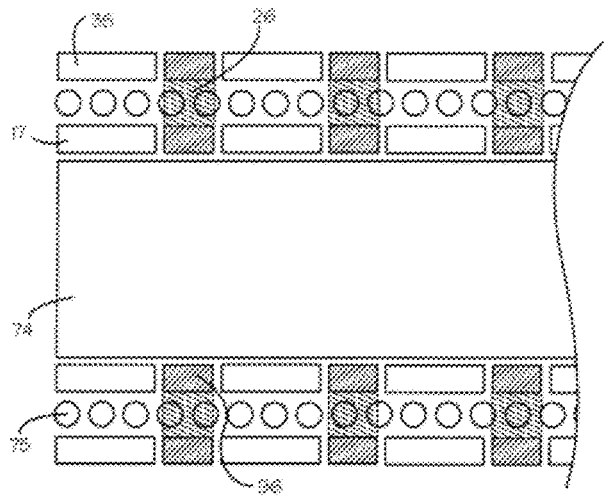

In another embodiment, the mapping electrode structure includes a mapping wire (see FIGS. 33A-33B). A pre-shaped core 74 can be used with a coil 75 wound tightly around it. The flex circuit main lead 17 of the flex circuit 89 can be wrapped and bonded over the surface of the coil 75. Multiple flex circuit main leads 17 can be used in the flex circuit 89 and the conductive layer 96 can be located at specific intervals. The mapping electrodes 51 can be formed circumferentially around the wire using conductive ink at each of the conductive sections 96 as described above. FIGS. 33C and 33D illustrate another embodiment of a mapping wire. In this embodiment, a pre-shaped core 74 can be used and a flex circuit 89 wrapped over it. An insulated coil 75 of a non-conductive material can be wound around the inner assembly, tightly at the proximal end and varying at the distal end. The sections that are not tightly wound can correspond to the conductive sections 96 of the lead 17. A conductive filler material 26, such as an adhesive, epoxy, or the like, can be used to fill the gaps between the flex circuit main lead 17 up to the surface of the coil 75. The mapping electrodes 51 can be formed circumferentially around the coil using conductive ink at each of the conductive sections 96.

Figure 34A:
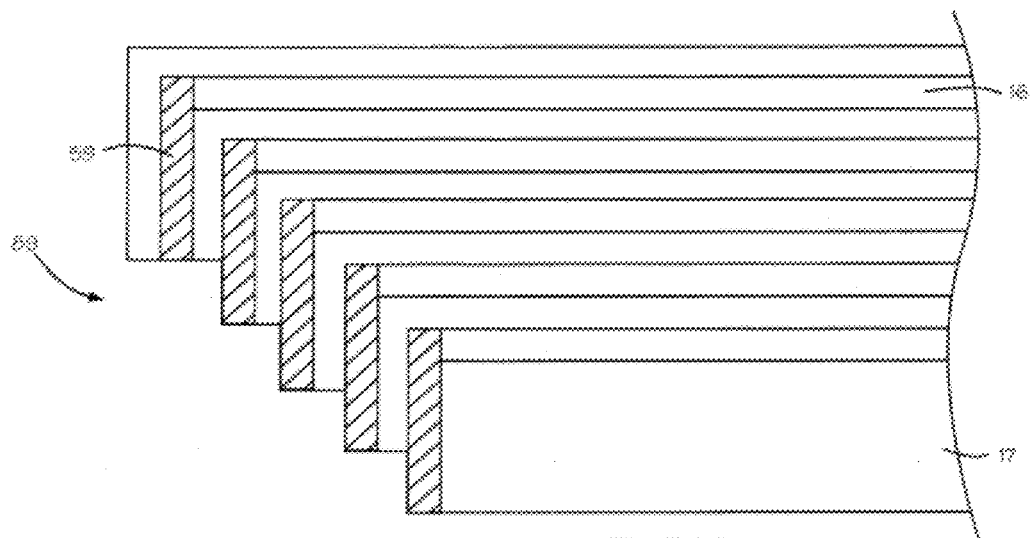
FIGS. 34A-34F illustrate embodiments of a flex circuit that can be used for a mapping electrode structure.
Figure 34B:
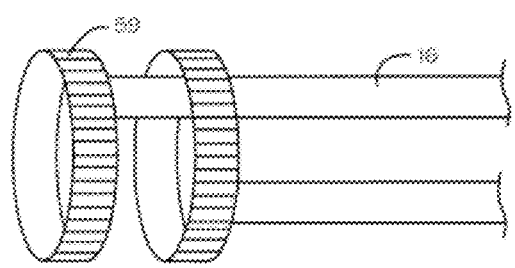
Figure 34C:
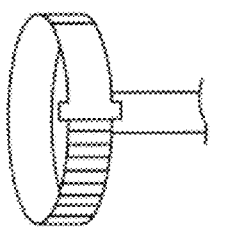
Figure 34D:
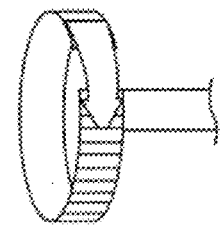
Figure 34E:
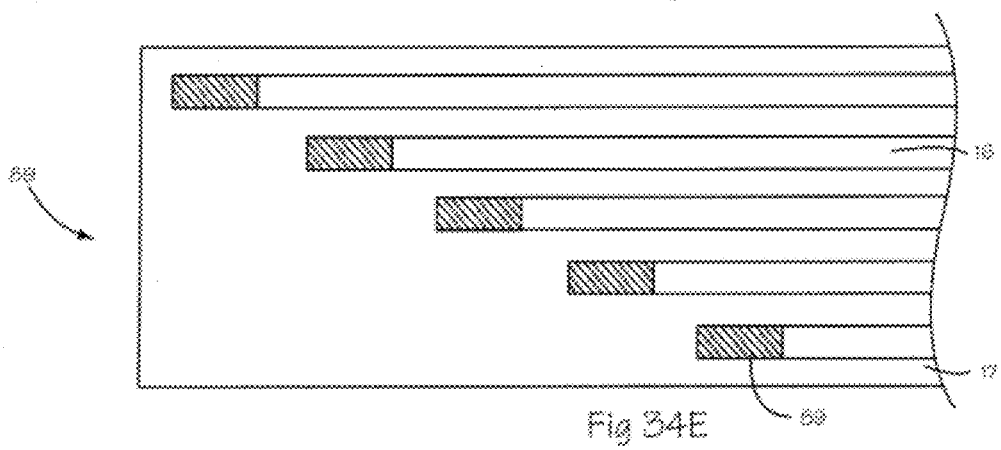
Figure 34F:
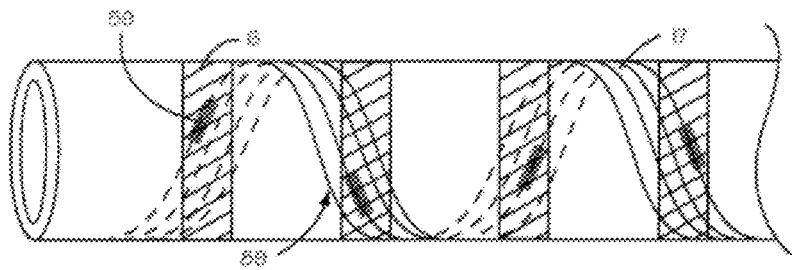

FIGS. 34A-34F show various embodiments of a flex circuit 89 that can be used for the mapping wire. Conductive traces 16 on a flex circuit 89 can end in an L-shape. The proximal end of the lead 17 can be routed to the handle (not shown). The short L-arm of the trace 16 can be exposed and provide the conductive pad 59 for the electrodes. The flex circuit can be wrapped over the inner assembly of the mapping wire so that the conductive section forms a loop around the core and connects to itself as shown in FIG. 34B. The loops then can become the electrodes 51 themselves or the electrodes 51 are formed using the same or similar conductive material as described above. FIGS. 34C and 34D show two embodiments of the termination of the conductive section. In a first embodiment, the tabs at the end can be bonded or secured in place via adhesive or an outer bonding layer without disturbing the conductive pad. In another embodiment a self-locking mechanism can be used. FIG. 34E shows straight traces 16 on a flex circuit 89 with conductive tips 59 ending at different locations relative to the edge of the flex circuit 89. The flex circuit 89 can be wrapped over the inner assembly of the mapping wire with each conductive section ending at specific locations on the length of the catheter. Alternatively, as shown in FIG. 34F, the traces can be wound around the inner assembly similar to a coil. At each conductive section, electrodes 51 can be laid circumferentially around the inner assembly.

The devices and electrode assemblies described herein can also include one or more pairs of pacing and capture electrodes 91 to verify that the lesion created was effective in obtaining action potential block through the ablation line. As shown in FIG. 12, the large electrodes 6 can be used to create the ablation lesion lines for the treatment of atrial fibrillation, for example, as current 92 is passed between the adjacent electrodes 6. Current 92 can also skip over one electrode to reach the next to create the desired line as shown in FIG. 12. The pattern of electrodes 6 can be designed to create segments of interconnecting lines, for example to isolate the pulmonary veins and other areas in the heart. Multiple applications of energy can be applied by the electrodes 6 to adjacent or overlapping tissue regions. Pacing and capture electrodes 91 can be used, for example during creation of a lesion with the RF power on or in between delivery of energy. In an embodiment, two or more sets of pacing and capture electrodes 91 can be included. One set of electrodes 91 can deliver the pacing action potential and the other set of electrodes 91 can be located behind the lesion line to be created to sense or "capture" the action potential delivered. When the ablation line is complete and there are no open electrical gaps in the tissue, a single pair of these pacing and capture electrodes 91 (one pacing, one capturing) may be used to verify the action potential block. Whereas during creation of the first portion of the lesion line at the start of ablation energy application the action potential can travel around the lesion line to reach the capturing electrode. In this scenario, a larger number of (e.g. more than two) pacing and capture electrodes 91 can be used to identify the direction from which the action potential came. The pacing and capture electrodes 91 can be used to identify whether the action potential came through the lesion line or around it thus identifying where additional energy transmission may be necessary. The multiple pacing and capture electrodes 91 can detect direction of the action potential by identifying which electrode detected the action potential first, second, third, fourth and so on. With this feature, the user can verify signal blockage after each segment of the lesion instead of waiting until the overall lesion is created.

Control of Energy Transmission

Figure 35:
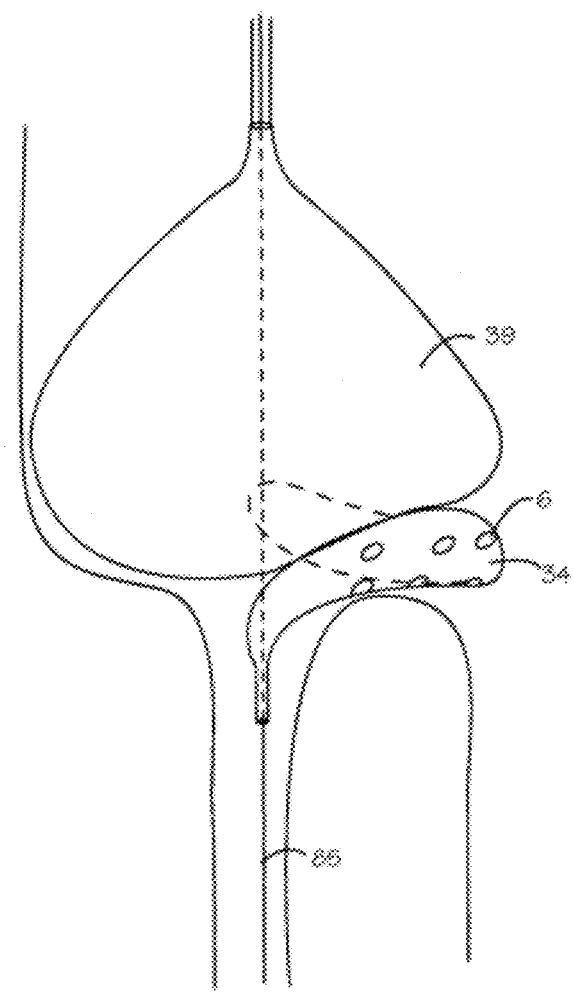
FIG. 35 illustrates an embodiment of an electrode support structure.

The electrode assemblies described herein are conformable such that they provide good contact with the target tissues, especially tissues having complex three-dimensional geometries. Mechanisms can be incorporated into the devices described herein that improve contact of the electrode assembly with the target tissues. In an embodiment a support structure such as a balloon can be used to press the electrode assembly against the target tissue (see FIG. 35). In this embodiment, a distal and relatively small expandable electrode structure 34 that includes electrodes 6 on its outer surface is positioned against the target tissue. A larger proximal support structure 39 can assist in positioning the electrode structure 34 by pushing the smaller electrode structure 34 against the tissue. A guidewire or guiding rod 85 is shown that can also be used to assist in positioning.

Figure 36A:
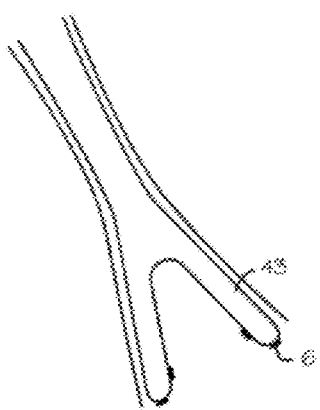
FIGS. 36A-36B illustrate an embodiment of an electrode system for use near a heat sink.
Figure 36B:
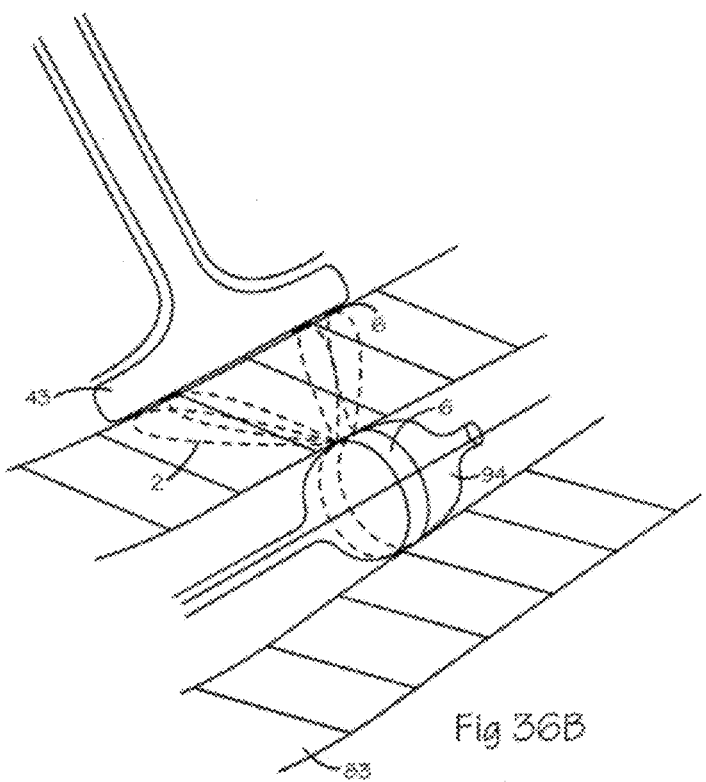

Heat and current can dissipate quickly away from a region to be treated if for example a heat sink is present such as a near-by pool of blood such as a large artery, vein, or the coronary sinus. This results in sections of the tissue not getting sufficient energy transmission and the failure of a conduction block. Because of the poor heat transfer of energy through gas compared to a liquid such as blood, a fluid-tight structure filled with a blood-safe gas, such as carbon dioxide or helium, can be provided near the location of energy delivery. As shown in FIGS. 36A-36B, a gas inflated balloon 94 can be placed in the coronary sinus for example and used such that current 2 can pass from the electrodes 6 on the electrode structure 43 to a reference electrode 6 on the gas-inflated balloon 94. The tissue between can then be appropriately ablated. The gas-filled structure can also be used for temperature measurement and feedback.

Figure 37A:
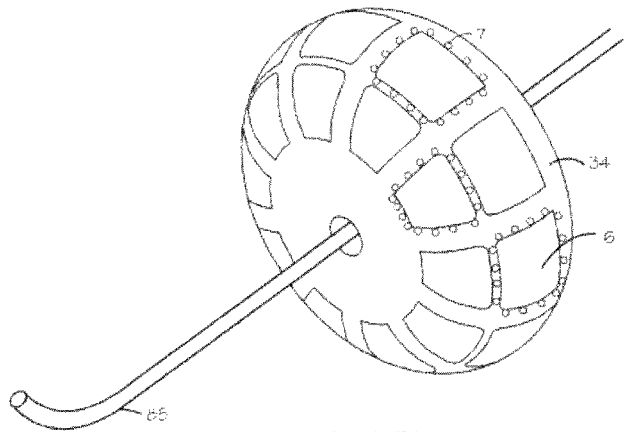
FIGS. 37A-37F illustrate embodiments of irrigation holes positioned near one or more electrodes.
Figure 37B:
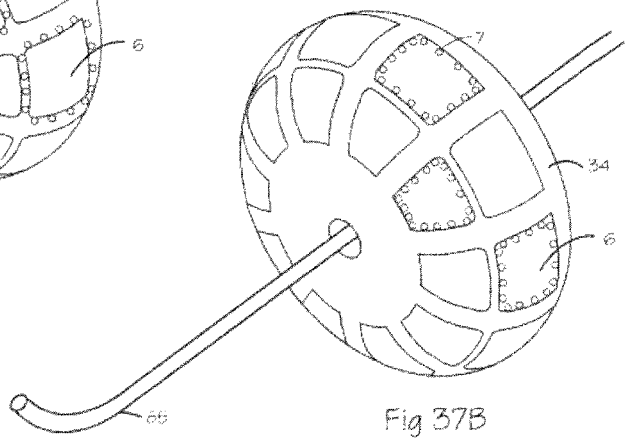
Figure 37C:
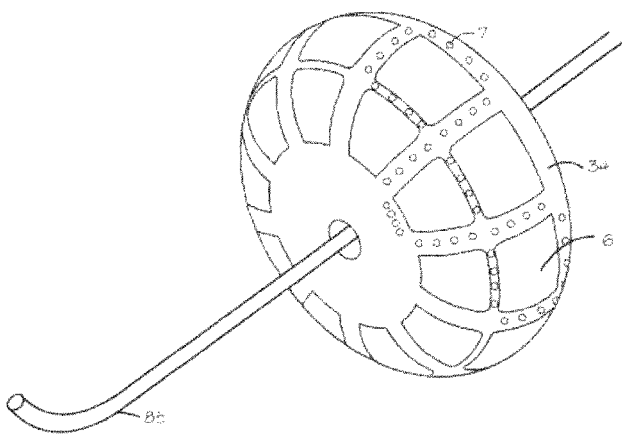
Figure 37D:
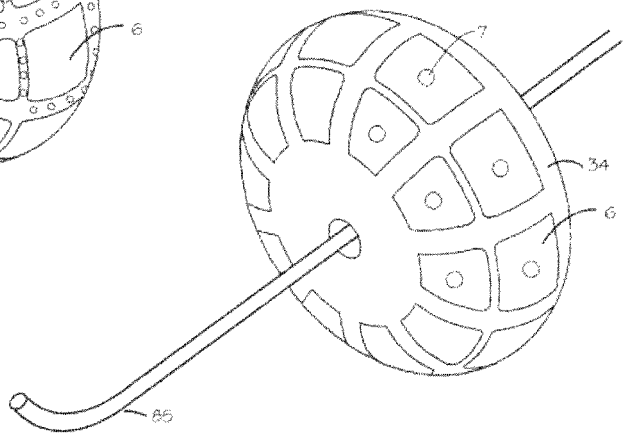

As described above, the flex circuit 89 can have temperature sensors 90 mounted on conductive traces 16 near, on or between electrodes 6 in contact with the tissues. The temperature sensors 90 provide feed back to the user as to the temperature of the target and surrounding tissues such that the device and/or the user can modulate energy supply and charring or excessive coagulation can be avoided. Controlling the temperature, for example using irrigation at or near the tissue treatment site, is another way in which charring can be prevented. As shown in FIGS. 37A-37C, irrigation holes 7 can be positioned near one or more of the electrodes 6 to deliver a cooling fluid to the region and maintain consistent, predictable pattern of energy transmission. The fluid can include a non-conductive or conductive irrigation medium. The figures show irrigation holes 7 for three electrodes 6, but it should be appreciated that more or less than three electrodes 6 can have irrigation holes. In an embodiment, all electrodes 6 have one or more irrigation holes 7. The irrigation holes 7 can be contacting or adjacent to an electrode, for example surrounding the border of the electrode 6. In another embodiment such as shown in FIG. 37B, the irrigation holes 7 can be placed directly on the surface of the electrode 6 near the edge of the electrode 6. It should be appreciated that the irrigation hole may be placed anywhere on the electrode 6. FIG. 37C shows yet another embodiment with irrigation holes 7 located in between two electrodes 6 so adjacent electrodes 6 share a set of irrigation holes 7. It should be appreciated that the configuration of irrigation holes 7 to electrodes 6 can vary and that the configurations provided in the figures are for example only. FIG. 37D shows a single irrigation hole 7 located at the center of each electrode (only six holes are shown). In one embodiment, these irrigation holes 7 can match with holes placed on the flex circuit conductive pad 59 (see FIG. 3B). In one embodiment the flow rate of the irrigation fluid can vary and be controlled to a desired level. The irrigation flow rate can be set to a minimum level to maintain pressure within a closed membrane, such as a balloon for example, while positioning or orienting the catheter. Alternatively, cooling fluid can be circulated within a closed membrane without the use of irrigation holes.

When irrigation fluid delivery is the means by which the balloon inflation is maintained, the size and number of holes becomes important. The fluid resistance of the sum of the holes should be such that for the required flow of irrigation fluid the pressure drop across the sum of the holes is that required to maintain the balloon inflation. As the pressure drop across a hole for a given flow rate varies as a 4th order function of the diameter, a preferred embodiment has many smaller holes such that more averaging can occur. In addition to averaging, when lower exit fluid velocities are desired, many smaller holes provides an advantage over fewer larger holes.

Figure 37E:
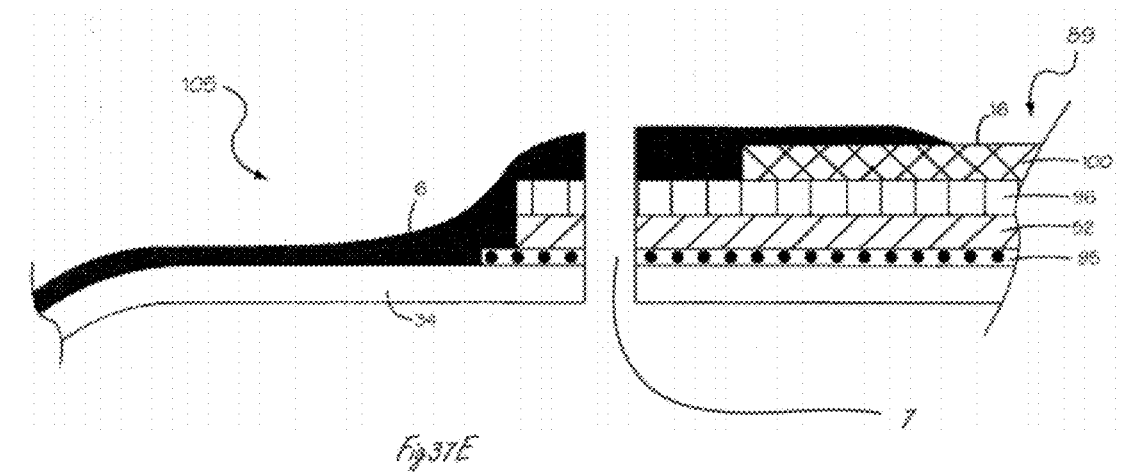
Figure 37F:
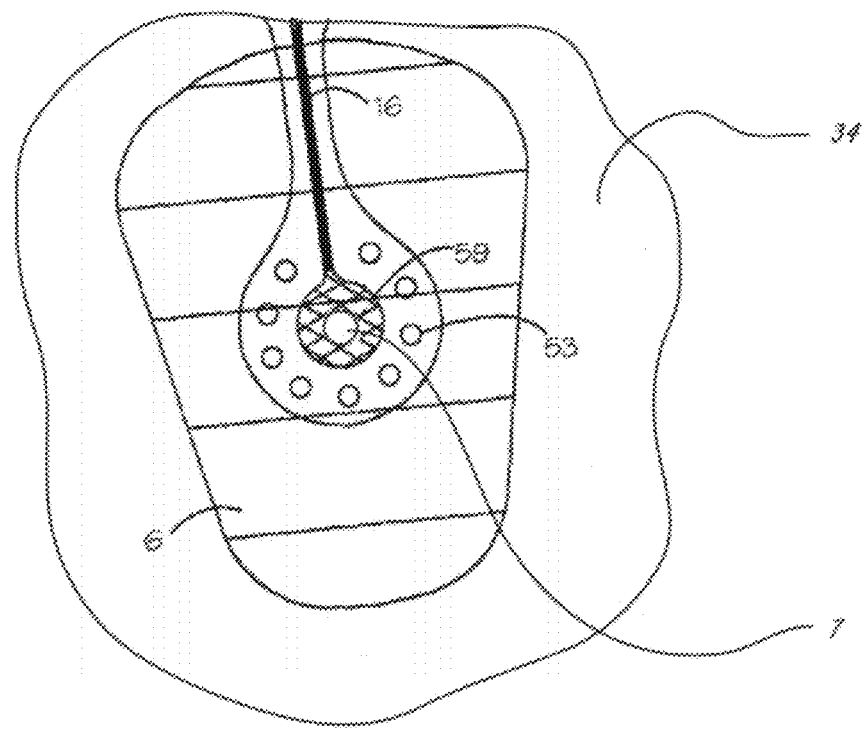

In FIGS. 37E-37F are illustrated irrigation holes 7 incorporated as part of the flex circuit 89. When the irrigation hole 7 is configured in this fashion the increased stiffness associated with the flex circuit substrate 52 singly or in combination with the conductive layer 96 and other layers may be used to advantage as a means to provide extra strength to the irrigation hole and thereby prevent tearing of the membrane 34 at the irrigation hole during manufacture or use. The flex circuit in proximity to the hole can be affixed to the expanded membrane 34 via an adhesive 95 or other bonding process during manufacture. The hole 7 in flex circuit 89 can additionally be used as a template for hole placement by drilling, puncture, or other suitable process during manufacture. In this fashion placement relative to the electrodes and the size of hole may be more closely controlled, which are both factors important in the process of irrigation. Both hole placement relative to the electrode and the cross section and cross sectional area of the hole 7 will be important in controlling the volume flow of irrigation fluid in proximity to the electrode 6. The irrigation hole as illustrated in FIGS. 37E-37F has been shown such that the irrigation hole passes through all the electrode 96, substrate 52, and adhesive 95, layers of the electrode assembly structure 105 of FIG. 1A. The irrigation hole 7 as described may, however, be used in any electrode structure 105 herein described incorporating a flex circuit 89. The irrigation hole 7 may also be configured such that it passes through any or none of the layers associated with the disclosed structures of electrode structure 105 so long as the irrigation hole 7 passes at least one of the layers associated with the flex circuit 89.

The devices and electrode assemblies described herein can incorporate a variety of mechanisms that allow the user to assess the extent, orientation and quality of treatment line as well as the orientation of the electrode assembly itself in real-time during a procedure without the need to remove the device. For example, energy transmission can be visualized and assessed through the deployable membrane of the device such as, for example, using incorporated fiber optics or a camera on a chip. FIGS. 38A-38G show a balloon 34 having electrodes 6 mounted on its surface as well as a fiber optic scope 38 to visualize the tissue as it is being ablated. The scope 38 can be positioned on an interior of the expandable structure 34 as shown in the figures or an exterior surface of the expandable structure 34.

Figure 38A:
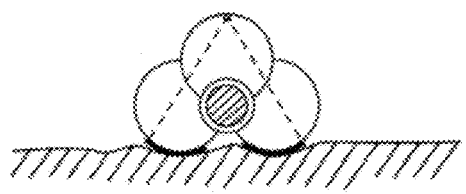
FIGS. 38A-38I illustrate embodiments of a visualization system for use with an electrode assembly.
Figure 38B:
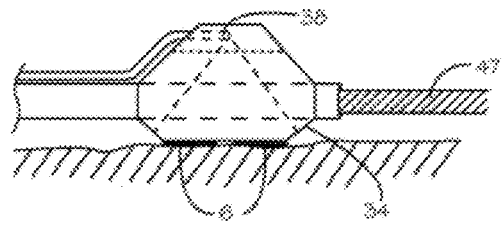
Figure 38C:
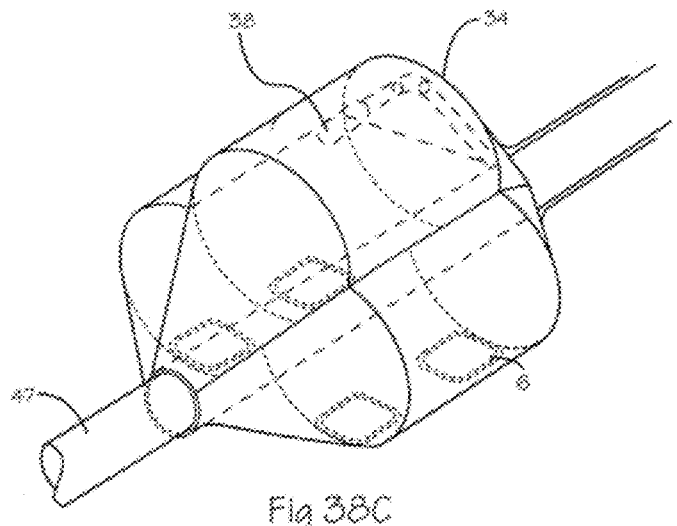
Figure 38D:
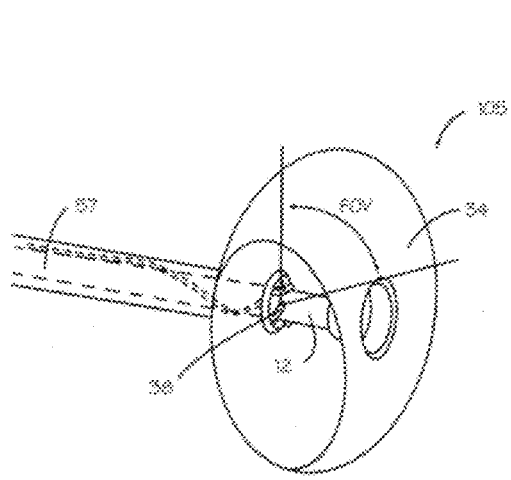
Figure 38E:
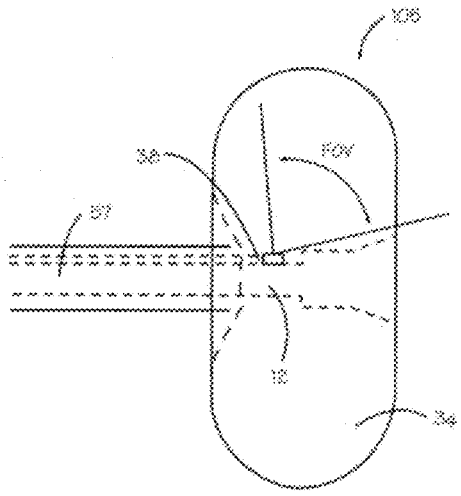
Figure 38F:
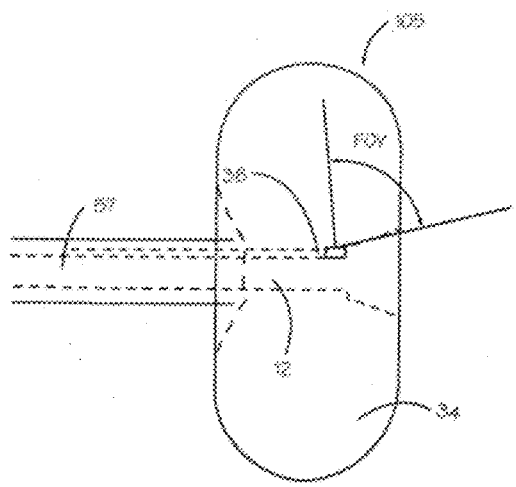
Figure 38G:
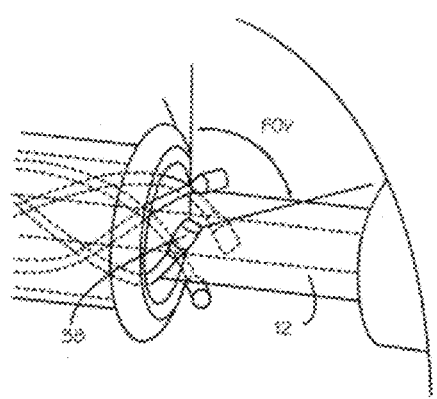
Figure 38H:
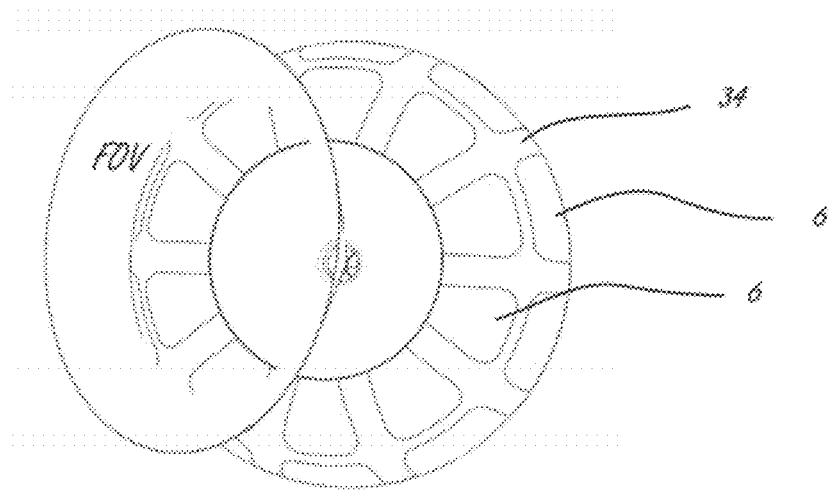
Figure 38I:
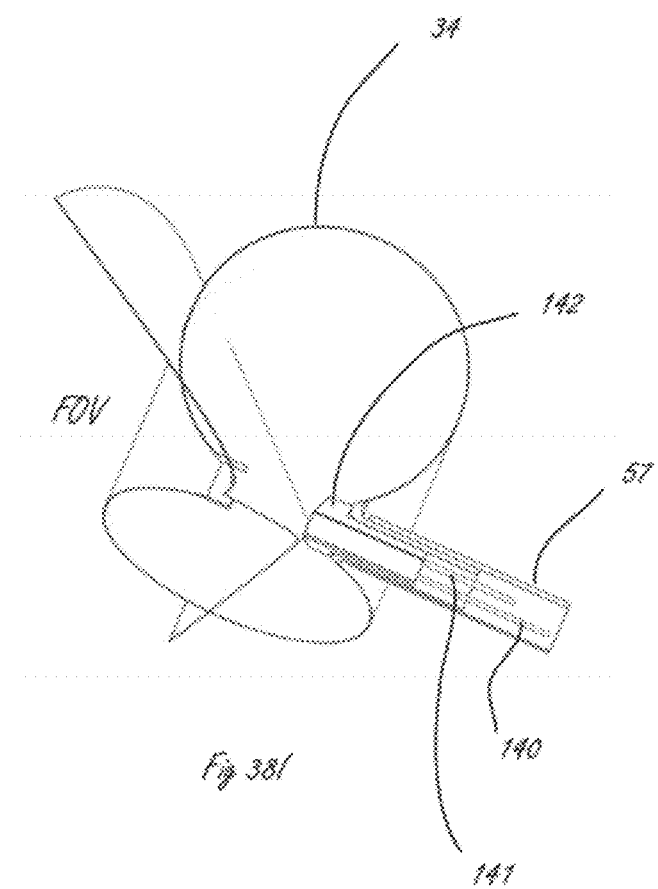

In an embodiment, more than one fiber optic scope 38 can be used in the electrode assembly 105 (see FIGS. 38D-38G). The fiber optic scopes 38 can be wrapped helically around an inner shaft 12 with a flexible shaft 57 or be placed adjacent to the inner shaft 12 to achieve a desired field of view ("FOV"). The scope(s) 38 can also be fitted with angular viewing optics to achieve a different view. For example, FIG. 38D illustrates the scope 38 wrapped around the inner shaft 12 to achieve the FOV shown. The same scope 38 in FIG. 38E goes straight through the shaft 12 but to achieve the same FOV, an angular viewing optic can be used. In one embodiment, the fiber optics scope 38 can be movable along the axial length within the membrane 34. This can aid in the confirmation of good apposition to the tissue when the electrode assembly 105 is already in place. FIG. 38G shows a close-up view of four scopes 38 wrapped helically around an inner shaft. Radiopaque markers can also be used to aid in determining the orientation of the electrode apparatus during use. FIG. 20A shows radiopaque visual orientation markers 49 coupled to the support arms 44. The orientation markers 49 can have a variety of specific shapes that can be used, for example by a software projection algorithm from the fluoroscope output. Mapping data can be combined with orientation data from the markers 49 to visualize and allow the user to select which electrodes 6 to activate and use for the desired energy transmission. A user interface can display the orientation of the device, for example on a screen on the RF generator, and this image can also be superimposed on a fluoroscopic view. FIG. 38H illustrates a front view of an electrode assembly 105 incorporating visualization system and the field of view for one of four such optical sub-assemblies incorporated in the optical assembly. Each of the optical sub assemblies incorporates an optics structure 142, which interfaces to an illumination fiber 141, a 200 micron fiber bundle 140, such as the Sumitomo Image Guide IGN-02/03, and an optics structure 142. A quarter section of the electrode assembly 105, with flex circuit 89 (not shown) and inner shaft 57 for visualization of the fibers, is depicted in FIG. 38I. Illumination fiber 141 and image guide 140, in the depicted embodiment, travel within inflation lumen 36 (see FIG. 6C) to handle 1006 (not shown) and on to visualization system control 1004 (not shown). The sub-assemblies are fitted into the toroidal expandable membrane 34 singly and locked in place around the inner shaft 57 at the time of assembly of the visualization system. Other arrangements not depicted route the fiber bundle and illumination fiber through an additional lumen in the inner shaft 134 (not shown).

In any of the embodiments represented in FIGS. 38 A through I, the visualization systems incorporating fiber scopes and fiber optic illumination may be replaced with visualization systems which incorporate either cameras and/or LEDs at the distal end of the ablation system. FIG. 38J depicts a component sub assembly of such a visualization system comprised of two sub assemblies. The two sub assemblies comprising sub assembly 210 are a camera sub assembly and an illumination sub assemble, each fabricated by molding the active components into an optical grade of polymer. The visualization system of FIG. 38J is configured similarly to the structure described in FIG. 38I, however the optical fibers which comprised the fiber optics scope or imaging bundle 140 has been replaced with camera 240, and the illumination fiber 141 has been replaced with LED 241. The camera is mounted in optic structure 242 and the LED is mounted in optic structure 243. As depicted the three visualization sub assemblies comprise a total visualization system 200. The three sub assemblies comprising the total system provide for a smaller fabrication cross section and ensuing advantages as described elsewhere here in. Such a complete system is depicted in FIG. 38K mounted within a toroidal flexible membrane 34 structure for carrying ablation electrodes as described herein. A visualization system alternatively may incorporate more or less subassemblies 210. A flex circuit as described herein can be adapted to interface a camera when used.

The visualization system of FIGS. 38 J, K, and L are structured such that the FOV for both the camera element and the illumination element are fixed relative to the directions in which they point, which as depicted are at an angle of about 60 degrees relative to the cylindrical or longitudinal axis of inner shaft 134. Camera elements 240 and LED elements 241 are distributed about 120 degrees apart from adjacent camera elements and LEDs, respectively, around the longitudinal axis. The camera elements and LEDs are offset with respect to each other by about 60 degrees. In this fashion the FOV's for the camera elements and those for the LED elements overlap as depicted in FIG. 38L. Such embodiments have an added advantage in that during delivery they can flex in towards the center of the opposite of what is shown and thereby present a reduced cross sectional profile. Where such a feature is desirable, the camera might be placed proximal to the LED.

Another alternative visualization system in which the direction in which the FOV's for the camera and illumination elements may be adjusted is depicted in FIGS. 38M through 38Q. In this embodiment the optics structures 242, along with associated camera and LED, are mounted on flex circuit branches 87 of a flex circuit 89, as depicted in FIG. 38M, where only one optics structure 242 is shown mounted to one of the three branches for clarity. As the two ends of the flex circuit 89 are displaced axially relative to one another, the branches 87 flex, thereby adjusting the direction relative to the cylindrical axis of the shaft (not shown) to which the visualization system is pointed. In an embodiment such as that of FIG. 62, the distal end of the visualization system is attached to an inner shaft and the proximal end to an outer shaft or the associated hubs of the toroidal balloon. The distal end of the visualization system of FIGS. 38M and O is that closest to the camera. The flexing branches 87 of the flex circuit 89 may be modified to facilitate preferential bending at bend points 245. The substrate may be narrowed at these points such that the width is reduced and or the substrate and or electrical traces may be thinned at these points. Alternatively a NiTi element may be incorporated in the flex circuit at these points.

In one embodiment of the optics structure 242, the structure is cast in an optical grade of polymer. In such an embodiment some or all of the optics associated with camera and illumination source may be features of the optics structure. Such features known to those skilled in the art are not shown here. The optics structure 242 may additionally incorporate features which allow for better mechanical interfacing with flex circuit branch 87. The optics structure may also incorporate optical dams to isolate the source light from entering the camera from within the optics structure. Alternate preferred embodiments may be fabricated by injection molding as used for fabricating optics.

In the embodiments depicted in FIG. 38 the fluid used to inflate the flexible membrane 34 and the flexible membrane itself will be transparent to the illumination and camera optical pass bands. An exemplary inflation fluid is saline with or without a radiopaque contrast media. A few of the many possible materials appropriate for the flexible membrane are PET and Polyurethanes. In some alternatives $CO_2$ may be used to inflate the membrane. This is particularly advantageous when a camera capable of imaging in the IR is used. Such a system would have particular advantage in monitoring electrode and/or tissue temperature during an ablation procedure.

FIGS. 38 N and O illustrate the visualization system of FIG. 38M and associated FOV's for the sub assemblies 210 in two different states of flexure. In FIG. 38N, the flex elements are flexed at about 60 degrees relative to the shaft longitudinal axis and in FIG. 38O they are not flexed and the FOV's are pointing in a direction substantially normal to the shaft's longitudinal axis. As can be seen in FIGS. 38N and O there are FOV overlap regions 252 associated with some range of angles off of the shaft axis and there are some range of angles for which there is no overlap. When working with multiple cameras, these overlap regions have particular value. At a minimum, in regions where such overlaps exist, a contiguous image of the target tissue is available. Additionally the features within the overlap regions may be used as a basis to process the individual images and knit them together into one contiguous image for presentation to the operator. In addition elliptical and cylindrical lenses can be used to enhance overlap of FOVs. Image processing protocols may also be used to remove distortions associated with such lens use and variations in camera angle.

The adjustable visualization system of FIGS. 38 M through Q has additional advantage when camera optics are required to be simple such as for cost related or camera volume related concerns. In such situations a camera with a small FOV may be manipulated to view image particular features and/or multiple images which can be knit together to create an image which covers a larger area.

When capturing multiple images from multiple cameras either sequentially or in parallel, or when capturing multiple images from a single camera sequentially, or both, areas within the images that have sharp features and are imaged in multiple FOV have particular value. FIG. 38P illustrates the visualization system of FIG. 38M mounted in a fashion similar to that depicted in FIG. 38I where the toroidal balloon comprises three electrodes 6. The illustration characterizes cameras which are facing five degrees off of the shaft angle. The electrodes are marked to facilitate identification of specific locations within the FOVs. As illustrated they are numbered 1 through 3 and the numbers have been placed both on and off the electrodes. Marking features other than numbers could also be used such as varying the shape of the electrode. Alternatively, any of the means described for the use of radio opaque markers could be used, for instance those illustrated in FIG. 40B. In the illustration of FIG. 38P the cameras will image the region between the two circles 258 which represent the surface of the toroidal balloon which is in contact with a tissue surface. The full extent of the FOV's 250 for the three cameras is shown, but it should be understood that the portions of the FOVs outside the image region will not image tissue. In the illustration of FIG. 38P the three cameras image the area 253 where all three FOVs intersect. Pairs of cameras FOVs intersect in areas 252 and areas 251 are imaged by only one camera. In this example the multiple overlap regions and the locational features greatly facilitate the image processing required to knit the images into a contiguous whole. The illustration of FIG. 38Q characterizes cameras with a tilt of about 45 degrees. In both figures the FOV for the cameras is about 120 degree.

Figure 38R:
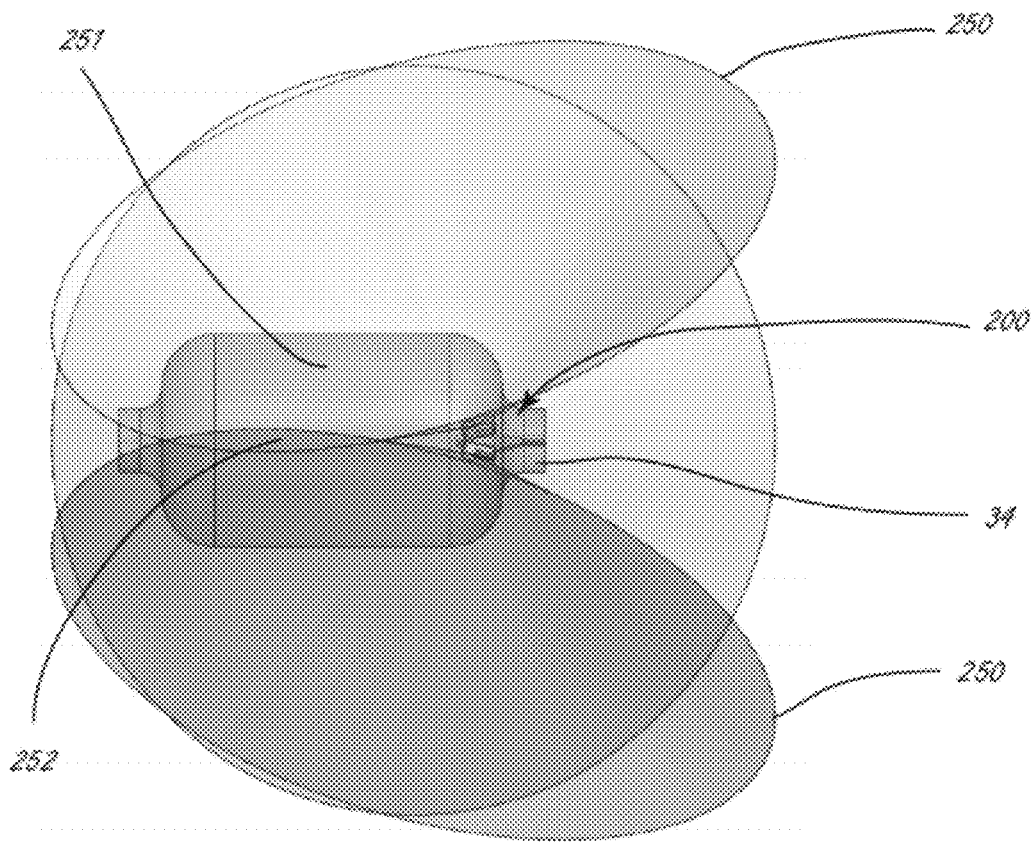

In alternate embodiments the visualization systems described herein can be comprised of expandable structures with configurations other than toroidal. FIG. 38R illustrates the visualization system of FIG. 38M with a cylindrical balloon structure. The distal direction is to left on the page, and the remainder of the system has been left out for clarity. As illustrated, the camera has a FOV of substantially 120 degrees and is pointed at substantially 15 degrees off the shaft axis. In such a configuration a contiguous image of the surface to which the balloon structure is adjacent will be recorded by the tree cameras. The height of the contiguous image will be the maximum length of the FOV overlap region 252. In this configuration when the cameras are pointed at less than about 10 degrees the captured image will not be contiguous. In yet another embodiment the fixed visualization system of FIG. 38J may be used. The design of the visualization system can be adjusted to accommodate the constraints of the particular intended use. More cameras can be used when the constraints require fixed cameras and/or cameras with smaller FOV. Alternatively, larger FOV and/or steerable cameras can be used when constraints require less volume or cost amongst other considerations. In yet another embodiment a single fixed or steerable camera can be used and rotated thereby capturing multiple sequential images which can, by image processing procedures, be knit into a contiguous image.

Two additional exemplary features of the embodiments of the visualization systems presented herein are the delivery profile of the completed visualization system and fabrication profile of the visualization system or its components. The delivery profile is the profile of the visualization system which is normal to the shaft axis in the delivery configuration. The fabrication profile is the profile of the smallest component which can be assembled within the expandable member. The fixed visualization systems described herein are comprised of multiple sub-elements 242 and 243 which when assembled comprise the completed distal portion of the visualization system 200. FIG. 38K is exemplary of such a design using three sub-assemblies 210 to comprise the whole assemble 200 that has a fabrication profile equivalent to the front face subassemblies 242 and 243. The fabrication profile for the steerable visualization assembly distal section described herein is approximately the front facing surface of the optical structure 242 for the configuration where each of the branches 87 are separate at the beginning of fabrication and can thereby be introduced into the expandable structure separately. In preferred embodiments the optical structure will be designed such that these profiles are minimized. Following introduction the distal ends are then fixed together. The delivery configuration for the steerable visualization system can in some embodiments be made smaller by allowing the individual branches to compress into the center of the delivery lumen. In some embodiments the delivery profile is smaller than the outer shaft.

In yet other embodiments the distal end of the visualization system of FIG. 38M can be left free floating such that on delivery the device can be compressed but on deployment it can spring into a delivery configuration.

Thermochromic inks can be used to create locational markings as is indicated by the ring in FIG. 38P electrode number 3. Alternatively the entire back surface of the electrode could be covered with a thermochromic ink, in which case temperature uniformity of the electrode can be evaluated. Electrode 2 in the figure is represented as a group of parallel lines of conductor separated by spaces and ringed by a common conductor. Such an electrode facilitates viewing the tissue behind the electrode during the ablation process.

Figure 39A:
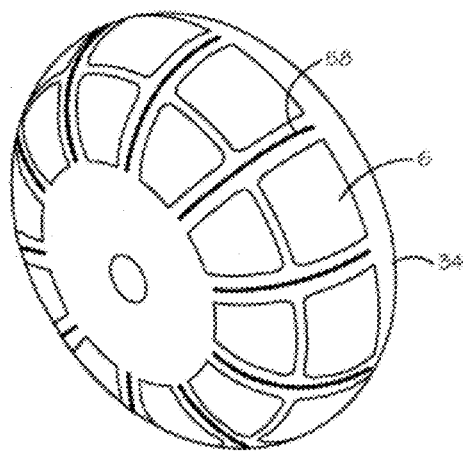
FIGS. 39A-39E illustrate various embodiments of radiopaque marker systems.
Figure 39B:
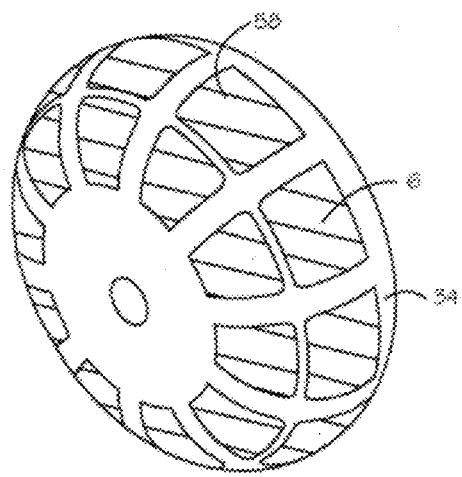
Figure 39C:
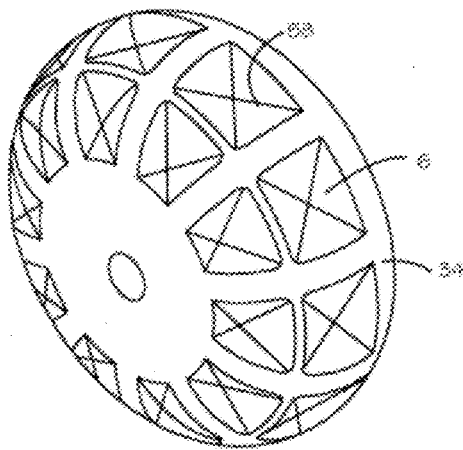
Figure 39D:
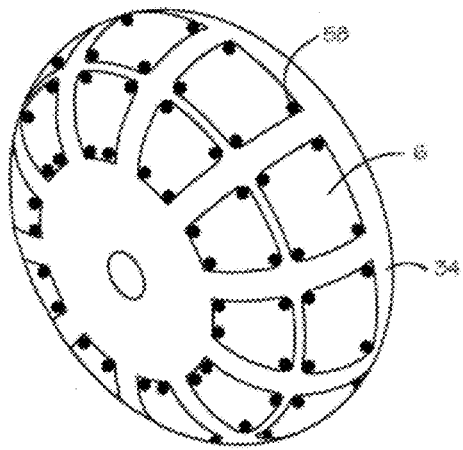
Figure 39E:
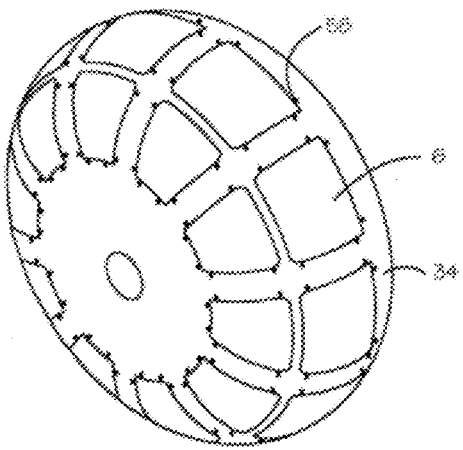

FIGS. 3B, 39A-39E, and 40A-40B show various embodiments of radiopaque patterns that can be used with an expandable membrane structure 34 for the visualization and orientation of the placement of the electrodes 6 onto the tissue as well as the overall shape of the expandable membrane structure 34. In an embodiment, the radiopaque markers 58 can be thin lines or "spines" along the longitudinal axis either between the electrodes 6 as shown in FIG. 39A or directly across the center of the electrodes as shown in FIG. 39B or 39C. These spines of radiopaque markers 58 provide an indication of distance between electrodes 6 and overall shape of the balloon 34 against the tissue. In another embodiment, radiopaque markers 58 can be incorporated into the flex circuits that are used to connect each electrode 6. Layers of denser, radiopaque material such as gold can be added to the conductive pads of the flex circuit 89 for visualization. The denser material can also be placed at the distal branch of the flex circuit to create the thin spines. In this embodiment a thin layer of additional material can be used such that the surface or thickness of the electrodes is not altered and an overall low profile of the device maintained.

In another embodiment the radiopaque markers 58 can form lines angled across the electrodes 6 giving the user a sense of whether the electrode 6 is, for example on the anterior or posterior side (see FIG. 39B). In another embodiment, the radiopaque markers 58 can be in the shape of an "X" across the electrode 6 allowing for the center and edges of the electrodes 6 to be pinpointed (see FIG. 39C). An outline of the electrode 6 can also be traced with radiopaque materials. In other embodiments, the radiopaque markers 58 can include dots around or directly on top of the edges of the electrodes 6 such that they outline the shape of each electrode (see FIGS. 39D and 39E), or they may be centered within the electrode (not shown) as dots or other shapes. Alternatively an electrode material which is both radiopaque and conductive may be used to facilitate these embodiments. In such cases the thickness of the electrode may be varied to adjust the radiopacity. In such an embodiment where it is desired to enhance the radiopacity of the center of the electrode, the full electrode is masked then printed then re-masked to define the thickened area and printed again. This or alternate electrode fabricating techniques can be used in any of the cases where the patterns previously described are applied to the electrodes. Other configurations, shapes, sizes of the radiopaque markers are possible.

The radiopaque markers can be placed on an electrode assembly at circumferentially asymmetrical intervals along the membrane 34. If the deployable membrane of the electrode assembly has an expandable structure such as a balloon, the radiopaque markers can be placed at adjacent quadrants of the balloon or between specified electrodes that are not evenly spaced apart. The markers can be the same or have varying shapes and sizes. Alternatively, the markers can create a distinguishing pattern over the surface of the membrane. In an example, a first quadrant marker can be one dot, a second quadrant marker can have two dots, and a third quadrant marker can have three dots and so on. The markers can include matching markers mounted on the shaft at the same spacing.

Figure 40A:
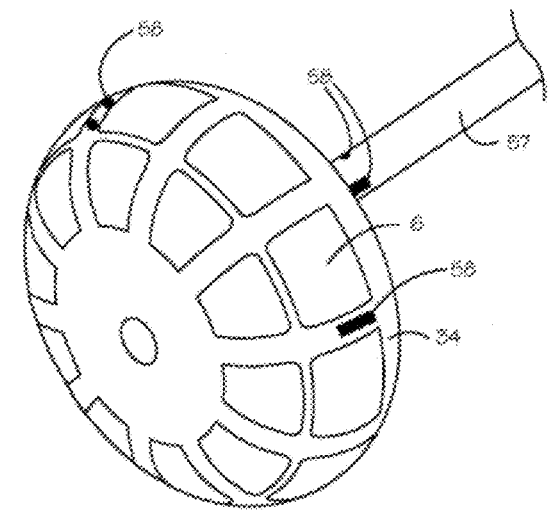
FIGS. 40A-40E illustrate various embodiments of radiopaque marker systems.
Figure 40B:
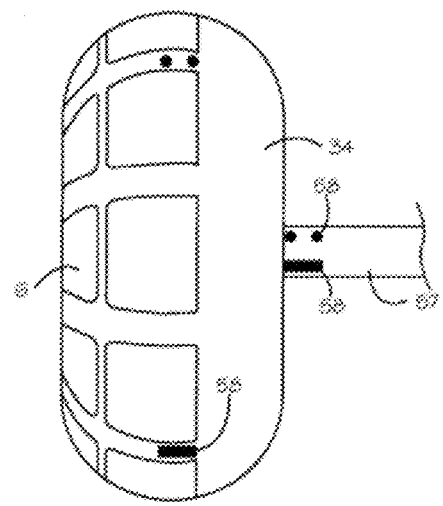
Figure 40C:
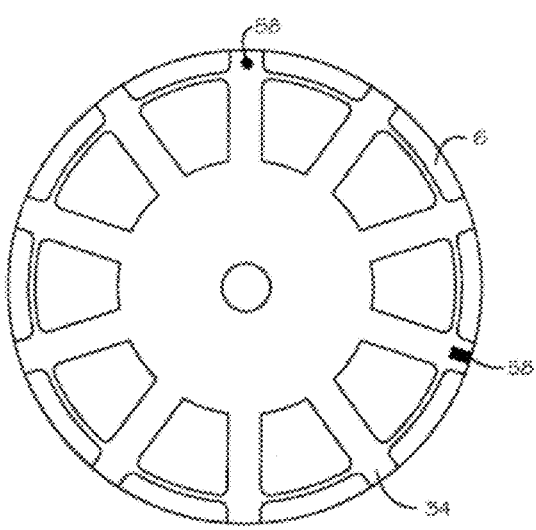
Figure 40D:
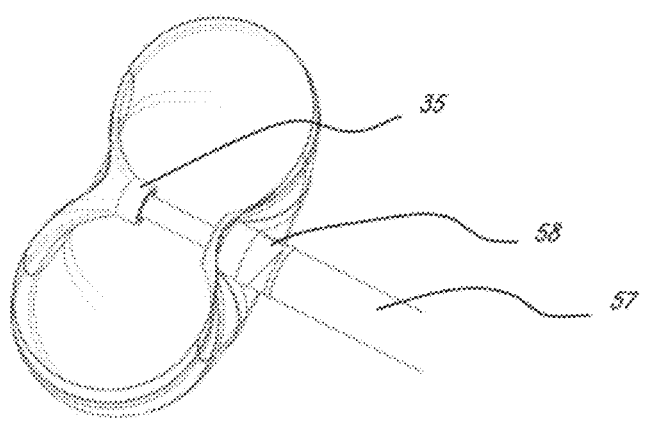
Figure 40E:
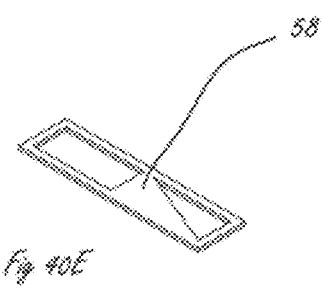

As shown in FIGS. 40A-40C, a radiopaque marker system can be incorporated on the membrane 34 of an electrode assembly. In an embodiment, two dissimilar markers 58 can be placed at just over 90 degrees apart (quadrants 1 and 2) and three electrode widths apart. Matching markers 58 to those on the membrane 34 can be located on the distal end of the shaft 57. Under fluoroscopy, the user can determine the orientation of the electrode structure 105 based on the location of the markers 58. The use of dissimilar markers 58 as shown, or varying numbers of dots on each consecutive quadrant as described above, allows a user to determine the orientation of the membrane 34 and determine the target energy transmission location. Such patterns may in addition be facilitated by using the techniques described with reference to FIGS. 39D and 39E, where the patterns are created on the electrodes and not all electrodes receive the same treatment. Where rotational orientation is sought, radiopaque markers may alternatively be added to structures other than those located on the membrane 34. Such an embodiment is illustrated in FIGS. 40D-40E. FIG. 40D illustrates a radiopaque ring 58 affixed on the OD of shaft 57. FIG. 40E illustrates the ring in an unwrapped configuration where the one of a number of possible set features are more easily seen. The transparent portion of the projection passing across the longitudinal axis of the ring created by the triangle and square cut outs has an image which continuously and uniquely varies through 360 degrees of rotation. The ring can be configured to be located in alternate locations such as on the ID of outer shaft 57 or other cylindrical structures within, or on the of thickened membrane section 35 of membrane 34, amongst others.

FIG. 3B illustrates the integration of a radiopaque marker system 58 directly onto the flex circuit 89. A set of markers 58 is shown on two separate branches 87 of the flex circuit 89, for example 1 line and 2 dots. In the embodiment of FIG. 3D a number of the flex arms of the flex circuit can be modified to enhance the radiopacity by incorporating a unique layer of appropriately radiopaque material, or modifying a conductive layer material, or conductive layer thickness, or both. In such an embodiment the arm incorporating electrode pad 59c, and the forth, and seventh arms, counting from left to right, incorporate a radiopaque layer which extends from the proximal tab 116 to the distal tab 116 for the first arm, ⅔ that distance for fourth arm and ⅓ that distance for seventh arm. Such a unique layer may additionally be created by adhering a foil of a radiopaque material such as silver, tungsten, tantalum, platinum, or gold to the branches of the completed flex circuit or be adhered to the flexible membrane 34 independent of the flexible circuit.

The spacing, number, shape and size of the markers 58 can play an important role in defining the geometry and orientation of the device as well as ease of use of the marker. The branches 87 of the flex circuit 89 can be located at unique latitudes on the membrane 34, in particular an embodiment of a membrane 34 similar to those of FIGS. 18A-18M. The marker system 58 can then lie at unique positions on the membrane 34. If the markers are spaced out in adjacent quadrants, for example, and are of different shape and/or number, the user can readily recognize a particular marker as quadrant I. Additionally, the temperature sensors 90 and electrodes themselves can serve as radiopaque markers which provide an indication of overall shape of the expandable membrane 34. In some embodiments thermistors of different sizes may be used and distributed in such a way that sections of the electrode assembly between the thermistors are identifiable.

Other mechanisms can be included in the devices or electrode assemblies described herein that allow a user to assess orientation and quality of energy transmission without the removal or repositioning of the device. For example, sensors located at or near the electrodes can be incorporated to detect tissue contact with the electrodes or the amount of pressure exerted on the tissue during a procedure. Because the amount of contact and pressure can have a dramatic influence on the depth and quality of the lesion being created, it can be important to assess in real-time the extent of contact made with the tissue and the degree of pressure being exerted. The depth of energy penetration and the ability to detect tissue contact with the electrodes during transmission allows a user to avoid thrombus formation and inadvertent charring of the tissue.

Tissue contact can be measured using a variety of techniques. In an embodiment, software can be programmed such that no significant hardware need be implemented. For example, the measurement of electrocardiograms through the electrodes on the membrane. Signals obtained by the electrocardiogram allow a user to determine whether the electrode is in contact or not. Algorithms can be employed to determine partial contact as well.

Another method to determine tissue contact with the electrode is to incorporate heat dissipation pattern recognition into the software. A short burst of RF heating can be applied to the electrodes and based on the behavior of heat dissipation the software can recognize whether the electrode is in contact with tissue or is in contact with only blood, for example. A faster dissipation of the heat applied would indicate contact with flowing blood instead of tissue, which would retain the heat longer.

Yet another method to detect tissue contact with the electrode is through impedance measurements. Contact with tissue can show a change in impedance as compared to blood. The amount of contact force may also be assessed through impedance measurements. This allows for proper determination of not only electrode-tissue contact but amount of force in which they are in contact, which could more accurately predict the depth of the energy transmission to be performed. A number of variables (frequency and amplitude) can be adjusted to achieve the desirable threshold and accuracy to determine the difference between tissue and flowing blood.

Figure 41A:
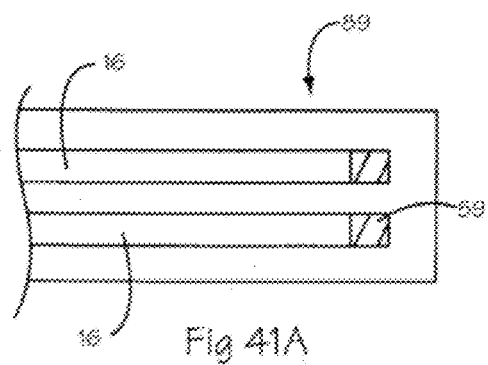
FIGS. 41A-41B illustrates embodiments for sensing tissue contact via impedance measurements.
Figure 41B:
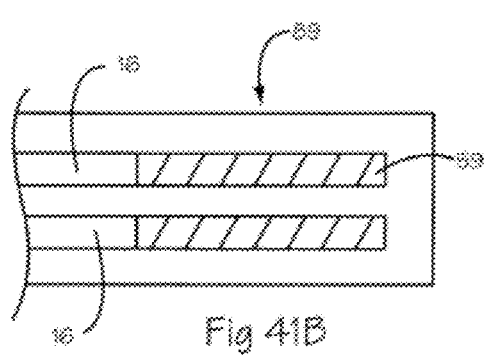

FIGS. 41A-41B illustrate another sensing mechanism using impedance measurements. The flex circuit 89 can contain two conductive traces 16 having non-insulated conductive pads 59 near their distal end and located near or adjacent to the electrodes (not shown), which are in proximity to one another. Impedance can be measured between the two conductive pads 59. In an example, when both conductive pads 59 are in contact with tissue, the impedance measurement will be generally high. When only one conductive pad 59 is in contact with tissue or both ends are not in contact, the impedance measurement will be generally lower. FIG. 41B shows a similar method that allows for larger conductive pads 59. This may allow for partial tissue detection based on a larger range of impedance measurements.

Pressure sensors are known in the art and can be incorporated into the flex circuit. An example is a piezoresistive pressure sensor which can be covered with gel, silicon or another material. Examples of these sensors include GE NPD-240, GE NovaSensor P1602 and Silicon Microstructures SM5102, EPCOS ASB1200V and T5300, and Intersema MS7212. The sensor can be placed on the flex circuits near or at the electrodes.

Figure 41C:
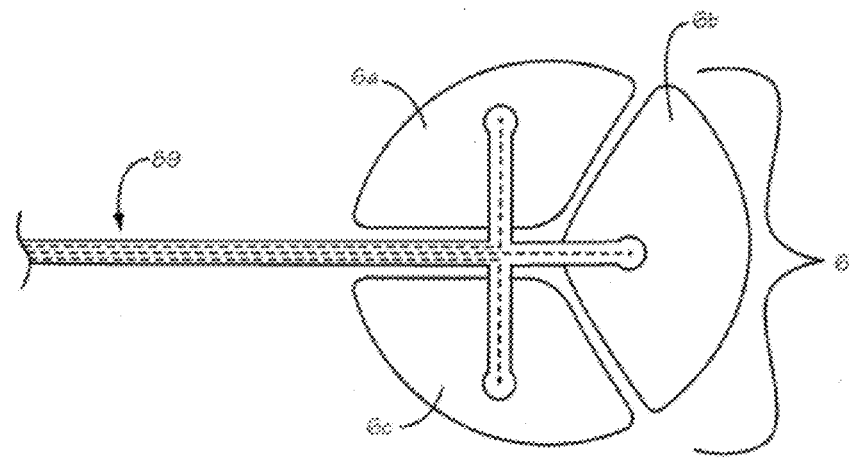
FIGS. 41C-41D illustrate various embodiments of microswitches that can be used to activate electrodes.
Figure 41D:
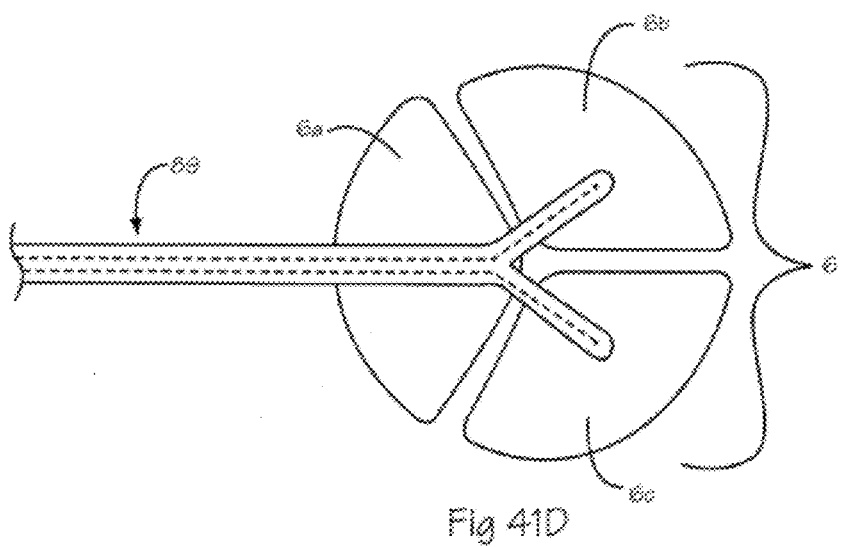

Micro-switches can be located at each electrode, for example with additional hardware and/or software integration. FIGS. 41C and 41D illustrate an example of an electrode 6 broken down into 3 separate conductive patches 6a, 6b, and 6c. Each conductive patch 6a, 6b, and 6c can have a corresponding micro-switch that is physically activated when tissue is in contact with the electrode. The switch and conductive patch are connected when in contact with the tissue. Once all three patches 6a, 6b, and 6c are connected the electrode 6 can be activated. The flex circuit 89 can be arranged differently between the two figures which may define the overall flexibility and foldability of the assembly.

Figure 42:
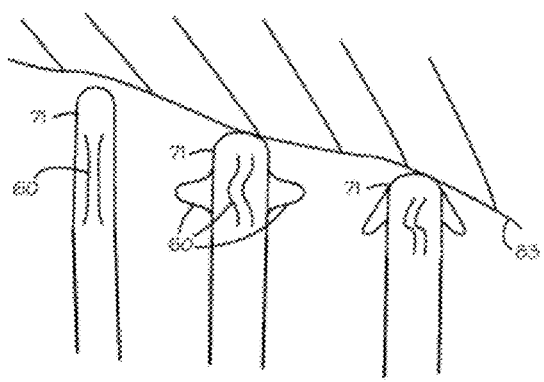
FIG. 42 illustrates an embodiment of a tissue contact assessment mechanism that can be incorporated into the electrode assembly.
Figure 43:
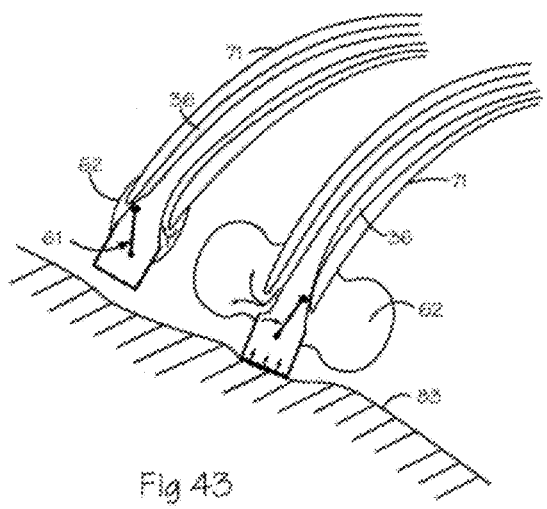
FIG. 43 illustrates another embodiment of a tissue contact assessment mechanism that can be incorporated into the electrode assembly.

In another embodiment shown in FIG. 42, an electrode catheter 71 can incorporate radiopaque, longitudinal "arms" 60 that protrude out when the appropriate amount of pressure is being applied by the electrode catheter 71 against the tissue 83. If there is no pressure exerted against the tissue 83 or not enough pressure being exerted, the electrode catheter 71 has a slender profile with no protrusion of the arms. If too much pressure is being exerted, the arms 60 splay such that they can point backward. A specific shape of the arms can be an indicator of proper contact pressure. FIG. 43 shows an electrode catheter 71 that includes an expandable element 62 such as a balloon that can be controlled by a valve 61 or other fluid-control mechanism. When the appropriate amount of pressure is being exerted by the electrode catheter 71 on the tissue 83, the valve 61 allows the expandable element 62 to be inflated via an inflation lumen 36. Electrodes (not shown) can be placed on the distal tip of the electrode catheter 71 for activation when the expandable element 62 reaches the proper size. The expandable element 62 can be inflated with a radiopaque dye or radiopaque dye can be injected into the bloodstream for visualization.

Electrode Assembly Anchors

The devices described herein can incorporate various structural elements that provide further assistance in the manipulation and repositioning of the electrode assembly without the need for removing the device and reorienting the device. For example, the electrode apparatus can be independently translatable over an anchor catheter or guide element that is fixed in place at or near the target tissue. The anchor can provide a stable reference point and act as an efficient, quick and controlled repositioning device that the electrode assembly can slidably or rotatably move over, for example to contact the ablation pattern region just created. This allows a user to perform additional energy transmissions, for example in areas that did not result in full trans-mural ablation. Or a user can map and verify the effectiveness of the therapy, for example in areas of the tissue that are thicker or require a higher dosage of energy or several passes of energy transmission.

The configuration of the anchor device can vary including, but not limited to, a suction catheter, an expandable member such as a balloon or basket, or suction pods that incorporate electrodes and suction mechanisms simultaneously. In an embodiment where cells outside the pulmonary vein are to be treated, for example in atrial fibrillation, an expandable element can be inserted within the pulmonary vein.

Figure 44A:
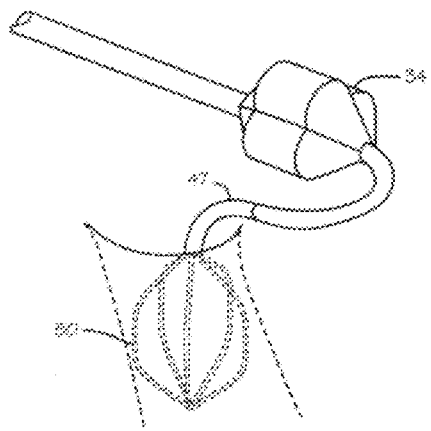
FIGS. 44A-44F illustrate various embodiments of an anchoring system to create ablation lines.
Figure 44B:
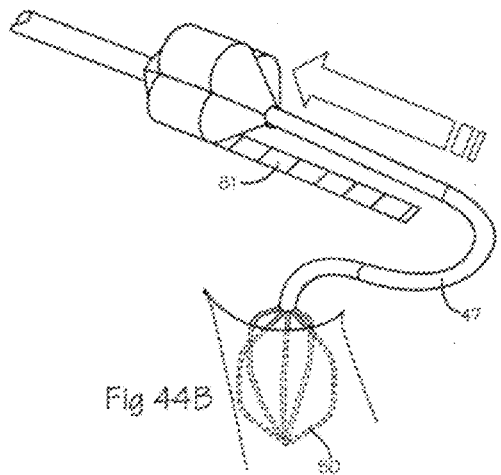
Figure 44C:
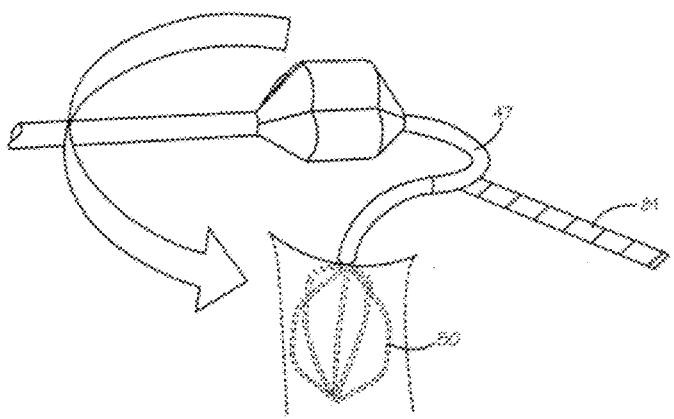
Figure 44D:
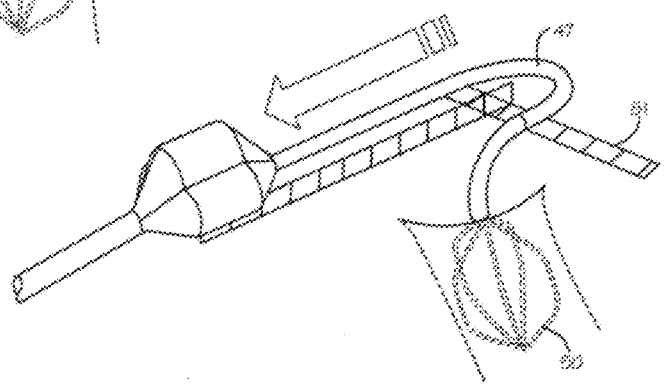
Figure 44E:
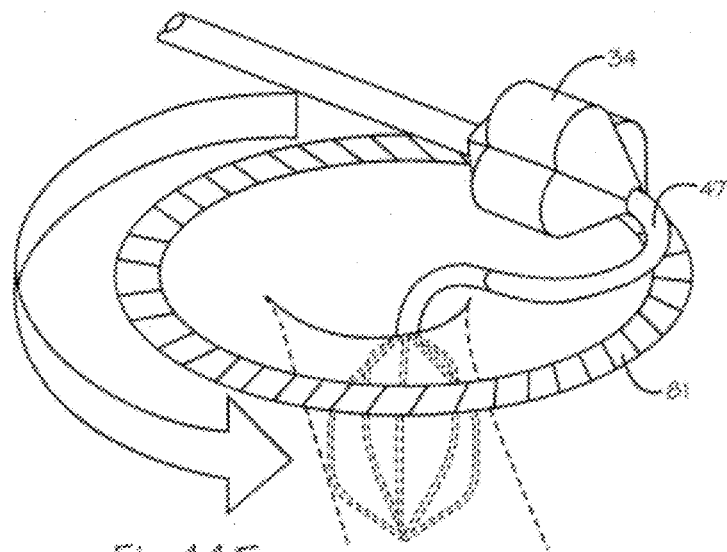
Figure 44F:
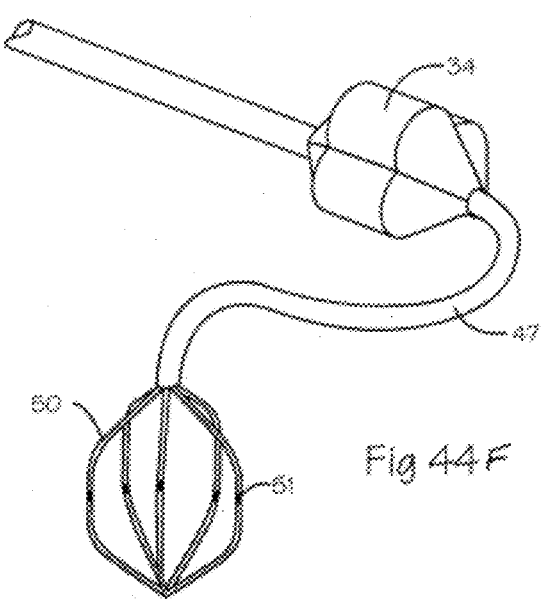

FIGS. 44A-44F show an embodiment of a membrane 34 that includes an anchoring basket 50. The membrane 34 is shown as having a balloon structure, but the membrane 34 can have another shape and configuration as described above such as a single catheter that extends to an anchoring basket 50. FIG. 44A shows a guide 47 (catheter or wire) that can be anchored at the distal end by deploying the anchoring basket 50. The guide 47 can be deployed along the desired line 81. Once the guide 47 is in place and optionally a visualization balloon and scope assembly (not shown) advanced over the guide to confirm correct placement and tissue contact, the membrane 34 can be retracted (or advanced) while activating electrodes to achieve the desired linear lesion 81 (FIG. 44B). After the first linear lesion is made 81, the guide 47 can be rotated around the anchor 50 and re-oriented to create a secondary lesion (FIGS. 44C-44D). Alternatively, a fully or partially circumferential lesion 81 can be created around the antrum of the pulmonary vein or in combination with the linear lesions described above (FIG. 44E). This can be done by maintaining the membrane 34 position relative to the guide 47, and rotating the membrane 34 around the axis of the anchor. Once the desired lesion set is completed, conduction can be tested for example by monitoring electrical potentials via mapping electrodes 51 located on anchor 50 deployed within the pulmonary vein (FIG. 44F) as discussed above.

Figure 45A:
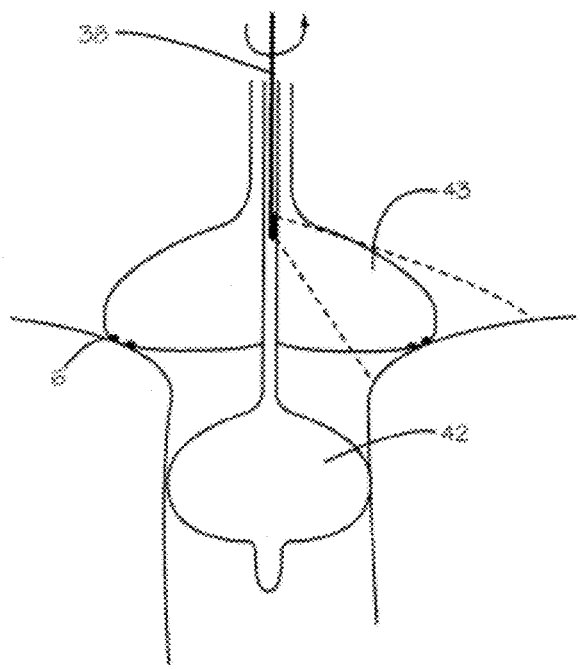
FIGS. 45A-45B illustrate embodiments of an anchoring system for use with an electrode assembly.
Figure 45B:
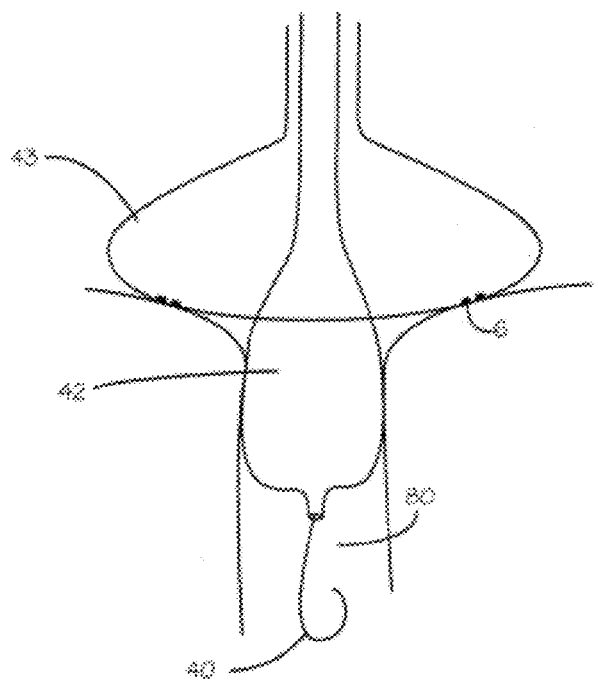

As shown in FIGS. 45A and 45B, the anchor can also have an expandable structure such as a balloon. The anchor 42 can have a variety of shapes. In this embodiment, the anchor 42 can be deployed, for example in the pulmonary vein 80 for anchoring and positioning of an element 43. A guidewire 40 can be introduced in the pulmonary vein 80 to assist in the location of the anchor 42. The electrode element 43 is shown having electrodes 6 on its outer surface and a fiber optic scope 38 that can be rotated for visualization around the circumference of the electrode element 43.

Controlled repositioning mechanisms using suction can also be used such that some portion of the anchor is in contact with the tissue while another portion is being repositioned. In an embodiment, suction tip catheters can be used to anchor the electrode assembly. The suction tip can be deployed within the pulmonary vein. A suction tip 1 can also be used for controlled repositioning of the electrode element. For example, one or more suction regions can be alternately turned on or off to allow a user to guide and move the device, such as an electrode catheter as shown in FIGS. 48A-48B, 49A-49D, 50, 51A-51C, and 52A-52D. Suction can be incorporated with an optional inflatable element to improve energy transmission achieved in addition to anchoring such as shown in FIGS. 44A-44F, 47, 53A-53E, 54A-54D and 55A-55C.

An anchoring catheter 15 can have a suction tip 18 to anchor on the myocardium wall of the pulmonary vein 80 to be used in conjunction with a separate electrode sheath 76 (see FIG. 14A-14B). Alternatively, an electrode sheath 76 can be a single catheter that extends to an anchoring basket distal end 50 or terminates in a suction tip 18. FIGS. 46A-46B and 47, show close-up views of the electrode element having an aspiration lumen 4 and a distal region that has an elliptical, rounded or funnel-shaped suctioning tip 1. The suction tip 1 allows the electrode element to locate and anchor onto an area of the myocardium 83 as well as transmit energy in the same region using electrodes 6. The tissue 83 can be pulled inside the suction tip 1 for anchoring and energy transmission. As shown in FIG. 46A, the electrodes 6 can be used in a bipolar configuration allowing the current 2 to move from one side of the suction tip 1 to the other. Current 2 can pass through the tissue 83 in a pattern similar to lines 2. Alternatively, the electrodes 6 of the electrode element can be used in a monopolar RF energy delivery. The electrodes 6 can be on the inside surface of the suction tip 1 to contact the tissue 83 directly or through a fluid layer such as saline. Irrigation holes 7 and irrigation lumens 8 can be included to reduce the chance of clotting and charring at the electrode site as well as prevent excessive heat build-up. The irrigation holes 7 can be placed on the inside and or outside of the suction tip 1. As shown in FIG. 47, the catheter 71 can be a catheter having a flexible and torque-able shaft that can be laser cut in a puzzle like pattern 3 out of metal or hard polymer. The main flex circuit lead 17 can connect the electrode 6 to the proximal end.

Figure 48A:
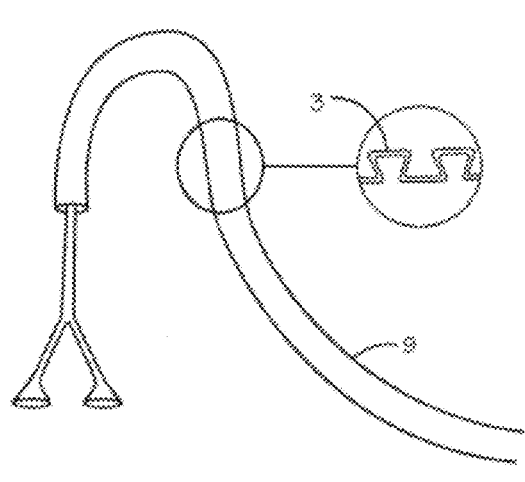
FIGS. 48A-48B illustrate an embodiment of a two arm suction tip anchoring and electrode assembly.
Figure 48B:
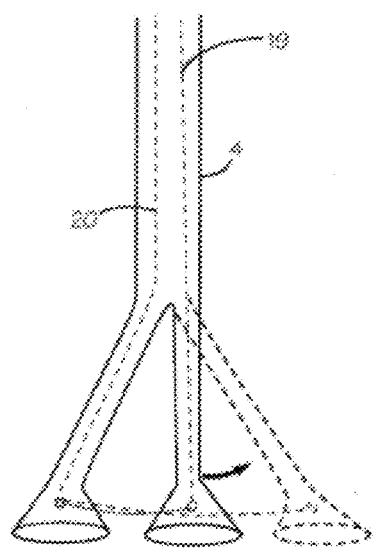

FIG. 48A shows a steerable sheath 9 and a two arm catheter 63 extending from the distal end of the sheath 9. The two arm catheter 63 can include two suction tips 1 each of which can have electrodes to allow RF energy transmission between the two suction tips 1 of the catheter 63. The two suction tips 1 can have a funnel shape each disposed with an electrode 6. The suction tips 1 allow the electrode to be anchored independently. One suction tip 1 of the catheter can anchor onto the tissue, for example by activating the suction, and the other suction tip 1 arm moved to the next target tissue region. Movement can occur by moving the suction tip 1 guided for example by the pre-determined spacing between the tips 1 and a tension wire 20 that can be controlled by the user (see FIG. 48B). The tension wire 20 can be pulled to bring the two tips 1 towards one another. Release or relaxation of the tension wire 20 can allow for the two suction tips 1 to spread apart such as due to a spring force in the material of the tips 1 and/or catheter 63.

Once the catheter 63 is positioned ablation can be initiated. The suction tips 1 can include one or more electrodes and one or more temperature sensors. The two suction tips 1 can be spread apart and suction turned on through both tips 1 before energy is applied. Alternatively, the suction can be turned on for a first tip 1 and then turned on for the second tip 1 before energy is applied. To continue the energy pattern one of the suction tips is turned off and is positioned in another location, for example by rotation or changing the distance between the tips using the tension wire 20. To achieve the desired position, the user can alternately turn on and off either of the tips 1 and orient the catheter 63 as desired. When creating a particular pattern, the use can keep suction active on one of the suction tips 1 and inactive on the tip or tips being moved. The main body of the sheath 9 or the catheter 63 can have great flexibility and torque-ability. The sheath 9 or the catheter 63 can include a laser cut pattern 3 or have a braided shaft that allows for the catheter to maintain one-to-one torque control, such as after taking out the slack, while providing flexibility/bendability and enhance the ease of positioning of the electrodes.

Figures 49A, 49B, 49C, 49D:
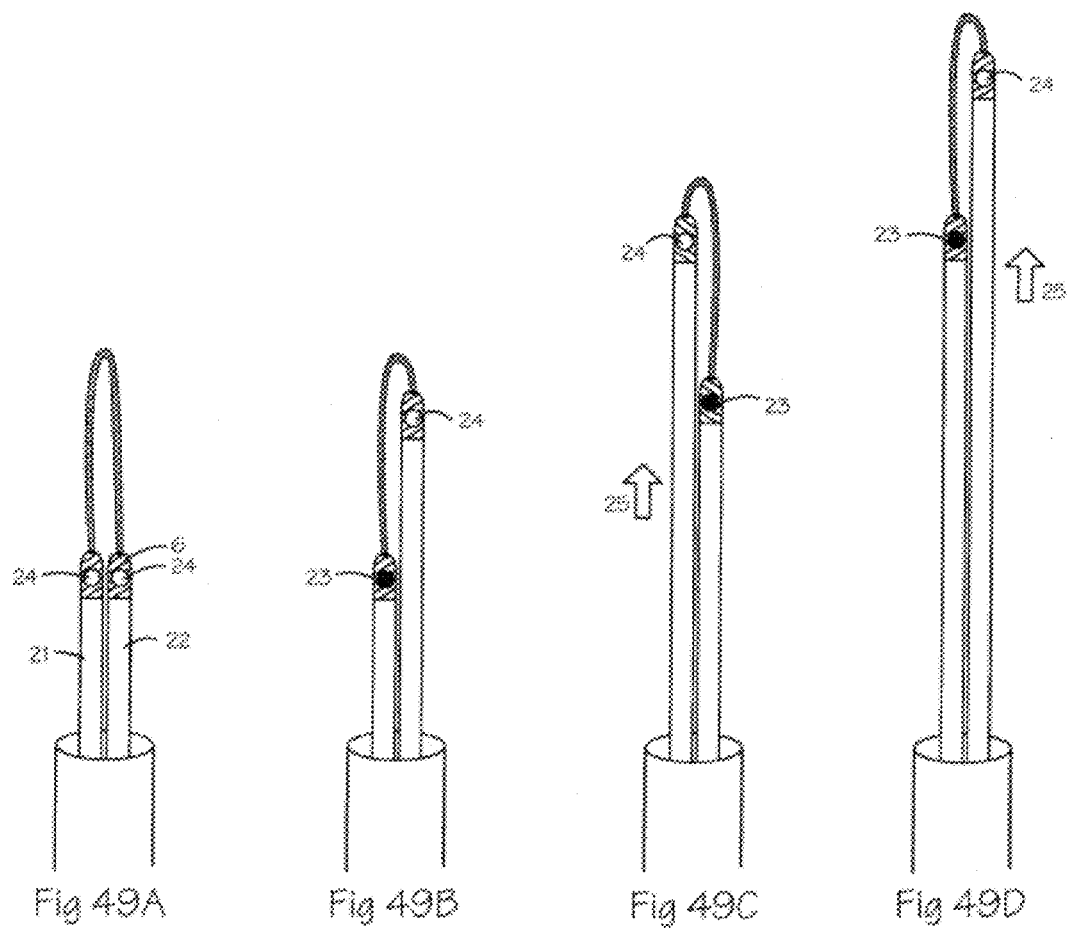
FIGS. 49A-49D illustrate an embodiment of a suction tip anchoring and electrode assembly for creating continuous energy transmission lines.

In another embodiment, the catheter can include suction pods and two control arms. FIGS. 49A-49D show a schematic representation of the suction catheter having two proximal control arms 21, 22. The control arms 21, 22 can be positioned next to each other as shown in FIG. 49A. Motion of the control arms 21, 22 can allow for the catheter to be anchored and positioned as the user desires in a deliberate and repeatable manner. The user can position the catheter in proximity to the region of treatment and turn the suction on through one of the suction holes. FIG. 49A shows both suction holes turned off 24 (shown as a white circles). The suction hole can be turned on 23 (shown as a darkened circle) to anchor to the tissue. The other suction hole can remain turned off 24, for example to allow its associated control arm 22 to be advanced distally (see FIG. 49B). Once positioned, the suction hole is turned on 23 while the other suction hole is turned off 24 and the associated control arm 21 moved in similar fashion (see FIGS. 49C and 49D). The control arms 21, 22 can also be moved in a proximal direction using a similar on-off alternating suction mechanism.

The two control arms 21, 22 can also be concentric or in apposition to each other (e.g., as opposed to linearly displaced) with the inner tip extended distal to the outer. In the concentric embodiment, the inner tip can move distally while the outer tip is anchored. Then the distal tip suction can be turned on and the outer tip is moved until just proximal to the distal tip. The catheter can rotate around the suction pods (i.e. control arms with suction holes) to achieve lateral motion and/or energy transmission. The suction pods can be made out of conductive material or coated with such to act as the electrodes 6. RF current can be passed between each of the suction pods/electrodes to perform the ablation, sensing, stimulating and/or mapping. There can be two or more suction pods/electrodes per catheter.

Figure 50:
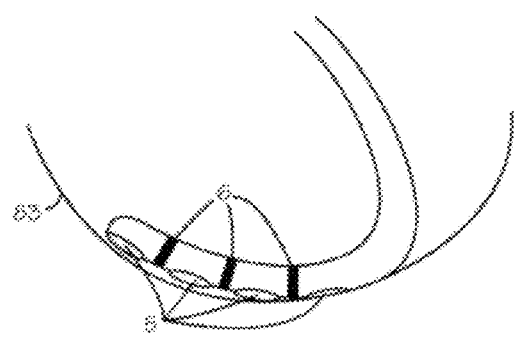
FIG. 50 illustrates an embodiment of a suction anchoring and electrode assembly.

As shown in FIG. 50, the catheter 63 can include suction holes 5 or pods without the use of multi-tipped configuration described above. The catheter 63 can incorporate multiple suction holes 5 and electrodes 6 can be placed adjacent to or near the suction holes 5 to anchor the electrodes 6 to the tissue 83. Movement of the catheter 63 and suction holes 5 along the tissue 83 can occur without the use of cables or tension wires for movement. A long continuous energy transmission line along the tissue 83 can be created.

Figure 51A:
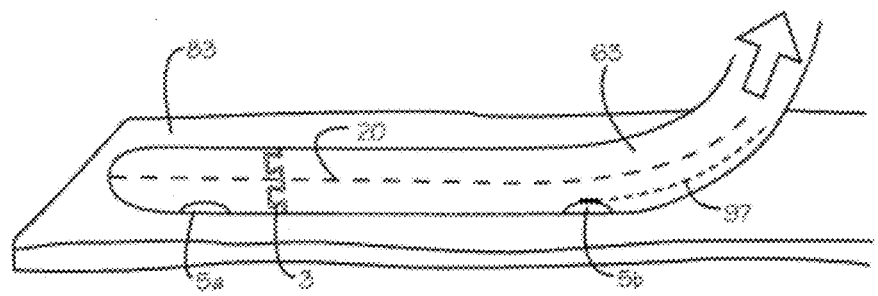
FIGS. 51A-51C illustrate an embodiment of a suction anchoring and electrode assembly for creating continuous energy transmission lines.
Figure 51B:
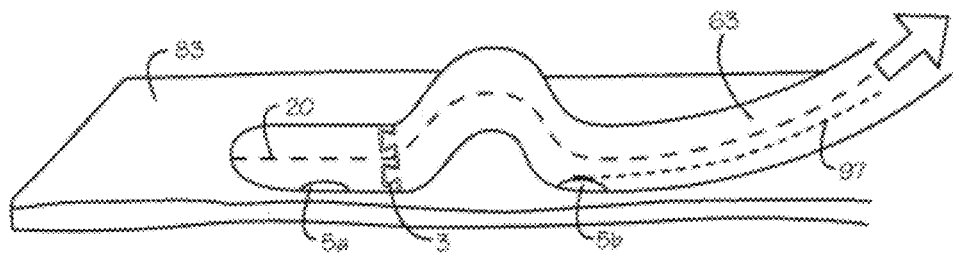
Figure 51C:
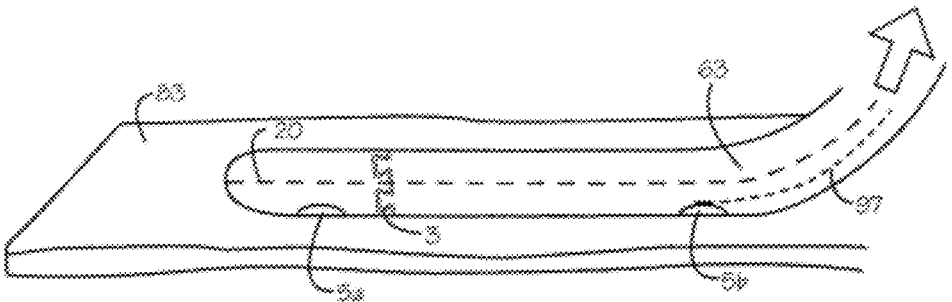
Figure 52A:
FIGS. 52A-52D illustrate an embodiment of an electrode system including an inner suction catheter and an outer electrode catheter.
Figure 52B:
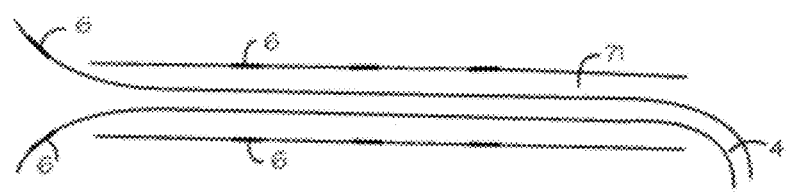
Figure 52C:
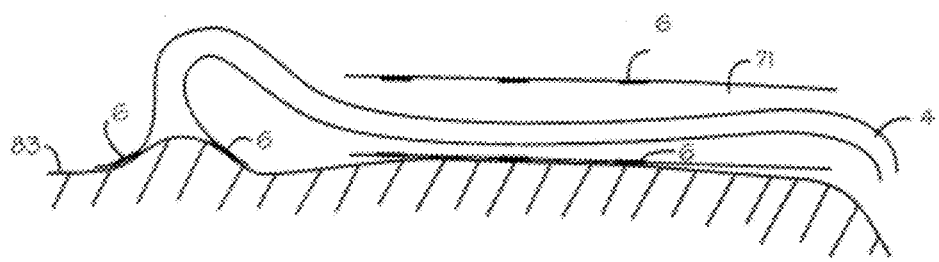
Figure 52D:
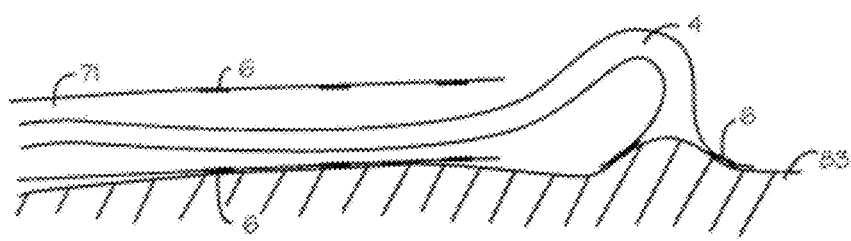
Figure 53A:
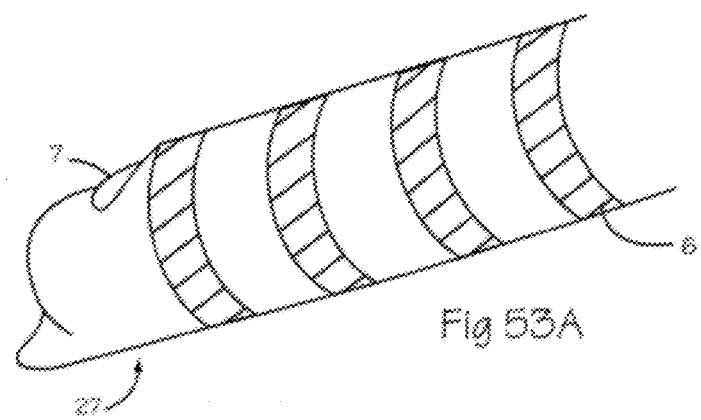
FIGS. 53A-53E illustrate an embodiment of a suction electrode catheter having an expandable region.
Figure 53B:
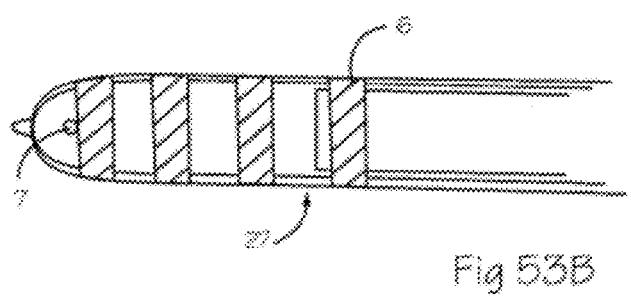
Figure 53C:
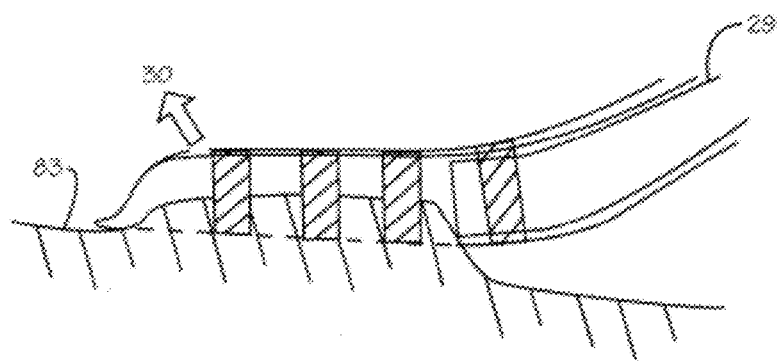
Figure 53D:
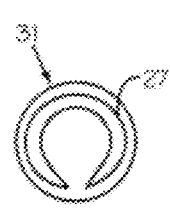
Figure 53E:
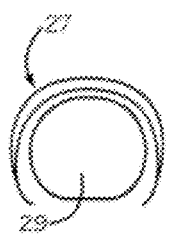

FIGS. 51A-51C show a closer view of the suction catheter 63 creating a long continuous energy transmission line along the tissue 83 and the manipulation of the distal tip of the suction catheter 63. The catheter 63 can be moved over the tissue 83 without losing initial position. The catheter 63 manipulation sequence can vary. In an embodiment, both suction holes 5a, 5b can be turned on such that the catheter 63 is anchored onto the tissue 83 (FIG. 51A). The suction in the distal hole 5a can be turned off and a pull wire 20 withdrawn proximally to bend the catheter 63 and cause a backward motion (FIG. 51B). Suction can then be turned on in the distal hole 5a and turned off in the proximal hole 5b to allow the catheter 63 to straighten out (FIG. 51C). The suction can then be turned on in the proximal hole 5b and energy transmission initiated. This process can be repeated to create an energy transmission line in a first direction (e.g. proximally). Suction can also be activated in the opposite manner such that the catheter is moved forward (e.g. distally). The catheter 63 can include a laser cut pattern 3, for example between each suction hole 5a, 5b that increases flexibility and allows for lateral movement of the catheter 63.

In an alternate design, suction can be turned on to maintain the position but not for anchoring the catheter 63 for movement. In this embodiment, the push element 97 can be used as an alternative to suction forces to oppose the pull force provided by the pull wire 20 to bring the distal tip closer to the proximal tip as shown in FIG. 51B. The push element 97 can also be used to straighten the catheter 63 or to orient it using the flexible laser cut pattern 3.

FIGS. 52A-52D illustrate another example of an electrode system including a concentric inner suction catheter 4 and an outer electrode catheter 71. The inner catheter incorporating suction lumen 4 can be movable and steerable and can extend beyond the distal tip of the electrode catheter 71. Once the suction tip is firmly anchored onto the tissue 83, the electrode catheter 71 can be manipulated to be in contact against the tissue 83. Electrodes 6 can be mounted on the electrode catheter 71 and can also be mounted at the tip of the suction catheter 4. After an energy transmission line is created the electrode catheter 71 can pivot or swivel around the suction catheter tip 4 and transmit energy to the opposite side without losing its initial position. An irrigation mechanism can be included and used in conjunction with the electrode system to keep the tissue cool during the procedure as described above.

FIGS. 53A-53E illustrate another embodiment of a suction catheter that includes an expandable portion. The electrode catheter 27 can include a single aspiration lumen and a movable inner shaft 29. The electrode catheter 27 has an internal lumen with multiple openings which the movable inner shaft 29 can translate over and cover. In this manner, the inner shaft 29 can selectively control the amount of suction by covering the specific sections of the catheter 27. In this embodiment, no separate suction lumen need be connected to each of the aspiration ends all the way back to the handle. The catheter 27 can be contained within an outer sheath 31 for ease in delivery (see FIG. 53D). The main body of the electrode catheter 27 (between the outer sheath 31 and the retractable shaft 29) can be made of a flexible or super-elastic material such as Nitinol or other material. Also, shown in this embodiment is a mechanism that allows for the passage of a cooling fluid onto the surface of the catheter through holes 7 to cool the electrodes 6 and the surrounding tissue 83. Saline 30 can be used for irrigation through the holes 7 also as described in more detail above.

Figure 54A:
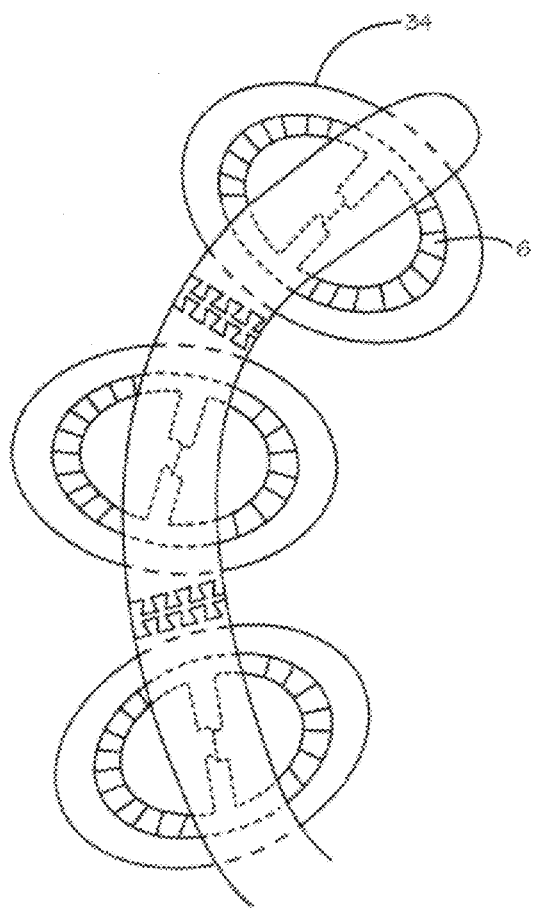
FIGS. 54A-54D illustrate an embodiment of a suction electrode catheter having more than one expandable region.
Figures 54B, 54C, 54D:
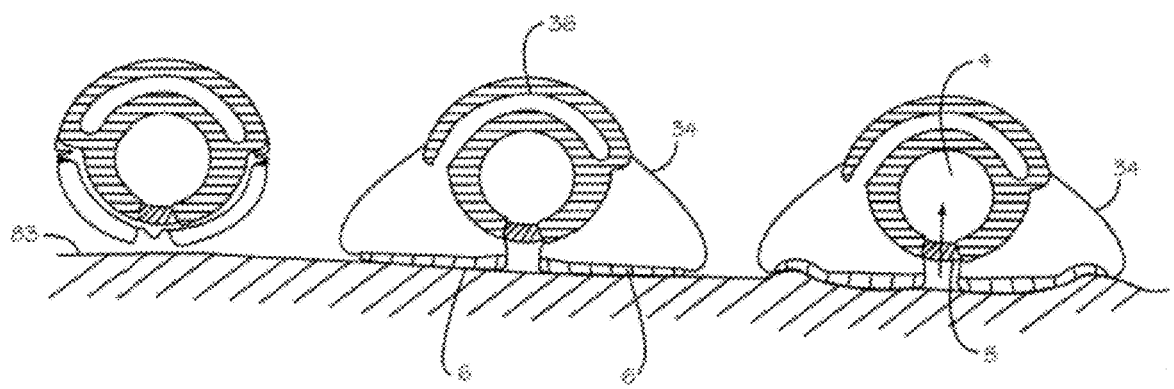

FIGS. 54A-54D show another embodiment of a suction electrode catheter that includes an expandable portion. In this embodiment, the catheter electrode system includes inflatable elements 34 having electrodes 6 disposed thereon, such as on the surface of the inflatable elements 34. The inflatable elements 34 can be an inflatable balloon with a corresponding inflation lumen(s) 36. A suction lumen 4 and corresponding suction holes 5 can form multiple suction pods 67 disposed along the length of the catheter at various intervals that stabilize the catheter and assure good contact with the target tissue to be ablated, for example a moving target tissue such as the myocardium. The catheter between each suction pod 67 can include a laser cut pattern 3 for increased flexibility in positioning of the electrodes, as described herein. FIGS. 54B-54D show the various stages of the catheter from pre-inflation to fully inflated and engaged with the tissue.

Figure 55A:
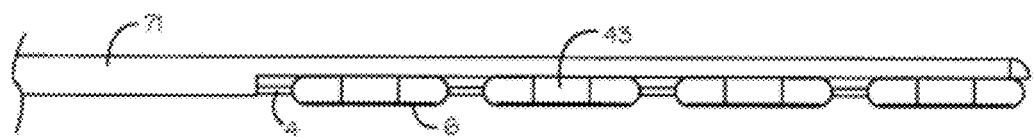
FIGS. 55A-55C illustrate an embodiment of a suction electrode catheter having more than one expandable region.
Figure 55B:
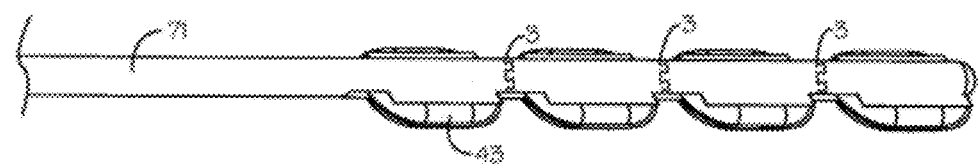
Figure 55C:
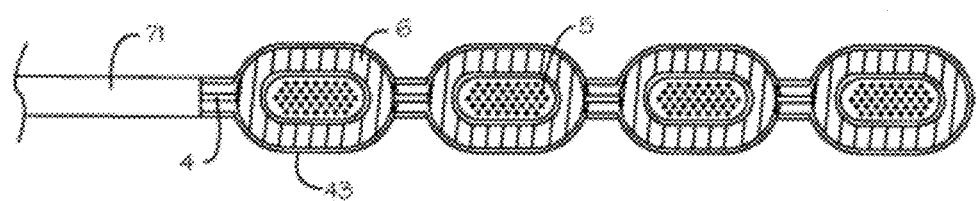

FIGS. 55A-55C show another embodiment of a suction electrode catheter that includes an expandable portion. The catheter electrode system can include expandable elements 43 having electrodes 6 disposed thereon. The linear electrode catheter 71 can use a combination of expandable elements 43 and aspiration to anchor the device and transmit energy to the target tissue. The expandable elements 43 can be flexible membranes or balloons having electrodes 6 of electro-conductive ink deposited thereon as described above. The expandable elements 43 can be shaped to create an opening to the tissue when inflated and allow for aspiration and anchoring. An aspiration lumen 4 can connect each of the expandable elements 43 and can be controlled at the handle (not shown). A retractable shaft can be used to control suction of the individual suction pods. In another embodiment, each suction pod can be individually controlled via separate aspiration lumens. The aspiration holes 5 create a gap between the aspiration lumen 4 and the tissue. This separation allows for the tissue to be drawn into the opening of the expandable element 43 and be in full contact with the electrodes 6 without blocking flow to the aspiration lumen 4 itself. The distal end of electrode catheter 71 can be flexible between each suction pod or may include a laser cut pattern 3 and can be manipulated for best apposition to the tissue. Irrigation holes (not shown) can also be included at each suction pod to allow for saline to flow through and prevent clotting of blood in the suction pods. An electrode assembly 105 that includes one or more suctions elements can be used to treat the internal space of an organ target tissue via electrodes positioned inside or outside the organ. For example, for treatment of atrial fibrillation within the left atrium, the electrode assembly can produce endocardial or epicardial ablation lesion lines.

Figure 56A:
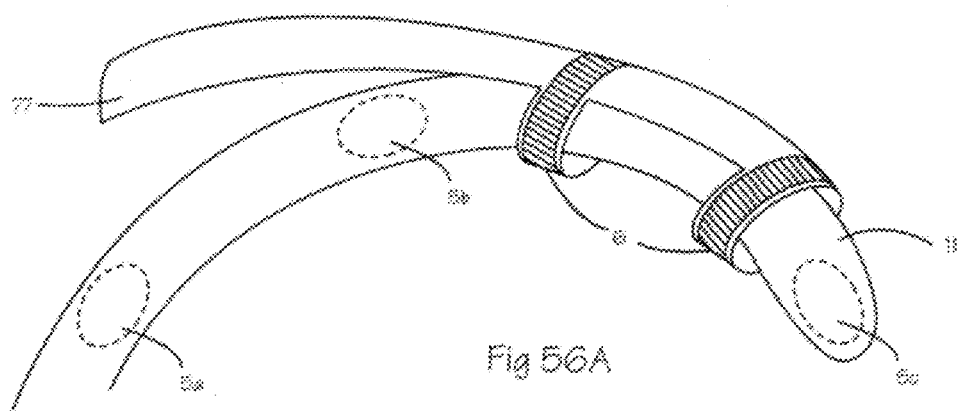
FIGS. 56A-56E illustrate various embodiments of a rapid exchange electrode sheath and anchoring catheter.
Figure 56B:
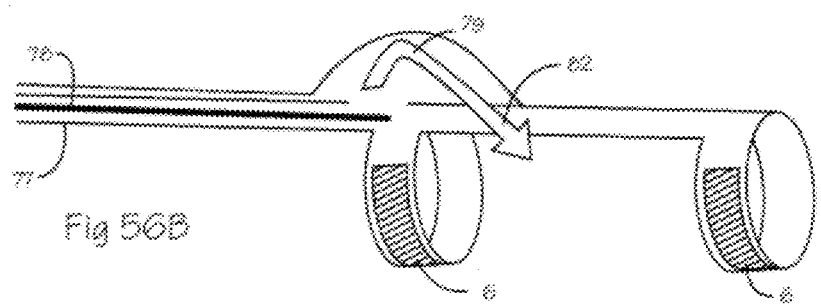
Figure 56C:
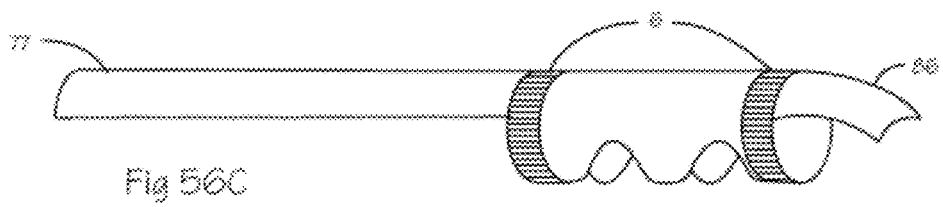

FIGS. 56A-56E illustrate various embodiments of a rapid exchange electrode sheath 77 that can be positioned over an anchoring catheter 11 that is fixed to the tissue via suction holes 5a, 5b, 5c as described in embodiments above. In this embodiment, the electrode catheter 77 can have one or more rings 64 near the distal end through which the anchoring catheter 11 can extend. These rings 64 as well as the proximal portion of the electrode catheter 77 can be oriented such that they do not obstruct the suction holes 5a, 5b, 5c as shown in FIG. 56A. It should be appreciated that although only three suction holes are depicted in the figure, more or fewer suction holes are considered herein. FIG. 56B shows the electrodes 6 coupled to an anterior portion of one or more of the rings 64 of the catheter 77 to minimize interference with the suction holes 5a, 5b, and 5c. An expandable element 66 can be included that has an inside reflecting surface 79 to allow for vision through a fiberscope 78 with an angle of view 82 towards the tissue. The reflecting surface 79 can have holes (not shown) that allow for a mechanism such as a water jet to contact the tissue and provide a clear field of view for the fiberscope 78. Although a reflecting surface 79 and water jet are depicted, it should be appreciated that vision can be accomplished with the use of only the fiberscope 78. FIG. 56C shows an electrode catheter 77 having a distal curved tip 86 that can press in a downward direction on the anchoring catheter 11. This mechanism helps to keep the suction hole(s) 5a, 5b, 5c against the tissue and to provide for a better anchoring.

Figure 56D:
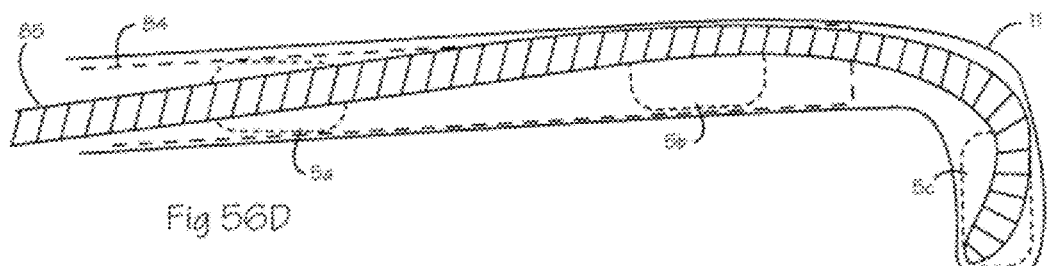
Figure 56E:
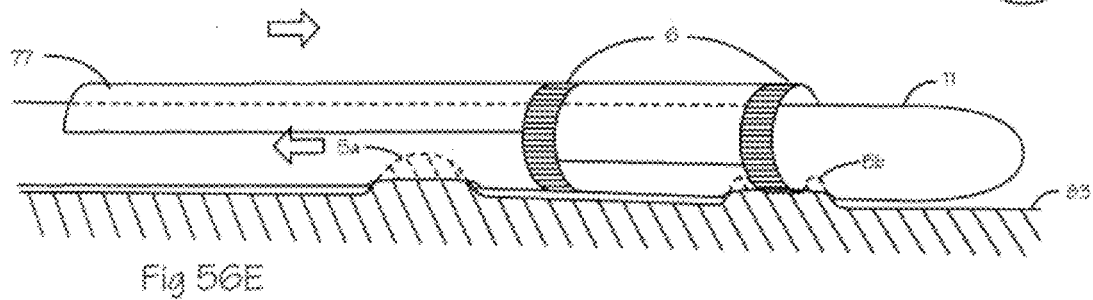

FIG. 56D shows a guiding wire 85 extending through the anchoring catheter 11 that can be used to orient the anchoring catheter 11 to an optimal or better place for the suction holes 5a, 5b, and 5c to press against the tissue. As mentioned in previous embodiments, the anchoring catheter 11 can be flexible with little torque resistance to enhance its ability to orient the suction holes 5a, 5b, and 5c against the surface of the tissue at a variety of angles. The anchoring catheter 11 can also include a retractable hollow shaft 84 to provide more rigidity and torque control for placing the suction holes 5a, 5b, 5c against the tissue. In an example, a user can orient the wire 85 to obtain contact and anchoring of the most distal suction hole 5c against the tissue. The user can pull back and rotate the shaft 84 in combination with manipulating the wire 85 to orient the second most distal suction hole 5b to contact and engage with the tissue. The next most proximal hole 5a can be similarly oriented and the shaft retracted to allow for all the suction holes 5a, 5b, 5c to be actively anchored against the tissue. Once the anchoring catheter 11 is properly oriented and stable, the electrode catheter 77 can be advanced and retracted over the suction holes 5 without loosing adhesion against the tissue. This provides for a quicker and more efficient energy transmission, for example for the purpose of ablation and mapping. FIG. 56E shows the electrode catheter 77 movement relative to the anchoring catheter 11 against the tissue 83.

Methods of Manufacture and Materials

Various techniques can be employed in the manufacture of the devices described herein. In an embodiment, the flex circuit 89 can be constructed to optimize for an overall low profile of the electrode assembly 105. The flex circuit 89 can have temperature sensors 90 that can be powered through one of the conductive traces 16 of the flex circuit 89. This eliminates the need for an additional assembly junction on the membrane 64. The temperature sensors 90 can share a conductive trace 16 with a mapping electrode 51. Sharing the conductive traces 16 allows for narrower flex circuits 89 and an overall lower profile of the electrode assembly 105. A single flex circuit 89 can split into at least two branches 87 to reduce the number of parts and ease of assembly. There can be only one flex circuit 89 that splits into all the branches 87 of the flex circuit 89 needed to power the electrodes 6. The distal end of the flex circuit branches 87 can contain sacrificial tabs 102 that allow for proper positioning of the branches of the flex circuit 89 during assembly.

The flex circuit main leads 17 of the flex circuits 89 can be routed from the proximal end (near a handle or actuator) of a catheter shaft 57 through the catheter lumen to the distal end. The flex circuit main leads 17 can divide into two or more branches 87 and can be folded over the membrane 34 from either a proximal region or a distal region of the membrane 34. The membrane 34 can be mounted on a temporary mandrel support with inflation ports to maintain a constant expanded state during assembly. The flex circuit sacrificial tabs 102 can be mated to an assembly fixture for consistent tensioning of all branches of the flex circuit. The fixture can be designed to hold the membrane 34 and the flex circuit 89 in a pre-determined position relative to the other. For a streamlined bond of the flex circuit 89 to the membrane 34, the flex circuit branches 87 can be pressed firmly against the membrane 34 surface while an agent, such as adhesive, is applied and cured. This can minimize the profile due to, for example, an excessive amount of agent applied. Adhesive can be applied to the underneath surface or bottom substrate layer of the flex circuit 89, which will be in contact with the membrane 34. This can be accomplished through the use of a robotic system, which can apply precise amounts of adhesive at appropriate locations on the flex circuit 89.

Figure 59:
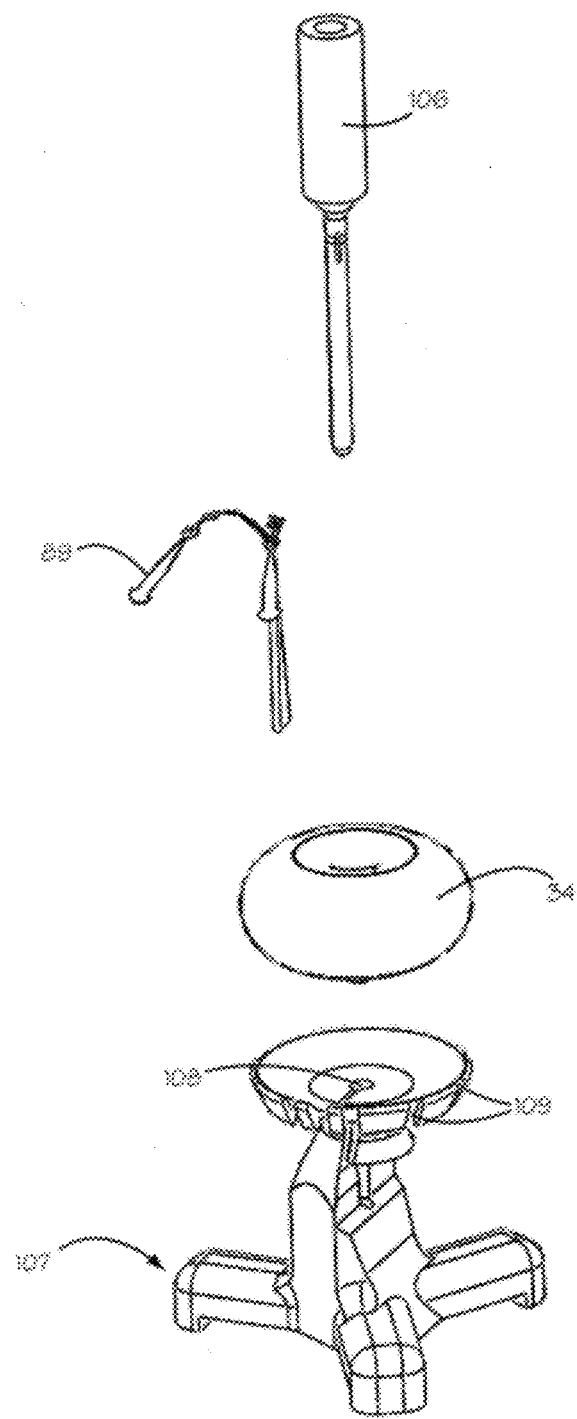
FIG. 59 illustrates a device that can be used to assemble the electrode assembly.

As shown in FIG. 59, the assembly fixture can include a centering and inflation pin 106 and the fixture base 107. The flex circuit 89 can be inserted through a central slot 108 in the fixture base 107 and the branches 87 directed to their respective radial pattern slots 109. The membrane 34, a toroid-shaped balloon in this example, can be mounted on the centering and inflation pin 106 and the pin is inserted through the center slot 108 of the fixture base 107 and secured in place. A regulated, low pressure air supply can be used to inflate the membrane 34 to the desired level once on the fixture 107. The sacrificial tabs 102 of the flex circuit 89 can be mated to the radially-spaced slots 109 of the perimeter of the fixture base 107, maintaining a consistent position of the flex circuit 89 relative to the expandable membrane 34. Once the flex circuit 89 and the membrane 34 are properly located and secured, the agent can be applied and cured.

In FIGS. 61A-61C, 62A and 62B are illustrated various means by which catheter shafts may be interfaced to the expandable membranes 34 associated with the electrode assembly 105. FIG. 61A and detailed views FIGS. 61B and 61C illustrate how the outer diameter (OD) of an inner shaft 134 and an outer shaft 57 may be interfaced to the various surfaces of an expandable member 34. In FIG. 61B is illustrated an expanded view of an interface in which the outer surface 135 of the expandable membrane 34 is interfaced to the OD of the inner shaft 134 and the inner surface of the expandable membrane 34 is interfaced with the OD of outer shaft 57. In FIG. 61C the interface to the outer shaft remains the same as that illustrated in FIG. 61B, however the inner surface of expandable membrane 34 is interfaced with the OD of inner shaft 134. Although not shown, a single shaft may also be used to interface with the distal and proximal interfaces of the expandable membrane 34. In this embodiment, a spacer can be used at the distal end. Alternatively, both interfaces on the expandable structure can be fabricated at the same inner diameter (ID).

FIGS. 62A and 62B illustrate the interface of FIG. 61B where the expandable member portion of the interface incorporates a thickened section 35. FIGS. 63A and 63B illustrate the interface of FIG. 61C where the where the expandable member portion of the interface incorporates a thickened section 35 and additional structure associated with the electrode assembly 105 are also incorporated. The interface of FIGS. 63A-63C has particular advantage when presenting electrodes on the distal surface of the electrode assembly 105 as all portions of the shaft to which the expandable member 34 is interfaced reside proximal to the distal end of the shafts on inflation or a portion of the expandable member 34 is substantially distal to the distal end of the assembly or the distal end of the shaft.

The electrodes 6 can be sprayed onto the flex circuit 89 and membrane 34 while still mounted on the temporary support mandrel. The electrodes 6 can cover each conductive pad 59 for electrical connection to the flex circuit trace 16 and a relatively large portion of the surrounding membrane 34 surface and over the insulated portions of the flex circuit 89 itself. The electrodes 6 can be formed by using a mask over the membrane 34 during the deposition process, which can spray over the membrane and the mask alike. Once the ink is cured, the mask can be removed. An alternate technique is to use automated robotic systems which may be programmed to precisely and accurately spray only the desired electrode surfaces without the presence of a mask.

The electrodes 6 can be formed before or after the flex circuit is bonded to the base membrane structure. FIG. 2A shows an electrode 6 deposited onto the membrane 34 first. The trace 16 of the flex circuit 89 can be laid over the membrane 34 with the conductive pad 59 positioned directly over the electrode 6. An electrically conductive adhesive layer 95 can be laid over portions of the electrode 6 to adhere to the exposed conductive layer 96. Non-conductive adhesive 95 can be used to bond to the rest of the membrane 34 and trace 16. FIG. 2B shows that the trace 16 can be first bonded to the membrane 34 using an adhesive which does not need to be conductive. The conductive pad 59 can face outward from the membrane 34 surface such that it is not in direct contact with the membrane 34. The electrode 6 can then be laid over the conductive pad 59, the adjacent insulated flex circuit 89 portion, and the membrane 34.

FIG. 2C shows the trace 16 of the flex circuit 89 traveling from inside the membrane 34 through the membrane surface. The electrode 6 can alternatively be placed first, in which case the exposed conductive pad 59 of the trace 16 can face inwards to be in contact with the electrode 6. FIG. 2D shows the flex circuit 89 manufactured at the same time as the membrane 34. As shown, a layer of membrane 34 material can be the inner-most layer, followed by placement of the flex circuit 89 and traces 16 with the exposed conductive pad 59 facing out. The conductive pad 59 of the trace 16 can be masked to deposit the remaining layers of membrane material to encapsulate the flex circuit 89. Lastly, the electrode 6 can be laid over the exposed conductive pad 59 of the trace 16 and the membrane 34. The electrode 6 in this embodiment can also be a polymer impregnated with conductive material. FIG. 2E shows an embodiment where the electrode 6 is manufactured at the same time as the membrane 34. The electrode 6 can be embedded with the membrane 34 layer and the electrode material may be impregnated with the membrane material to enhance adherence. The trace 16 can then be placed over the electrode 6 with the exposed conductive pad 59 in contact with the electrode 6.

Methods of Use

As described previously, the devices and method described herein are not limited to use for atrial fibrillation. It should be appreciated that the following is for example only and that other indications are considered herein.

The devices described herein can be used for the ablation of the myocardium, for example for the treatment of atrial fibrillation. The pulmonary veins, which are known to cause irregular signals, can be electrically isolated from the rest of the atrium. Aberrant tissue on other areas of the atrium that can cause irregular electrical signals can be found and ablated. The electrode assemblies described herein can conform to the different anatomical sites within the atrium to electrically eliminate these abnormal signals. In an embodiment, the electrode assembly for use in treating atrial fibrillation includes a balloon shaped membrane in the shape of a sphere or a toroid allowing for large diameter to be positioned against the antrum of the pulmonary vein for circumferential lesions. Another site where such electrode assemblies have application is in the treatment of mitral prolapse. In this treatment the electrode structure may delivered to the mitral valve, inflated, such that the electrode structures interface with the annulus of the mitral valve. When lesions are induced in the annulus of the mitral valve, the collagenous tissues comprising the annulus will shrink. Such treatments are effected by other means with the outcome of decreasing mitral valve regurgitation. Such a treatment can be useful in any of the valves of the heart. Alternatively, an electrode assembly incorporating a cylindrical balloon shaped membrane element may be used to treat atrial fibrillation within the pulmonary vein, where a helical lesion pattern can be used to advantage as a means of limiting stenosis resultant from the ablative injury. Yet another site where such a configuration has particular advantage is in the treatment of hyper tension by ablating sympathetic nerves peripheral to the renal arteries. The ability to create a helical lesion within the renal artery without requiring repositioning of the electrode structure, either by activation of a set of helically arrayed electrodes or addressing a subset of a rectilinear array to create a helical lesion as described herein has advantage over the art presently in use. With reference to the luminal treatments just described, patterns other the helical lesion can provide the same outcome. Such patterns are those in which the projection of lesions on a plane normal to the long axis of the treatment lumen create a complete circle of overlapping regions.

Figure 57A:
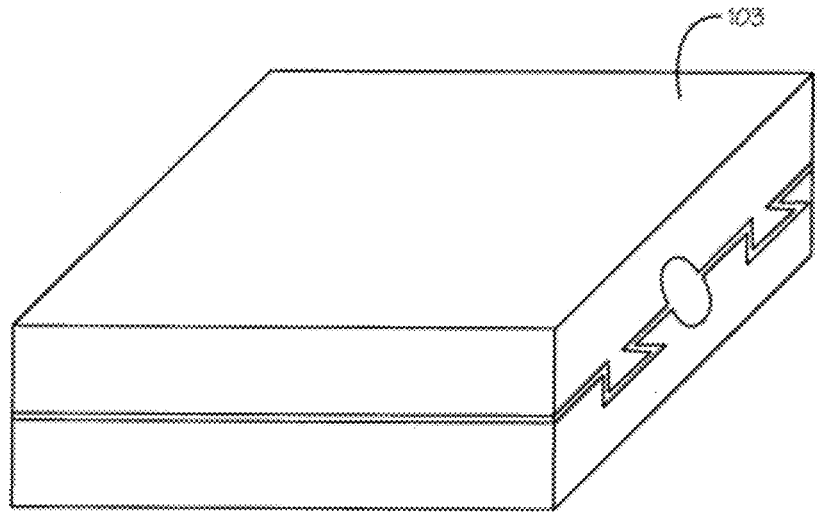
FIGS. 57A-57C illustrate a sheathing device that can be used to sheath an electrode assembly for minimally-invasive delivery.
Figure 57B:
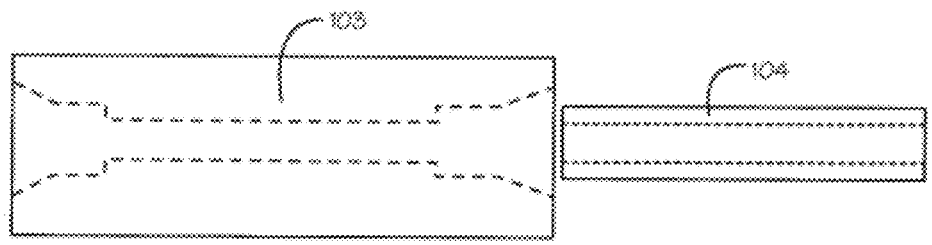
Figure 57C:
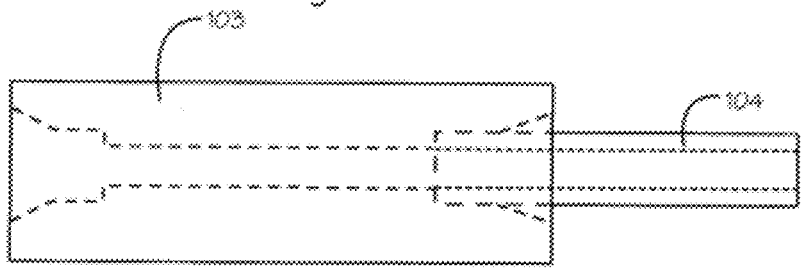
Figure 58A:
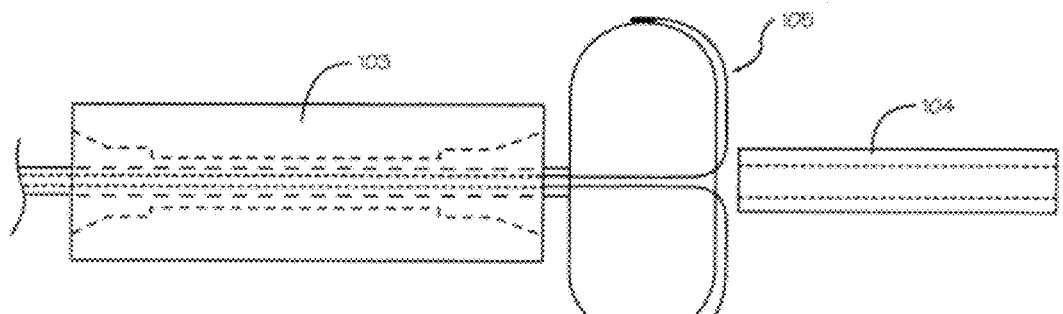
FIGS. 58A-58K illustrate a method of sheathing the electrode assembly for minimally-invasive delivery.
Figure 58B:
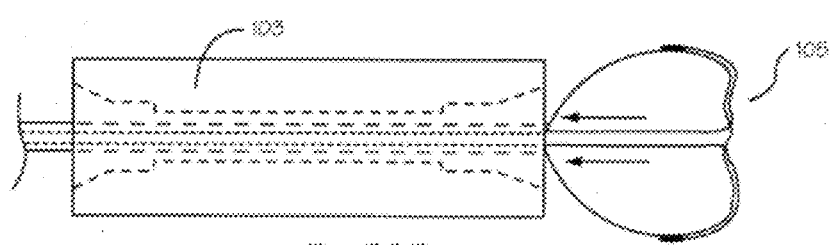
Figure 58C:
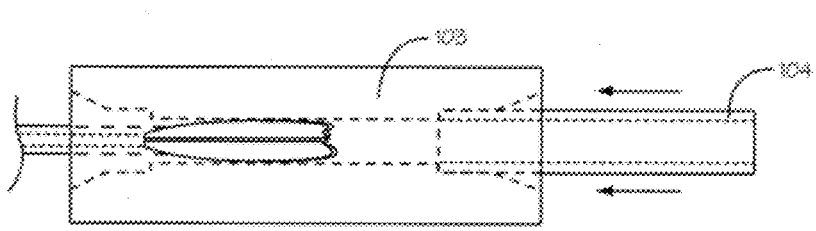
Figure 58D:
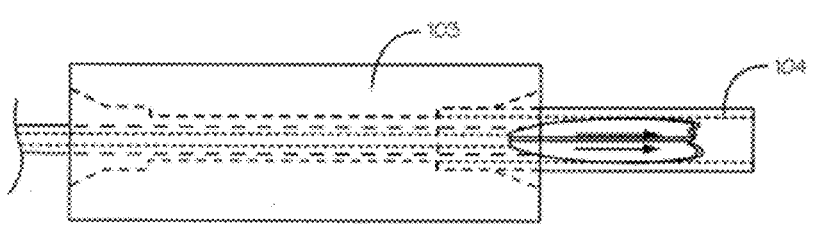
Figure 58E:
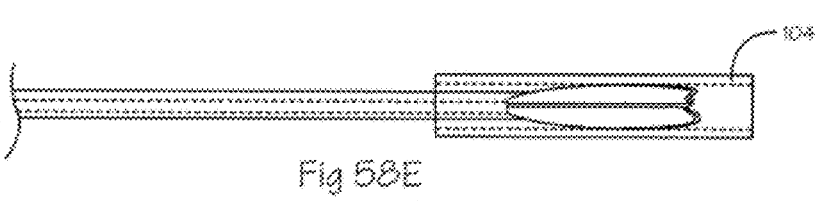

In an embodiment, the electrode assembly 105 can be sheathed using a sheathing fixture 103 and introduced into a sheath that is placed at the appropriate entry point, the femoral vein for example (see FIGS. 57A-57C). The sheathing fixture 103 can be a block with a predefined internal diameter for the electrode assembly 105. The fixture 103 can be manufactured as two halves that are slidable and interlockable to each other as shown in FIG. 57A. A sheathing tube 104 can be used in conjunction with the sheathing fixture 103 in that the tube 104 can slide into the sheathing fixture 103 until it reaches a hard stop as shown in FIGS. 57B and 57C. The inner diameter of the tube 104 can match that of the fixture 103. To sheath the ablation assembly 105, the catheter can be placed within the sheathing fixture 103 such that the assembly 105 is outside of the fixture 103 at one end as shown in FIG. 58A. The shaft 57 can also be placed with the two halves of the sheathing fixture 103 still separated. The assembly 105 can be pulled into the inner portion of the sheathing fixture 103. The tube 104 can be inserted into the fixture 103 until it reaches a hard stop. The shaft 57 and the electrode assembly 105 can be pushed into the tube 104 and seated within the tube 104. Once the assembly 105 and shaft 57 are securely sheathed into the tube 104, the fixture 103 can be removed from the assembly 105 by separating the two halves of the sheathing fixture 103. The sheathing tube 104 can be to introduce the assembly 105 into a sheath that is placed to reach the desired target tissue. The assembly 105 is then pushed out of the sheathing tube 104 and travels within the introducer to reach the target site. The sheathing tube 104 remains proximal to the assembly and does not travel within the introducer sheath 117.

Figure 58F:
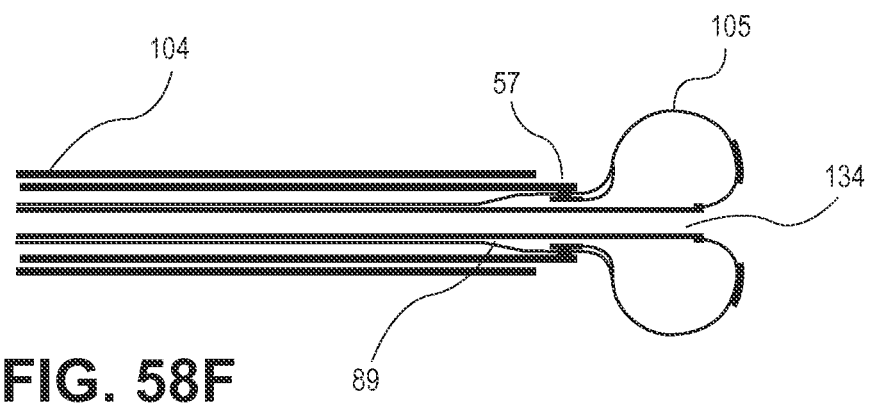
Figure 58G:
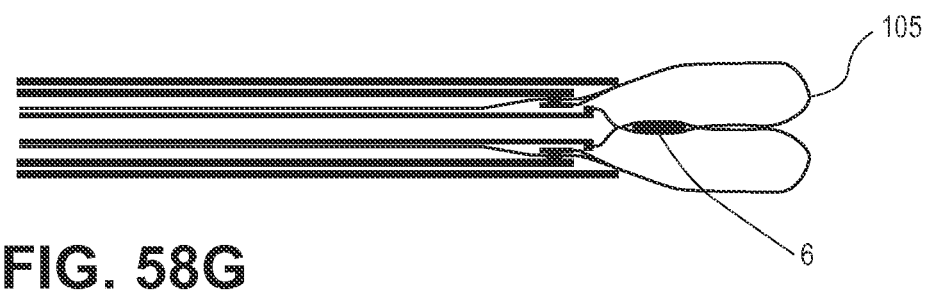
Figure 58H:
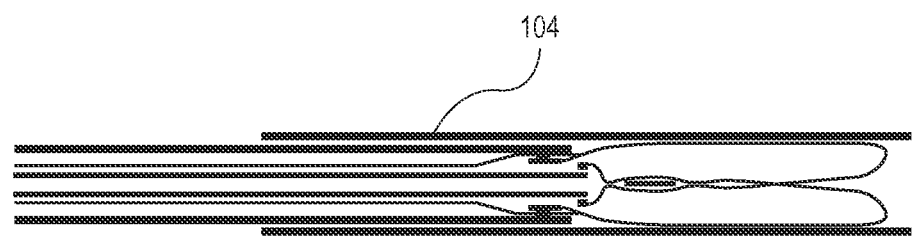

An alternate means of sheathing prior to introduction to the introducer is illustrated in FIGS. 58F-58H. The three primary stages of this process are represented in FIGS. 58F-58H and are described as follows. In this embodiment an alternate sheathing tube 128 is mounted on the outer shaft 57 at the time of manufacture as shown in FIG. 58F. The sheathing tube 128 and assembly 105 are moved relative to one another such that assembly 105 is collapsed by alternate sheathing tube 128 as indicated in FIG. 58G. As the relative motions are continued electrode assembly 105 is captured and contained within the alternate sheathing tube as shown in FIG. 58H. The alternate sheathing tube 128 and electrode assembly 105 are then introduced through an introducer valve 126 into the introducer sheath 127. Sheathing tube 128 may be a short section which interfaces with the proximal section of outer shaft 57, or may be close to the entire length of the outer shaft 57 such that it can be operated from the handle and can be used while the electrode assembly 105 is resident in within the luminal system under treatment.

Figure 58I:
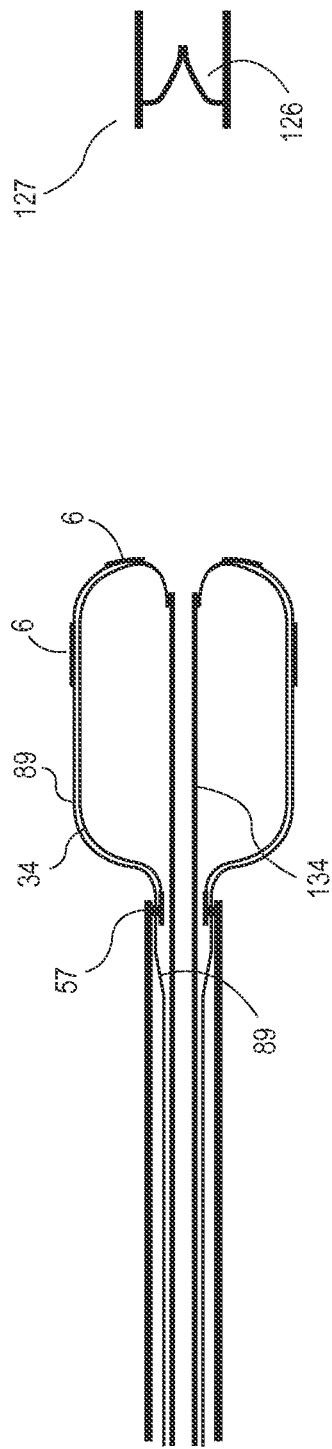
Figure 58J:
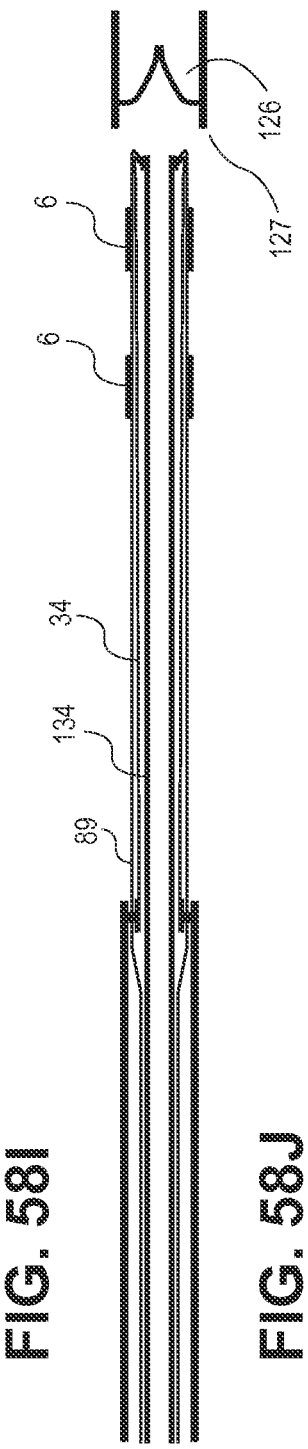
Figure 58K:
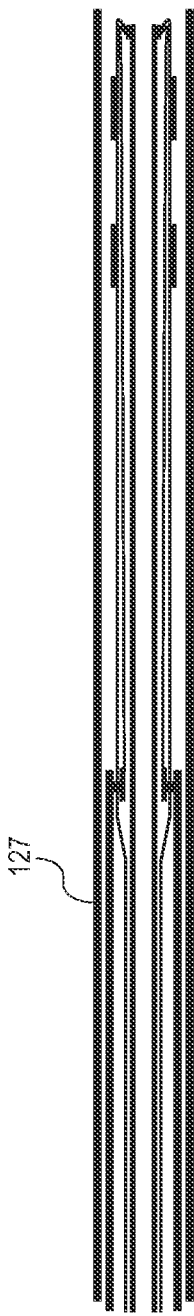

In yet another embodiment a sheathing tube may or may not be required. This embodiment is represented in FIGS. 58I-58K. In this embodiment the inner shaft 58 and the outer shaft 57 are moved relative to one another such that the electrode assembly 105 is shifted from its expanded configuration to a delivery configuration as indicated in the transition pictured from 58I-58J. As illustrated in FIG. 58K, electrode assembly 105 is shifted into introducer sheath 128 through and introducer valve 126 and the device is ready for transport to the treatment site. Alternately, the device in the configuration of FIG. 58J may be delivered with a sheathing tube such as those described herein.

The alternate delivery sheath 128 is illustrated in FIG. 65. The alternate sheathing tube can have multiple tubing layers and is configured to be captured on the outer shaft and present a soft and compliant member at the interface to the electrode assembly 105. It is typically mounted on the outer shaft at the time of manufacture. The device is described as follows. A soft jacket 129 fabricated from a compliant material such as PEBAX encapsulates at least the distal end of a stiff jacket 130. The soft jacket 129 also extends beyond the distal end of the stiff jacket 130 such that as the alternate delivery sheath 128 interfaces with the electrode assembly 105 a compliant member is presented assuring no damage to the electrode assembly occurs as it is being compressed into its sheathed configuration. The stiff jacket 130 can be manufactured of stiff materials such as polyimide. This proximal end of this assembly is surrounded by base tube 122 which can be manufactured of materials having strength such as polyimide. At the proximal end mounted within the base tube 132 is the stop tube 131 which is configured to collide with a feature on the outer shaft 57 (not shown). The stop tube 131 can be manufactured of materials such as polyimide. Given the characteristics of the materials presented others can be appropriately chosen as replacements by those with knowledge in the art.

The assembly 105 can be delivered to the left atrium and the membrane expanded and placed at the antrum of one of the pulmonary veins. The overall shape of the membrane can be visualized using the electrodes themselves as the conductive metallic material of the electrodes can provide visualization under fluoroscopy. The radiopaque markers can be used to determine exact location of each electrode based on the marker orientation. The mapping electrodes can be used to measure initial electrical signals and can later confirm electrical conduction block post ablation. The user can select which electrodes to turn on, which ones to leave off, and which ones to set to a higher or lower power setting based on their contact with the tissue. The various methods of contact detection as described above or a fiber optic can be used to confirm contact of the electrodes with the tissue. The device is then set to the appropriate power and temperature settings, irrigation turned on to the desired level, and energy transmission initiated. The mapping electrodes can be used now to determine successful conduction block. Once conduction block is achieved, the catheter and moved over to the next target location, another pulmonary vein or atrial wall, for ablation.

FIG. 64 illustrates a complete system 1000 for using the electrode assembly 105. The system incorporates a visualization system 1004, a source of ablative power 1002, an irrigation fluid source 1003 interfaced to a pump possibly incorporating an irrigation fluid cooling means 1005, an interface cable 1001, a catheter handle 1006 incorporating additional controls, a catheter incorporating a shaft 57 connected to the distal end of the electrode assembly 105 and associated inner assemblies, the electrode structure 105, and a guide wire 1007.

It should be appreciated that variations of the disclosed devices, assemblies, and methods can exist. It should also be appreciated that a variety of elements described herein can be used individually or in a variety of combinations. Features described herein in the context with or respect to one exemplary device or assembly can be implemented separately or in any suitable sub-combination with other exemplary devices or systems.

It is to be understood that this subject matter described herein is not limited to particular embodiments described, as such may of course vary. It is also to be understood that the terminology used herein is for the purpose of describing particular embodiments only, and is not intended to be limiting. Unless defined otherwise, all technical terms used herein have the same meaning as commonly understood by one skilled in the art to which this subject matter belongs.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A catheter and electrode assembly comprising:
an elongate catheter body comprising a distal portion; and
an expandable electrode structure coupled to the distal portion, the expandable electrode structure comprising
an inflatable membrane having an expanded configuration,
a substrate disposed over and secured to the inflatable membrane,
at least two electrically conductive traces disposed on and secured to the substrate, a first trace electrically coupled to a first electrode and a second trace electrically coupled to a second electrode different than the first electrode, the first and second electrodes being individually addressable, and wherein the first electrode is disposed over a portion of the substrate and a portion of an external surface of the membrane not covered by the substrate.

2. The assembly of claim 1, wherein the expandable electrode structure comprises at least four electrodes disposed on the inflatable membrane such that they are distally facing when the membrane is in the expanded configuration.

3. The assembly of claim 1, wherein first and second opposite sides of a surface of the membrane are coupled to the catheter body.

4. The assembly of claim 1 wherein the expanded configuration is an inflated configuration.

5. The assembly of claim 1 wherein the first electrode is disposed distally to the second electrode.

6. The assembly of claim 1 wherein the first trace extends further distally along the inflatable membrane than the second trace.

7. The assembly of claim 1 wherein the second electrode is disposed over a portion of the substrate and a portion of an external surface of the membrane not covered by the substrate.

8. A catheter and electrode assembly comprising:
an elongate catheter comprising an inner elongate member axially movable relative to an outer elongate member; and
an expandable member comprising
an inflatable membrane with a proximal end secured to the outer elongate member and a distal end secured to the inner elongate member,
a substrate disposed over and secured to the inflatable membrane,
at least two electrically conductive traces disposed over on and secured to the substrate, a first trace electrically coupled to a first electrode and a second trace electrically coupled to a second electrode different than the first electrode, the first and second electrodes being individually addressable, and wherein the first electrode is disposed over a portion of the substrate and a portion of an external surface of the membrane not covered by the substrate.

9. The catheter of claim 8 wherein the inflatable membrane is configured to have a toroid shape when inflated.

10. The catheter of claim 8 wherein the inflatable membrane has a distal region that is drawn into itself.

11. The catheter of claim 8 wherein the expandable member comprises a plurality of electrodes that comprises a ring of electrodes, radially distributed about a catheter shaft longitudinal axis, on a distal region of the inflatable membrane.

12. The catheter of claim 11 wherein the ring of electrodes comprises at least four electrodes.

13. The catheter of claim 11 wherein the plurality of electrodes further comprises a second ring of electrodes, radially distributed about the catheter shaft longitudinal axis on the inflatable membrane and radially outward relative to the first ring of electrodes when the inflatable membrane is inflated.

14. The catheter of claim 8 wherein the inner elongate member is a guidewire lumen.

15. The catheter of claim 8 wherein at least one of the first and second electrodes is distally facing when the inflatable membrane is in the inflated configuration.

16. The catheter of claim 8 wherein a first surface of the inflatable membrane is secured to the outer elongate member and a second surface of the inflatable membrane is secured to the inner elongate member.

17. A catheter and electrode assembly comprising:
an elongate catheter; and
an expandable member comprising
an inflatable membrane with a first surface secured to a distal region of the elongate catheter and a second surface different than the first surface secured to the distal region of the elongate catheter, wherein a distal end of the inflatable membrane is drawn into itself when the inflatable membrane is in an inflated configuration,
a substrate disposed over and secured to the inflatable membrane, and
at least two electrically conductive traces disposed on and secured to the substrate, a first trace electrically coupled to a first electrode and a second trace electrically coupled to a second electrode different than the first electrode, the first and second electrodes being individually addressable, and wherein the first electrode is disposed over a portion of the substrate and a portion of an external surface of the membrane not covered by the membrane.

18. The catheter of claim 17 wherein the inflatable membrane is configured to have a toroid shape when inflated.

19. The catheter of claim 17 wherein the expandable member comprises a plurality of electrodes that comprises a ring of electrodes, radially distributed about a catheter shaft longitudinal axis, on a distal region of the inflatable membrane.

20. The catheter of claim 19 wherein the ring of electrodes comprises at least four electrodes.

21. The catheter of claim 19 wherein the plurality of electrodes further comprises a second ring of electrodes radially outward relative to the first ring of electrodes when the inflatable membrane is inflated.

22. The catheter of claim 17 wherein at least one of the first and second electrodes is distally facing when the inflatable membrane is in the inflated configuration.

* * * * *